US008226943B2

(12) United States Patent
Gurney et al.

(10) Patent No.: US 8,226,943 B2
(45) Date of Patent: Jul. 24, 2012

(54) ANTIBODIES TO NOTCH RECEPTORS

(75) Inventors: Austin L. Gurney, San Francisco, CA (US); Timothy Charles Hoey, Hillsborough, CA (US); Edward Thein Htun van der Horst, Palo Alto, CA (US); Aaron Ken Sato, Burlingame, CA (US); Yuan Ching Liu, Fremont, CA (US); Maureen Fitch Bruhns, San Mateo, CA (US); John A. Lewicki, Los Gatos, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 254 days.

(21) Appl. No.: 12/499,627

(22) Filed: Jul. 8, 2009

(65) Prior Publication Data

US 2010/0111958 A1 May 6, 2010

Related U.S. Application Data

(60) Provisional application No. 61/112,699, filed on Nov. 7, 2008, provisional application No. 61/112,701, filed on Nov. 7, 2008, provisional application No. 61/079,095, filed on Jul. 8, 2008.

(51) Int. Cl.
*A61K 39/395* (2006.01)
*C07K 16/28* (2006.01)
*C07K 14/705* (2006.01)
*C12N 5/00* (2006.01)

(52) U.S. Cl. ............... 424/130.1; 424/133.1; 424/141.1; 424/143.1; 435/326; 435/331; 435/334; 530/350; 530/387.1; 530/388.1; 530/388.15; 530/388.22

(58) Field of Classification Search ........................ None
See application file for complete search history.

(56) References Cited

U.S. PATENT DOCUMENTS

| | | | |
|---|---|---|---|
| 5,648,464 A | 7/1997 | Artavanis-Tsakonas et al. | |
| 5,786,158 A | 7/1998 | Artavanis-Tsakonas et al. | |
| 5,789,195 A | 8/1998 | Artavanis-Tsakonas et al. | |
| 6,004,528 A | 12/1999 | Bergstein | |
| 6,080,588 A | 6/2000 | Glick | |
| 6,083,904 A | 7/2000 | Artavanis-Tsakonas | |
| 6,090,922 A | 7/2000 | Artavanis-Tsakonas et al. | |
| 6,180,370 B1 | 1/2001 | Queen et al. | |
| 6,379,925 B1 | 4/2002 | Kitajewski et al. | |
| 6,537,775 B1 | 3/2003 | Tournier-Lasserve et al. | |
| 6,689,744 B2 | 2/2004 | Gao et al. | |
| 6,984,522 B2 | 1/2006 | Clarke et al. | |
| 7,091,323 B2 * | 8/2006 | Pan et al. ................ | 530/388.15 |
| 7,115,360 B2 | 10/2006 | Clarke et al. | |
| 7,432,364 B2 * | 10/2008 | Pan et al. ................ | 536/23.53 |
| 7,632,926 B2 | 12/2009 | Kim et al. | |
| 7,713,710 B2 | 5/2010 | Clarke et al. | |
| 7,754,206 B2 | 7/2010 | Clarke et al. | |
| 7,850,961 B2 | 12/2010 | Clarke et al. | |
| 7,919,092 B2 * | 4/2011 | Lewicki et al. ............ | 424/141.1 |
| 8,088,617 B2 | 1/2012 | Gurney et al. | |
| 2002/0086014 A1 | 7/2002 | Korman et al. | |
| 2002/0119565 A1 | 8/2002 | Clarke et al. | |
| 2002/0122802 A1 | 9/2002 | Wands et al. | |
| 2003/0082651 A1 | 5/2003 | Gao et al. | |
| 2003/0083465 A1 | 5/2003 | Zimrin et al. | |
| 2003/0186290 A1 | 10/2003 | Tournier-Lasserve et al. | |
| 2004/0229301 A1 | 11/2004 | Wang | |
| 2005/0026831 A1 | 2/2005 | Bodmer et al. | |
| 2005/0089518 A1 | 4/2005 | Clarke et al. | |
| 2005/0112121 A1 | 5/2005 | Artavanis-Tsakonas et al. | |
| 2005/0142635 A1 | 6/2005 | Tsuchiya et al. | |
| 2005/0187179 A1 | 8/2005 | Miele et al. | |
| 2005/0232927 A1 | 10/2005 | Clarke et al. | |
| 2006/0030694 A1 | 2/2006 | Kitajewski et al. | |
| 2006/0051325 A1 | 3/2006 | Clarke et al. | |
| 2006/0073125 A1 | 4/2006 | Clarke et al. | |
| 2006/0083682 A1 | 4/2006 | Bergstein | |
| 2006/0263774 A1 | 11/2006 | Clark et al. | |
| 2007/0036800 A1 | 2/2007 | Bergstein | |
| 2007/0036801 A1 | 2/2007 | Bergstein | |
| 2007/0036804 A1 | 2/2007 | Bergstein | |
| 2007/0041984 A1 | 2/2007 | Bergstein | |
| 2007/0196047 A9 | 8/2007 | Levner et al. | |
| 2007/0212737 A1 | 9/2007 | Clarke et al. | |
| 2007/0265246 A1 | 11/2007 | Clevers et al. | |
| 2008/0076670 A1 | 3/2008 | Sivan et al. | |
| 2008/0112940 A1 | 5/2008 | Liaw | |
| 2008/0118520 A1 | 5/2008 | Li et al. | |
| 2008/0131434 A1 | 6/2008 | Lewicki et al. | |
| 2008/0131908 A1 | 6/2008 | Li et al. | |
| 2008/0132423 A1 | 6/2008 | Kondo | |
| 2008/0178305 A1 | 7/2008 | Clarke et al. | |

(Continued)

FOREIGN PATENT DOCUMENTS

EP     0 662 827 B2     7/1995

(Continued)

OTHER PUBLICATIONS

Al-Hajj et al., "Prospective Identification of Tumorigenic Breast Cancer Cells", Cell Biology 100:3983-3988 (2003), Proceedings of the National Academy of Science, 700 11th Street, NW Suite 450 Washington, DC 20001.

(Continued)

*Primary Examiner* — Bridget E Bunner
(74) *Attorney, Agent, or Firm* — Sterne, Kessler, Golstein & Fox P.L.L.C.

(57) ABSTRACT

The present invention relates to Notch-binding agents and Notch antagonists and methods of using the agents and/or antagonists for treating diseases such as cancer. The present invention provides antibodies that specifically bind to a non-ligand binding region of the extracellular domain of one or more human Notch receptor, such as Notch2 and/or Notch3, and inhibit tumor growth. The present invention further provides methods of treating cancer, the methods comprising administering a therapeutically effective amount of an antibody that specifically binds to a non-ligand binding region of the extracellular domain of a human Notch receptor protein and inhibits tumor growth.

23 Claims, 44 Drawing Sheets

U.S. PATENT DOCUMENTS

Figure 1B:
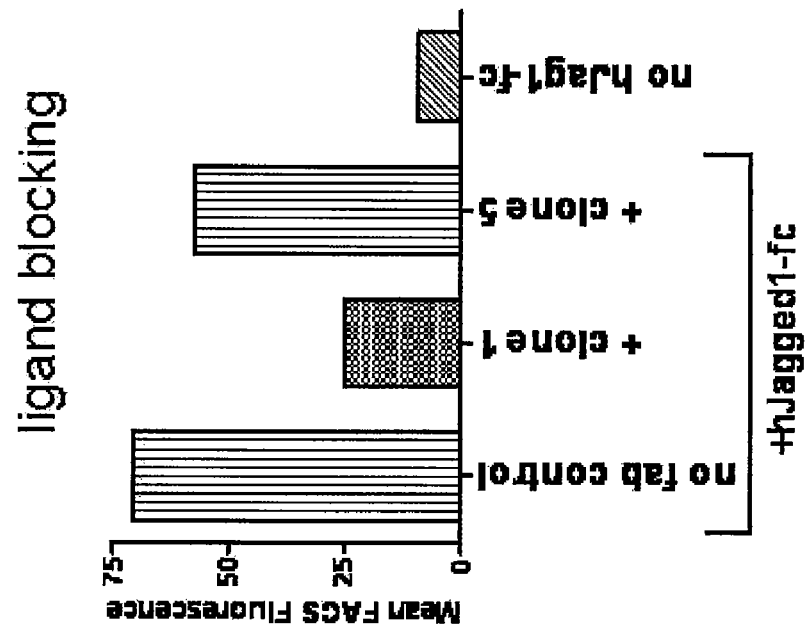

| | | |
|---|---|---|
| 2008/0187532 A1 | 8/2008 | Gurney et al. |
| 2008/0188405 A1 | 8/2008 | Di Fiore et al. |
| 2008/0194022 A1 | 8/2008 | Clarke et al. |
| 2008/0226621 A1 | 9/2008 | Fung et al. |
| 2008/0260734 A1 | 10/2008 | Clarke et al. |
| 2009/0004205 A1 | 1/2009 | Clarke et al. |
| 2009/0028856 A1 | 1/2009 | Chen et al. |
| 2009/0047285 A1 | 2/2009 | Gurney et al. |
| 2009/0208491 A1 | 8/2009 | Gurney et al. |
| 2011/0033481 A1 | 2/2011 | Clarke et al. |
| 2011/0092378 A1 | 4/2011 | Clarke et al. |
| 2011/0195065 A1 | 8/2011 | Lewicki et al. |

FOREIGN PATENT DOCUMENTS

| | | |
|---|---|---|
| WO | WO 94/07474 A1 | 4/1994 |
| WO | WO 97/37004 A1 | 10/1997 |
| WO | WO 97/45143 A1 | 12/1997 |
| WO | WO 98/57621 A1 | 12/1998 |
| WO | WO 00/20576 A2 | 4/2000 |
| WO | WO 00/52143 A2 | 9/2000 |
| WO | WO 02/00576 A1 | 1/2002 |
| WO | WO 02/12447 A2 | 2/2002 |
| WO | WO 02/18544 A2 | 3/2002 |
| WO | WO 03/042246 A2 | 5/2003 |
| WO | WO 03/050502 A2 | 6/2003 |
| WO | WO 03/062273 A2 | 7/2003 |
| WO | WO 04/001004 A2 | 12/2003 |
| WO | WO 2004/091383 A2 | 10/2004 |
| WO | WO 2005/026334 A2 | 3/2005 |
| WO | WO 2005/054434 A2 | 6/2005 |
| WO | WO 2005/074633 A2 | 8/2005 |
| WO | WO 2006/110581 A2 | 10/2006 |
| WO | WO 2008/051797 A3 | 5/2008 |
| WO | WO 2008/057144 A2 | 5/2008 |
| WO | WO 2008/076960 A2 | 6/2008 |
| WO | WO 2008/091641 A2 | 7/2008 |
| WO | WO 2008/108910 A2 | 9/2008 |
| WO | WO 2008/136848 A2 | 11/2008 |
| WO | WO 2009/025867 A2 | 2/2009 |
| WO | WO 2009/035522 A1 | 3/2009 |
| WO | WO 2010/005567 A2 | 1/2010 |

OTHER PUBLICATIONS

Arias et al., "Csl-Independent Notch Signalling: A Checkpoint in Ceu Fate Decisions During Development?", Current Opinion in Genetics & Development, 12:524-533 (2002), Elsevier Science Ltd, The Boulevard, Langford Lane, Kidlington, Oxford, OX5 1 GB, UK.

Artavanis-Tsakonas et al., "Notch Signaling: Cell Fate Control and Signal Integration in Development", Science 284:770-776 (1999), American Association for the Advancement of Science, 1200 New York Avenue, NW, Washington, DC 20005.

Brennan and Brown, "Is There a Role for Notch Signalling in Human Breast Cancer?", Breast Cancer Research, 5:69-75 (2003), BioMed Central Ltd, London WC1X 8HL, United Kingdom.

Brennan et al., "Repression by Notch is Required Before Wingless Signalling During Muscle Progenitor Cell Development in *Drosophila*", Current Biology, 9:707-710 (1991), Current Biology Publications, 34-42 Cleveland Street, London W1 P GLE, UK.

Cole et al., "The Ebv-Hybridoma Technique and its Application to Human Lung Cancer", Monoclonal Antibodies and Cancer Therapy, 77-96 (1985), Alan R. Liss, Inc, 41 East11th Street, New York, NY 10003.

Del Amo et al., "Cloning, Analysis, and Chromosomal Localization of Notch-1, a Mouse Homolog of *Drospohila* Notch," Genomics, 15:259-264 (1993), Academic Press, Inc.

Domenga et al., "Notch3 is required for arterial identity and maturation of vascular smooth muscle cells," Genes & Development, 18:2730-2735 (2004), Cold Spring Harbor Laboratory Press.

Duncan et al., "Integration of Notch and Wnt Signaling in Hematopoietic Stem Cell Maintenance", Nature Immunology 6:314-322 (2005), Nature Publishing Group, 345 Park Avenue South, New York, NY 10010-1707.

Ellisen et al., "Tan•1, The Human Homolog of the *Drosophila* Notch Gene, Is Broken by Chromosomal Translocations in T Lymphoblastic Neoplasms", Cell, 66:649-661 (1991), Cell Press, 50 Church Street, Cambridge, Massachusetts 02138.

Gale et al., "Haploinsufficiency of Delta-Like 4 Ligand Results in Embryonic Lethality Due to Major Defects in Arterial and Vascular Development", PNAS, 101:15949-15954 (2004), National Academy of Science, 700 11th Street, NW Suite 450 Washington, DC 20001.

Gallahan et al., "Expression of a Truncated Int3 Gene in Developing Secretory Mammary Epithelium Specifically Retards Lobular Differentiation Resulting in Tumorigenesis", Cancer Research, 56:1775-1785 (1996), American Association for Cancer Research, Inc, Public Ledger Bldg., Suite 816, 150 South Independence Mall West, Philadelphia, PA 19106-3483.

Gridley, T., "Notch signaling and inherited disease syndromes," Human Molecular Genetics 12:R9-R13 (2003), Oxford University Press.

Gridley, T., "Notch signaling during vascular development," PNAS, 98:5377-5378 (2001), National Academy of Sciences, Washington, DC 20001.

Gridley, T., "Vessel guidance," Nature, 445:722-723 (2007) Nature Publishing Group, New York, NY 10013-1917, USA.

Gridley, T., "Notch Signaling in Vertebrate Development and Disease," Mol. Cell. Neurosci, 9:103-108, (1997), Academic Press, 6277 Sea Harbor Drive, Orlando, FL 32887-4900.

Hadland et al., "A requirement for Notchl distinguishes 2 phases of definitive hematopoiesis during development," Blood, 104:3097-3105 (2004), The American Society of Hematology.

Hainaud et al., "The Role of the Vascular Endothelial Growth Factor-Delta-like 4 Ligand/Notch4-Ephrin B2 Cascade in Tumor Vessel Remodeling and Endothelial Cell Functions," Cancer Res, 66:8501-8510, (2006), American Association for Cancer Research.

Hallahan et al., "The SmoAl Mouse Model Reveals that Notch Signaling is Critical for the Growth and Survival of Some Hedgehog-Induced Medulloblastomas", Cancer Research, 64:7794-7800 (2004), American Association for Cancer Research, Philadelphia, PA 19106-4404.

Hitoshi et al., "Notch Pathway Molecules are Essential for Tile Maintenance, but not the Generation of Mammalian Neural Stem Cells", Genes &. Development, 16:846-858 (2002), Cold Spring Harbor Laboratory Press, Cold Spring Harbor Laboratory Press 500 Sunnyside Boulevard Woodbury, New York 11797.

Iso et al., "Notch Signaling in Vascular Development", Arterioscler Thrombosis and Vascular Biology, 23:543-553 (2003), Lippincott Williams & Wilkins , Philadelphia, PA 19106.

Jhappan et al., "Expression of an Activated Notch-Related Int-3 Transgene Interferes with Cell Differentiation and Induces Neoplastic Transformation in Mammary and Salivary Glands", Genes & Development, 6:345-355 (1992), Cold Spring Harbor Laboratory Press, Box 100, 1 Bungtown Road, Cold Spring Harbor, New York 11724-2203.

Joutel and Tournier-Lasserve., "Notch Signalling Pathway and Human Diseases", Seminars in Cell & Departmental Biology, 9:619-625 (1998), Academic Press, Orlando, FL 32887.

Joutel et al., "Notch3 Mutations in Cadasil, A Herediraty Adult Onset Consition Causing Stroke and Dementia", Nature, 383:707-710 (1996), Macmillan Magazines Ltd., 4 Little Essex Street, London WC2R 3LF.

Karanu et al., "The Notch Ligand Jagged-L Represents a Novel Growth Factor of Human Hematopoietic Stem Cells", J. Exp. Med, 192: 1365-1372 (Nov. 6, 2000), The Rockefeller University Press, 1114 First Avenue, New York, 10021.

Kidd et al., "Sequence of the Notch Locus of *Drosophila melanogaster*: Relationship of the Encoded Protein to Mammalian Clotting and Growth Factors", Molecular and Cellular Biology, 6: 3094-3108 (1986), American Society for Microbiology, 1913 I St., NW, Washington, DC 20006.

Kopper and Hajdú"Tumor Stem Cells", Pathology Oncology Research, 10:69-73 (2004), Arányi Lajos Foundation, Budapest.

Krebs et al., "Notch Signaling is Essential for Vascular Morphogenesis in Mice", Genes & Development, 14:1343-1352 (2000), Cold Spring Harbor Laboratory Press, Box 100, 1 Bungtown Road, Cold Spring Harbor, New York 11724-2203.

Kuukasjärvi et al., "Genetic Heterogeneity and Clonal Evolution Underlying Development of Asynchronous Metastasis in Human Breast Cancer", Cancer Research, 57:1597-1604 (Apr. 15, 1997), American Association for Cancer Research, Inc., P.O. Box 3000, Denville, NJ 7834.

Lapidot et al., "A Cell Initiating Human Acute Myeloid Leukaemia after Transplantation into SCID Mice", Nature, 367:645-648 (1994), Macmillan Magazines Ltd., 4 Little Essex Street, London WC2R 3LF.

Lawrence et al., "Notch Signaling Targets the Wingless Responsiveness of a Ubx Visceral Mesoderm Enhancer in *Drosophila*", Current Biology, 11:375-385 (2001), Cell Press, 1100 Massachusetts Avenue, Cambridge, MA 02138.

Leethanakul et al., "Distinct Pattern of Expression of Differentiation and Growth-Related Genes in Squamous Cell Carcinomas of the Head and Neck Revealed by the Use of Laser Capture Microdissection and Cdna Arrays", Oncogene, 19:3220-3224 (2000), Nature Publishing Group, Houndmills, Basingstoke, Hampshire RG21 6XS, UK.

Leong and Karsan, "Recent insights into the role of Notch signaling in tumorigenesis," Blood, 107:2223-2233 (2006), American Society of Hematology.

Leong et al., "Activated Notch4 Inhibits Angiogenesis: Role of β1-Integrin Activartion," Mol. Cell. Biol., 22:2830-2841, (2002) American Society for Microbiology.

McCright et al., "Defects in Development of the Kidney, Heart and Eye Vasculature in Mice Homozygous for a Hypomorphic Notch2 Mutation", Development, 128:491-502 (2001), The Company of Biologists Limited, Bidder Building, 140 Cowley Road, Cambridge CB4 ODL, UK.

Mohr, "Character Caused by Mutation of an Entire Region of a Chromosome in *Drosophila*", Genetics, 4:275-282 (1919), The Genetics Society of America, Genetics Mellon Institute, Box I 4400 Fifth Avenue Pittsburgh, Pennsylvania 15213-2683.

Parr et al., "The Possible Correlation of Notch-1 and Notch-2 with Clinical Outcome and Tumor Clinicpathological Parameters in Human Breast Cancer", International Journal of Molecular Medicine, 14:779-786 (2004), Springer Verlag, Tiergartenstasse 17, 69121 Heidelberg, Germany.

Pear and Aster, "T Cell Acute Lymphoblastic Leukemia/Lymphoma: A Human Cancer Commonly Associated with Aberrant Notch1 Signaling", Current Opinion in Hematology, 11:426-433 (2004), Lippincott Williams & Wilkins, Philadelphia, PA 19106.

Politi et al., "Notch in Mammary Gland Development and Breast Cancer", Seminars in Cancer Biology, 14:341-347 (2004), Academic Press, 6277 Sea Harbor Drive, Orlando, FL, 32887-4900.

Purow et al., "Expression of Notch-1 and Its Ligands, Delta-Like-1 and Jagged-1, is Critical for Glioma Cell Survival and Proliferation", Clinical Research, 65:2354-2363 (2005), American Association for Cancer Research, Philadelphia, PA 19106-4404.

Rae et al., "Novel Association of a Diverse Range of Genes with Renal Cell Carcinoma as Identified by Differential Display", Inter. J. Cancer, 88:726-732 (2000), John Wiley & Sons Inc, 350 Main Street, Malden MA 02148, USA.

Rebay et al., "Specific Egf Repeats of Notch Mediate Interactions with Delta and Serrate: Implications for Notch as a Multifunctional Receptor", Cell, 67:687-699 (1991), Cell Press, 50 Church Street, Cambridge, Massachusetts 02138.

Reya et al., "Stem Cells, Cancer and Cancer Stem Cells", Nature, 414:105-111 (2001), Nature Publishing Group, New York, NY 10013-1917, USA.

Robey et al., "An Activated Form of Notch Influences the Choice Between Cd4 and Cd8 T Cell Lineages", Cell, 87:483-492 (1996), Cell Press, 50 Church Street, Cambridge, Massachusetts 02138.

Smith et al., "Constitutive Expression of a Truncated Int3 Gene in Mouse Mammary Epithelium Impairs Differentiation and Functional Development", Cell Growth & Differentiation, 6: 563-577 (1995), American Association for Cancer Research, Philadelphia, PA 19106-4404.

Soriano et al., "Expression of an Activated Notch4(Int-3) Oncoprotein Disrupts Morphogenesis and Induces an Invasive Phenotype in Mammary Epithelial Cells in Vitro", Intl. J. Cancer, 86: 652-659 (2000), John Wiley & Sons Inc, 350 Main Street, Malden MA 02148, USA.

Suzuki et al., "Imbalanced Expression of Tan-L and Human Notch4 in Endometrial Cancers", International Journal of Oncology, 17: 1131-1139 (2000), Spandidos-publications, Athens 116 10, Greece.

Swiatek et al., "Notch1 is essential for postimplantation development in mice," Genes & Development, 8:707-719, (1994) Cold Spring Harbor Laboratory.

Takeshita et al., "Crictical Role of Endothelial Notch1 Signaling in Postnatal Angiogenesis," Cir. Res. 100:70-78 (2007), American Heart Association, Inc.

Tavares et al., "Inhibition of Vascular Endothelium by the Notch-Ligand Delta-4 Unveils a Novel Therapeutic Target," Vascular Wall Biology, Poster Board #-Session: 115-II, Abstract# 1944, pp. 531a, (2003), American Society of Hematology, San Diego, California.

Uyttendaele et al., "Notch4 and Wnt-L Proteins Function to Regulate Branching Morphogenesis of Malnmary Epithelial Cells in an Opposing Fashion", Developmental Biology, 196:204-217 (1998), Academic Press, Orlando, FL 32887-4900.

Van Es and Clevers, "Notch and Wnt Inhibitors as Potential New Drugs for Intestinal Neoplastic Disease", Trends in Molecular Medicine, 11: 496-502 (2005), Elsevier, London, UK WCIX 8RR.

Van Limpt et al., "Sage Analysis of Neuroblastoma Reveals a High Expression of the Human Homologue of the *Drosophila* Delta Gene", Medical and Pediatric Oncology, 35:554-558 (2000), Wiley-Liss, Inc, 605 Third Avenue, New York, NY 10158-0012.

Varnum-Finney et al., "Pluripotent, Cytokine-dependent, Hematopoietic Stem Cells are Immortalized by Constitutive Notch1 Signaling", Nature Medicine, 6:1278-1281 (2000), Nature Publishing Group, New York, NY 10013-1917, USA.

Weijzen et al., "Activation of Notch-L Signaling Maintains the Neoplastic Phenotype in Human Ras-Transformed Cells", Nature Medicine, 8 :979-986 (2002), Nature Publishing Group, New York, NY 10013-1917, USA.

Wharton et al., "Nucleotide Sequence from the Neurogenic Locus Notch Implies a Gene Product that Shares Homology with Proteins Containing Egf-Like Repeats", Cell, 43:567-581 (1985), Cell Press, 50 Church Street, Cambridge, Massachusetts 02138.

Xu et al., "Regions of *Drosophila* Notch that Contribute to Ligand Binding and the Modulatory Influence of Fringe", The Journal of Biological Chemistry, 280: 30158-30165 (2005), American Society for Biochemistry and Molecular Biology, Inc., 9650 Rockville Pike, Bethesda, MD 20814 U.S.A.

Xue et al., "Embryonic Lethality and Vascular Defects in Mice Lacking the Notch Ligand Jagged1", Human Molecular Genetics, 8: 723-730 (1999), Oxford University Press, McLean, VA 22101-0850, USA.

Zagouras et al., "Alterations in Notch Signaling in Neoplastic Lesions of the Human Cervix", PNAS, 92: 6414-6418 (1995), National Academy of Sciences, Washington, DC 20001.

The Extended European Search Report issued in European Application No. EP 07 777 332.3, on Aug. 11, 2009 (10 pages).

Kei Sakamoto et al., "Distinct roles of EGF repeats for the Notch signaling system," *Experimental Cell Research*, 2005, 281-291, 302(2), Elsevier, Orlando, FL, XP-004649921.

Li Shao et al., "Fringe modifies O-fucose on mouse Notch1 at epidermal growth factor-like repeats within the ligand-binding site and the Abruptex region," *The Journal of Biological Chemistry*, 2003, 7775-7782, 278(10), American Society for Biochemistry and Molecular Biology, Bethesda, MD, XP-002538409.

Nils Peters et al., "CADASIL-associated Notch3 mutations have differential effects both on ligand binding and ligand-induced Notch3 receptor signaling through RBP-Jk," *Experimental Cell Research*, 2004, 454-464, 299 (2), Elsevier, Orlando, FL, XP-004537012.

Shimizu, K., et al., "Physical 1-15 interaction of Delta1, Jagged1, and Jagged2 with Notch1 and Notch3 receptors," Biochem. Biophys. Res. Commun. 276:385-389, Academic Press, United States (2000).

Rand, M., et al,, "Calcium binding to tandem repeats of EGF-like modules. Expression and characterization of the EGF-like modules of human Notch-1 implicated in receptor-ligand interactions," Protein Science 6:2059-2071, Cambridge University Press, United Kingdom (1997).

Hambleton, S., et al., "Structural and Functional Properties of the Human Notch-I Ligand Binding Region," Structure 12:2173-2183, Current Biology, Ltd., United States (2004).

Miele, L., Gamma-Secretase and Notch Signaling: Novel Therapeutic Targets in Breast Cancer, DTIC (Online), accessed at http://www.dtic.mil/cgi-bin/GetTRDoc?Location=U2&doc=GetTRDoc.pdf&AD=ADA446389 (retrieved on Jan. 12, 2010).

Dikic, I., et al., "Notch: Implications of endogenous inhibitors for therapy," *Bioessays* 32:481-487, John Wiley & Sons, United States (2010).

Lin, L., et al., "Targeting Specific Regions of the Notch3 Ligand-Binding Domain Induces Apoptosis and Inhibits Tumor Growth in Lung Cancer," Can. Res. 70: 632-638, American Assoc. for Cancer Research, United States (2010).

Bheeshmachar, G., et al., "Evidence for a Role for Notch Signaling in the Cytokine-Dependent Survival of Activated T cells," J. Immunol. 177:5041-5050, XP008112523, American Association of Immunologists, Inc., United States (2006).

Extended European Search Report of European Appl. No. 08 72 4737.5, European Patent Office, Munich, Germany, dated Sep. 24, 2010.

"Biologicals Product: Mouse Monoclonal anti-Notch 1 (A6) antibody datasheet," XP008115324, NOVUS, accessed at http://www.novusbio.com/data_sheet/pdf_data_sheet/5985, downloaded 2008.

Allenspach, E.J., et al., "Notch Signaling in Cancer," *Cancer Biol.* 1:466-476, Landes Bioscience, United States (2002).

Armstrong, F., et al., "NOTCH is a key regulator of human T-cell acute leukemia initiating cell activity," *Blood* 113:1730-1740, The American Society of Hematology, United States (2009).

Bellavia, D., et al., "Constitutive activtion of NF-Kβ and T-cell leukemia/lymphoma in Notch3 transgenic mice," *EMBO J.* 19:3337-3348, Oxford University Press, United States (2000).

Callahan, R. & Raafat, A. "Notch Signaling in Mammary Gland Tumorigenesis," *Journal of Mammary Gland Biology and Neoplasia* 6:23-36, Plenum Publishing Corporation, United States (2001).

Campbell, A.M., "Monoclonal antibody technology," vol. 13, pp. v-29, Elsevier Science Publishers B.V, The Netherlands, 1984.

Cox, C.V., et al., "Characterization of acute lymphoblastic leukemia progenitor cells," *Blood* 104:2919-2925, The American Society of Hematology, United States (2004).

Deftos, M.L., et al., "Correlating notch signaling with thymocyte maturation," *Immunity* 9:777-786, Cell Press, United States (1998).

English language Abstract of WIPO Patent Publication No. WO 02/00576 A1, Jan. 3, 2002.

Fleming, R.J., et al., "The Notch receptor and its ligands," *Trends in Cell Biol.* 7:437-441, Elsevier Science Ltd., The Netherlands (1997).

Fre, S., et al., "Notch signals control the fate of immature progenitor cells in the intestine," *Nature* 435:964-968, Nature Publishing Group, England (2005).

Gallahan, D., and Callahan, R., "The mouse mammary tumor associated gene INT3 is a unique member of the *NOTCH* gene family (*NOTCH4*)," *Oncogene* 14:1838-1890, Stockton Press, United States (1997).

Grabher, C., et al., "Notch 1 activation in the molecular pathogensis of T-cell acute lymphoblastic leukaemia," *Nature Reviews Cancer* 6:347-359, Nature Publishing Group, England (2006).

Imatani, A. and Callahan, R., "Identification of a novel *NOTCH-4/INT-3* RNA species encoding, an activated gene product in certain human tumor cell lines," *Oncogene* 19:223-231, Macmillan Publishers Ltd., England (2000).

International Search Report for International Application No. PCT/US08/00884, United States Patent and Trademark Office, U.S.A., mailed on Oct. 1, 2008.

International Search Report for International Application No. PCT/US09/03995, United States Patent and Trademark Office, U.S.A., mailed on Mar. 2, 2010.

International Search Report for International Application No. PCT/US2008/001948, USPTO, mailed on Oct. 15, 2008.

Jang, M.S., et al.,"Notch signaling as a target in multimodality cancer therapy," *Curr. Opin. Mol. Ther.* 2(1):55-65, Thomson Reuters (Scientific) Ltd., England (Feb. 2000).

Jarriault, S., et al., "Signaling downstream of activated mammalian Notch," *Nature* 377:355-358, Nature Publishing Group, England (1995).

Jehn, B.M., et al., "Cutting edge: protective effects of Notch-1 on TCR-induced apoptosis," *J. Immunol.* 162:635-638, The American Association of Immunologists, United States (1999).

Jundt, F., et al., "Activated Notch1 signaling promotes tumor cell proliferation and survival in Hodgkin and anaplastic large cell lymphoma," *Blood* 99:3398-3403, The American Society of Hematology, United States (2002).

Lee, J-S, et al., "Intracisternal Type A Particle-Mediated Activation of the *Notch4/int3* Gene in a Mouse Mammary Tumor: Generation of Truncated *Notch4/int3* mRNAs by Retroviral Splicing Events." *J. Virol.* 73:5166-5171, American Society for Microbiology, United States (1999).

Lee, S-H, et al., "Mutational analysis of *NOTCH1*, 2, 3 and 4 genes in common solid cancers and acute leukemias," *APMIS* 115:1357-1363, The Authors Journal Compilation, United States (2007).

Li, K., et al., "Modulation of Notch Signaling by Antibodies Specific for the Extracellular Negative Regulatory Region of NOTCH3," *J. Biol. Chem.* 283:8046-8054, The American Society for Biochemistry and Molecular Biology, Inc., United States (2008).

Li, L., et al., "The Human Homolog of Rat *Jagged1* Expressed by Marrow Stroma Inhibits Differentiation of 32D Cells through Interaction with Notch1," *Immunity* 8:43-55, Cell Press, United States (1998).

Li, L., et al., "Cloning, Characterization, and the Complete 56.8-Kilobase DNA Sequence of the Human NOTCH4 Gene," *Genomics* 51:45-48, Academic Press, United States (1998).

Lindsell, C.E., et al., "Jagged: A Mammalian Ligand That Activates Notch1," *Cell* 80:909-917, Cell Press, United States (1995).

Liu, Z., et al., "Notch1 loss of heterozygosity causes cascular tumors and lethal hemorrhage in mice," *J. Clin. Invest.* 121(2):800-8, American Society for Clinical Investigation, United States (Feb. 2011;Epub Jan. 25, 2011).

Miele, L., & Osborne, B., "Arbiter of Differentiation and Death: Notch Signaling Meets Apoptosis," *J. Cell Physiol.* 181:393-409, Wiley-Liss, Inc., United States (1999).

Nam, Y., et al., "Notch signaling as a therapeutic target," *Curr. Opin. Chem. Biol.* 6:501-509, Elsevier Science Ltd., Holland (2002).

Pelegrin, A., et al., "[Immunotargeting of tumors: state of the art and prospects in 2000]," *Bull. Cancer* 87(11):777-91, John Libbey Eurotext, France (Nov. 2000) in the English language.

Pelegrin, A., et al.,"[Immunotargeting of tumors: state of the art and prospects in 2000]," *Bull. Cancer* 87(11):777-91, Johon Libbey Eurotext, France (Nov. 2000) in the French language.

Sambandam, A., et al., "Notch signaling controls the generation and differentiation of early T lineage progenitors," *Nature Immunol.* 6:663-670, Nature Publishing Group, England (2005).

Sugaya, K., et al., "Gene organization of human NOTCH4 and (CTG)n polymorphism in this human counterpart gene of mouse proto-oncogene *Int3*," *Gene* 189:235-244, Elsevier Science B.V., Holland (1997).

Summons to attend oral proceedings pursuant to Rule 115(1) EPC for European Patent Application 05722705.0-2402/1718767, European Patent Office, Germany, mailed on Feb. 9, 2011.

Thelu, J., et al., "Notch signaling is linked to epidermal cell differentiation level in basal cell carcinoma, psoriasis and wound healing," *BMC Dermatology* 2:7, BioMed Central, England (2002).

Van Es, J.H., et al., "Notch/γ-secretase inhibition turns proliferative cells in intestinal crypts and adenomas into goblet cells," *Nature* 435:959-963, Nature Publishing Group, England (2005).

Weng, A.P., and Aster, J.C., "Multiple niches for Notch in cancer: context is everything," *Curr. Opin. Genet. Dev.* 14(1):48-54, Elsevier, England (Feb. 2004).

Weng, A.P., et al., "Activating Mutations of *NOTCH1* in Human T Cell Acute Lymphoblastic Leukemia," *Science* 306:269-271, Nature Publishing Group, England (2004).

Weng, A.P., et al., "Growth Suppression of Pre-T Acute Lymphoblastic Leukemia Cells by Inhibition of Notch Signaling," *Mol. Cell Biol.* 23:655-644, American Society for Microbiology, United States (2003).

Duan, Z., et al., "A Novel Notch Protein, N2N, Targeted by Neutrophil Elastase and Implicated in Hereditary Neutropenia," *Mol. Cell. Biol.* 24(1):58-70, American Society for Microbiology, United States (Jan. 2004).

Huang, E.Y., et al., "Surface Expression of Notch1 on Thymocytes: Correlation with the Double-Negative to Double-Positive Transition," *J. Immunol.* 171(5):2296-304, American Association of Immunologists, United States (Sep. 1, 2003).

Santa Cruz Biotechnology, Inc., "Notch 2 (25-255): sc-5545 datasheet," downloaded on Dec. 2, 2009.

Axelson, H., "Notch signaling and cancer: emerging complexity," *Semin. Cancer Biol.* 14:317-319, Elsevier Ltd., England (2004).

Curry, C.L., et al., "Gamma secretase inhibitor blocks Notch activation and induces apoptosis in Kaposi's sarcoma tumor cells," *Oncogene* 24:6333-6344, Nature Publishing Group, England (2005).

Dontu, G., et al., "Role of Notch signaling in cell-fate determination of human mammary stem/progenitor cells," *Breast Cancer Res.* 6:R605-R615, BioMed Central Ltd., England (2004).

Harper, J.A., et al., "Notch signaling in development and disease," *Clin. Genet.* 64:461-472, Blackwell Munksgaard, Denmark (2003).

Hopfer, O., et al., "The Notch pathway in ovarian carcinomas and adenomas," *Br. J. Cancer* 93:709-718, Cancer Research UK, England (2005).

Maillard, I., et al., "Mastermind critically regulates Notch-mediated lymphoid cell fate decisions," *Blood* 104:1696-1702, The American Society of Hematology, United States (2004).

Qin, J.Z., et al., "p53-independent NOXA induction overcomes apoptotic resistance of malignant melanomas," *Mol. Cancer Ther.* 3:895-902, American Association for Cancer Research, United States (2004).

Pei, Z. And Baker, N., "Competition between Delta and the Abruptex domain of Notch," *BMC Dev. Biol.* 8:4, BioMed Central, United Kingdom (2008).

Luo, B., et al., "Isolation and functional analysis of a cDNA for human Jagged2, a gene encoding a ligand for the Notch1 receptor," *Mol. Cell. Biol.* 17:6057-6067, American Society for Microbiology, United States (1997).

International Search Report for International Application No. PCT/US09/03994, ISA/US, Alexandria, Virginia, USA, mailed on Jul. 23, 2010.

International Search Report for International Application No. PCT/US11/21135, International Searching Authority, Alexandria, Virginia, United States, mailed Jul. 20, 2011.

NCBI Entrez, GenBank Report, Accession No. P01724, Burstein, Y. and Schechter, I, Entry Date Jul. 21, 1986, last updated Nov. 4, 2008.

NCBI Entrez, GenBank Report, Accession No. Q8VDC9, SEMBI, P., Entry Date Mar. 1, 2002, last updated Oct. 31, 2006.

Written Opinion of the International Searching Authority for International Application No. PCT/US11/21135, International Searching Authority, Alexandria, Virginia, United States, mailed Jul. 20, 2011.

\* cited by examiner

PN8 PANCREATIC TUMOR

B44 BREAST TUMOR

T1 BREAST TUMOR

PE13 Breast Tumor

C28 Colon Tumor

Colo205 Colon Tumor

17A

17B

*: p < 0.05 vs. Control
**: p < 0.05 vs. Gemcitabine

*: p < 0.05 vs. Control
**: p < 0.05 vs. Taxol

SEQUENCE LISTING

<160> NUMBER OF SEQ ID NOS: 60

<210> SEQ ID NO 1
<211> LENGTH: 1383
<212> TYPE: DNA
<213> ORGANISM: Homo sapiens

<400> SEQUENCE: 1

```
atgaaacacc tgtggttctt cctcctgctg gtggcagctc ccagatgggt cctgtcccag      60
gtgcaattgg tggaaagcgg cggcggcctg gtgcaaccgg gcggcagcct gcgtctgagc     120
tgcgcggcct ccggatttac ctttcttct tctggtatgt cttgggtgcg ccaagccct      180 gggaagggtc tcgagtgggt gagcgttatc gcttcttctg gtagcaatac ctattatgcg     240
gatagcgtga aaggccgttt taccatttca cgtgataatt cgaaaaacac cctgtatctg     300
caaatgaaca gcctgcgtgc ggaagatacg gccgtgtatt attgcgcgcg tggtattttt     360
tttgctattt ggggccaagg cacccctggtg acggttagct cagccagcac aaagggccct    420
agcgtcttcc ctctggctcc ctgcagcagg agcaccagcg agagcacagc cgccctgggc     480
tgcctggtca aggactactt ccccgaaccg gtgacggtgt cgtggaactc aggcgctctg     540
accagcggcg tgcacacctt cccagctgtc ctacagtcct caggactcta ctccctcagc     600
agcgtggtga ccgtgccctc cagcaacttc ggcacccaga cctacacctg caacgtagat     660
```

```
cacaagccca gcaacaccaa ggtggacaag acagttgagc gcaaatgttg tgtcgagtgc    720
ccaccgtgcc cagcaccacc tgtggcagga ccgtcagtct tcctcttccc cccaaaaccc    780
aaggacaccc tcatgatctc ccggacccct gaggtcacgt gcgtggtggt ggacgtgagc    840
cacgaagacc ccgaggtcca gttcaactgg tacgtggacg gcgtggaggt gcataatgcc    900
aagacaaagc cacgggagga gcagttcaac agcacgttcc gtgtggtcag cgtcctcacc    960
gttgtgcacc aggactggct gaacggcaag gagtacaagt gcaaggtctc caacaaaggc   1020
ctcccagccc ccatcgagaa aaccatctcc aaaaccaaag gcagccccg agaaccacag    1080
gtgtacaccc tgcccccatc ccgggaggag atgaccaaga accaggtcag cctgacctgc   1140
ctggtcaaag gcttctaccc cagcgacatc gccgtggagt gggagagcaa tgggcagccg   1200
gagaacaact acaagaccac acctcccatg ctggactccg acggctcctt cttcctctac   1260
agcaagctca ccgtggacaa gagcaggtgg cagcagggga acgtcttctc atgctccgtg   1320
atgcatgagg ctctgcacaa ccactacacg cagaagagcc tctccctgtc tccgggtaaa   1380
tga                                                                1383

<210> SEQ ID NO 2
<211> LENGTH: 460
<212> TYPE: PRT
<213> ORGANISM: Homo sapiens

<400> SEQUENCE: 2

Met Lys His Leu Trp Phe Phe Leu Leu Leu Val Ala Ala Pro Arg Trp
1               5                  10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Ser Gly Met Ser Trp Val Arg Gln Ala Pro Gly Lys Gly Leu
    50                  55                  60

Glu Trp Val Ser Val Ile Ala Ser Ser Gly Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Ile Phe Phe Ala Ile Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240
```

| | | | | | | | | | | | |
|---|---|---|---|---|---|---|---|---|---|---|---|
|Pro|Pro|Cys|Pro|Ala|Pro|Val|Ala|Gly|Pro|Ser|Val|Phe|Leu|Phe|
| | | |245| | |250| | | |255| |

Pro Pro Lys Pro Lys Asp Thr Leu Met Ile Ser Arg Thr Pro Glu Val
           260                 265                 270

Thr Cys Val Val Val Asp Val Ser His Glu Asp Pro Glu Val Gln Phe
         275                 280                 285

Asn Trp Tyr Val Asp Gly Val Glu Val His Asn Ala Lys Thr Lys Pro
   290                 295                 300

Arg Glu Glu Gln Phe Asn Ser Thr Phe Arg Val Val Ser Val Leu Thr
305                 310                 315               320

Val Val His Gln Asp Trp Leu Asn Gly Lys Glu Tyr Lys Cys Lys Val
         325                 330                 335

Ser Asn Lys Gly Leu Pro Ala Pro Ile Glu Lys Thr Ile Ser Lys Thr
         340                 345                 350

Lys Gly Gln Pro Arg Glu Pro Gln Val Tyr Thr Leu Pro Pro Ser Arg
         355                 360                 365

Glu Glu Met Thr Lys Asn Gln Val Ser Leu Thr Cys Leu Val Lys Gly
   370                 375                 380

Phe Tyr Pro Ser Asp Ile Ala Val Glu Trp Glu Ser Asn Gly Gln Pro
385                 390                 395               400

Glu Asn Asn Tyr Lys Thr Thr Pro Pro Met Leu Asp Ser Asp Gly Ser
         405                 410                 415

Phe Phe Leu Tyr Ser Lys Leu Thr Val Asp Lys Ser Arg Trp Gln Gln
         420                 425                 430

Gly Asn Val Phe Ser Cys Ser Val Met His Glu Ala Leu His Asn His
         435                 440                 445

Tyr Thr Gln Lys Ser Leu Ser Leu Ser Pro Gly Lys
   450                 455                 460

<210> SEQ ID NO 3
<211> LENGTH: 708
<212> TYPE: DNA
<213> ORGANISM: Homo sapiens

<400> SEQUENCE: 3

```
atggtgttgc agacccaggt cttcatttct ctgttgctct ggatctctgg tgcctacggg      60
gatatcgtgc tgacccagag cccggcgacc ctgagcctgt ctccgggcga acgtgcgacc    120
ctgagctgca gagcgagcca gtctgttcgt tctaattatc tggcttggta ccagcagaaa    180
ccaggtcaag caccgcgtct attaatttat ggtgcttctt ctcgtgcaac tggggtcccg    240
gcgcgtttta gcggctctgg atccggcacg gattttaccc tgaccattag cagcctggaa    300
cctgaagact ttgcggttta ttattgccag cagtattcta attttcctat tacctttggc    360
cagggtacga agttgaaat taaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacaggggag agtgttag               708
```

<210> SEQ ID NO 4
<211> LENGTH: 236
<212> TYPE: PRT
<213> ORGANISM: Homo sapiens -continued

<400> SEQUENCE: 4

```
Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln
        35                  40                  45

Ser Val Arg Ser Asn Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Tyr Ser Asn Phe Pro Ile Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 5
<211> LENGTH: 6
<212> TYPE: PRT
<213> ORGANISM: Homo sapiens

<400> SEQUENCE: 5

```
Ser Ser Ser Gly Met Ser
1               5
```

<210> SEQ ID NO 6
<211> LENGTH: 17
<212> TYPE: PRT
<213> ORGANISM: Homo sapiens

<400> SEQUENCE: 6

```
Val Ile Ala Ser Ser Gly Ser Asn Thr Tyr Tyr Ala Asp Ser Val Lys
1               5                   10                  15

Gly
```

<210> SEQ ID NO 7
<211> LENGTH: 6
<212> TYPE: PRT
<213> ORGANISM: Homo sapiens

<400> SEQUENCE: 7

```
Gly Ile Phe Phe Ala Ile
```

<210> SEQ ID NO 8
<211> LENGTH: 12
<212> TYPE: PRT
<213> ORGANISM: Homo sapiens

<400> SEQUENCE: 8

Arg Ala Ser Gln Ser Val Arg Ser Asn Tyr Leu Ala
1               5                   10

<210> SEQ ID NO 9
<211> LENGTH: 7
<212> TYPE: PRT
<213> ORGANISM: Homo sapiens

<400> SEQUENCE: 9

Gly Ala Ser Ser Arg Ala Thr
1               5

<210> SEQ ID NO 10
<211> LENGTH: 8
<212> TYPE: PRT
<213> ORGANISM: Homo sapiens

<400> SEQUENCE: 10

Gln Gln Tyr Ser Asn Phe Pro Ile
1               5

<210> SEQ ID NO 11
<211> LENGTH: 130
<212> TYPE: PRT
<213> ORGANISM: Homo sapiens

<400> SEQUENCE: 11

Met Lys Lys Thr Ala Ile Ala Ile Ala Val Ala Leu Ala Gly Phe Ala
1               5                   10                  15

Thr Val Ala Gln Ala Asp Ile Val Leu Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Ser Val Arg Ser Asn Tyr Leu Ala Trp Tyr Gln Gln Lys Pro Gly Gln
        50                  55                  60

Ala Pro Arg Leu Leu Ile Tyr Gly Ala Ser Ser Arg Ala Thr Gly Val
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Tyr Ser Asn Phe Pro Ile Thr Phe Gly Gln Gly Thr Lys Val Glu Ile
        115                 120                 125

Lys Arg
    130

<210> SEQ ID NO 12
<211> LENGTH: 137
<212> TYPE: PRT
<213> ORGANISM: Homo sapiens

<400> SEQUENCE: 12

Met Lys Gln Ser Thr Ile Ala Leu Ala Leu Leu Pro Leu Leu Phe Thr
1               5                   10                  15

```
Pro Val Thr Lys Ala Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Ser Gly Met Ser Trp Val Arg Gln Ala Pro Gly Lys
    50                  55                  60

Gly Leu Glu Trp Val Ser Val Ile Ala Ser Ser Gly Ser Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Gly Ile Phe Phe Ala Ile Trp Gly Gln
        115                 120                 125

Gly Thr Leu Val Thr Val Ser Ser Ala
    130                 135
```

<210> SEQ ID NO 13
<211> LENGTH: 109
<212> TYPE: PRT
<213> ORGANISM: Homo sapiens

<400> SEQUENCE: 13

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser Asn Phe Pro
                85                  90                  95

Ile Thr Phe Gly Gln Gly Thr Lys Val Glu Ile Lys Arg
            100                 105
```

<210> SEQ ID NO 14
<211> LENGTH: 116
<212> TYPE: PRT
<213> ORGANISM: Homo sapiens

<400> SEQUENCE: 14

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Gly Ile Phe Phe Ala Ile Trp Gly Gln Gly Thr Leu Val Thr
            100                 105                 110

Val Ser Ser Ala
        115

<210> SEQ ID NO 15
<211> LENGTH: 1383
<212> TYPE: DNA
<213> ORGANISM: Homo sapiens

<400> SEQUENCE: 15

| | | | | | |
|---|---|---|---|---|---|
| atgaagcacc | tgtggttctt | tctgctgctg | gtcgccgctc | ctagatgggt | gctgtccgag | 60 |
| gtgcagctgg | tcgagtctgg | cggcggactg | gtgcagcctg | gcggctccct | gagactgtcc | 120 |
| tgcgctgcct | ccggcttcac | cttctcctcc | tccggcatgt | cctgggtgcg | ccaggctccc | 180 |
| ggcaagggcc | tggagtgggt | gtccgtgatc | gcctccagcg | gctccaacac | ctactacgcc | 240 |
| gactccgtga | agggccggtt | caccatctcc | cgggacaact | ccaagaacac | cctgtacctg | 300 |
| cagatgaact | ccctgcgggc | cgaggacacc | gccgtgtact | actgcgccag | gggcatcttc | 360 |
| ttcgccatct | ggggccaggg | caccctggtg | accgtgtcct | ccgcctccac | caagggccct | 420 |
| tccgtgttcc | ctctggcccc | ttgctcccgg | tccacctccg | agtccaccgc | cgctctgggc | 480 |
| tgcctggtga | aggactactt | ccctgagcct | gtgacagtgt | cctggaactc | tggcgccctg | 540 |
| acctccggcg | tgcacacctt | ccctgccgtg | ctgcagtcct | ccggcctgta | ctccctgtcc | 600 |
| tccgtggtga | cagtgccttc | ctccaacttc | ggcacccaga | cctacacctg | caacgtggac | 660 |
| cacaagcctt | ccaacaccaa | ggtggacaag | accgtggagc | ggaagtgctg | cgtggagtgc | 720 |
| cctccttgcc | ctgcccctcc | tgtggctggc | cctagcgtgt | tcctgttccc | tcctaagcct | 780 |
| aaggacaccc | tgatgatctc | ccggacccct | gaggtgacct | gcgtggtggt | ggacgtgtcc | 840 |
| cacgaggacc | ctgaggtgca | gttcaattgg | tacgtggacg | gcgtggaggt | gcacaacgcc | 900 |
| aagaccaagc | ctcgggagga | acagttcaac | tccaccttcc | gggtggtgtc | cgtgctgacc | 960 |
| gtggtgcacc | aggactggct | gaacggcaag | gaatacaagt | gcaaagtctc | caacaagggc | 1020 |
| ctgcctgccc | ctatcgagaa | aaccatcagc | aagaccaagg | ccagcctcg | cgagcctcag | 1080 |
| gtgtacaccc | tgcctccatc | cagggaggaa | atgaccaaga | accaggtgtc | cctgacctgt | 1140 |
| ctggtgaagg | gcttctaccc | ttccgatatc | gccgtggagt | gggagtccaa | cggccagcct | 1200 |
| gagaacaact | acaagaccac | ccctccctatg | ctggactccg | acggctcctt | cttcctgtac | 1260 |
| tccaagctga | cagtggacaa | gtcccggtgg | cagcagggca | acgtgttctc | ctgctccgtg | 1320 |
| atgcacgagg | ccctgcacaa | ccactacacc | cagaagtccc | tgtccctgag | ccctggcaag | 1380 |
| tag | | | | | | 1383 |

<210> SEQ ID NO 16
<211> LENGTH: 460
<212> TYPE: PRT
<213> ORGANISM: Homo sapiens

<400> SEQUENCE: 16

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Ser Gly Met Ser Trp Val Arg Gln Ala Pro Gly Lys Gly Leu

```
              50                  55                  60
Glu Trp Val Ser Val Ile Ala Ser Ser Gly Ser Asn Thr Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Gly Ile Phe Phe Ala Ile Trp Gly Gln Gly Thr
                115                 120                 125

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Asn Phe Gly Thr Gln Thr Tyr Thr Cys Asn Val Asp His Lys Pro Ser
210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
                275                 280                 285

Asn Trp Tyr Val Asp Gly Val Glu Val His Asn Ala Lys Thr Lys Pro
290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
                355                 360                 365

Glu Glu Met Thr Lys Asn Gln Val Ser Leu Thr Cys Leu Val Lys Gly
                370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
450                 455                 460

<210> SEQ ID NO 17
<211> LENGTH: 711
```

```
<212> TYPE: DNA
<213> ORGANISM: Homo sapiens

<400> SEQUENCE: 17
atggtgctgc agacccaggt gttcatctcc ctgctgctgt ggatctccgg cgcctacggc      60
gagatcgtgc tgacccagtc ccctgccaca ctgagcctga gccctggcga gagagccacc     120
ctgagctgca ggcgggcctc ccagtccgtg cggtccaact acctggcttg gtatcagcag     180
aaacccggac aggcccctcg gctgctgatc tacggcgcct cctcccgggc taccggcatc     240
cctgccggt tctccggctc cggcagcggc accgacttca ccctgaccat ctcctccctg      300
gagcctgagg acttcgccgt gtactactgc agcagtact ccaacttccc tatcaccttc      360
ggccagggca ccaaggtgga gatcaagcgg accgtggccg ctccttccgt gttcatcttc     420
cccccttccg acgagcagct gaagtccggc accgcctccg tggtgtgcct gctgaacaac     480
ttctacccctc gggaggccaa ggtgcagtgg aaggtggaca cgccctgca gtccggcaac    540
tcccaggaat ccgtcaccga gcaggactcc aaggacagca cctactcccct gtcctccacc    600
ctgaccctgt ccaaggccga ctacgagaag cacaaggtgt acgcctgcga ggtgacccac    660
cagggcctgt ccagccctgt gaccaagtcc ttcaaccggg gcgagtgcta g              711

<210> SEQ ID NO 18
<211> LENGTH: 235
<212> TYPE: PRT
<213> ORGANISM: Homo sapiens

<400> SEQUENCE: 18

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Arg Ser Asn Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Tyr
            100                 105                 110

Ser Asn Phe Pro Ile Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

225            230            235

<210> SEQ ID NO 19
<211> LENGTH: 110
<212> TYPE: PRT
<213> ORGANISM: Homo sapiens

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Arg Ala Ser Gln Ser Val Arg Ser
            20                  25                  30

Asn Tyr Leu Ala Trp Tyr Gln Lys Pro Gly Gln Ala Pro Arg Leu
        35                  40                  45

Leu Ile Tyr Gly Ala Ser Arg Ala Thr Gly Ile Pro Ala Arg Phe
    50                  55                  60

Ser Gly Ser Gly Ser Gly Thr Asp Phe Thr Leu Thr Ile Ser Ser Leu
65                  70                  75                  80

Glu Pro Glu Asp Phe Ala Val Tyr Tyr Cys Gln Gln Tyr Ser Asn Phe
                85                  90                  95

Pro Ile Thr Phe Gly Gln Gly Thr Lys Val Glu Ile Lys Arg
            100                 105                 110

<210> SEQ ID NO 20
<211> LENGTH: 116
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Phe Phe Ala Ile Trp Gly Gln Gly Thr Leu Val Thr
            100                 105                 110

Val Ser Ser Ala
        115

<210> SEQ ID NO 21
<211> LENGTH: 723
<212> TYPE: PRT
<213> ORGANISM: Homo sapiens

<400> SEQUENCE: 21

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

```
Gly Tyr Cys Lys Cys Pro Glu Gly Phe Leu Gly Glu Tyr Cys Gln His
     50                  55                  60

Arg Asp Pro Cys Glu Lys Asn Arg Cys Gln Asn Gly Gly Thr Cys Val
 65              70                  75                      80

Ala Gln Ala Met Leu Gly Lys Ala Thr Cys Arg Cys Ala Ser Gly Phe
                 85                  90                  95

Thr Gly Glu Asp Cys Gln Tyr Ser Thr Ser His Pro Cys Phe Val Ser
                100                 105                 110

Arg Pro Cys Leu Asn Gly Gly Thr Cys His Met Leu Ser Arg Asp Thr
            115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480
```

```
Leu Cys Met Pro Gly Phe Lys Gly Val His Cys Glu Leu Arg Ala
                485                 490                 495
Asp Lys Thr His Thr Cys Pro Pro Cys Pro Ala Pro Glu Leu Leu Gly
            500                 505                 510
Gly Pro Ser Val Phe Leu Phe Pro Pro Lys Pro Lys Asp Thr Leu Met
            515                 520                 525
Ile Ser Arg Thr Pro Glu Val Thr Cys Val Val Val Asp Val Ser His
            530                 535                 540
Glu Asp Pro Glu Val Lys Phe Asn Trp Tyr Val Asp Gly Val Glu Val
545                 550                 555                 560
His Asn Ala Lys Thr Lys Pro Arg Glu Glu Gln Tyr Asn Ser Thr Tyr
                565                 570                 575
Arg Val Val Ser Val Leu Thr Val Leu His Gln Asp Trp Leu Asn Gly
                580                 585                 590
Lys Glu Tyr Lys Cys Lys Val Ser Asn Lys Ala Leu Pro Ala Pro Ile
                595                 600                 605
Glu Lys Thr Ile Ser Lys Ala Lys Gly Gln Pro Arg Glu Pro Gln Val
            610                 615                 620
Tyr Thr Leu Pro Pro Ser Arg Asp Glu Leu Thr Lys Asn Gln Val Ser
625                 630                 635                 640
Leu Thr Cys Leu Val Lys Gly Phe Tyr Pro Ser Asp Ile Ala Val Glu
                645                 650                 655
Trp Glu Ser Asn Gly Gln Pro Glu Asn Asn Tyr Lys Thr Thr Pro Pro
                660                 665                 670
Val Leu Asp Ser Asp Gly Ser Phe Phe Leu Tyr Ser Lys Leu Thr Val
            675                 680                 685
Asp Lys Ser Arg Trp Gln Gln Gly Asn Val Phe Ser Cys Ser Val Met
            690                 695                 700
His Glu Ala Leu His Asn His Tyr Thr Gln Lys Ser Leu Ser Leu Ser
705                 710                 715                 720
Pro Gly Lys

<210> SEQ ID NO 22
<211> LENGTH: 6
<212> TYPE: PRT
<213> ORGANISM: Homo sapiens

<400> SEQUENCE: 22

Ser Ile Phe Tyr Pro Thr
1               5

<210> SEQ ID NO 23
<211> LENGTH: 6
<212> TYPE: PRT
<213> ORGANISM: Homo sapiens

<400> SEQUENCE: 23

Ser Ser Phe Phe Ala Ser
1               5

<210> SEQ ID NO 24
<211> LENGTH: 6
<212> TYPE: PRT
<213> ORGANISM: Homo sapiens

<400> SEQUENCE: 24

Ser Ser Phe Tyr Ala Ser
1               5
```

<210> SEQ ID NO 25
<211> LENGTH: 6
<212> TYPE: PRT
<213> ORGANISM: Homo sapiens

<400> SEQUENCE: 25

Ser Ser Phe Phe Ala Thr
1               5

<210> SEQ ID NO 26
<211> LENGTH: 6
<212> TYPE: PRT
<213> ORGANISM: Homo sapiens

<400> SEQUENCE: 26

Ser Ile Phe Tyr Pro Ser
1               5

<210> SEQ ID NO 27
<211> LENGTH: 6
<212> TYPE: PRT
<213> ORGANISM: Homo sapiens

<400> SEQUENCE: 27

Ser Ser Phe Phe Ala Asn
1               5

<210> SEQ ID NO 28
<211> LENGTH: 5
<212> TYPE: PRT
<213> ORGANISM: Homo sapiens

<400> SEQUENCE: 28

His Lys Gly Ala Leu
1               5

<210> SEQ ID NO 29
<211> LENGTH: 5
<212> TYPE: PRT
<213> ORGANISM: Homo sapiens

<400> SEQUENCE: 29

His Glu Asp Ala Ile
1               5

<210> SEQ ID NO 30
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is Gly or Ser
<220> FEATURE:
<221> NAME/KEY: MISC_FEATURE
<222> LOCATION: (2)..(2)
<223> OTHER INFORMATION: X is Ile or Ser
<220> FEATURE:
<221> NAME/KEY: MISC_FEATURE
<222> LOCATION: (4)..(4)
<223> OTHER INFORMATION: X is Phe or Tyr
<220> FEATURE:
<221> NAME/KEY: MISC_FEATURE
<222> LOCATION: (5)..(5)
<223> OTHER INFORMATION: X is Ala or Pro
<220> FEATURE:
<221> NAME/KEY: MISC_FEATURE
<222> LOCATION: (6)..(6)

<223> OTHER INFORMATION: X is Ile, Thr, Ser, or Asn

<400> SEQUENCE: 30

Xaa Xaa Phe Xaa Xaa Xaa
1               5

<210> SEQ ID NO 31
<211> LENGTH: 2471
<212> TYPE: PRT
<213> ORGANISM: Homo sapiens

<400> SEQUENCE: 31

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
            35                  40                  45

Gly Tyr Cys Lys Cys Pro Glu Gly Phe Leu Gly Glu Tyr Cys Gln His
        50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

-continued

```
Cys Ile Asp Arg Val Ala Ser Phe Ser Cys Met Cys Pro Glu Gly Lys
            355                 360                 365

Ala Gly Leu Leu Cys His Leu Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
```

```
                    770             775             780
Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
                835                 840                 845

Lys Glu Ser Pro Asn Phe Glu Ser Tyr Thr Cys Leu Cys Ala Pro Gly
850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
                900                 905                 910

Asp Asp Cys Leu Ala Asn Pro Cys Gln Asn Gly Gly Ser Cys Met Asp
            915                 920                 925

Gly Val Asn Thr Phe Ser Cys Leu Cys Leu Pro Gly Phe Thr Gly Asp
            930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
                980                 985                 990

Glu Ser Ser Cys Phe Asn Gly Gly Thr Cys Val Asp Gly Ile Asn Ser
            995                 1000                1005

Phe Ser Cys Leu Cys Pro Val Gly Phe Thr Gly Ser Phe Cys Leu
        1010                1015                1020

His Glu Ile Asn Glu Cys Ser Ser His Pro Cys Leu Asn Glu Gly
        1025                1030                1035

Thr Cys Val Asp Gly Leu Gly Thr Tyr Arg Cys Ser Cys Pro Leu
        1040                1045                1050

Gly Tyr Thr Gly Lys Asn Cys Gln Thr Leu Val Asn Leu Cys Ser
        1055                1060                1065

Arg Ser Pro Cys Lys Asn Lys Gly Thr Cys Val Gln Lys Lys Ala
        1070                1075                1080

Glu Ser Gln Cys Leu Cys Pro Ser Gly Trp Ala Gly Ala Tyr Cys
        1085                1090                1095

Asp Val Pro Asn Val Ser Cys Asp Ile Ala Ala Ser Arg Arg Gly
        1100                1105                1110

Val Leu Val Glu His Leu Cys Gln His Ser Gly Val Cys Ile Asn
        1115                1120                1125

Ala Gly Asn Thr His Tyr Cys Gln Cys Pro Leu Gly Tyr Thr Gly
        1130                1135                1140

Ser Tyr Cys Glu Glu Gln Leu Asp Glu Cys Ala Ser Asn Pro Cys
        1145                1150                1155

Gln His Gly Ala Thr Cys Ser Asp Phe Ile Gly Gly Tyr Arg Cys
        1160                1165                1170

Glu Cys Val Pro Gly Tyr Gln Gly Val Asn Cys Glu Tyr Glu Val
        1175                1180                1185
```

```
Asp Glu Cys Gln Asn Gln Pro Cys Gln Asn Gly Gly Thr Cys Ile
1190                    1195                1200

Asp Leu Val Asn His Phe Lys Cys Ser Cys Pro Gly Thr Arg
1205                    1210                1215

Gly Leu Leu Cys Glu Glu Asn Ile Asp Asp Cys Ala Arg Gly Pro
1220                    1225                1230

His Cys Leu Asn Gly Gly Gln Cys Met Asp Arg Ile Gly Gly Tyr
1235                    1240                1245

Ser Cys Arg Cys Leu Pro Gly Phe Ala Gly Glu Arg Cys Glu Gly
1250                    1255                1260

Asp Ile Asn Glu Cys Leu Ser Asn Pro Cys Ser Ser Glu Gly Ser
1265                    1270                1275

Leu Asp Cys Ile Gln Leu Thr Asn Asp Tyr Leu Cys Val Cys Arg
1280                    1285                1290

Ser Ala Phe Thr Gly Arg His Cys Glu Thr Phe Val Asp Val Cys
1295                    1300                1305

Pro Gln Met Pro Cys Leu Asn Gly Gly Thr Cys Ala Val Ala Ser
1310                    1315                1320

Asn Met Pro Asp Gly Phe Ile Cys Arg Cys Pro Pro Gly Phe Ser
1325                    1330                1335

Gly Ala Arg Cys Gln Ser Ser Cys Gly Gln Val Lys Cys Arg Lys
1340                    1345                1350

Gly Glu Gln Cys Val His Thr Ala Ser Gly Pro Arg Cys Phe Cys
1355                    1360                1365

Pro Ser Pro Arg Asp Cys Glu Ser Gly Cys Ala Ser Ser Pro Cys
1370                    1375                1380

Gln His Gly Gly Ser Cys His Pro Gln Arg Gln Pro Pro Tyr Tyr
1385                    1390                1395

Ser Cys Gln Cys Ala Pro Pro Phe Ser Gly Ser Arg Cys Glu Leu
1400                    1405                1410

Tyr Thr Ala Pro Pro Ser Thr Pro Pro Ala Thr Cys Leu Ser Gln
1415                    1420                1425

Tyr Cys Ala Asp Lys Ala Arg Asp Gly Val Cys Asp Glu Ala Cys
1430                    1435                1440

Asn Ser His Ala Cys Gln Trp Asp Gly Gly Asp Cys Ser Leu Thr
1445                    1450                1455

Met Glu Asn Pro Trp Ala Asn Cys Ser Ser Pro Leu Pro Cys Trp
1460                    1465                1470

Asp Tyr Ile Asn Asn Gln Cys Asp Glu Leu Cys Asn Thr Val Glu
1475                    1480                1485

Cys Leu Phe Asp Asn Phe Glu Cys Gln Gly Asn Ser Lys Thr Cys
1490                    1495                1500

Lys Tyr Asp Lys Tyr Cys Ala Asp His Phe Lys Asp Asn His Cys
1505                    1510                1515

Asp Gln Gly Cys Asn Ser Glu Glu Cys Gly Trp Asp Gly Leu Asp
1520                    1525                1530

Cys Ala Ala Asp Gln Pro Glu Asn Leu Ala Glu Gly Thr Leu Val
1535                    1540                1545

Ile Val Val Leu Met Pro Pro Glu Gln Leu Leu Gln Asp Ala Arg
1550                    1555                1560

Ser Phe Leu Arg Ala Leu Gly Thr Leu Leu His Thr Asn Leu Arg
1565                    1570                1575

Ile Lys Arg Asp Ser Gln Gly Glu Leu Met Val Tyr Pro Tyr Tyr
1580                    1585                1590
```

```
Gly Glu Lys Ser Ala Ala Met Lys Lys Gln Arg Met Thr Arg Arg
    1595                1600                1605

Ser Leu Pro Gly Glu Gln Glu Gln Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
    1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
    1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
    1730                1735                1740

Val Ser Glu Ala Asn Leu Ile Gly Thr Gly Thr Ser Glu His Trp
    1745                1750                1755

Val Asp Asp Glu Gly Pro Gln Pro Lys Lys Val Lys Ala Glu Asp
    1760                1765                1770

Glu Ala Leu Leu Ser Glu Glu Asp Asp Pro Ile Asp Arg Arg Pro
    1775                1780                1785

Trp Thr Gln Gln His Leu Glu Ala Ala Asp Ile Arg Arg Thr Pro
    1790                1795                1800

Ser Leu Ala Leu Thr Pro Pro Gln Ala Glu Gln Glu Val Asp Val
    1805                1810                1815

Leu Asp Val Asn Val Arg Gly Pro Asp Gly Cys Thr Pro Leu Met
    1820                1825                1830

Leu Ala Ser Leu Arg Gly Gly Ser Ser Asp Leu Ser Asp Glu Asp
    1835                1840                1845

Glu Asp Ala Glu Asp Ser Ser Ala Asn Ile Ile Thr Asp Leu Val
    1850                1855                1860

Tyr Gln Gly Ala Ser Leu Gln Ala Gln Thr Asp Arg Thr Gly Glu
    1865                1870                1875

Met Ala Leu His Leu Ala Ala Arg Tyr Ser Arg Ala Asp Ala Ala
    1880                1885                1890

Lys Arg Leu Leu Asp Ala Gly Ala Asp Ala Asn Ala Gln Asp Asn
    1895                1900                1905

Met Gly Arg Cys Pro Leu His Ala Ala Val Ala Ala Asp Ala Gln
    1910                1915                1920

Gly Val Phe Gln Ile Leu Ile Arg Asn Arg Val Thr Asp Leu Asp
    1925                1930                1935

Ala Arg Met Asn Asp Gly Thr Thr Pro Leu Ile Leu Ala Ala Arg
    1940                1945                1950

Leu Ala Val Glu Gly Met Val Ala Glu Leu Ile Asn Cys Gln Ala
    1955                1960                1965

Asp Val Asn Ala Val Asp Asp His Gly Lys Ser Ala Leu His Trp
    1970                1975                1980

Ala Ala Ala Val Asn Asn Val Glu Ala Thr Leu Leu Leu Leu Lys
```

-continued

```
            1985                1990                1995
Asn Gly Ala Asn Arg Asp Met Gln Asp Asn Lys Glu Glu Thr Pro
    2000                2005                2010
Leu Phe Leu Ala Ala Arg Glu Gly Ser Tyr Glu Ala Ala Lys Ile
    2015                2020                2025
Leu Leu Asp His Phe Ala Asn Arg Asp Ile Thr Asp His Met Asp
    2030                2035                2040
Arg Leu Pro Arg Asp Val Ala Arg Asp Arg Met His His Asp Ile
    2045                2050                2055
Val Arg Leu Leu Asp Glu Tyr Asn Val Thr Pro Ser Pro Pro Gly
    2060                2065                2070
Thr Val Leu Thr Ser Ala Leu Ser Pro Val Ile Cys Gly Pro Asn
    2075                2080                2085
Arg Ser Phe Leu Ser Leu Lys His Thr Pro Met Gly Lys Lys Ser
    2090                2095                2100
Arg Arg Pro Ser Ala Lys Ser Thr Met Pro Thr Ser Leu Pro Asn
    2105                2110                2115
Leu Ala Lys Glu Ala Lys Asp Ala Lys Gly Ser Arg Arg Lys Lys
    2120                2125                2130
Ser Leu Ser Glu Lys Val Gln Leu Ser Glu Ser Val Thr Leu
    2135                2140                2145
Ser Pro Val Asp Ser Leu Glu Ser Pro His Thr Tyr Val Ser Asp
    2150                2155                2160
Thr Thr Ser Ser Pro Met Ile Thr Ser Pro Gly Ile Leu Gln Ala
    2165                2170                2175
Ser Pro Asn Pro Met Leu Ala Thr Ala Ala Pro Ala Pro Val
    2180                2185                2190
His Ala Gln His Ala Leu Ser Phe Ser Asn Leu His Glu Met Gln
    2195                2200                2205
Pro Leu Ala His Gly Ala Ser Thr Val Leu Pro Ser Val Ser Gln
    2210                2215                2220
Leu Leu Ser His His His Ile Val Ser Pro Gly Ser Gly Ser Ala
    2225                2230                2235
Gly Ser Leu Ser Arg Leu His Pro Val Pro Val Pro Ala Asp Trp
    2240                2245                2250
Met Asn Arg Met Glu Val Asn Glu Thr Gln Tyr Asn Glu Met Phe
    2255                2260                2265
Gly Met Val Leu Ala Pro Ala Glu Gly Thr His Pro Gly Ile Ala
    2270                2275                2280
Pro Gln Ser Arg Pro Pro Glu Gly Lys His Ile Thr Thr Pro Arg
    2285                2290                2295
Glu Pro Leu Pro Pro Ile Val Thr Phe Gln Leu Ile Pro Lys Gly
    2300                2305                2310
Ser Ile Ala Gln Pro Ala Gly Ala Pro Gln Pro Gln Ser Thr Cys
    2315                2320                2325
Pro Pro Ala Val Ala Gly Pro Leu Pro Thr Met Tyr Gln Ile Pro
    2330                2335                2340
Glu Met Ala Arg Leu Pro Ser Val Ala Phe Pro Thr Ala Met Met
    2345                2350                2355
Pro Gln Gln Asp Gly Gln Val Ala Gln Thr Ile Leu Pro Ala Tyr
    2360                2365                2370
His Pro Phe Pro Ala Ser Val Gly Lys Tyr Pro Thr Pro Pro Ser
    2375                2380                2385
```

```
Gln His Ser Tyr Ala Ser Ser Asn Ala Ala Glu Arg Thr Pro Ser
    2390            2395                2400

His Ser Gly His Leu Gln Gly Glu His Pro Tyr Leu Thr Pro Ser
    2405            2410                2415

Pro Glu Ser Pro Asp Gln Trp Ser Ser Ser Ser Pro His Ser Ala
    2420            2425                2430

Ser Asp Trp Ser Asp Val Thr Thr Ser Pro Thr Pro Gly Gly Ala
    2435            2440                2445

Gly Gly Gly Gln Arg Gly Pro Gly Thr His Met Ser Glu Pro Pro
    2450            2455                2460

His Asn Asn Met Gln Val Tyr Ala
    2465            2470

<210> SEQ ID NO 32
<211> LENGTH: 2321
<212> TYPE: PRT
<213> ORGANISM: Homo sapiens

<400> SEQUENCE: 32

Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Pro Pro Cys Leu Asp Gly Ser Pro
            35                  40                  45

Cys Ala Asn Gly Gly Arg Cys Thr Gln Leu Pro Ser Arg Glu Ala Ala
        50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285
```

```
Gly Thr Cys Phe Asn Thr Leu Gly Gly His Ser Cys Val Cys Val Asn
290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
                340                 345                 350

Asp Ala Cys Val Ser Asn Pro Cys His Glu Asp Ala Ile Cys Asp Thr
                355                 360                 365

Asn Pro Val Asn Gly Arg Ala Ile Cys Thr Cys Pro Pro Gly Phe Thr
370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
                420                 425                 430

Asn Glu Cys Leu Ser Gly Pro Cys Arg Asn Gln Ala Thr Cys Leu Asp
                435                 440                 445

Arg Ile Gly Gln Phe Thr Cys Ile Cys Met Ala Gly Phe Thr Gly Thr
450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
                500                 505                 510

Ser Thr Pro Cys Arg Asn Gly Ala Lys Cys Val Asp Gln Pro Asp Gly
                515                 520                 525

Tyr Glu Cys Arg Cys Ala Glu Gly Phe Glu Gly Thr Leu Cys Asp Arg
                530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
                580                 585                 590

His Gly Gly Lys Cys Leu Asp Leu Val Asp Lys Tyr Leu Cys Arg Cys
                595                 600                 605

Pro Ser Gly Thr Thr Gly Val Asn Cys Glu Val Asn Ile Asp Asp Cys
610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
                660                 665                 670

Val Asp Gly Glu Asn Gly Phe Arg Cys Leu Cys Pro Pro Gly Ser Leu
                675                 680                 685

Pro Pro Leu Cys Leu Pro Pro Ser His Pro Cys Ala His Glu Pro Cys
                690                 695                 700

Ser His Gly Ile Cys Tyr Asp Ala Pro Gly Gly Phe Arg Cys Val Cys
705                 710                 715                 720
```

```
Glu Pro Gly Trp Ser Gly Pro Arg Cys Ser Gln Ser Leu Ala Arg Asp
            725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
            770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                    805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                    885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
            930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                    965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
            995                 1000                1005

Cys Gln Asn Gly Gly Arg Cys Val Gln Thr Gly Ala Tyr Cys Leu
    1010                1015                1020

Cys Pro Pro Gly Trp Ser Gly Arg Leu Cys Asp Ile Arg Ser Leu
    1025                1030                1035

Pro Cys Arg Glu Ala Ala Ala Gln Ile Gly Val Arg Leu Glu Gln
    1040                1045                1050

Leu Cys Gln Ala Gly Gly Gln Cys Val Asp Glu Asp Ser Ser His
    1055                1060                1065

Tyr Cys Val Cys Pro Glu Gly Arg Thr Gly Ser His Cys Glu Gln
    1070                1075                1080

Glu Val Asp Pro Cys Leu Ala Gln Pro Cys Gln His Gly Gly Thr
    1085                1090                1095

Cys Arg Gly Tyr Met Gly Gly Tyr Met Cys Glu Cys Leu Pro Gly
    1100                1105                1110

Tyr Asn Gly Asp Asn Cys Glu Asp Asp Val Asp Glu Cys Ala Ser
    1115                1120                1125

Gln Pro Cys Gln His Gly Gly Ser Cys Ile Asp Leu Val Ala Arg
```

-continued

```
             1130                1135                1140

Tyr Leu Cys Ser Cys Pro Pro Gly Thr Leu Gly Val Leu Cys Glu
    1145                1150                1155

Ile Asn Glu Asp Asp Cys Gly Pro Gly Pro Leu Asp Ser Gly
    1160                1165                1170

Pro Arg Cys Leu His Asn Gly Thr Cys Val Asp Leu Val Gly Gly
    1175                1180                1185

Phe Arg Cys Thr Cys Pro Pro Gly Tyr Thr Gly Leu Arg Cys Glu
    1190                1195                1200

Ala Asp Ile Asn Glu Cys Arg Ser Gly Ala Cys His Ala Ala His
    1205                1210                1215

Thr Arg Asp Cys Leu Gln Asp Pro Gly Gly Gly Phe Arg Cys Leu
    1220                1225                1230

Cys His Ala Gly Phe Ser Gly Pro Arg Cys Gln Thr Val Leu Ser
    1235                1240                1245

Pro Cys Glu Ser Gln Pro Cys Gln His Gly Gly Gln Cys Arg Pro
    1250                1255                1260

Ser Pro Gly Pro Gly Gly Leu Thr Phe Thr Cys His Cys Ala
    1265                1270                1275

Gln Pro Phe Trp Gly Pro Arg Cys Glu Arg Val Ala Arg Ser Cys
    1280                1285                1290

Arg Glu Leu Gln Cys Pro Val Gly Val Pro Cys Gln Gln Thr Pro
    1295                1300                1305

Arg Gly Pro Arg Cys Ala Cys Pro Pro Gly Leu Ser Gly Pro Ser
    1310                1315                1320

Cys Arg Ser Phe Pro Gly Ser Pro Pro Gly Ala Ser Asn Ala Ser
    1325                1330                1335

Cys Ala Ala Ala Pro Cys Leu His Gly Gly Ser Cys Arg Pro Ala
    1340                1345                1350

Pro Leu Ala Pro Phe Phe Arg Cys Ala Cys Ala Gln Gly Trp Thr
    1355                1360                1365

Gly Pro Arg Cys Glu Ala Pro Ala Ala Ala Pro Glu Val Ser Glu
    1370                1375                1380

Glu Pro Arg Cys Pro Arg Ala Ala Cys Gln Ala Lys Arg Gly Asp
    1385                1390                1395

Gln Arg Cys Asp Arg Glu Cys Asn Ser Pro Gly Cys Gly Trp Asp
    1400                1405                1410

Gly Gly Asp Cys Ser Leu Ser Val Gly Asp Pro Trp Arg Gln Cys
    1415                1420                1425

Glu Ala Leu Gln Cys Trp Arg Leu Phe Asn Asn Ser Arg Cys Asp
    1430                1435                1440

Pro Ala Cys Ser Ser Pro Ala Cys Leu Tyr Asp Asn Phe Asp Cys
    1445                1450                1455

His Ala Gly Gly Arg Glu Arg Thr Cys Asn Pro Val Tyr Glu Lys
    1460                1465                1470

Tyr Cys Ala Asp His Phe Ala Asp Gly Arg Cys Asp Gln Gly Cys
    1475                1480                1485

Asn Thr Glu Glu Cys Gly Trp Asp Gly Leu Asp Cys Ala Ser Glu
    1490                1495                1500

Val Pro Ala Leu Leu Ala Arg Gly Val Leu Val Leu Thr Val Leu
    1505                1510                1515

Leu Pro Pro Glu Glu Leu Leu Arg Ser Ser Ala Asp Phe Leu Gln
    1520                1525                1530
```

-continued

```
Arg Leu Ser Ala Ile Leu Arg Thr Ser Leu Arg Phe Arg Leu Asp
    1535                1540                1545

Ala His Gly Gln Ala Met Val Phe Pro Tyr His Arg Pro Ser Pro
    1550                1555                1560

Gly Ser Glu Pro Arg Ala Arg Arg Glu Leu Ala Pro Glu Val Ile
    1565                1570                1575

Gly Ser Val Val Met Leu Glu Ile Asp Asn Arg Leu Cys Leu Gln
    1580                1585                1590

Ser Pro Glu Asn Asp His Cys Phe Pro Asp Ala Gln Ser Ala Ala
    1595                1600                1605

Asp Tyr Leu Gly Ala Leu Ser Ala Val Glu Arg Leu Asp Phe Pro
    1610                1615                1620

Tyr Pro Leu Arg Asp Val Arg Gly Glu Pro Leu Glu Pro Pro Glu
    1625                1630                1635

Pro Ser Val Pro Leu Leu Pro Leu Leu Val Ala Gly Ala Val Leu
    1640                1645                1650

Leu Leu Val Ile Leu Val Leu Gly Val Met Val Ala Arg Arg Lys
    1655                1660                1665

Arg Glu His Ser Thr Leu Trp Phe Pro Glu Gly Phe Ser Leu His
    1670                1675                1680

Lys Asp Val Ala Ser Gly His Lys Gly Arg Arg Glu Pro Val Gly
    1685                1690                1695

Gln Asp Ala Leu Gly Met Lys Asn Met Ala Lys Gly Glu Ser Leu
    1700                1705                1710

Met Gly Glu Val Ala Thr Asp Trp Met Asp Thr Glu Cys Pro Glu
    1715                1720                1725

Ala Lys Arg Leu Lys Val Glu Glu Pro Gly Met Gly Ala Glu Glu
    1730                1735                1740

Ala Val Asp Cys Arg Gln Trp Thr Gln His His Leu Val Ala Ala
    1745                1750                1755

Asp Ile Arg Val Ala Pro Ala Met Ala Leu Thr Pro Pro Gln Gly
    1760                1765                1770

Asp Ala Asp Ala Asp Gly Met Asp Val Asn Val Arg Gly Pro Asp
    1775                1780                1785

Gly Phe Thr Pro Leu Met Leu Ala Ser Phe Cys Gly Gly Ala Leu
    1790                1795                1800

Glu Pro Met Pro Thr Glu Glu Asp Glu Ala Asp Asp Thr Ser Ala
    1805                1810                1815

Ser Ile Ile Ser Asp Leu Ile Cys Gln Gly Ala Gln Leu Gly Ala
    1820                1825                1830

Arg Thr Asp Arg Thr Gly Glu Thr Ala Leu His Leu Ala Ala Arg
    1835                1840                1845

Tyr Ala Arg Ala Asp Ala Ala Lys Arg Leu Leu Asp Ala Gly Ala
    1850                1855                1860

Asp Thr Asn Ala Gln Asp His Ser Gly Arg Thr Pro Leu His Thr
    1865                1870                1875

Ala Val Thr Ala Asp Ala Gln Gly Val Phe Gln Ile Leu Ile Arg
    1880                1885                1890

Asn Arg Ser Thr Asp Leu Asp Ala Arg Met Ala Asp Gly Ser Thr
    1895                1900                1905

Ala Leu Ile Leu Ala Ala Arg Leu Ala Val Glu Gly Met Val Glu
    1910                1915                1920

Glu Leu Ile Ala Ser His Ala Asp Val Asn Ala Val Asp Glu Leu
    1925                1930                1935
```

-continued

Gly Lys Ser Ala Leu His Trp Ala Ala Ala Val Asn Asn Val Glu
1940                1945                1950

Ala Thr Leu Ala Leu Leu Lys Asn Gly Ala Asn Lys Asp Met Gln
1955                1960                1965

Asp Ser Lys Glu Glu Thr Pro Leu Phe Leu Ala Ala Arg Glu Gly
1970                1975                1980

Ser Tyr Glu Ala Ala Lys Leu Leu Leu Asp His Phe Ala Asn Arg
1985                1990                1995

Glu Ile Thr Asp His Leu Asp Arg Leu Pro Arg Asp Val Ala Gln
2000                2005                2010

Glu Arg Leu His Gln Asp Ile Val Arg Leu Leu Asp Gln Pro Ser
2015                2020                2025

Gly Pro Arg Ser Pro Pro Gly Pro His Gly Leu Gly Pro Leu Leu
2030                2035                2040

Cys Pro Pro Gly Ala Phe Leu Pro Gly Leu Lys Ala Ala Gln Ser
2045                2050                2055

Gly Ser Lys Lys Ser Arg Arg Pro Pro Gly Lys Ala Gly Leu Gly
2060                2065                2070

Pro Gln Gly Pro Arg Gly Arg Gly Lys Lys Leu Thr Leu Ala Cys
2075                2080                2085

Pro Gly Pro Leu Ala Asp Ser Ser Val Thr Leu Ser Pro Val Asp
2090                2095                2100

Ser Leu Asp Ser Pro Arg Pro Phe Gly Gly Pro Ala Ser Pro
2105                2110                2115

Gly Gly Phe Pro Leu Glu Gly Pro Tyr Ala Ala Thr Ala Thr
2120                2125                2130

Ala Val Ser Leu Ala Gln Leu Gly Gly Pro Gly Arg Ala Gly Leu
2135                2140                2145

Gly Arg Gln Pro Pro Gly Gly Cys Val Leu Ser Leu Gly Leu Leu
2150                2155                2160

Asn Pro Val Ala Val Pro Leu Asp Trp Ala Arg Leu Pro Pro Pro
2165                2170                2175

Ala Pro Pro Gly Pro Ser Phe Leu Leu Pro Leu Ala Pro Gly Pro
2180                2185                2190

Gln Leu Leu Asn Pro Gly Thr Pro Val Ser Pro Gln Glu Arg Pro
2195                2200                2205

Pro Pro Tyr Leu Ala Val Pro Gly His Gly Glu Glu Tyr Pro Val
2210                2215                2220

Ala Gly Ala His Ser Ser Pro Pro Lys Ala Arg Phe Leu Arg Val
2225                2230                2235

Pro Ser Glu His Pro Tyr Leu Thr Pro Ser Pro Glu Ser Pro Glu
2240                2245                2250

His Trp Ala Ser Pro Ser Pro Pro Ser Leu Ser Asp Trp Ser Glu
2255                2260                2265

Ser Thr Pro Ser Pro Ala Thr Ala Thr Gly Ala Met Ala Thr Thr
2270                2275                2280

Thr Gly Ala Leu Pro Ala Gln Pro Leu Pro Leu Ser Val Pro Ser
2285                2290                2295

Ser Leu Ala Gln Ala Gln Thr Gln Leu Gly Pro Gln Pro Glu Val
2300                2305                2310

Thr Pro Lys Arg Gln Val Leu Ala
2315                2320

```
<210> SEQ ID NO 33
<211> LENGTH: 1479
<212> TYPE: DNA
<213> ORGANISM: Homo sapiens

<400> SEQUENCE: 33
atgcccgccc tgcgcccgc tctgctgtgg gcgctgctgg cgctctggct gtgctgcgcg      60
gcccccgcgc atgcattgca gtgtcgagat ggctatgaac cctgtgtaaa tgaaggaatg     120
tgtgttacct accacaatgg cacaggatac tgcaaatgtc cagaaggctt cttgggggaa     180
tattgtcaac atcgagaccc ctgtgagaag aaccgctgcc agaatggtgg gacttgtgtg     240
gcccaggcca tgctggggaa agccacgtgc cgatgtgcct cagggtttac aggagaggac     300
tgccagtact caacatctca tccatgcttt gtgtctcgac cctgcctgaa tggcggcaca     360
tgccatatgc tcagccggga tacctatgag tgcacctgtc aagtcgggtt tacaggtaag     420
gagtgccaat ggacggatgc ctgcctgtct catccctgtg caaatggaag tacctgtacc     480
actgtggcca accagttctc ctgcaaatgc ctcacaggct tcacagggca gaaatgtgag     540
actgatgtca atgagtgtga cattccagga cactgccagc atggtggcac ctgcctcaac     600
ctgcctggtt cctaccagtg ccagtgccct cagggcttca caggccagta ctgtgacagc     660
ctgtatgtgc cctgtgcacc ctcaccttgt gtcaatggag gcacctgtcg cagactggt      720 gacttcactt tgagtgcaa ctgccttcca ggttttgaag ggagcacctg tgagaggaat     780
attgatgact gccctaacca caggtgtcag aatggagggg tttgtgtgga tggggtcaac     840
acttacaact gccgctgtcc cccacaatgg acaggacagt tctgcacaga ggatgtggat     900
gaatgcctgc tgcagcccaa tgcctgtcaa atgggggca cctgtgccaa ccgcaatgga     960
ggctatggct gtgtatgtgt caacggctgg agtggagatg actgcagtga aacattgat     1020 gattgtgcct tcgcctcctg tactccaggc tccacctgca tcgaccgtgt ggcctccttc    1080
tcttgcatgt gcccagaggg gaaggcaggt ctcctgtgtc atctggatga tgcatgcatc    1140
agcaatcctt gccacaaggg ggcactgtgt gacaccaacc cctaaatgg gcaatatatt     1200 tgcacctgcc cacaaggcta caagggggct gactgcacag aagatgtgga tgaatgtgcc    1260
atggccaata gcaatccttg tgagcatgca ggaaaatgtg tgaacacgga tggcgccttc    1320
cactgtgagt gtctgaaggg ttatgcagga cctcgttgtg agatggacat caatgagtgc    1380
cattcagacc cctgccagaa tgatgctacc tgtctggata agattggagg cttcacatgt    1440
ctgtgcatgc caggtttcaa aggtgtgcat tgtgaatta                            1479

<210> SEQ ID NO 34
<211> LENGTH: 493
<212> TYPE: PRT
<213> ORGANISM: Homo sapiens

<400> SEQUENCE: 34

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
            35                  40                  45

Gly Tyr Cys Lys Cys Pro Glu Gly Phe Leu Gly Glu Tyr Cys Gln His
        50                  55                  60

Arg Asp Pro Cys Glu Lys Asn Arg Cys Gln Asn Gly Gly Thr Cys Val
65                  70                  75                  80
```

-continued

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu
                485                 490

<210> SEQ ID NO 35

```
<211> LENGTH: 43
<212> TYPE: PRT
<213> ORGANISM: Homo sapiens

<400> SEQUENCE: 35

Leu Asn Asp Ala Cys Ile Ser Asn Pro Cys Asn Glu Gly Ser Asn Cys
1               5                   10                  15

Asp Thr Asn Pro Val Asn Gly Lys Ala Ile Cys Thr Cys Pro Ser Gly
                20                  25                  30

Tyr Thr Gly Pro Ala Cys Ser Gln Asp Val Asp
            35                  40

<210> SEQ ID NO 36
<211> LENGTH: 43
<212> TYPE: PRT
<213> ORGANISM: Homo sapiens

<400> SEQUENCE: 36

Leu Asp Asp Ala Cys Ile Ser Asn Pro Cys His Lys Gly Ala Leu Cys
1               5                   10                  15

Asp Thr Asn Pro Leu Asn Gly Gln Tyr Ile Cys Thr Cys Pro Gln Gly
                20                  25                  30

Tyr Lys Gly Ala Asp Cys Thr Glu Asp Val Asp
            35                  40

<210> SEQ ID NO 37
<211> LENGTH: 43
<212> TYPE: PRT
<213> ORGANISM: Homo sapiens

<400> SEQUENCE: 37

Leu Asp Asp Ala Cys Val Ser Asn Pro Cys His Glu Asp Ala Ile Cys
1               5                   10                  15

Asp Thr Asn Pro Val Asn Gly Arg Ala Ile Cys Thr Cys Pro Pro Gly
                20                  25                  30

Phe Thr Gly Gly Ala Cys Asp Gln Asp Val Asp
            35                  40

<210> SEQ ID NO 38
<211> LENGTH: 43
<212> TYPE: PRT
<213> ORGANISM: Homo sapiens

<400> SEQUENCE: 38

Leu Glu Asp Met Cys Leu Ser Gln Pro Cys His Gly Asp Ala Gln Cys
1               5                   10                  15

Ser Thr Asn Pro Leu Thr Gly Ser Thr Leu Cys Leu Cys Gln Pro Gly
                20                  25                  30

Tyr Ser Gly Pro Thr Cys His Gln Asp Leu Asp
            35                  40

<210> SEQ ID NO 39
<211> LENGTH: 129
<212> TYPE: PRT
<213> ORGANISM: Homo sapiens

<400> SEQUENCE: 39

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
                20                  25                  30
```

-continued

Leu Ser Pro Gly Glu Arg Ala Thr Leu Ser Cys Arg Ala Ser Gln Ser
          35                  40                  45

Val Arg Ser Asn Tyr Leu Ala Trp Tyr Gln Gln Lys Pro Gly Gln Ala
 50                      55                  60

Pro Arg Leu Leu Ile Tyr Gly Ala Ser Ser Arg Ala Thr Gly Val Pro
 65                  70                  75                  80

Ala Arg Phe Ser Gly Ser Gly Ser Gly Thr Asp Phe Thr Leu Thr Ile
              85                  90                  95

Ser Ser Leu Glu Pro Glu Asp Phe Ala Val Tyr Tyr Cys Gln Gln Tyr
             100                 105                 110

Ser Asn Phe Pro Ile Thr Phe Gly Gln Gly Thr Lys Val Glu Ile Lys
             115                 120                 125

Arg

<210> SEQ ID NO 40
<211> LENGTH: 135
<212> TYPE: PRT
<213> ORGANISM: Homo sapiens

<400> SEQUENCE: 40

Met Lys His Leu Trp Phe Phe Leu Leu Leu Val Ala Ala Pro Arg Trp
 1               5                  10                  15

Val Leu Ser Gln Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
          35                  40                  45

Ser Ser Ser Gly Met Ser Trp Val Arg Gln Ala Pro Gly Lys Gly Leu
 50                      55                  60

Glu Trp Val Ser Val Ile Ala Ser Ser Gly Ser Asn Thr Tyr Tyr Ala
 65                  70                  75                  80

Asp Ser Val Lys Gly Arg Phe Thr Ile Ser Arg Asp Asn Ser Lys Asn
              85                  90                  95

Thr Leu Tyr Leu Gln Met Asn Ser Leu Arg Ala Glu Asp Thr Ala Val
             100                 105                 110

Tyr Tyr Cys Ala Arg Gly Ile Phe Phe Ala Ile Trp Gly Gln Gly Thr
             115                 120                 125

Leu Val Thr Val Ser Ser Ala
        130                 135

<210> SEQ ID NO 41
<211> LENGTH: 38
<212> TYPE: PRT
<213> ORGANISM: Homo sapiens

<400> SEQUENCE: 41

Gln Ala Asp Pro Cys Ala Ser Asn Pro Cys Ala Asn Gly Gly Gln Cys
 1               5                  10                  15

Leu Pro Phe Glu Ala Ser Tyr Ile Cys His Cys Pro Pro Ser Phe His
             20                  25                  30

Gly Pro Thr Cys Arg Gln
         35

<210> SEQ ID NO 42
<211> LENGTH: 37
<212> TYPE: PRT
<213> ORGANISM: Homo sapiens

<400> SEQUENCE: 42

```
Thr Asp Ala Cys Leu Ser His Pro Cys Ala Asn Gly Ser Thr Cys Thr
1               5                   10                  15

Thr Val Ala Asn Gln Phe Ser Cys Lys Cys Leu Thr Gly Phe Thr Gly
            20                  25                  30

Gln Lys Cys Glu Thr
        35
```

<210> SEQ ID NO 43
<211> LENGTH: 40
<212> TYPE: PRT
<213> ORGANISM: Homo sapiens

<400> SEQUENCE: 43

```
Ser Asp Val Asp Glu Cys Arg Val Gly Glu Pro Cys Arg His Gly Gly
1               5                   10                  15

Thr Cys Leu Asn Thr Pro Gly Ser Phe Arg Cys Gln Cys Pro Ala Gly
            20                  25                  30

Tyr Thr Gly Pro Leu Cys Glu Asn
        35                  40
```

<210> SEQ ID NO 44
<211> LENGTH: 37
<212> TYPE: PRT
<213> ORGANISM: Homo sapiens

<400> SEQUENCE: 44

```
Arg Asp Phe Cys Ser Ala Asn Pro Cys Val Asn Gly Gly Val Cys Leu
1               5                   10                  15

Ala Thr Tyr Pro Gln Ile Gln Cys His Cys Pro Pro Gly Phe Glu Gly
            20                  25                  30

His Ala Cys Glu Arg
        35
```

<210> SEQ ID NO 45
<211> LENGTH: 2555
<212> TYPE: PRT
<213> ORGANISM: Homo sapiens

<400> SEQUENCE: 45

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160
```

```
Ser Tyr Ile Cys His Cys Pro Pro Ser Phe His Gly Pro Thr Cys Arg
                165                 170                 175
Gln Asp Val Asn Glu Cys Gly Gln Lys Pro Gly Leu Cys Arg His Gly
            180                 185                 190
Gly Thr Cys His Asn Glu Val Gly Ser Tyr Arg Cys Val Cys Arg Ala
        195                 200                 205
Thr His Thr Gly Pro Asn Cys Glu Arg Pro Tyr Val Pro Cys Ser Pro
    210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
    290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
    370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Val Ser Asn Pro Cys Gln Asn Asp
    450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
    530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
```

```
                580             585             590
Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
        610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
                660                 665                 670

Ser Met Cys Asn Ile Asn Ile Asp Glu Cys Ala Gly Asn Pro Cys His
                675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
        770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
                835                 840                 845

Asp Tyr Glu Ser Phe Ser Cys Val Cys Pro Thr Gly Trp Gln Gly Gln
        850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
        900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
        930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
                980                 985                 990

Phe Asn Gly Gly Thr Cys Val Asp  Gly Ile Asn Ser Phe Thr Cys Leu
        995                 1000                1005
```

```
Cys Pro Pro Gly Phe Thr Gly Ser Tyr Cys Gln His Asp Val Asn
1010                1015                1020

Glu Cys Asp Ser Gln Pro Cys Leu His Gly Gly Thr Cys Gln Asp
1025                1030                1035

Gly Cys Gly Ser Tyr Arg Cys Thr Cys Pro Gln Gly Tyr Thr Gly
1040                1045                1050

Pro Asn Cys Gln Asn Leu Val His Trp Cys Asp Ser Ser Pro Cys
1055                1060                1065

Lys Asn Gly Gly Lys Cys Trp Gln Thr His Thr Gln Tyr Arg Cys
1070                1075                1080

Glu Cys Pro Ser Gly Trp Thr Gly Leu Tyr Cys Asp Val Pro Ser
1085                1090                1095

Val Ser Cys Glu Val Ala Ala Gln Arg Gln Gly Val Asp Val Ala
1100                1105                1110

Arg Leu Cys Gln His Gly Gly Leu Cys Val Asp Ala Gly Asn Thr
1115                1120                1125

His His Cys Arg Cys Gln Ala Gly Tyr Thr Gly Ser Tyr Cys Glu
1130                1135                1140

Asp Leu Val Asp Glu Cys Ser Pro Ser Pro Cys Gln Asn Gly Ala
1145                1150                1155

Thr Cys Thr Asp Tyr Leu Gly Gly Tyr Ser Cys Lys Cys Val Ala
1160                1165                1170

Gly Tyr His Gly Val Asn Cys Ser Glu Glu Ile Asp Glu Cys Leu
1175                1180                1185

Ser His Pro Cys Gln Asn Gly Gly Thr Cys Leu Asp Leu Pro Asn
1190                1195                1200

Thr Tyr Lys Cys Ser Cys Pro Arg Gly Thr Gln Gly Val His Cys
1205                1210                1215

Glu Ile Asn Val Asp Asp Cys Asn Pro Pro Val Asp Pro Val Ser
1220                1225                1230

Arg Ser Pro Lys Cys Phe Asn Asn Gly Thr Cys Val Asp Gln Val
1235                1240                1245

Gly Gly Tyr Ser Cys Thr Cys Pro Pro Gly Phe Val Gly Glu Arg
1250                1255                1260

Cys Glu Gly Asp Val Asn Glu Cys Leu Ser Asn Pro Cys Asp Ala
1265                1270                1275

Arg Gly Thr Gln Asn Cys Val Gln Arg Val Asn Asp Phe His Cys
1280                1285                1290

Glu Cys Arg Ala Gly His Thr Gly Arg Arg Cys Glu Ser Val Ile
1295                1300                1305

Asn Gly Cys Lys Gly Lys Pro Cys Lys Asn Gly Gly Thr Cys Ala
1310                1315                1320

Val Ala Ser Asn Thr Ala Arg Gly Phe Ile Cys Lys Cys Pro Ala
1325                1330                1335

Gly Phe Glu Gly Ala Thr Cys Glu Asn Asp Ala Arg Thr Cys Gly
1340                1345                1350

Ser Leu Arg Cys Leu Asn Gly Gly Thr Cys Ile Ser Gly Pro Arg
1355                1360                1365

Ser Pro Thr Cys Leu Cys Leu Gly Pro Phe Thr Gly Pro Glu Cys
1370                1375                1380

Gln Phe Pro Ala Ser Ser Pro Cys Leu Gly Gly Asn Pro Cys Tyr
1385                1390                1395

Asn Gln Gly Thr Cys Glu Pro Thr Ser Glu Ser Pro Phe Tyr Arg
1400                1405                1410
```

```
Cys Leu Cys Pro Ala Lys Phe Asn Gly Leu Leu Cys His Ile Leu
    1415                1420                1425

Asp Tyr Ser Phe Gly Gly Gly Ala Gly Arg Asp Ile Pro Pro Pro
    1430                1435                1440

Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
```

-continued

```
             1805                1810                1815

Glu  Thr  Lys  Lys  Phe  Arg  Phe  Glu  Glu  Pro  Val  Val  Leu  Pro  Asp
     1820                1825                1830

Leu  Asp  Asp  Gln  Thr  Asp  His  Arg  Gln  Trp  Thr  Gln  Gln  His  Leu
     1835                1840                1845

Asp  Ala  Ala  Asp  Leu  Arg  Met  Ser  Ala  Met  Ala  Pro  Thr  Pro  Pro
     1850                1855                1860

Gln  Gly  Glu  Val  Asp  Ala  Asp  Cys  Met  Asp  Val  Asn  Val  Arg  Gly
     1865                1870                1875

Pro  Asp  Gly  Phe  Thr  Pro  Leu  Met  Ile  Ala  Ser  Cys  Ser  Gly  Gly
     1880                1885                1890

Gly  Leu  Glu  Thr  Gly  Asn  Ser  Glu  Glu  Glu  Glu  Asp  Ala  Pro  Ala
     1895                1900                1905

Val  Ile  Ser  Asp  Phe  Ile  Tyr  Gln  Gly  Ala  Ser  Leu  His  Asn  Gln
     1910                1915                1920

Thr  Asp  Arg  Thr  Gly  Glu  Thr  Ala  Leu  His  Leu  Ala  Ala  Arg  Tyr
     1925                1930                1935

Ser  Arg  Ser  Asp  Ala  Ala  Lys  Arg  Leu  Leu  Glu  Ala  Ser  Ala  Asp
     1940                1945                1950

Ala  Asn  Ile  Gln  Asp  Asn  Met  Gly  Arg  Thr  Pro  Leu  His  Ala  Ala
     1955                1960                1965

Val  Ser  Ala  Asp  Ala  Gln  Gly  Val  Phe  Gln  Ile  Leu  Ile  Arg  Asn
     1970                1975                1980

Arg  Ala  Thr  Asp  Leu  Asp  Ala  Arg  Met  His  Asp  Gly  Thr  Thr  Pro
     1985                1990                1995

Leu  Ile  Leu  Ala  Ala  Arg  Leu  Ala  Val  Glu  Gly  Met  Leu  Glu  Asp
     2000                2005                2010

Leu  Ile  Asn  Ser  His  Ala  Asp  Val  Asn  Ala  Val  Asp  Asp  Leu  Gly
     2015                2020                2025

Lys  Ser  Ala  Leu  His  Trp  Ala  Ala  Ala  Val  Asn  Asn  Val  Asp  Ala
     2030                2035                2040

Ala  Val  Val  Leu  Leu  Lys  Asn  Gly  Ala  Asn  Lys  Asp  Met  Gln  Asn
     2045                2050                2055

Asn  Arg  Glu  Glu  Thr  Pro  Leu  Phe  Leu  Ala  Ala  Arg  Glu  Gly  Ser
     2060                2065                2070

Tyr  Glu  Thr  Ala  Lys  Val  Leu  Leu  Asp  His  Phe  Ala  Asn  Arg  Asp
     2075                2080                2085

Ile  Thr  Asp  His  Met  Asp  Arg  Leu  Pro  Arg  Asp  Ile  Ala  Gln  Glu
     2090                2095                2100

Arg  Met  His  His  Asp  Ile  Val  Arg  Leu  Leu  Asp  Glu  Tyr  Asn  Leu
     2105                2110                2115

Val  Arg  Ser  Pro  Gln  Leu  His  Gly  Ala  Pro  Leu  Gly  Gly  Thr  Pro
     2120                2125                2130

Thr  Leu  Ser  Pro  Pro  Leu  Cys  Ser  Pro  Asn  Gly  Tyr  Leu  Gly  Ser
     2135                2140                2145

Leu  Lys  Pro  Gly  Val  Gln  Gly  Lys  Lys  Val  Arg  Lys  Pro  Ser  Ser
     2150                2155                2160

Lys  Gly  Leu  Ala  Cys  Gly  Ser  Lys  Glu  Ala  Lys  Asp  Leu  Lys  Ala
     2165                2170                2175

Arg  Arg  Lys  Lys  Ser  Gln  Asp  Gly  Lys  Gly  Cys  Leu  Leu  Asp  Ser
     2180                2185                2190

Ser  Gly  Met  Leu  Ser  Pro  Val  Asp  Ser  Leu  Glu  Ser  Pro  His  Gly
     2195                2200                2205
```

-continued

Tyr Leu Ser Asp Val Ala Ser Pro Pro Leu Leu Pro Ser Pro Phe
    2210            2215                2220

Gln Gln Ser Pro Ser Val Pro Leu Asn His Leu Pro Gly Met Pro
    2225            2230                2235

Asp Thr His Leu Gly Ile Gly His Leu Asn Val Ala Ala Lys Pro
    2240            2245                2250

Glu Met Ala Ala Leu Gly Gly Gly Arg Leu Ala Phe Glu Thr
    2255            2260                2265

Gly Pro Pro Arg Leu Ser His Leu Pro Val Ala Ser Gly Thr Ser
    2270            2275                2280

Thr Val Leu Gly Ser Ser Ser Gly Gly Ala Leu Asn Phe Thr Val
    2285            2290                2295

Gly Gly Ser Thr Ser Leu Asn Gly Gln Cys Glu Trp Leu Ser Arg
    2300            2305                2310

Leu Gln Ser Gly Met Val Pro Asn Gln Tyr Asn Pro Leu Arg Gly
    2315            2320                2325

Ser Val Ala Pro Gly Pro Leu Ser Thr Gln Ala Pro Ser Leu Gln
    2330            2335                2340

His Gly Met Val Gly Pro Leu His Ser Ser Leu Ala Ala Ser Ala
    2345            2350                2355

Leu Ser Gln Met Met Ser Tyr Gln Gly Leu Pro Ser Thr Arg Leu
    2360            2365                2370

Ala Thr Gln Pro His Leu Val Gln Thr Gln Val Gln Pro Gln
    2375            2380                2385

Asn Leu Gln Met Gln Gln Gln Asn Leu Gln Pro Ala Asn Ile Gln
    2390            2395                2400

Gln Gln Gln Ser Leu Gln Pro Pro Pro Pro Pro Gln Pro His
    2405            2410                2415

Leu Gly Val Ser Ser Ala Ala Ser Gly His Leu Gly Arg Ser Phe
    2420            2425                2430

Leu Ser Gly Glu Pro Ser Gln Ala Asp Val Gln Pro Leu Gly Pro
    2435            2440                2445

Ser Ser Leu Ala Val His Thr Ile Leu Pro Gln Glu Ser Pro Ala
    2450            2455                2460

Leu Pro Thr Ser Leu Pro Ser Ser Leu Val Pro Pro Val Thr Ala
    2465            2470                2475

Ala Gln Phe Leu Thr Pro Pro Ser Gln His Ser Tyr Ser Ser Pro
    2480            2485                2490

Val Asp Asn Thr Pro Ser His Gln Leu Gln Val Pro Glu His Pro
    2495            2500                2505

Phe Leu Thr Pro Ser Pro Glu Ser Pro Asp Gln Trp Ser Ser Ser
    2510            2515                2520

Ser Pro His Ser Asn Val Ser Asp Trp Ser Glu Gly Val Ser Ser
    2525            2530                2535

Pro Pro Thr Ser Met Gln Ser Gln Ile Ala Arg Ile Pro Glu Ala
    2540            2545                2550

Phe Lys
    2555

<210> SEQ ID NO 46
<211> LENGTH: 2003
<212> TYPE: PRT
<213> ORGANISM: Homo sapiens

<400> SEQUENCE: 46

-continued

```
Met Gln Pro Pro Ser Leu Leu Leu Leu Leu Leu Leu Leu Leu
1               5                   10                  15

Cys Val Ser Val Val Arg Pro Arg Gly Leu Leu Cys Gly Ser Phe Pro
            20              25              30

Glu Pro Cys Ala Asn Gly Gly Thr Cys Leu Ser Leu Ser Leu Gly Gln
        35              40              45

Gly Thr Cys Gln Cys Ala Pro Gly Phe Leu Gly Glu Thr Cys Gln Phe
        50              55              60

Pro Asp Pro Cys Gln Asn Ala Gln Leu Cys Gln Asn Gly Gly Ser Cys
65              70              75              80

Gln Ala Leu Leu Pro Ala Pro Leu Gly Leu Pro Ser Ser Pro Ser Pro
                85              90              95

Leu Thr Pro Ser Phe Leu Cys Thr Cys Leu Pro Gly Phe Thr Gly Glu
        100             105             110

Arg Cys Gln Ala Lys Leu Glu Asp Pro Cys Pro Pro Ser Phe Cys Ser
        115             120             125

Lys Arg Gly Arg Cys His Ile Gln Ala Ser Gly Arg Pro Gln Cys Ser
        130             135             140

Cys Met Pro Gly Trp Thr Gly Glu Gln Cys Gln Leu Arg Asp Phe Cys
145             150             155             160

Ser Ala Asn Pro Cys Val Asn Gly Gly Val Cys Leu Ala Thr Tyr Pro
                165             170             175

Gln Ile Gln Cys His Cys Pro Pro Gly Phe Glu Gly His Ala Cys Glu
                180             185             190

Arg Asp Val Asn Glu Cys Phe Gln Asp Pro Gly Pro Cys Pro Lys Gly
        195             200             205

Thr Ser Cys His Asn Thr Leu Gly Ser Phe Gln Cys Leu Cys Pro Val
        210             215             220

Gly Gln Glu Gly Pro Arg Cys Glu Leu Arg Ala Gly Pro Cys Pro Pro
225             230             235             240

Arg Gly Cys Ser Asn Gly Gly Thr Cys Gln Leu Met Pro Glu Lys Asp
                245             250             255

Ser Thr Phe His Leu Cys Leu Cys Pro Pro Gly Phe Ile Gly Pro Asp
                260             265             270

Cys Glu Val Asn Pro Asp Asn Cys Val Ser His Gln Cys Gln Asn Gly
            275             280             285

Gly Thr Cys Gln Asp Gly Leu Asp Thr Tyr Thr Cys Leu Cys Pro Glu
        290             295             300

Thr Trp Thr Gly Trp Asp Cys Ser Glu Asp Val Asp Glu Cys Glu Thr
305             310             315             320

Gln Gly Pro Pro His Cys Arg Asn Gly Gly Thr Cys Gln Asn Ser Ala
                325             330             335

Gly Ser Phe His Cys Val Cys Val Ser Gly Trp Gly Gly Thr Ser Cys
                340             345             350

Glu Glu Asn Leu Asp Asp Cys Ile Ala Ala Thr Cys Ala Pro Gly Ser
            355             360             365

Thr Cys Ile Asp Arg Val Gly Ser Phe Ser Cys Leu Cys Pro Pro Gly
        370             375             380

Arg Thr Gly Leu Leu Cys His Leu Glu Asp Met Cys Leu Ser Gln Pro
385             390             395             400

Cys His Gly Asp Ala Gln Cys Ser Thr Asn Pro Leu Thr Gly Ser Thr
                405             410             415

Leu Cys Leu Cys Gln Pro Gly Tyr Ser Gly Pro Thr Cys His Gln Asp
        420             425             430
```

```
Leu Asp Glu Cys Leu Met Ala Gln Gln Gly Pro Ser Pro Cys Glu His
        435                 440                 445

Gly Gly Ser Cys Leu Asn Thr Pro Gly Ser Phe Asn Cys Leu Cys Pro
        450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
            485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
        515                 520                 525

His Asp Leu Leu Asn Gly Phe Gln Cys Ile Cys Leu Pro Gly Phe Ser
        530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
            565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
        595                 600                 605

Gly Ala Phe Phe Cys Leu Cys Pro Ser Gly Phe Thr Gly Gln Leu Cys
        610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
            645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
        675                 680                 685

Glu Ala Glu Leu Gly Gly Cys Ile Ser Ala Pro Cys Ala His Gly Gly
        690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
            725                 730                 735

Pro Cys Leu Asn Gly Gly Ser Cys Asn Pro Ser Pro Gly Gly Tyr Tyr
            740                 745                 750

Cys Thr Cys Pro Pro Ser His Thr Gly Pro Gln Cys Gln Thr Ser Thr
        755                 760                 765

Asp Tyr Cys Val Ser Ala Pro Cys Phe Asn Gly Gly Thr Cys Val Asn
        770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
            805                 810                 815

Asn Arg Ala Thr Cys Gln Asp Ser Pro Gln Gly Pro Arg Cys Leu Cys
            820                 825                 830

Pro Thr Gly Tyr Thr Gly Gly Ser Cys Gln Thr Leu Met Asp Leu Cys
        835                 840                 845

Ala Gln Lys Pro Cys Pro Arg Asn Ser His Cys Leu Gln Thr Gly Pro
```

```
                    850             855             860
Ser Phe His Cys Leu Cys Leu Gln Gly Trp Thr Gly Pro Leu Cys Asn
865                     870                 875                 880

Leu Pro Leu Ser Ser Cys Gln Lys Ala Ala Leu Ser Gln Gly Ile Asp
                    885                 890                 895

Val Ser Ser Leu Cys His Asn Gly Gly Leu Cys Val Asp Ser Gly Pro
                    900                 905                 910

Ser Tyr Phe Cys His Cys Pro Pro Gly Phe Gln Gly Ser Leu Cys Gln
                915                 920                 925

Asp His Val Asn Pro Cys Glu Ser Arg Pro Cys Gln Asn Gly Ala Thr
            930                 935                 940

Cys Met Ala Gln Pro Ser Gly Tyr Leu Cys Gln Cys Ala Pro Gly Tyr
945                 950                 955                 960

Asp Gly Gln Asn Cys Ser Lys Glu Leu Asp Ala Cys Gln Ser Gln Pro
                965                 970                 975

Cys His Asn His Gly Thr Cys Thr Pro Lys Pro Gly Gly Phe His Cys
                980                 985                 990

Ala Cys Pro Pro Gly Phe Val Gly Leu Arg Cys Glu Gly Asp Val Asp
            995                 1000                1005

Glu Cys Leu Asp Gln Pro Cys His Pro Thr Gly Thr Ala Ala Cys
1010                1015                1020

His Ser Leu Ala Asn Ala Phe Tyr Cys Gln Cys Leu Pro Gly His
    1025                1030                1035

Thr Gly Gln Trp Cys Glu Val Glu Ile Asp Pro Cys His Ser Gln
    1040                1045                1050

Pro Cys Phe His Gly Gly Thr Cys Glu Ala Thr Ala Gly Ser Pro
    1055                1060                1065

Leu Gly Phe Ile Cys His Cys Pro Lys Gly Phe Glu Gly Pro Thr
    1070                1075                1080

Cys Ser His Arg Ala Pro Ser Cys Gly Phe His His Cys His His
    1085                1090                1095

Gly Gly Leu Cys Leu Pro Ser Pro Lys Pro Gly Phe Pro Pro Arg
    1100                1105                1110

Cys Ala Cys Leu Ser Gly Tyr Gly Gly Pro Asp Cys Leu Thr Pro
    1115                1120                1125

Pro Ala Pro Lys Gly Cys Gly Pro Pro Ser Pro Cys Leu Tyr Asn
    1130                1135                1140

Gly Ser Cys Ser Glu Thr Thr Gly Leu Gly Gly Pro Gly Phe Arg
    1145                1150                1155

Cys Ser Cys Pro His Ser Ser Pro Gly Pro Arg Cys Gln Lys Pro
    1160                1165                1170

Gly Ala Lys Gly Cys Glu Gly Arg Ser Gly Asp Gly Ala Cys Asp
    1175                1180                1185

Ala Gly Cys Ser Gly Pro Gly Gly Asn Trp Asp Gly Gly Asp Cys
    1190                1195                1200

Ser Leu Gly Val Pro Asp Pro Trp Lys Gly Cys Pro Ser His Ser
    1205                1210                1215

Arg Cys Trp Leu Leu Phe Arg Asp Gly Gln Cys His Pro Gln Cys
    1220                1225                1230

Asp Ser Glu Glu Cys Leu Phe Asp Gly Tyr Asp Cys Glu Thr Pro
    1235                1240                1245

Pro Ala Cys Thr Pro Ala Tyr Asp Gln Tyr Cys His Asp His Phe
    1250                1255                1260
```

-continued

His Asn Gly His Cys Glu Lys Gly Cys Asn Thr Ala Glu Cys Gly
1265                1270                1275

Trp Asp Gly Gly Asp Cys Arg Pro Glu Asp Gly Asp Pro Glu Trp
1280                1285                1290

Gly Pro Ser Leu Ala Leu Leu Val Val Leu Ser Pro Pro Ala Leu
1295                1300                1305

Asp Gln Gln Leu Phe Ala Leu Ala Arg Val Leu Ser Leu Thr Leu
1310                1315                1320

Arg Val Gly Leu Trp Val Arg Lys Asp Arg Asp Gly Arg Asp Met
1325                1330                1335

Val Tyr Pro Tyr Pro Gly Ala Arg Ala Glu Glu Lys Leu Gly Gly
1340                1345                1350

Thr Arg Asp Pro Thr Tyr Gln Glu Arg Ala Ala Pro Gln Thr Gln
1355                1360                1365

Pro Leu Gly Lys Glu Thr Asp Ser Leu Ser Ala Gly Phe Val Val
1370                1375                1380

Val Met Gly Val Asp Leu Ser Arg Cys Gly Pro Asp His Pro Ala
1385                1390                1395

Ser Arg Cys Pro Trp Asp Pro Gly Leu Leu Leu Arg Phe Leu Ala
1400                1405                1410

Ala Met Ala Ala Val Gly Ala Leu Glu Pro Leu Leu Pro Gly Pro
1415                1420                1425

Leu Leu Ala Val His Pro His Ala Gly Thr Ala Pro Pro Ala Asn
1430                1435                1440

Gln Leu Pro Trp Pro Val Leu Cys Ser Pro Val Ala Gly Val Ile
1445                1450                1455

Leu Leu Ala Leu Gly Ala Leu Leu Val Leu Gln Leu Ile Arg Arg
1460                1465                1470

Arg Arg Arg Glu His Gly Ala Leu Trp Leu Pro Pro Gly Phe Thr
1475                1480                1485

Arg Arg Pro Arg Thr Gln Ser Ala Pro His Arg Arg Arg Pro Pro
1490                1495                1500

Leu Gly Glu Asp Ser Ile Gly Leu Lys Ala Leu Lys Pro Lys Ala
1505                1510                1515

Glu Val Asp Glu Asp Gly Val Val Met Cys Ser Gly Pro Glu Glu
1520                1525                1530

Gly Glu Glu Val Gly Gln Ala Glu Glu Thr Gly Pro Pro Ser Thr
1535                1540                1545

Cys Gln Leu Trp Ser Leu Ser Gly Gly Cys Gly Ala Leu Pro Gln
1550                1555                1560

Ala Ala Met Leu Thr Pro Pro Gln Glu Ser Glu Met Glu Ala Pro
1565                1570                1575

Asp Leu Asp Thr Arg Gly Pro Asp Gly Val Thr Pro Leu Met Ser
1580                1585                1590

Ala Val Cys Cys Gly Glu Val Gln Ser Gly Thr Phe Gln Gly Ala
1595                1600                1605

Trp Leu Gly Cys Pro Glu Pro Trp Glu Pro Leu Leu Asp Gly Gly
1610                1615                1620

Ala Cys Pro Gln Ala His Thr Val Gly Thr Gly Glu Thr Pro Leu
1625                1630                1635

His Leu Ala Ala Arg Phe Ser Arg Pro Thr Ala Ala Arg Arg Leu
1640                1645                1650

Leu Glu Ala Gly Ala Asn Pro Asn Gln Pro Asp Arg Ala Gly Arg
1655                1660                1665

| | | | | | | | | | | |
|---|---|---|---|---|---|---|---|---|---|---|
|Thr|Pro|Leu|His|Ala|Val|Ala|Ala|Asp|Ala|Arg|Glu|Val|Cys|
| |1670| | | |1675| | | |1680| |

Thr Pro Leu His Ala Val Ala Ala Asp Ala Arg Glu Val Cys
    1670            1675            1680

Gln Leu Leu Leu Arg Ser Arg Gln Thr Ala Val Asp Ala Arg Thr
    1685            1690            1695

Glu Asp Gly Thr Thr Pro Leu Met Leu Ala Ala Arg Leu Ala Val
    1700            1705            1710

Glu Asp Leu Val Glu Glu Leu Ile Ala Ala Gln Ala Asp Val Gly
    1715            1720            1725

Ala Arg Asp Lys Trp Gly Lys Thr Ala Leu His Trp Ala Ala Ala
    1730            1735            1740

Val Asn Asn Ala Arg Ala Ala Arg Ser Leu Leu Gln Ala Gly Ala
    1745            1750            1755

Asp Lys Asp Ala Gln Asp Asn Arg Glu Gln Thr Pro Leu Phe Leu
    1760            1765            1770

Ala Ala Arg Glu Gly Ala Val Glu Val Ala Gln Leu Leu Leu Gly
    1775            1780            1785

Leu Gly Ala Ala Arg Glu Leu Arg Asp Gln Ala Gly Leu Ala Pro
    1790            1795            1800

Ala Asp Val Ala His Gln Arg Asn His Trp Asp Leu Leu Thr Leu
    1805            1810            1815

Leu Glu Gly Ala Gly Pro Pro Glu Ala Arg His Lys Ala Thr Pro
    1820            1825            1830

Gly Arg Glu Ala Gly Pro Phe Pro Arg Ala Arg Thr Val Ser Val
    1835            1840            1845

Ser Val Pro Pro His Gly Gly Gly Ala Leu Pro Arg Cys Arg Thr
    1850            1855            1860

Leu Ser Ala Gly Ala Gly Pro Arg Gly Gly Gly Ala Cys Leu Gln
    1865            1870            1875

Ala Arg Thr Trp Ser Val Asp Leu Ala Ala Arg Gly Gly Gly Ala
    1880            1885            1890

Tyr Ser His Cys Arg Ser Leu Ser Gly Val Gly Ala Gly Gly Gly
    1895            1900            1905

Pro Thr Pro Arg Gly Arg Arg Phe Ser Ala Gly Met Arg Gly Pro
    1910            1915            1920

Arg Pro Asn Pro Ala Ile Met Arg Gly Arg Tyr Gly Val Ala Ala
    1925            1930            1935

Gly Arg Gly Gly Arg Val Ser Thr Asp Asp Trp Pro Cys Asp Trp
    1940            1945            1950

Val Ala Leu Gly Ala Cys Gly Ser Ala Ser Asn Ile Pro Ile Pro
    1955            1960            1965

Pro Pro Cys Leu Thr Pro Ser Pro Glu Arg Gly Ser Pro Gln Leu
    1970            1975            1980

Asp Cys Gly Pro Pro Ala Leu Gln Glu Met Pro Ile Asn Gln Gly
    1985            1990            1995

Gly Glu Gly Lys Lys
    2000

<210> SEQ ID NO 47
<211> LENGTH: 645
<212> TYPE: DNA
<213> ORGANISM: Homo sapiens

<400> SEQUENCE: 47
gacatcgtgc tgacccagtc ccccgccaca ctgtccctgt ctcccggcga gagagccacc    60

```
ctgagctgtc gggcctccca gtccgtgcgg tccaactacc tggcctggta tcagcagaag    120
cccggccagg cccctcggct gctgatctac ggcgcctcct ccagggctac cggcgtgcct    180
gcccggttct ccggctccgg ctctggcacc gacttcaccc tgaccatctc cagcctggag    240
cctgaggact tcgccgtgta ctactgccag cagtactcca acttccctat caccttcggc    300
cagggcacca aggtggagat caagcggacc gtggccgctc cttccgtgtt catcttcccc    360
ccttccgacg agcagctgaa gtccggcacc gcctccgtgg tgtgcctgct gaacaacttc    420
taccctcggg aggccaaggt gcagtggaag gtggacaacg ccctgcagtc cggcaactcc    480
caggagtccg tcaccgagca ggactccaag gactctacct actccctgtc ctccaccctg    540
accctgagca aggccgacta cgagaagcac aaggtgtacg cctgcgaggt gacccaccag    600
ggcctgtcct ctcccgtgac caagtccttc aaccggggcg agtgc                    645

<210> SEQ ID NO 48
<211> LENGTH: 1323
<212> TYPE: DNA
<213> ORGANISM: Homo sapiens

<400> SEQUENCE: 48
gaggtgcagc tggtcgagtc tggcggcgga ctggtgcagc ctggcggctc cctgagactg     60
tcctgcgccg cttccggctt caccttctcc tccagcggca tgtcctgggt gcgccaggca    120
cctggcaaag gactcgagtg ggtgtccgtg atcgcctcct ccggctccaa cacctactac    180
gccgactccg tgaagggccg gttcaccatc tcccgggaca actccaagaa caccctgtac    240
ctgcagatga actccctgcg ggccgaggac accgccgtgt actactgcgc ccggtccatc    300
ttctacacca cctggggcca gggcaccctg gtgaccgtgt cctccgcctc caccaagggc    360
ccctccgtgt tccctctggc cccttgctcc cggtccacct ctgagtctac cgccgctctg    420
ggctgcctgg tgaaggacta cttccctgag cctgtgaccg tgtcctggaa ctctggcgcc    480
ctgacctctg gcgtgcacac cttccctgcc gtgctgcagt cctccggcct gtactccctg    540
tcctccgtgg tgaccgtgcc ttcctccaac ttcggcaccc agacctacac ctgcaacgtg    600
gaccacaagc cttccaacac caaggtggac aagaccgtgg agcggaagtg ctgcgtggag    660
tgccctcctt gtcctgctcc tcctgtggct ggcccttctg tgttcctgtt ccctcctaag    720
cctaaggaca ccctgatgat ctcccggacc cctgaagtga cctgcgtggt ggtggacgtg    780
tcccacgagg accctgaggt gcagttcaat tggtacgtgg acggcgtgga ggtgcacaac    840
gccaagacca gcctcggga ggaacagttc aactccacct tccgggtggt gtctgtgctg    900
accgtggtgc accaggactg gctgaacggc aagaatacaa agtgcaaggt gtccaacaag    960
ggcctgcctg cccctatcga aaagaccatc tctaagacca agggccagcc tcgcgagcct   1020
caggtctaca ccctgcctcc tagccgggag gaaatgacca agaaccaggt gtccctgacc   1080
tgtctggtga agggcttcta cccttccgat atcgccgtgg agtgggagtc taacggccag   1140
cctgagaaca actacaagac cacccctcct atgctggact ccgacggctc cttcttcctg   1200
tactccaagc tgacagtgga caagtcccgg tggcagcagg gcaacgtgtt ctcctgctcc   1260
gtgatgcacg aggccctgca caaccactac acccagaagt ccctgtccct gtctcctggc   1320
aag                                                                1323

<210> SEQ ID NO 49
<211> LENGTH: 441
<212> TYPE: PRT
<213> ORGANISM: Homo sapiens
```

-continued

```
<400> SEQUENCE: 49

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Ser
             20                  25                  30

Gly Met Ser Trp Val Arg Gln Ala Pro Gly Lys Gly Leu Glu Trp Val
         35                  40                  45

Ser Val Ile Ala Ser Ser Gly Ser Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ile Phe Tyr Thr Thr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415
```

```
Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 50
<211> LENGTH: 118
<212> TYPE: PRT
<213> ORGANISM: Homo sapiens

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Phe Tyr Thr Thr Trp Gly Gln Gly Thr Leu Val Thr
            100                 105                 110

Val Ser Ser Ala Ser Thr
        115

<210> SEQ ID NO 51
<211> LENGTH: 6
<212> TYPE: PRT
<213> ORGANISM: Homo sapiens

<400> SEQUENCE: 51

Ser Ile Phe Tyr Thr Thr
1               5

<210> SEQ ID NO 52
<211> LENGTH: 116
<212> TYPE: PRT
<213> ORGANISM: Homo sapiens

<400> SEQUENCE: 52

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Phe Tyr Pro Thr Trp Gly Gln Gly Thr Leu Val Thr
            100                 105                 110

Val Ser Ser Ala
        115
```

<210> SEQ ID NO 53
<211> LENGTH: 116
<212> TYPE: PRT
<213> ORGANISM: Homo sapiens

<400> SEQUENCE: 53

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Phe Ala Ser Trp Gly Gln Gly Thr Leu Val Thr
            100                 105                 110

Val Ser Ser Ala
        115

<210> SEQ ID NO 54
<211> LENGTH: 116
<212> TYPE: PRT
<213> ORGANISM: Homo sapiens

<400> SEQUENCE: 54

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Tyr Ala Ser Trp Gly Gln Gly Thr Leu Val Thr
            100                 105                 110

Val Ser Ser Ala
        115

<210> SEQ ID NO 55
<211> LENGTH: 116
<212> TYPE: PRT
<213> ORGANISM: Homo sapiens

<400> SEQUENCE: 55

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val

```
                35                  40                  45
Ser Val Ile Ala Ser Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Phe Ala Thr Trp Gly Gln Gly Thr Leu Val Thr
                100                 105                 110

Val Ser Ser Ala
        115

<210> SEQ ID NO 56
<211> LENGTH: 116
<212> TYPE: PRT
<213> ORGANISM: Homo sapiens

<400> SEQUENCE: 56

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
                 20                  25                  30

Gly Met Ser Trp Val Arg Gln Ala Pro Gly Lys Gly Leu Glu Trp Val
         35                  40                  45

Ser Val Ile Ala Ser Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ile Phe Tyr Pro Ser Trp Gly Gln Gly Thr Leu Val Thr
                100                 105                 110

Val Ser Ser Ala
        115

<210> SEQ ID NO 57
<211> LENGTH: 116
<212> TYPE: PRT
<213> ORGANISM: Homo sapiens

<400> SEQUENCE: 57

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
                 20                  25                  30

Gly Met Ser Trp Val Arg Gln Ala Pro Gly Lys Gly Leu Glu Trp Val
         35                  40                  45

Ser Val Ile Ala Ser Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Phe Ala Asn Trp Gly Gln Gly Thr Leu Val Thr
                100                 105                 110

Val Ser Ser Ala
        115
```

<210> SEQ ID NO 58
<211> LENGTH: 354
<212> TYPE: DNA
<213> ORGANISM: Homo sapiens

<400> SEQUENCE: 58

```
gaggtgcagc tggtcgagtc tggcggcgga ctggtgcagc ctggcggctc cctgagactg      60
tcctgcgccg cttccggctt caccttctcc tccagcggca tgtcctgggt gcgccaggca     120
cctggcaaag gactcgagtg ggtgtccgtg atcgcctcct ccggctccaa cacctactac     180
gccgactccg tgaagggccg gttcaccatc tcccgggaca actccaagaa cacctgtac      240 ctgcagatga actccctgcg ggccgaggac accgccgtgt actactgcgc ccggtccatc     300
ttctacacca cctggggcca gggcaccctg gtgaccgtgt cctccgcctc cacc           354
```

<210> SEQ ID NO 59
<211> LENGTH: 327
<212> TYPE: DNA
<213> ORGANISM: Homo sapiens

<400> SEQUENCE: 59

```
gatatcgtgc tgacccagag cccggcgacc ctgagcctgt ctccgggcga acgtgcgacc      60
ctgagctgca gagcgagcca gtctgttcgt tctaattatc tggcttggta ccagcagaaa     120
ccaggtcaag caccgcgtct attaatttat ggtgcttctt ctcgtgcaac tggggtcccg     180
gcgcgtttta gcggctctgg atccggcacg gattttaccc tgaccattag cagcctggaa     240
cctgaagact ttgcggttta ttattgccag cagtattcta attttcctat tacctttggc     300
cagggtacga agttgaaat taaacgt                                           327
```

<210> SEQ ID NO 60
<211> LENGTH: 348
<212> TYPE: DNA
<213> ORGANISM: Homo sapiens

<400> SEQUENCE: 60

```
caggtgcaat tggtggaaag cggcggcggc ctggtgcaac cggcggcag cctgcgtctg       60 agctgcgcgg cctccggatt tacctttct tcttctggta tgtcttgggt gcgccaagcc      120
cctgggaagg gtctcgagtg ggtgagcgtt atcgcttctt ctggtagcaa taccattat     180 gcggatagcg tgaaaggccg ttttaccatt tcacgtgata attcgaaaaa cacctgtat      240 ctgcaaatga acagcctgcg tgcggaagat acggccgtgt attattgcgc gcgtggtatt     300
ttttttgcta tttggggca aggcaccctg gtgacggtta gctcagcc                   348
```

ANTIBODIES TO NOTCH RECEPTORS

CROSS-REFERENCE TO RELATED APPLICATIONS

This application claims the priority benefit of U.S. Provisional Application No. 61/112,699, filed Nov. 7, 2008, U.S. Provisional Application No. 61/112,701, filed Nov. 7, 2008, and U.S. Provisional Application No. 61/079,095, filed Jul. 8, 2008, each of which is hereby incorporated by reference herein in its entirety.

BACKGROUND OF THE INVENTION

1. Field of the Invention

The present invention relates to compositions comprising an agent that binds a human Notch receptor and methods of using those compositions for the treatment of cancer and other diseases. More specifically, the present invention provides, for example, antibodies that specifically bind to a non-ligand binding region of the extracellular domain of a human Notch receptor and inhibit tumor growth. The present invention further provides methods of treating cancer, the method comprising administering a therapeutically effective amount of an antibody that specifically binds to a non-ligand binding region of the extracellular domain of a human Notch receptor protein and inhibits tumor growth.

2. Background

The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it can alter the developmental fate of tumor cells to maintain them in an undifferentiated and proliferative state (Brennan and Brown, 2003, *Breast Cancer Res.* 5:69). Thus carcinogenesis can proceed by usurping homeostatic mechanisms controlling normal development and tissue repair by stem cell populations (Beachy et al., 2004, *Nature* 432:324).

The Notch receptor was first identified in *Drosophila* mutants with haploinsufficiency resulting in notches at the wing margin, whereas loss-of-function produces an embryonic lethal "neurogenic" phenotype where cells of the epidermis switch fate to neural tissue (Moohr, 1919, *Genet.* 4:252; Poulson, 1937, *PNAS* 23:133; Poulson, 1940, *J. Exp. Zool.* 83:271). The Notch receptor is a single-pass transmembrane receptor containing numerous tandem epidermal growth factor (EGF)-like repeats and three cysteine-rich Notch/LIN-12 repeats within a large extracellular domain (Wharton et al., 1985, *Cell* 43:567; Kidd et al., 1986, *Mol. Cell. Biol.* 6:3094; reviewed in Artavanis et al., 1999, *Science* 284:770). Four mammalian Notch proteins have been identified (Notch1, Notch2, Notch3, and Notch4), and mutations in these receptors invariably result in developmental abnormalities and human pathologies including several cancers as described in detail below (Gridley, 1997, *Mol. Cell. Neurosci.* 9:103; Joutel & Tournier-Lasserve, 1998, *Semin. Cell Dev. Biol.* 9:619-25).

Notch receptors are activated by single-pass transmembrane ligands of the Delta, Serrated, Lag-2 (DSL) family. There are five known Notch ligands in mammals: Delta-like 1 (DLL1), Delta-like 3 (DLL3), Delta-like 4 (DLL4), Jagged 1 (JAG1) and Jagged 2 (JAG2) characterized by a DSL domain and tandem EGF-like repeats within the extracellular domain.

The extracellular domain of the Notch receptor interacts with that of its ligands, typically on adjacent cells, resulting in two proteolytic cleavages of Notch, one extracellular cleavage mediated by an ADAM (A Disintegrin And Metallopeptidase) protease and one cleavage within the transmembrane domain mediated by gamma secretase. This latter cleavage generates the Notch intracellular domain (ICD), which then enters the nucleus where it activates the CBF1, Suppressor of Hairless [Su(H)], Lag-2 (CSL) family of transcription factors as the major downstream effectors to increase transcription of nuclear basic helix-loop-helix transcription factors of the Hairy and Enhancer of Split [E(spl)] family (Artavanis et al., 1999, *Science* 284:770; Brennan and Brown, 2003, *Breast Cancer Res.* 5:69; Iso et al., 2003, *Arterioscler. Thromb. Vasc. Biol.* 23:543). Alternative intracellular pathways involving the cytoplasmic protein Deltex identified in *Drosophila* may also exist in mammals (Martinez et al., 2002, *Curr. Opin. Genet. Dev.* 12:524-33), and this Deltex-dependent pathway may act to suppress expression of Wnt target genes (Brennan et al., 1999, *Curr. Biol.* 9:707-710; Lawrence et al., 2001, *Curr. Biol.* 11:375-85).

Mammalian Notch receptors undergo cleavage to form the mature receptor and also following ligand binding to activate downstream signaling. A furin-like protease cleaves the Notch receptors during maturation to generate juxtamembrane heterodimers that comprise a non-covalently associated extracelluar subunit and a transmembrane subunit held together in an auto-inhibitory state. Ligand binding relieves this inhibition and induces cleavage of the Notch receptor by an ADAM-type metalloprotease and a gamma-secretase, the latter of which releases the intracellular domain (ICD) into the cytoplasm, allowing it to translocate into the nucleus to activate gene transcription. Cleavage by ADAM occurs within the non-ligand binding cleavage domain within the membrane proximal negative regulatory region.

Hematopoietic stem cells (HSCs) are the best understood stem cells in the body, and Notch signaling is implicated in their normal maintenance as well as in leukemic transformation (Kopper & Hajdu, 2004, *Pathol. Oncol. Res.* 10:69-73). HSCs are a rare population of cells that reside in a stromal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitor cells establishes immortalized cell lines that generate both lymphoid and myeloid cells in vitro and in long-term reconstitution assays (Varnum-Finney et al., 2000, *Nat. Med.* 6:1278-81), and the presence of Jagged1 increases engraftment of human bone marrow cell populations enriched for HSCs (Karanu et al., 2000, *J. Exp. Med.* 192:1365-72). More recently, Notch signaling has been demonstrated in HSCs in vivo and shown to be involved in inhibiting HSC differentiation. Furthermore, Notch signaling appears to be required for Wnt-mediated HSC self-renewal (Duncan et al., 2005, *Nat. Immunol.* 6:314).

The Notch signaling pathway also plays a central role in the maintenance of neural stem cells and is implicated in their normal maintenance as well as in brain cancers (Kopper & Hajdu, 2004, *Pathol. Oncol. Res.* 10:69-73; Purow et al., 2005, *Cancer Res.* 65:2353-63; Hallahan et al., 2004, *Cancer Res.* 64:7794-800). Neural stem cells give rise to all neuronal and glial cells in the mammalian nervous system during development, and more recently have been identified in the adult brain (Gage, 2000, *Science* 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS1 heterozygote mice (Nakamura et al., 2000, *J. Neurosci.* 20:283-93; Hitoshi et al., 2002, *Genes Dev.* 16:846-58). The reduction in neural stem cells appears to result from their premature differentiation into neurons (Hatakeyama et al., 2004, *Dev.* 131:5539-50) suggesting that Notch signaling regulates neural stem cell differentiation and self-renewal.

Aberrant Notch signaling is implicated in a number of human cancers. The Notch1 gene in humans was first identified in a subset of T-cell acute lymphoblastic leukemias as a translocated locus resulting in activation of the Notch pathway (Ellisen et al., 1991, *Cell* 66:649-61). Constitutive activation of Notch1 signaling in T-cells in mouse models similarly generates T-cell lymphomas suggesting a causative role (Robey et al., 1996, *Cell* 87:483-92; Pear et al., 1996, *J. Exp. Med.* 183:2283-91; Yan et al., 2001, *Blood* 98:3793-9; Bellavia et al., 2000, *EMBO J.* 19:3337-48). Notch1 point mutations, insertions, and deletions producing aberrant Notch1 signaling have also been found to be frequently present in both childhood and adult T-cell acute lymphoblastic leukemia/lymphoma (Pear & Aster, 2004, *Curr. Opin. Hematol.* 11:416-33).

The frequent insertion of the mouse mammary tumor virus into both the Notch1 and Notch4 locus in mammary tumors and the resulting activated Notch protein fragments first implicated Notch signaling in breast cancer (Gallahan & Callahan, 1987, *J. Virol.* 61:66-74; Brennan & Brown, 2003, *Breast Cancer Res.* 5:69; Politi et al., 2004, *Semin. Cancer Biol.* 14:341-7). Further studies in transgenic mice have confirmed a role for Notch in ductal branching during normal mammary gland development, and a constitutively active form of Notch4 in mammary epithelial cells inhibits epithelial differentiation and results in tumorigenesis (Jhappan et al., 1992, *Genes & Dev.* 6:345-5; Gallahan et al., 1996, *Cancer Res.* 56:1775-85; Smith et al., 1995, *Cell Growth Differ.* 6:563-77; Soriano et al., 2000, *Int. J. Cancer* 86:652-9; Uyttendaele et al., 1998, *Dev. Biol.* 196:204-17; Politi et al., 2004, *Semin. Cancer Biol.* 14:341-7). Evidence for a role for Notch in human breast cancer is provided by data showing the expression of Notch receptors in breast carcinomas and their correlation with clinical outcome (Weijzen et al., 2002, *Nat. Med.* 8:979-86; Parr et al., 2004, *Int. J. Mol. Med.* 14:779-86). Furthermore, overexpression of the Notch pathway has been observed in cervical cancers (Zagouras et al., 1995, PNAS 92:6414-8), renal cell carcinomas (Rae et al., 2000, *Int. J. Cancer* 88:726-32), head and neck squamous cell carcinomas (Leethanakul et al., 2000, *Oncogene* 19:3220-4), endometrial cancers (Suzuki et al., 2000, *Int. J. Oncol.* 17:1131-9), and neuroblastomas (van Limpt et al., 2000, *Med. Pediatr. Oncol.* 35:554-8), suggestive of a potential role for Notch in the development of a number of neoplasms. Interestingly, Notch signaling may play a role in the maintenance of the undifferentiated state of Apc-mutant neoplastic cells of the colon (van Es & Clevers, 2005, *Trends in Mol. Med.* 11:496-502).

The Notch pathway is also involved in multiple aspects of vascular development including proliferation, migration, smooth muscle differentiation, angiogenesis and arterial-venous differentiation (Iso et al., 2003, *Arterioscler. Thromb. Vasc. Biol.* 23:543). For example, homozygous null mutations in Notch1/4 and Jagged1 as well as heterozygous loss of DLL4 result in severe though variable defects in arterial development and yolk sac vascularization. Furthermore, DLL1-deficient and Notch2-hypomorphic mice embryos show hemorrhaging that likely results from poor development of vascular structures (Gale et al., 2004, PNAS, 101: 15949-54; Krebs et al., 2000, *Genes Dev.* 14:1343-52; Xue et al., 1999, *Hum. Mel. Genet.* 8:723-30; Hrabe de Angelis et al., 1997, *Nature* 386:717-21; McCright et al., 2001, *Dev.* 128: 491-502). In humans, mutations in Jagged1 are associated with Alagille syndrome, a developmental disorder that includes vascular defects, and mutations in Notch3 are responsible for an inherited vascular dementia (Cadasil) in which vessel homeostasis is defective (Joutel et al., 1996, *Nature* 383:707-10).

Anti-Notch antibodies and their possible use as anti-cancer therapeutics have been previously reported. See, e.g., U.S. Patent Application Publication No. 2008/0131434, which is incorporated by reference herein in its entirety. See also International Publication Nos. WO 2008/057144 and WO 2008/076960, as well as U.S. Patent Application Publication Nos. 2008/0226621, 2008/0118520, and 2008/0131908.

BRIEF SUMMARY OF THE INVENTION

The present invention provides novel Notch-binding agents and novel antagonists of one or more human Notch receptors, as well as methods of using those agents and antagonists. The present invention further provides novel polypeptides, such as antibodies that bind one or more human Notch receptors, fragments of such antibodies, and other polypeptides related to such antibodies. In certain embodiments, the invention provides antagonists of human Notch2 and/or human Notch3, including, but not limited to, antibodies that specifically bind human Notch2 and/or human Notch3. As used herein, the phrase "Notch2 and/or Notch3" means "Notch2," "Notch3," or "both Notch2 and Notch3." In certain embodiments, the antibodies or other antagonists bind to a region of the Notch receptor that is outside of the ligand-binding domain (e.g., EGF10 of Notch2 or EGF9 of Notch3). In certain embodiments, the antibodies specifically bind human Notch2. In certain embodiments, the antibodies specifically bind both human Notch2 and human Notch3. In some embodiments, the antibodies specifically bind human Notch3. Polynucleotides comprising nucleic acid sequences encoding the polypeptides are also provided, as are vectors comprising the polynucleotides. Cells comprising the polypeptides and/or polynucleotides of the invention are further provided. Compositions (e.g., pharmaceutical compositions) comprising the novel Notch antagonists are also provided. Methods of using the agents and antagonists are also provided, such as methods of using the Notch antagonists to inhibit tumor growth, reduce the tumorigenicity of tumors, inhibit angiogenesis, and/or treat cancer or other diseases associated with angiogenesis.

In one aspect, the invention provides an agent (e.g., an antibody) that specifically binds to an EGF10 domain (or an equivalent of an EGF10 domain) of one or more human Notch receptors. In certain embodiments, the agent is an antibody. In certain embodiments, the agent is an antagonist. In certain embodiments, the agent specifically binds to EGF10 of human Notch2 and/or EGF9 of human Notch3. EGF9 is the EGF within human Notch3 that is equivalent to EGF10 in the other human Notch receptors Notch1, Notch2, and Notch4. In some embodiments, the agent specifically binds to EGF10 of Notch 2. In some embodiments, the agent specifically binds to EGF10 of Notch 2 and to EGF9 of Notch 3. In some embodiments, the agent specifically binds to EGF9 of Notch 3. In other embodiments, the agent binds to at least part of the sequence HKGAL (SEQ ID NO:28) within Notch2 EGF10. In some embodiments, the agent binds to at least part of the sequence HEDAI (SEQ ID NO:29) within Notch3 EGF9.

In certain embodiments of each of the aforementioned aspects or embodiments, as well as other aspects and/or embodiments described elsewhere herein, the agent inhibits binding of a ligand to human Notch2 and/or Notch3. In some embodiments, the agent inhibits binding of a ligand to human Notch2. In some embodiments, the agent inhibits binding of a ligand to Notch2 and Notch3. In other embodiments, the agent inhibits binding of a ligand to Notch3. In certain embodiments, the ligand is DLL4, JAG1 or JAG2. In other embodiments, the agent inhibits signaling of human Notch2 and/or Notch3. In some embodiments, the agent inhibits signaling of human Notch2. In some embodiments, the agent inhibits signaling of Notch2 and Notch3. In other embodiments, the agent inhibits signaling of Notch3. In some embodiments Notch2 and/or Notch3 signaling is induced by DLL4, JAG1 or JAG2. Pharmaceutical compositions comprising the agent and methods of using the agent for such uses as inhibiting angiogenesis, inhibiting tumor growth, reducing the tumorigenicity of a tumor, and/or treating cancer are also provided.

In a further aspect, the invention provides an antibody that specifically binds human Notch2 and/or Notch3, wherein the antibody comprises (a) a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising SIFYTT (SEQ ID NO:51); and/or (b) a light chain CDR1 comprising RASQSVRSNYLA (SEQ ID NO:8), a light chain CDR2 comprising GASSRAT (SEQ ID NO:9), and/or a light chain CDR3 comprising QQYSNFPI (SEQ ID NO:10). In some embodiments, the antibody comprises (a) a heavy chain CDR1 comprising SSSGMS (SEQ ID NO:5), or a variant thereof comprising 1, 2, 3, or 4 conservative amino acid substitutions; a heavy chain CDR2 comprising VIASSGSNTYYADSVKG (SEQ ID NO:6), or a variant thereof comprising 1, 2, 3, or 4 conservative amino acid substitutions; and/or a heavy chain CDR3 comprising SIFYTT (SEQ ID NO:51), or a variant thereof comprising 1, 2, 3, or 4 conservative amino acid substitutions; and/or (b) a light chain CDR1 comprising RASQSVRSNYLA (SEQ ID NO:8), or a variant thereof comprising 1, 2, 3, or 4 conservative amino acid substitutions; a light chain CDR2 comprising GASSRAT (SEQ ID NO:9), or a variant thereof comprising 1, 2, 3, or 4 conservative amino acid substitutions; and/or a light chain CDR3 comprising QQYSNFPI (SEQ ID NO:10), or a variant thereof comprising 1, 2, 3, or 4 conservative amino acid substitutions. Pharmaceutical compositions comprising the antibody and methods of using the antibody for such uses as inhibiting angiogenesis, inhibiting tumor growth, reducing the tumorigenicity of a tumor, and/or treating cancer are also provided.

In a further aspect, the invention provides an antibody that specifically binds human Notch2 and/or Notch3, wherein the antibody comprises (a) a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising GIFFAI (SEQ ID NO:7); and/or (b) a light chain CDR1 comprising RASQSVRSNYLA (SEQ ID NO:8), a light chain CDR2 comprising GASSRAT (SEQ ID NO:9), and/or a light chain CDR3 comprising QQYSNFPI (SEQ ID NO:10). In certain embodiments, the antibody specifically binds Notch2. In some embodiments, the antibody comprises (a) a heavy chain CDR1 comprising SSSGMS (SEQ ID NO:5), or a variant thereof comprising 1, 2, 3, or 4 conservative amino acid substitutions; a heavy chain CDR2 comprising VIASSGSNTYYADSVKG (SEQ ID NO:6), or a variant thereof comprising 1, 2, 3, or 4 conservative amino acid substitutions; and/or a heavy chain CDR3 comprising GIFFAI (SEQ ID NO:7), or a variant thereof comprising 1, 2, 3, or 4 conservative amino acid substitutions; and/or (b) a light chain CDR1 comprising RASQSVRSNYLA (SEQ ID NO:8), or a variant thereof comprising 1, 2, 3, or 4 conservative amino acid substitutions; a light chain CDR2 comprising GASSRAT (SEQ ID NO:9), or a variant thereof comprising 1, 2, 3, or 4 conservative amino acid substitutions; and/or a light chain CDR3 comprising QQYSNFPI (SEQ ID NO:10), or a variant thereof comprising 1, 2, 3, or 4 conservative amino acid substitutions. Pharmaceutical compositions comprising the antibody and methods of using the antibody for such uses as inhibiting angiogenesis, inhibiting tumor growth, reducing the tumorigenicity of a tumor, and/or treating cancer are also provided.

In another aspect, the invention provides an antibody that specifically binds human Notch2 and/or Notch3, wherein the antibody comprises (a) a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising (G/S)(I/S)F(F/Y)(A/P)(I/T/S/N) (SEQ ID NO:30); and/or (b) a light chain CDR1 comprising RASQSVRSNYLA (SEQ ID NO:8), a light chain CDR2 comprising GASSRAT (SEQ ID NO:9), and/or a light chain CDR3 comprising QQYSNFPI (SEQ ID NO:10). In some embodiments, the antibody comprises a heavy chain CDR3 comprising SIFYPT (SEQ ID NO:22). In some embodiments, the antibody comprises a heavy chain CDR3 comprising SSSFFAS (SEQ ID NO:23). In other embodiments, the antibody comprises a heavy chain CDR3 comprising SSFYAS (SEQ ID NO:24). In certain embodiments, the antibody comprises a heavy chain CDR3 comprising SSFFAT (SEQ ID NO:25). In some embodiments, the antibody comprises a heavy chain CDR3 comprising SIFYPS (SEQ ID NO:26). In yet other embodiments, the antibody comprises a heavy chain CDR3 comprising SSFFAN (SEQ ID NO:27). Pharmaceutical compositions comprising the antibody and methods of using the antibody for such uses as inhibiting angiogenesis, inhibiting tumor growth, reducing the tumorigenicity of a tumor, and/or treating cancer are also provided.

In another aspect, the invention provides a polypeptide that comprises: (a) a polypeptide (e.g., a heavy chain variable region) having at least about 80% sequence identity to SEQ ID NO:50, SEQ ID NO:14, SEQ ID NO:40, SEQ ID NO:52, SEQ ID NO:53, SEQ ID NO:54, SEQ ID NO:55, SEQ ID NO:56, SEQ ID NO:57, or SEQ ID NO:20 (with or without signal sequence); and/or (b) a polypeptide (e.g., a light chain variable region) having at least about 80% sequence identity to SEQ ID NO:13, SEQ ID NO:19 or SEQ ID NO:39 (with or without signal sequence). In certain embodiments, the polypeptide is an antibody. In certain embodiments, the polypeptide specifically binds human Notch2 and/or Notch3. In some embodiments, the polypeptide specifically binds to human Notch2. In some embodiments, the polypeptide binds to Notch2 and Notch3. In other embodiments, the polypeptide binds to Notch3. In certain embodiments, the polypeptide comprises a polypeptide having at least about 85%, at least about 90%, at least about 95%, at least about 98%, or about 100% sequence identity to SEQ ID NO:14, SEQ ID NO:13, or SEQ ID NO:50. Pharmaceutical compositions comprising the polypeptide and methods of using the polypeptide for such uses as inhibiting angiogenesis, inhibiting tumor growth, reducing the tumorigenicity of a tumor, and/or treating cancer are also provided.

In still another aspect, the invention provides a polypeptide (e.g., an antibody or a heavy chain or light chain of an antibody) comprising: (a) a polypeptide having at least about 80% sequence identity to SEQ ID NO:49, SEQ ID NO:16, or SEQ ID NO:2 (with or without signal sequence); and/or (b) a polypeptide having at least about 80% sequence identity to SEQ ID NO:18, or SEQ ID NO:4 (with or without signal sequence. In certain embodiments, the polypeptide comprises a polypeptide having at least about 85%, at least about 90%, at least about 95%, at least about 98%, or about 100% sequence identity to SEQ ID NO:39 or SEQ ID NO:40. Pharmaceutical compositions comprising the antibodies and methods of treating cancer comprising administering therapeutically effective amounts of the antibodies are also provided.

In another aspect, the invention provides a polypeptide (e.g., an antibody or a heavy chain or light chain of an antibody) comprises: (a) a polypeptide having at least about 80% sequence identity to SEQ ID NO:50; and/or (b) a polypeptide having at least about 80% sequence identity to SEQ ID NO:13. In certain embodiments, the polypeptide comprises a polypeptide having at least about 85%, at least about 90%, at least about 95%, at least about 98%, or about 100% sequence identity to SEQ ID NO:50 or SEQ ID NO:13. In certain embodiments, the polypeptide is an antibody that binds human Notch2 and/or human Notch3. Pharmaceutical compositions comprising the antibodies and methods of treating cancer comprising administering therapeutically effective amounts of the antibodies are also provided.

In another aspect, the invention provides an antibody that comprises, consists, or consists essentially of a 59R1 IgG2 antibody comprising the heavy chain and light chain of SEQ ID NOs:16 and 18 (with or without signal sequence), respectively, or as encoded by the DNA deposited with the American Type Culture Collection (ATCC), 10801 University Boulevard, Manassas, Va., USA, under the conditions of the Budapest Treaty on Oct. 15, 2008, and assigned designation number PTA-9547. Pharmaceutical compositions comprising the antibody and methods of using the antibody for such uses as inhibiting angiogenesis, inhibiting tumor growth, reducing the tumorigenicity of a tumor, and/or treating cancer are also provided.

In an additional aspect, the invention provides an antibody that comprises, consists or consists essentially of a 59R5 IgG2 antibody comprising the heavy chain and light chain of SEQ ID NO:49 and SEQ ID NO:18 (with or without signal sequence), respectively, or as encoded by the DNA deposited with the ATCC on Jul. 6, 2009, and assigned designation number PTA-10170. Pharmaceutical compositions comprising the antibody and methods of using the antibody for such uses as inhibiting angiogenesis, inhibiting tumor growth, reducing the tumorigenicity of a tumor, and/or treating cancer are also provided.

In another aspect, the invention provides an antibody that competes for specific binding to human Notch2 and/or Notch3 with an antibody comprising a heavy chain variable region comprising SEQ ID NO:14 and a light chain variable region comprising SEQ ID NO:13. In certain embodiments, the antibody competes for specific binding with a 59R1 IgG2 antibody comprising the heavy chain and light chain of SEQ ID NOs:16 and 18 (with or without signal sequence), respectively, or as encoded by the DNA deposited with the ATCC on Oct. 15, 2008, and assigned designation number PTA-9547. In some embodiments, the antibody competes for binding to human Notch2. In some embodiments, the antibody competes for binding to human Notch2 and Notch3. In other embodiments, the antibody competes for binding to human Notch3. Pharmaceutical compositions comprising the antibody and methods of using the antibody for such uses as inhibiting angiogenesis, inhibiting tumor growth, reducing the tumorigenicity of a tumor, and/or treating cancer are also provided.

In a further aspect, the antibody competes for specific binding to human Notch2 and/or Notch3 with an antibody comprising a heavy chain variable region comprising SEQ ID NO:50 and a light chain variable region comprising SEQ ID NO:13. In some embodiments, the antibody competes for specific binding with a 59R5 antibody comprising the heavy chain and light chain of SEQ ID NOs: 49 and 18, respectively, or as encoded by the DNA deposited with the ATCC on Jul. 6, 2009, and assigned designation number PTA-10170. In some embodiments, the antibody competes for binding to human Notch2. In some embodiments, the antibody competes for binding to human Notch2 and Notch3. In other embodiments, the antibody competes for binding to human Notch3. Pharmaceutical compositions comprising the antibody and methods of using the antibody for such uses as inhibiting angiogenesis, inhibiting tumor growth, reducing the tumorigenicity of a tumor, and/or treating cancer are also provided.

In certain other aspects, the invention provides a polypeptide (with or without a signal sequence) comprising a sequence selected from the group consisting of SEQ ID NO:2, SEQ ID NO:4, SEQ ID NO:16, SEQ ID NO:18, SEQ ID NO:13, SEQ ID NO:14, SEQ ID NO:39, SEQ ID NO:40, SEQ ID NO:19, SEQ ID NO:20, SEQ ID NO:49, SEQ ID NO:50, SEQ ID NO:52, SEQ ID NO:53, SEQ ID NO:54, SEQ ID NO:55, SEQ ID NO:56, and SEQ ID NO:57, as well as a polynucleotide encoding such a polypeptide. In certain embodiments, the polypeptide is an antibody. In certain embodiments, the antibody specifically binds to human Notch2 and/or human Notch3. In certain embodiments, the antibody specifically binds to human Notch2. In certain embodiments, the antibody specifically binds to human Notch2 and human Notch3. In certain embodiments, the antibody specifically binds to human Notch3. In another aspect, the invention provides a polynucleotide comprising a sequence selected from the group consisting of SEQ ID NO:1, SEQ ID NO:3, SEQ ID NO:15, SEQ ID NO:17, SEQ ID NO:47, SEQ ID NO:48, SEQ ID NO:58, SEQ ID NO: 59 and SEQ ID NO:60.

In another aspect, the invention provides a method of modulating the function of pericytes and/or vascular smooth muscle cells in a subject (e.g., at the site of a tumor or other aberrant angiogenesis in the subject). In certain embodiments, the method comprises administering an effective amount of an agent that specifically binds human Notch2 and/or human Notch3 to the subject. In certain embodiments, the agent is an antibody. In some embodiments, the agent is an antibody described in any one of the aforementioned aspects and/or embodiments, as well as other aspects and/or embodiments described herein. In certain embodiments, the agent is an antagonist. In certain embodiments, the agent specifically binds to and is an antagonist of human Notch3. In certain embodiments, the modulation of the function of the pericytes and/or vascular smooth muscle cells results in inhibition of angiogenesis and/or tumor growth.

In still another aspect, the invention provides a method of inhibiting angiogenesis (e.g., tumor angiogenesis) in a subject. In certain embodiments, the method comprises administering to the subject an effective amount of an agent that specifically binds human Notch2 and/or human Notch3. In certain embodiments, the agent is an antagonist. In some embodiments, the agent specifically binds to and is an antagonist of human Notch2. In certain embodiments, the agent specifically binds to and is an antagonist of human Notch3. In some embodiments, the agent is an antagonist of both Notch2 and Notch3. In some embodiments, the antagonist is an antibody. In certain embodiments, the agent is an antibody. In some embodiments, the agent is an antibody described in any one of the aforementioned aspects and/or embodiments, as well as other aspects and/or embodiments described herein. In some embodiments, the antagonist is not an antibody. In some embodiments, the method of inhibiting angiogenesis further comprises administering to the subject an antagonist of vascular endothelial cell growth factor (VEGF) or of a VEGF receptor. In certain embodiments, the method is a method of inhibiting angiogenesis by modulating the function of pericytes and/or vascular smooth muscle cells.

In a further aspect, the invention provides a method of inhibiting growth of a tumor in a subject. In certain embodiments, the method comprises administering to the subject a therapeutically effective amount of an antagonist of human Notch2 and/or human Notch3. In certain embodiments, the antagonist is an antibody that specifically binds human Notch2. In some embodiments, the antagonist is an antibody that specifically binds both human Notch2 and human Notch3. In certain embodiments, the antagonist is an antibody that specifically binds human Notch3. In some embodiments, the antagonist is an antibody described in any one of the aforementioned aspects and/or embodiments, as well as other aspects and/or embodiments described herein. In certain embodiments, the tumor comprises a deletion or other mutation in the phosphatase and tensin homolog (PTEN) gene. In certain embodiments, the tumor is a breast tumor.

In a still further aspect, the invention provides a method of selecting a subject for treatment with a human Notch2 and/or human Notch3 antagonist. In certain embodiments, the method comprises (a) determining if the tumor comprises a deletion or mutation in the phosphatase and tensin homolog (PTEN) gene; and (b) selecting the subject for treatment with a Notch2 and/or Notch3 antagonist if the tumor comprises the deletion or mutation. In some embodiments, the subject is treated with a Notch2 antagonist. In some embodiments, the subject is treated with an antagonist of Notch2 and Notch3. In some embodiments, the subject is treated with an antagonist of Notch3. In some embodiments the antagonist is an antibody. In certain embodiments, the tumor is a breast tumor.

In another aspect, the invention provides an antibody that specifically binds to a non-ligand binding region of an extracellular domain of at least one human Notch receptor (e.g., 1, 2, 3, or 4 Notch receptors). In certain embodiments, the non-ligand binding region comprises or consists of EGF repeat 10 of a human Notch receptor (or an equivalent of EGF10, such as EGF9 of human Notch3). In some embodiments, the antibody inhibits tumor growth. In some embodiments, the antibody inhibits binding of a ligand to a Notch receptor. In certain embodiments, the antibody inhibits signaling by the Notch receptor. In some embodiments, the Notch receptor is a human Notch1, Notch2, Notch3, or Notch4 receptor. In certain embodiments, the antibody specifically binds to Notch2 (for example, EGF10 of Notch2). In certain embodiments, the antibody specifically binds to Notch2 and at least one additional Notch receptor. In certain embodiments, the additional Notch receptor is Notch3. Pharmaceutical compositions comprising the antibodies and methods of treating cancer comprising administering therapeutically effective amounts of the antibodies are also provided.

In an additional aspect, the invention provides an antibody that specifically binds to two or more (i.e., at least two or two, three, or four) human Notch receptors. In certain embodiments, the antibody specifically binds to a non-ligand binding region of an extracellular domain of the two or more human Notch receptors. In certain embodiments, if the two or more human Notch receptors comprise Notch1, Notch2, or Notch4, the antibody binds to EGF10 of Notch1, Notch2, or Notch4, and if the two or more human Notch receptors comprise Notch3, the antibody binds to EGF9 of Notch3. In certain embodiments, the non-ligand binding region is not EGF4. In certain embodiments, the two or more human Notch receptors comprise Notch2. In certain embodiments, the two or more human Notch receptors comprise Notch3. In still further embodiments, the two or more human Notch receptors comprise Notch2 and Notch3. In certain embodiments, the antibody is an antagonist of the two or more human Notch receptors. In certain embodiments, the antibody inhibits tumor growth. Pharmaceutical compositions comprising the antibodies and methods of treating cancer comprising administering therapeutically effective amounts of the antibodies are also provided.

In yet another aspect, the invention provides an isolated antibody that specifically binds to a non-ligand binding region of an extracellular domain of a human Notch2 receptor and inhibits tumor growth, wherein the non-ligand binding region comprises or consists of EGF repeat 10 of the human Notch2 receptor (e.g., SEQ ID NO:36). In some embodiments, the antibody does not bind to any region of human Notch2 outside of EGF repeat 10. In certain embodiments, the antibody also specifically binds to EGF repeat 10 (or equivalent) of at least one additional human Notch receptor (e.g., EGF9 of Notch3). In some embodiments, the antibody binds to human Notch2 EGF10 and Notch3 EGF9. Pharmaceutical compositions comprising the antibodies and methods of treating cancer comprising administering therapeutically effective amounts of the antibodies are also provided.

In yet another aspect, the invention provides an isolated antibody that specifically binds to a non-ligand binding region of an extracellular domain of a human Notch3 receptor and inhibits tumor growth, wherein the non-ligand binding region comprises or consists of EGF repeat 9 of the human Notch3 receptor (equivalent to EGF10 in the other Notch receptors). In some embodiments, the antibody does not bind to any region of human Notch3 outside of EGF repeat 9. In certain embodiments, the antibody also specifically binds to EGF repeat 10 of at least one additional human Notch receptor. In some embodiments, the antibody binds to human Notch3 EGF9 and Notch2 EGF10. Pharmaceutical compositions comprising the antibodies and methods of treating cancer comprising administering therapeutically effective amounts of the antibodies are also provided.

In a still further aspect, the invention provides an antibody that binds a non-ligand binding region of an extracellular domain of a human Notch receptor and comprises: (a) a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising GIFFAI (SEQ ID NO:7); and/or (b) a light chain CDR1 comprising RASQSVRSNYLA (SEQ ID NO:8), a light chain CDR2 comprising GASSRAT (SEQ ID NO:9), and/or a light chain CDR3 comprising QQYSNFPI (SEQ ID NO:10). In certain embodiments, the human Notch receptor is Notch2. In certain embodiments, the antibody binds to EGF10 of a human Notch2 receptor and/or EGF9 of a human Notch3 receptor. In an additional aspect, the invention provides an antibody that competes with such an antibody for specific binding to a non-ligand binding region of an extracellular domain of Notch2 in a competitive binding assay. Pharmaceutical compositions comprising the antibodies and methods of treating cancer comprising administering therapeutically effective amounts of the antibodies are also provided. Methods of inhibiting angiogenesis comprising administering the compositions are also provided.

In another aspect, the invention provides an antibody that binds a non-ligand binding region of an extracellular domain of a human Notch receptor and comprises: (a) a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising SIFYTT (SEQ ID NO:51); and/or (b) a light chain CDR1 comprising RASQSVRSNYLA (SEQ ID NO:8), a light chain CDR2 comprising GASSRAT (SEQ ID NO:9), and/or a light chain CDR3 comprising QQYSNFPI (SEQ ID NO:10). In certain embodiments, the human Notch receptor is Notch2. In some embodiments, the antibody binds to the human Notch2 and Notch3 receptors. In certain embodiments, the antibody binds to EGF 10 of a human Notch2 receptor and/or EGF9 of a human Notch3 receptor. In another embodiment, the invention provides an antibody that competes with such an antibody for specific binding to a non-ligand binding region of an extracellular domain of Notch2 in a competitive binding assay. Pharmaceutical compositions comprising the antibodies and methods of treating cancer comprising administering therapeutically effective amounts of the antibodies are also provided. Methods of inhibiting angiogenesis comprising administering the compositions are also provided.

In certain embodiments of each of the aforementioned aspects or embodiments, as well as other aspects and/or embodiments described elsewhere herein, the antibody specifically binds to both human Notch2 and human Notch3.

In certain embodiments of each of the aforementioned aspects or embodiments, as well as other aspects and/or embodiments described elsewhere herein, the antibody is a recombinant antibody. In certain embodiments, the antibody is a monoclonal antibody. In certain embodiments, the antibody is a chimeric antibody. In certain embodiments, the antibody is a humanized antibody. In certain embodiments, the antibody is a human antibody. In some embodiments, the antibody is monovalent, bivalent or multivalent. In certain embodiments, the antibody is a monospecific antibody. In certain embodiments, an individual antigen-binding site of the antibody binds (or is capable of binding) a non-ligand binding region of the extracellular domain of more than one human Notch receptor (e.g., Notch2 and Notch3). In certain alternative embodiments, the antibody is a bispecific antibody. In certain embodiments, the antibody is an IgG1 antibody. In certain embodiments, the antibody is an IgG2 antibody. In certain embodiments, the antibody is conjugated to a cytotoxic moiety. In certain embodiments, the antibody is isolated. In still further embodiments, the antibody is substantially pure.

In certain embodiments of each of the aforementioned aspects or embodiments, as well as other aspects and/or embodiments described elsewhere herein, the cancer or tumor treated with the antibody is a breast, colorectal, lung, pancreatic, prostate, or head and neck cancer or tumor. In certain embodiments, the cancer or tumor is melanoma. In certain embodiments, the cancer or tumor is a breast cancer or tumor. In certain embodiments, the cancer or tumor is a colorectal cancer or tumor. In certain embodiments, the cancer or tumor is a pancreatic cancer or tumor. In certain embodiments, the cancer or tumor is a prostate cancer or tumor.

In certain embodiments of each of the aforementioned aspects or embodiments, as well as other aspects and/or embodiments described elsewhere herein, the methods of treating cancer comprise inhibiting tumor growth. In certain embodiments, the methods of treating cancer comprise reducing the tumorigenicity of tumors (e.g., by reducing the frequency of cancer stem cells in the tumor).

In certain embodiments of each of the aforementioned aspects or embodiments, as well as other aspects and/or embodiments described elsewhere herein, the antagonist or antibody is administered to a subject in combination with an additional treatment for cancer. In certain embodiments, the additional treatment for cancer comprises radiation therapy, chemotherapy, and/or an additional antibody therapeutic. In some embodiments, the additional treatment for cancer comprises a chemotherapeutic agent. In certain embodiments, the chemotherapy comprises paclitaxel (e.g., TAXOL), irinotecan, gemcitabine, and/or oxaliplatin. In certain embodiments, the additional antibody therapeutic is an antibody that specifically binds a human Notch receptor (e.g., Notch1, 2, 3, or 4) or a human Notch receptor ligand (e.g., DLL4 or JAG1). In some embodiments, the additional antibody therapeutic is an anti-DLL4 antibody. In certain alternative embodiments, the additional antibody therapeutic is an antibody that specifically binds vascular endothelial cell growth factor (VEGF). In certain embodiments, the additional therapeutic binds a VEGF receptor.

In certain embodiments of each of the aforementioned aspects or embodiments, as well as other aspects and/or embodiments described elsewhere herein, the antibody is administered to a subject in combination with a second therapeutic agent that is an anti-angiogenic agent.

Cell lines (e.g., hybridoma cell lines) comprising or producing the antibodies or other polypeptides described herein are further provided by the invention. Polynucleotides (e.g., vectors) comprising the polynucleotides described herein, including polynucleotides encoding the polypeptides or the light chain variable regions or heavy chain variable regions of the antibodies described herein are also provided, as are cell lines comprising such polynucleotides.

In certain embodiments, the present invention provides a method of treating cancer, wherein the cancer comprises cancer stem cells, comprising administering to the subject a therapeutically effective amount of an antibody which binds a Notch receptor. In a more particular aspect, the present invention provides a method of treating cancer, wherein the cancer comprises stem cells expressing one or more Notch receptor family members, comprising administering to the subject a therapeutically effective amount of an antibody that binds those Notch receptor family members. The present invention provides antibodies that bind to the non-ligand binding domain of the extracellular domain of a human Notch receptor and are therapeutically effective against cancer. Thus, in certain embodiments, the present invention provides an antibody that specifically binds to a non-ligand binding region of the extracellular domain of a human Notch receptor and that inhibits tumor growth. In certain embodiments, the present invention further provides a method of treating cancer, the method comprising administering a therapeutically effective amount of an antibody that specifically binds to a non-ligand binding region of the extracellular domain of a human Notch receptor protein and inhibits tumor growth.

Various advantages in using an antibody that binds Notch receptor family members or the ligands to those Notch receptors to treat such cancers are contemplated herein. In some embodiments, certain Notch receptors are highly expressed in certain solid tumors, for example, breast and colon, and this provides a sink for active drug where the drug binds to the Notch receptor. Antibodies that bind overexpressed Notch receptors are anticipated to have a better safety profile than currently available chemotherapeutic drugs.

The invention further provides a method of treating cancer in a human, wherein the cancer comprising cancer stem cells is not characterized by overexpression by the cancer stem cell of one or more Notch receptors, comprising administering to the human a therapeutically effective amount of an antibody which binds to a Notch receptor and blocks ligand activation of a Notch receptor.

The invention further provides a method of treating cancer in a human comprising administering to the human therapeutically effective amounts of (a) a first antibody which binds a Notch receptor and inhibits growth or proliferation of cancer stem cells which overexpress Notch receptors; and (b) a second antibody which binds a Notch receptor and blocks ligand activation of a Notch receptor.

The invention also provides a method of treating cancer, wherein the cancer is selected from the group consisting of breast, colon, rectal and colorectal cancer, comprising administering a therapeutically effective amount of an antibody which binds Notch. The invention also provides another method of treating cancer, wherein the cancer is selected from the group consisting of breast, colon, pancreatic, prostate, lung, rectal and colorectal cancer, comprising administering a therapeutically effective amount of an antibody that blocks ligand activation of a Notch receptor. The invention also provides still another method of treating cancer, wherein the cancer is selected from the group consisting of breast, colon, pancreatic, prostate, lung, rectal and colorectal cancer, comprising administering a therapeutically effective amount of an antibody that binds Notch and an antibody that blocks ligand activation of a Notch receptor.

In further embodiments, the invention provides articles of manufacture for use (among other things) in the above methods. For example, the invention provides an article of manufacture comprising a container and a composition contained therein, wherein the composition comprises an antibody that binds Notch, and further comprises a package insert indicating that the composition can be used to treat a cancer comprising cancer stem cells. In some embodiments, the invention provides an article of manufacture comprising a container and a composition contained therein, wherein the composition comprises an antibody that binds Notch, and further comprises a package insert indicating that the composition can be used to treat cancer comprising cancer stem cells that express one or more Notch receptors.

In certain embodiments, the invention additionally pertains to an article of manufacture comprising a container and a composition contained therein, wherein the composition comprises an antibody which binds a Notch receptor and blocks ligand activation of a Notch receptor, and further comprises a package insert indicating that the composition can be used to treat cancer, wherein the cancer comprises cancer stem cells that are not characterized by overexpression of the Notch receptor.

In certain embodiments, an article of manufacture is provided which comprises (a) a first container with a composition contained therein, wherein the composition comprises a first antibody that binds a Notch receptor and inhibits growth of cancer cells comprising cancer stem cells overexpressing Notch; and (b) a second container with a composition contained therein, wherein the composition comprises a second antibody which binds Notch and blocks ligand activation of a Notch receptor.

In some embodiments, a further article of manufacture is provided which comprises a container and a composition contained therein, wherein the composition comprises an antibody which binds Notch and blocks ligand activation of a Notch receptor, and further comprises a package insert indicating that the composition can be used to treat a cancer selected from the group consisting of colon, pancreatic, prostate, lung, rectal and colorectal cancer.

The invention additionally provides: an antibody (e.g., a human antibody or a humanized antibody) which binds Notch and blocks ligand activation of a Notch receptor; a composition comprising the antibody and a pharmaceutically acceptable carrier; and an immunoconjugate comprising the antibody conjugated with a cytotoxic agent.

In one aspect, the invention provides an isolated polynucleotide encoding any of the antibodies or polypeptides of the aforementioned aspects or embodiments, as well as other aspects and/or embodiments described elsewhere herein. In some embodiments, the invention provides a vector comprising the polynucleotide. In some embodiments, a host cell comprises the polynucleotide or the vector. In other embodiments, a process of producing the antibody comprises culturing a host cell comprising the polynucleotide so that the polynucleotide is expressed and, optionally, further comprises recovering the antibody from the host cell culture (e.g., from the host cell culture medium).

Moreover, the invention provides an isolated polynucleotide encoding a humanized or human antibody as described in the aforementioned embodiments or aspects, as well as described elsewhere herein; a vector comprising the polynucleotide; a host cell comprising the polynucleotide or the vector; as well as a process of producing the antibody comprising culturing a host cell comprising the polynucleotide so that the polynucleotide is expressed and, optionally, further comprising recovering the antibody from the host cell culture (e.g., from the host cell culture medium).

The invention further pertains to an immunoconjugate comprising an antibody that binds Notch conjugated to one or more calicheamicin molecules, and the use of such conjugates for treating a Notch expressing cancer, e.g., a cancer in which cancer stem cells overexpress Notch.

Where aspects or embodiments of the invention are described in terms of a Markush group or other grouping of alternatives, including, but not limited to, groups of alternatives separated by "and/or" or "or," the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention. For example, language such as "X and/or Y" encompasses "X" individually, "Y" individually, as well as "X" and "Y" together.

BRIEF DESCRIPTION OF THE
DRAWINGS/FIGURES

FIG. 1: 59R1 antibodies and variants bind human Notch2 and block ligand binding. (A) FACS analysis of binding by 59R1 Fab to human Notch2. "Clone 1" is 59R1 Fab which was shown to bind human Notch2 on stably transfected HEK293 cells. "Clone 5" is the Fab of a different clone isolated from the phage library which did not bind Notch2. (B) FACS analysis of blocking of ligand (JAG1) binding by 59R1 Fab. "Clone 1" is 59R1 Fab which was shown to block binding of a hJagged1 ECD-Fc fusion to human Notch2 on stably transfected HEK293 cells. "Clone 5" is the Fab of a different clone isolated from the phage library which did not block ligand binding in the assay. (C) FACS analysis of binding of 59R1 IgG2 antibody to human Notch2 on stably transfected HEK293 cells. 59R1 IgG2 antibody was shown to bind human Notch2 on stably transfected HEK293 cells. (D) FACS analysis of blocking of ligand (DLL4) binding by 59R1 IgG2 antibody. 59R1 IgG2 antibody was shown to block binding of a hDLL4 ECD-Fc fusion to human Notch2 on stably transfected HEK293 cells. (E) Affinity maturation strategy for heavy chain CDR3 of 59R1. The parental sequence of the heavy chain CDR3 of 59R1 is shown boxed. Allowed residue changes are as indicated below the parental sequence in the figure. (F) Screening of affinity matured 59R1 sequences for JAG1 blocking ability. Improved variants are indicated with arrows.

Figure 2:
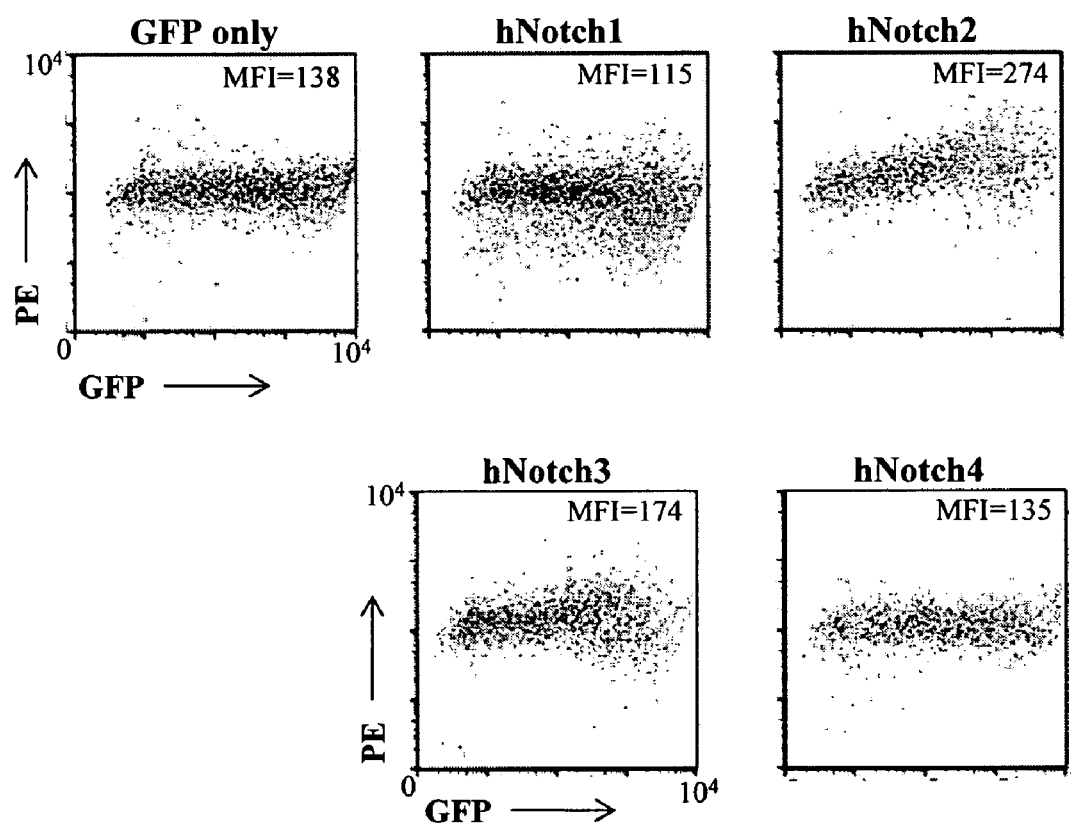

FIG. 2: FACS analysis of cross-reactivity of the 59R1 IgG2 antibody to the four human Notch homologues. 59R1 was found to bind hNotch2 and hNotch3 on transiently transfected HEK-293 cells but was found to not exhibit significant binding to hNotch1 and hNotch4 on the same cells.

FIG. 3: Epitope mapping of 59R1 antibody. (A) Anti-Notch2/3 antibody 59R1 binds to EGF repeat 10 of human Notch2. Supernatant from HEK 293 cells expressing recombinant Notch2-Fc fusion proteins with the indicated EGF repeats of Notch2 between 1 and 12 (x-axis) were used in ELISA with anti-Notch2/3 antibody 59R1. The OD (y-axis) indicated antibody binding (hatched bars) only to Notch2 fusion proteins comprising EGF repeat 10. (The figure shows data obtained from two separate experiments which are shown separately in the top and bottom graphs.) (B) EGF Repeats 11 and 12 are not involved in anti-Notch2/3 antibody 59R1 binding to full length hNotch2. FACS analysis of HEK 293 cells transfected with green fluorescent protein (GFP) (x-axis) alone (top left) or co-transfected with GFP and either full length Notch2 intact or with full length Notch 2 with EGF repeat 11 deleted ($\Delta$EGF11) or EGF repeat 12 deleted ($\Delta$EGF12). Binding of 59R1 is indicated along the y-axis (PE) to all three Notch2 proteins in GFP-expressing cells. (C) EGF repeat 10 is involved in anti-Notch2/3 antibody 59R1 binding to full-length hNotch2, but not in ligand binding. Binding by an anti-Notch2 antibody 59M70 that binds to EGF1-4 of hNotch2 is indicated as "anti-Notch2 binding." Binding by DLL4 is indicated as "ligand binding."

FIG. 4: Anti-Notch2/3 antibody 59R1 inhibits Notch2 signaling in luciferase reporter assays. (A) 59R1 blocks hDLL4-induced Notch2 reporter activity. (B) 59R1 blocks hJAG1-induced Notch2 reporter activity (C) 59R1 blocks hJAG2-induced Notch2 reporter activity FIG. 5: Notch2/3 Receptor Antibody 59R1 Inhibits Tumor Formation and Growth In vivo. (A) Anti-Notch2/3 (59R1) Inhibits the Formation of PE13 Breast Tumors. NOD/SCID mice injected with PE13 breast tumor cells were treated with control antibody (squares) or anti-Notch2/3 antibody 59R1 (open triangles) two days after cell injection and tumor volume (y-axis, mm$^3$) was measured across time (x-axis, days post cell injection). Treatment with 59R1 antibodies significantly inhibited tumor formation compared to control. (p<0.001) (B) Anti-Notch2/3 (59R1) Inhibits Formation of T3 Breast Tumors. NOD/SCID mice injected with T3 breast tumor cells were treated with control antibody (squares) or anti-Notch2/3 antibody 59R1 (open triangles) two days after cell injection, and tumor volume (y-axis, mm$^3$) was measured across time (x-axis, days post cell injection). Treatment with 59R1 antibodies significantly inhibited tumor formation compared to control. (p<0.001) (C) Anti-Notch2/3 (59R1) Inhibits the Growth of Colo-205 Colon Tumors. 6-8 week-old immunodeficient bg/nu XID female mice on a Swiss CD-1 background injected with Colo-205 colon tumor cells were treated with control antibody (squares) or anti-Notch2/3 antibody 59R1 (diamonds) after tumor volume reached a size between 65 to 200 mm$^3$. Mean tumor volume (y-axis, mm$^3$) was measured across time (x-axis, days post cell injection). Treatment with 59R1 antibodies inhibited tumor growth compared to control (* p<0.001 after day 40). (D) Anti-Notch2/3 (59R1) Inhibits the Growth of PN4 Pancreatic Tumors. NOD/SCID mice injected with PN4 pancreatic tumor cells were treated with control antibody (squares) or anti-Notch2/3 antibody 59R1 (diamonds) after tumor volume reached an a size between 65 to 200 mm$^3$. Mean tumor volume (y-axis, mm$^3$) was measured across time (x-axis, days post cell injection). Treatment with 59R1 antibodies inhibited tumor growth compared to control (* p<0.001 after day 70). (E) Anti-Notch2/3 (59R1) Inhibits the Growth of PE13 Breast Tumors. NOD/SCID mice injected with PE13 breast tumor cells were treated with control antibody (squares) or anti-Notch2/3 antibody 59R1 (diamonds) after tumor volume reached a size between 65 to 200 mm$^3$. Mean tumor volume (y-axis, mm$^3$) was measured across time (x-axis, days post cell injection). Treatment with 59R1 antibodies inhibited tumor growth compared to control (* p<0.05 after day 57). (F) Anti-Notch2/3 (59R1) Inhibits the Growth of T3 Breast Tumors. NOD/SCID mice injected with T3 breast tumor cells were treated with control antibody (solid bars) or anti-Notch2/3 antibody 59R1 (open bars) after tumor volume reached a size between 65 to 200 mm$^3$. Mean tumor volume was measured on days 18, 25, 39, and 42 post cell injection. Treatment with 59R1 antibodies inhibited tumor growth compared to control (*** p<0.001 on day 42).

Figure 6:
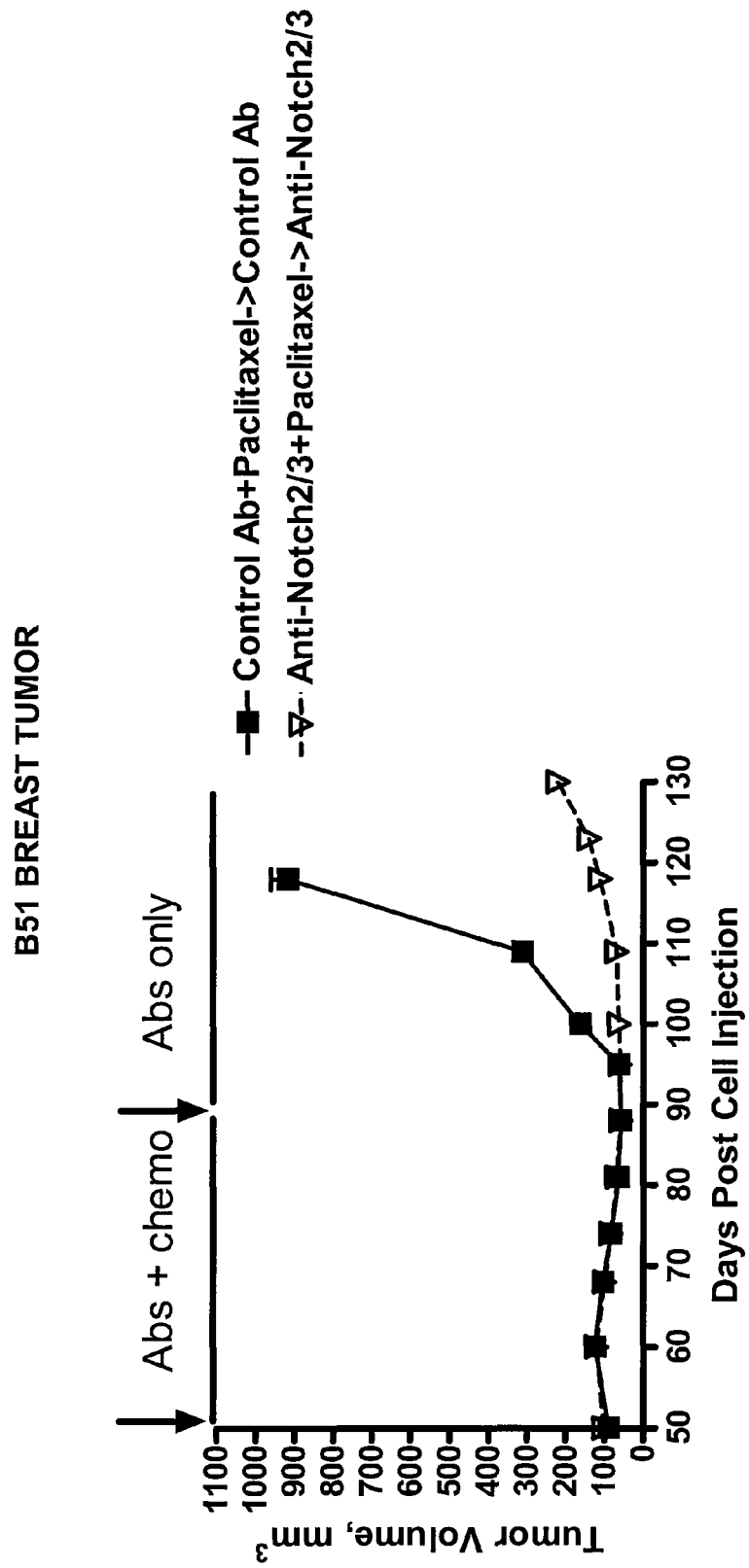

FIG. 6: Anti-Notch2/3 antibody 59R1 delays B51 breast tumor recurrence after paclitaxel treatment.

Figure 7:
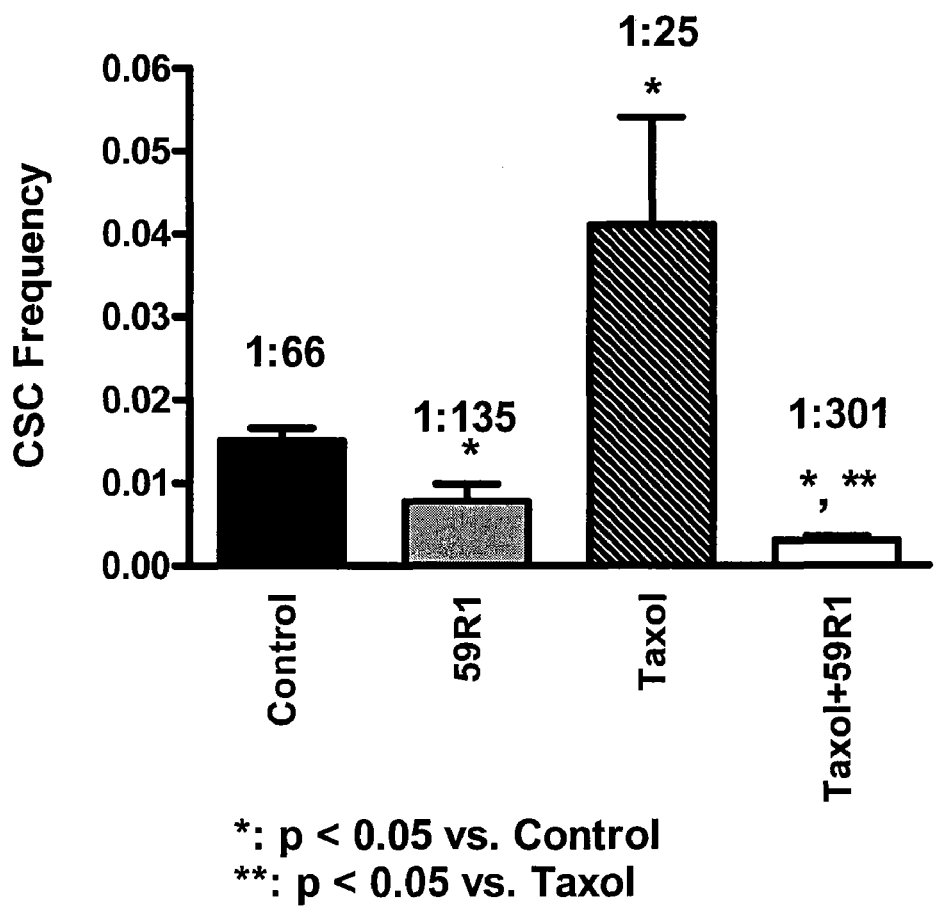

FIG. 7: Anti-Notch2/3 antibody 59R1 decreases cancer stem cell frequency in B51 breast tumor.

Figure 8:
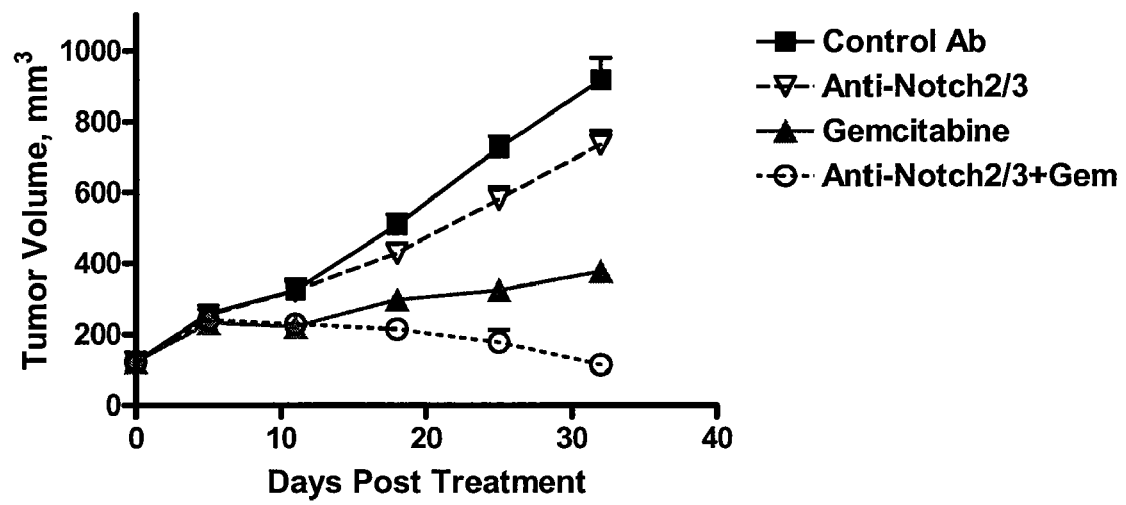

FIG. 8: In combination with gemcitabine, anti-Notch2/3 antibody 59R1 inhibits the growth of PN4 pancreatic tumors.

Figure 9:
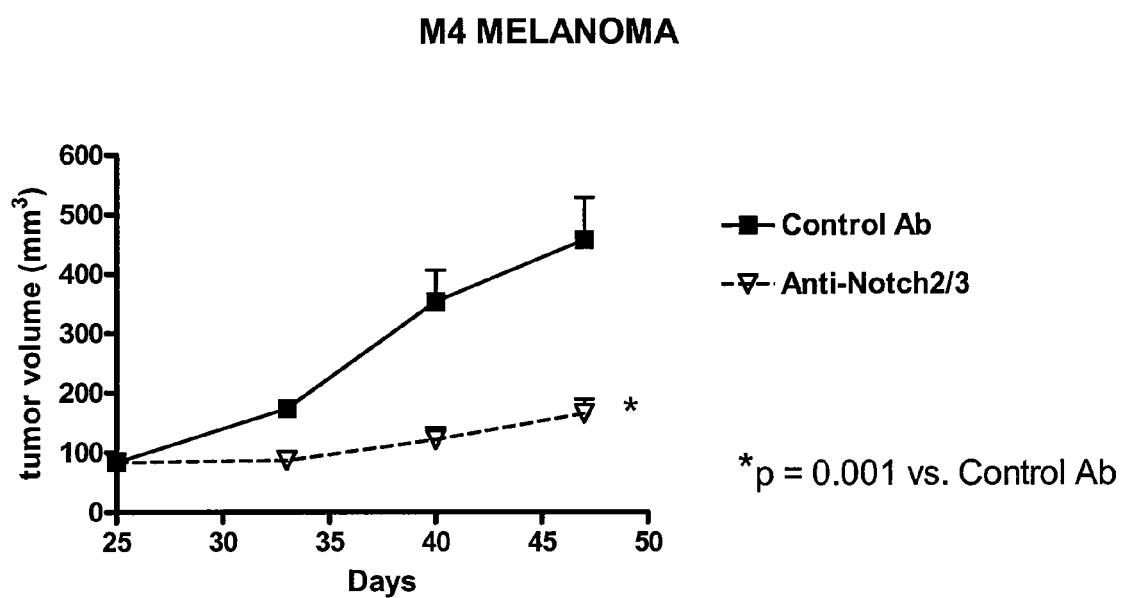

FIG. 9: Anti-Notch2/3 antibody 59R1 inhibits tumor growth in an M4 melanoma xenograft model.

Figure 10:
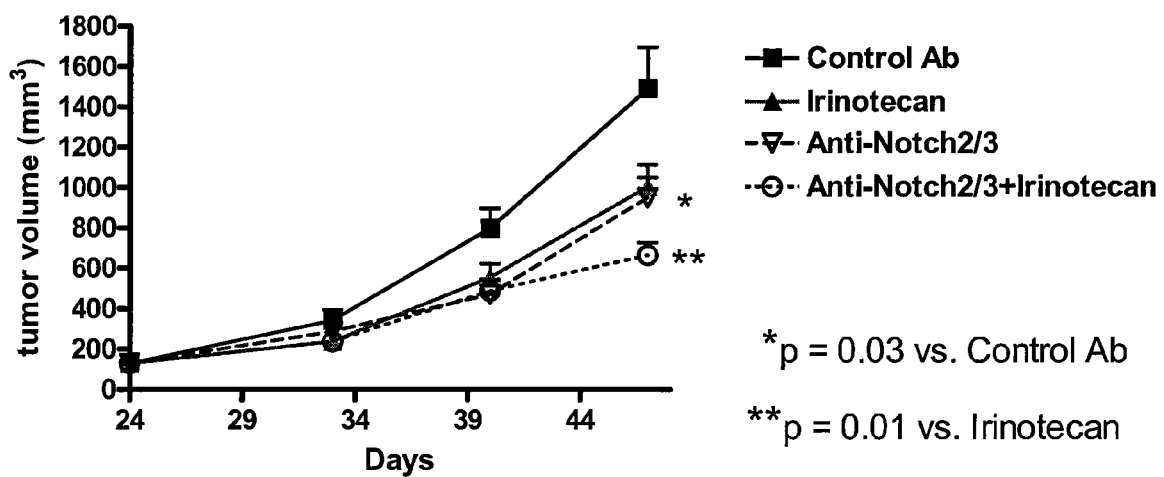

FIG. 10: Anti-Notch2/3 antibody 59R1 inhibits the growth of C28 colon tumors alone and in combination with irinotecan.

FIG. 11: 59R1 IgG2 antibody significantly inhibits tumor growth of established human tumor xenografts in vivo. Established Colo-205 (A), C8 (B), PN8 (C), B34 (D), B39 (E), B44 (F), PE-13 (G) and T1 (H) tumors (s.c, n=10 per group) were treated at 15 mg/kg once a week with the indicated antibodies (1B711, LZ-1 control antibody, black squares; 59R1, black triangles; AVASTIN, black circles; AVASTIN+59R1, black diamonds). Tumor volume (x-axis) is plotted over time (y-axis). In the Colo-205 xenograft model, combination therapy of 59R1 with AVASTIN was significantly more effective than either antibody treatment alone. In FIGS. 11B-11H, asterisks indicate significant tumor-growth inhibition at day shown: *, P<0.05; , P<0.01; *, P<0.001, Student's t-test; Symbols, mean; bars, SEM.

FIG. 12: Relative expression levels of selected genes are significantly regulated by 59R1 treatment in various xenograft tumor models. Expression levels of HEYL (A), Notch3 (B), RGS5 (C), ANGPT1 (D) and ANGPT2 (E) were individually tested by TaqMan® analysis from previously tested xenograft models. Notably, lack of estrogen (ne) abrogates effect of 59R1 in reducing ANGPT1 and ANGPT2 expression in host stroma of T1 harboring mice. Open circles correspond to individual tumors analyzed. Horizontal line, mean.

Figure 13:
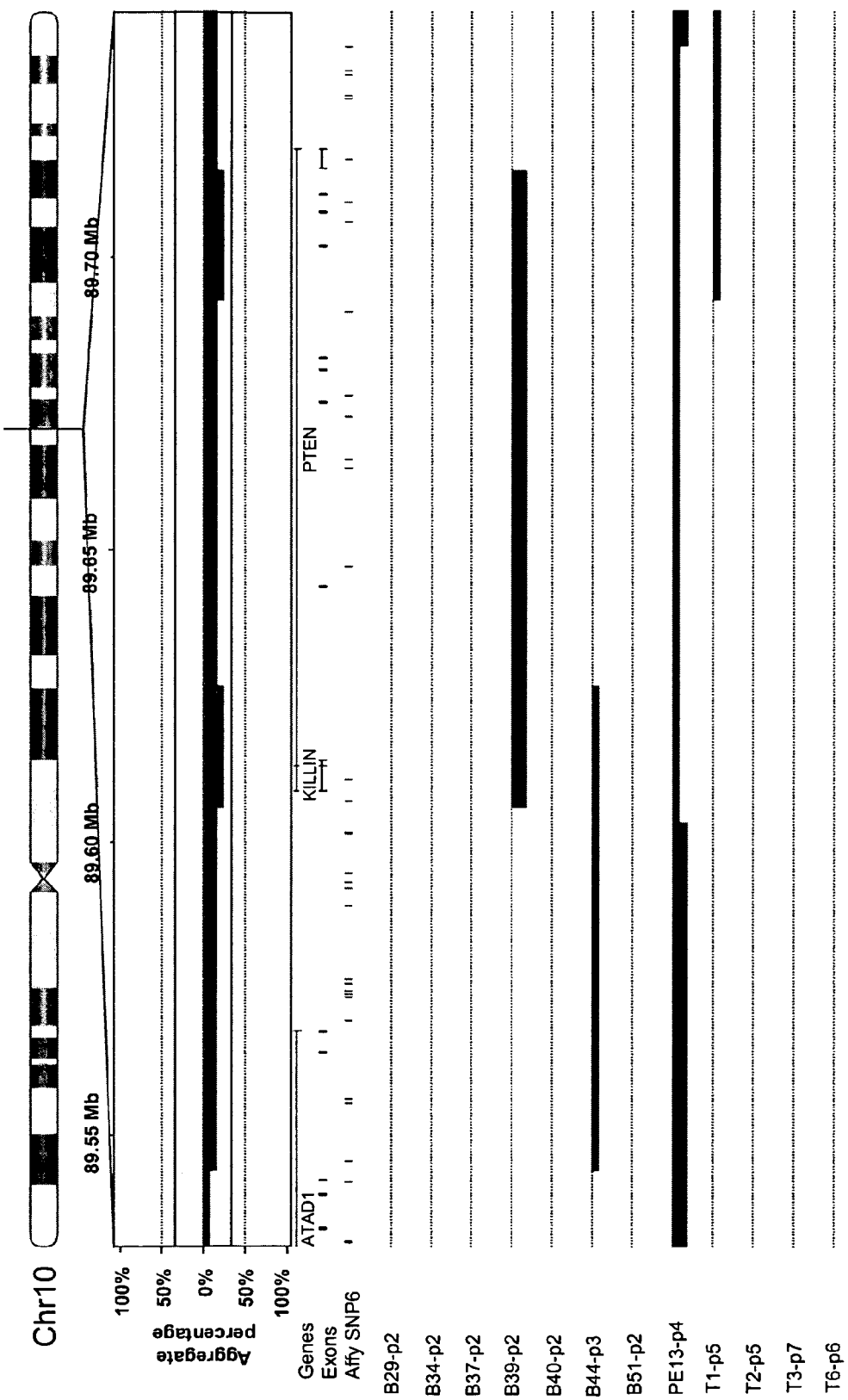

FIG. 13: The tumor suppressor PTEN gene is deleted in many of the breast tumors in which 59R1 showed anti-tumor efficacy. The PTEN exon, Affymetrix probe distribution, and the deletions in the PTEN gene in chromosome 10 are shown. The thick and thin gray-shaded bars indicate the homozygous and heterozygous deletions of the chromosome fragments, respectively.

Figure 14:
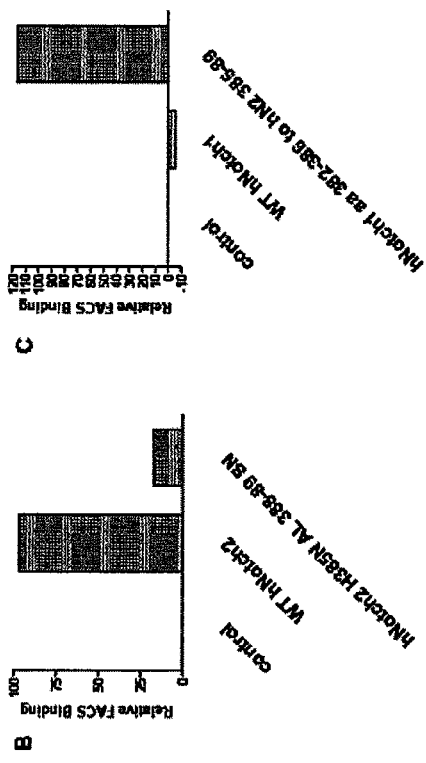

FIG. 14. Epitope mapping of 59R1 antibody. (A) Protein alignment of human Notch homologues. The alignment was performed by Clone Manager Software. The EGF 10 repeat of human Notch 1 (residues 356-418 of SEQ ID NO:45), Notch2 (residues 359-421 of SEQ ID NO: 31), and Notch4 (residues 376-439 of SEQ ID NO:46) and the equivalent EGF in human Notch3, EGF9 (residues 335-397 of SEQ ID NO: 32), is as indicated. The boxed area indicates a region containing one or more amino acid(s) that make up at least part of the 59R1 epitope as defined by FACS binding of 59R1 IgG2 antibody to an hNotch2 H385N AL 388-89 SN mutant (FIG. 14B) and to an hNotch1 construct in which aa 382-386 have been mutated to correspond to the hNotch2 sequence (FIG. 14C). (B) 59R1 IgG2 antibody binds to hNotch2, but not a mutant hNotch2 in which certain EGF 10 residues have been mutated to hNotch1 residues (H385N AL 388-89 SN). (C) 59R1 IgG2 antibody does not bind to hNotch1, but does bind to a mutant hNotch1 in which certain EGF 10 residues (aa 382-387) have been mutated to match the hNotch2 residues 385-389.

Figure 15A:
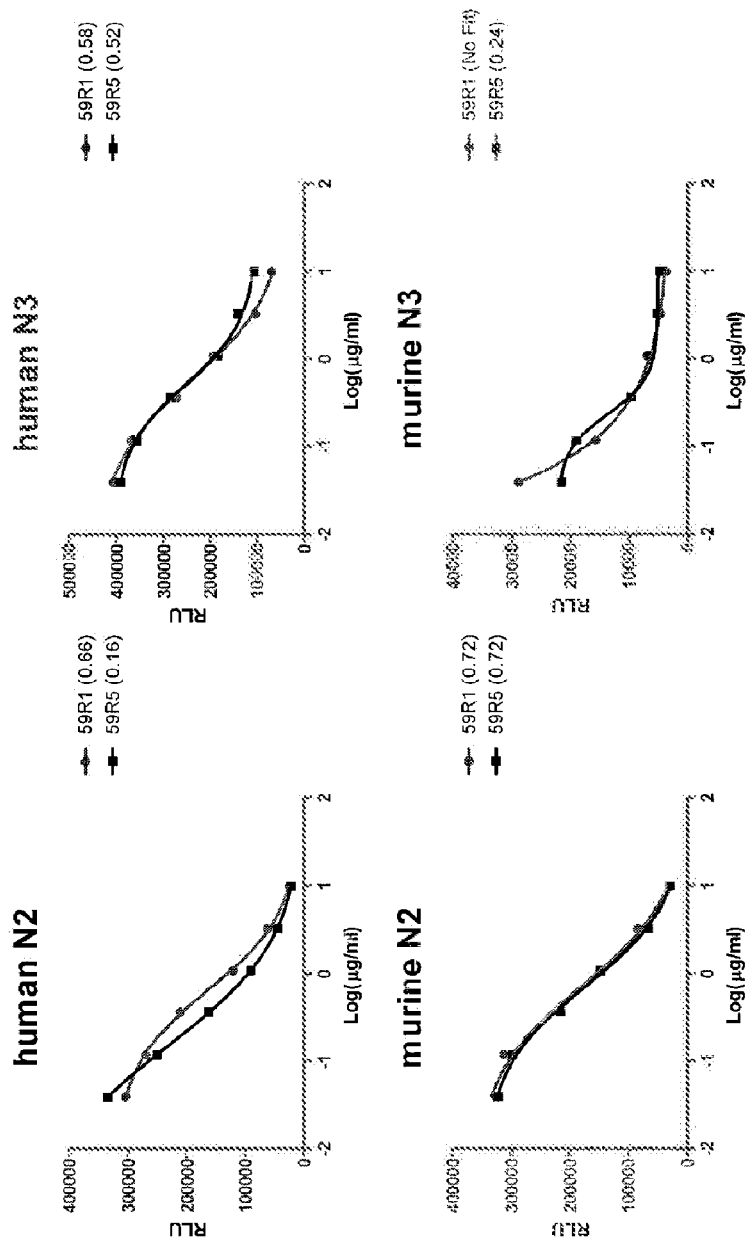
Figure 15B:
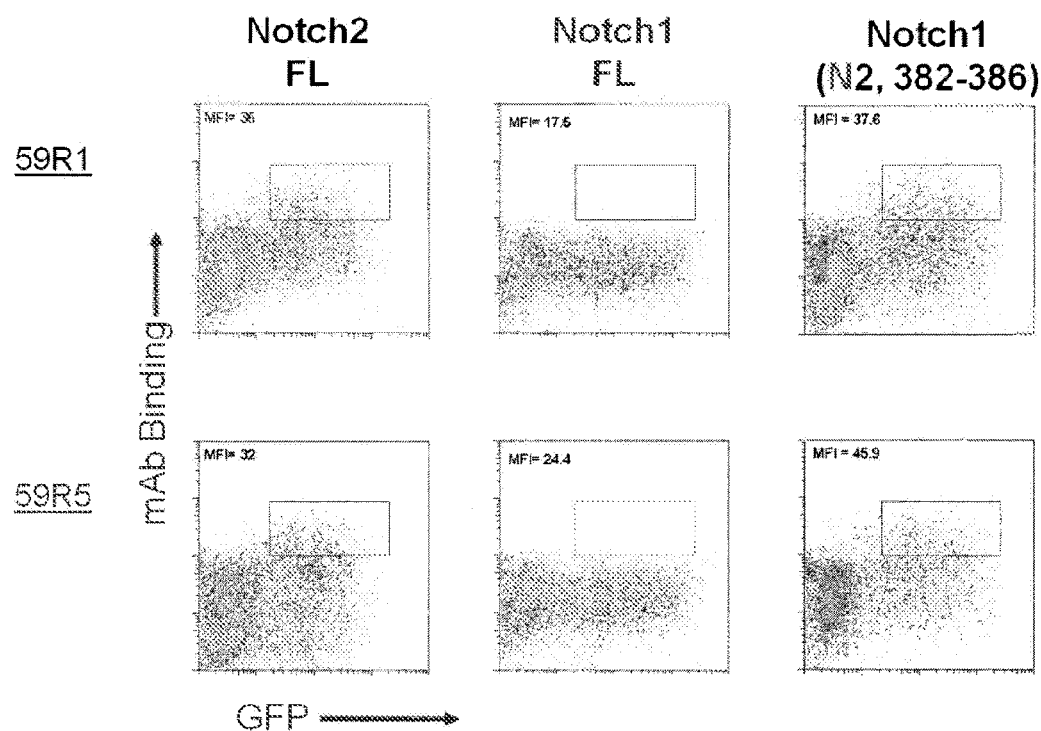

FIG. 15. In vitro characterization of 59R5. (A) FIG. 15A shows that antibody 59R5 is able to block ligand-induced signaling of Notch2 and Notch3. PC3 tumor cells were transiently transfected with human or mouse Notch receptor (hN2, human Notch2; mN2, murine Notch2; hN3, human Notch3; mN3, murine Notch3) and GFP inducible reporter construct. Transfected cells were incubated with different concentrations of antibody 59R1 and 59R5 in the presence of passively immobilized DLL4 Fc. (B) FIG. 15B shows that 59R5 binds to a similar epitope as 59R1. HEK 293 cells were transiently transfected with expression vectors encoding human Notch2, human Notch1, or human Notch1 with residues 382-386 mutated to the corresponding human Notch2 residues. Cells were also co-transfected with a plasmid encoding green fluorescent protein (GFP) to mark those cells that received transfected plasmid. Cells were incubated with 59R1 or 59R5 and fluorescent secondary antibody and then examined by FACS. The regions highlighted by the boxes suggest that cells transfected with the indicated Notch expression vector were able to bind to 59R1 or 59R5.

Figure 16A:
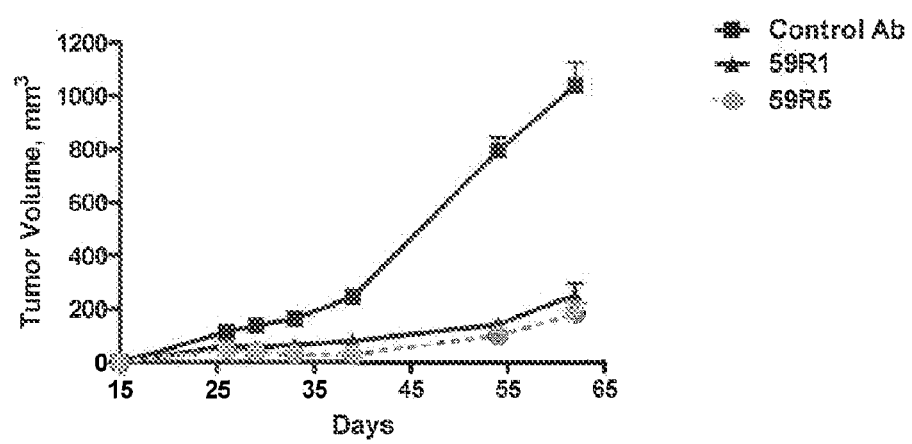
Figure 16B:
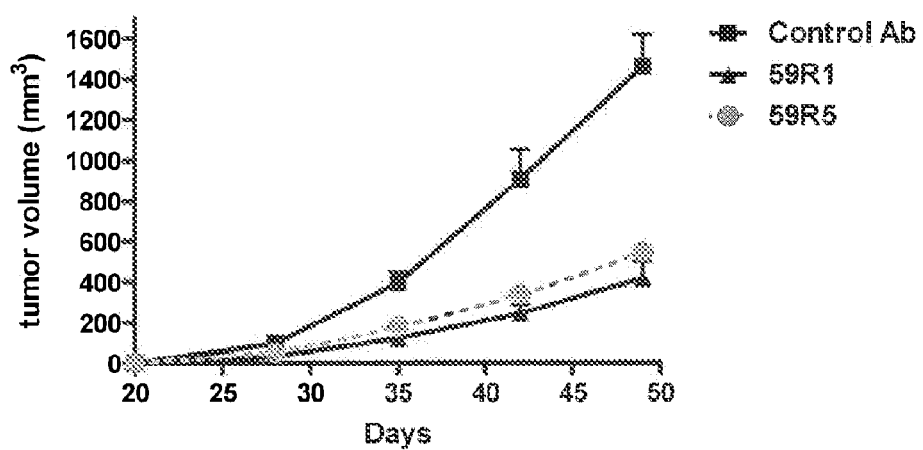
Figure 16C:
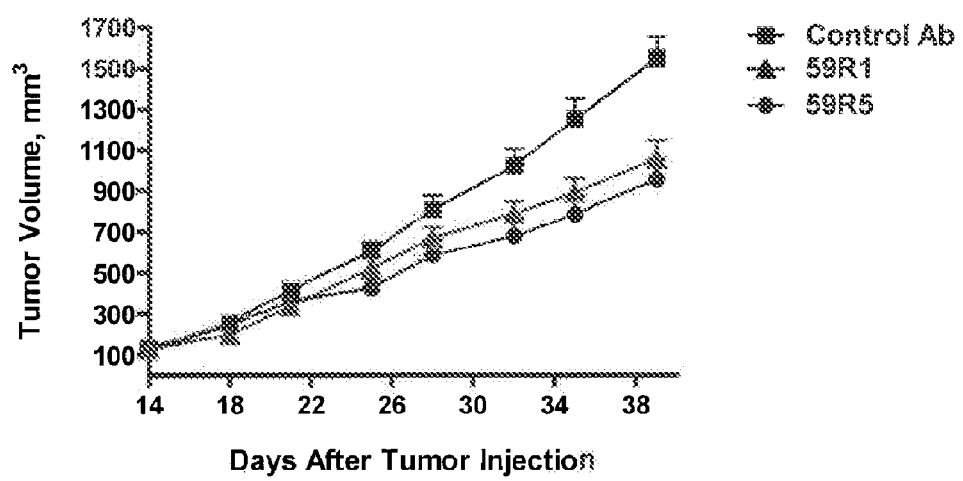

FIG. 16. Notch receptor antibody 59R5 inhibits tumor formation and growth in vivo. FIG. 16A shows in vivo treatment of PE13 breast tumor cells with antibody 59R5. FIG. 16B shows in vivo treatment of C28 colon cells with antibody 59R5. FIG. 16C shows in vivo treatment of Colo205 colon cells with antibody 59R5.

Figure 17:
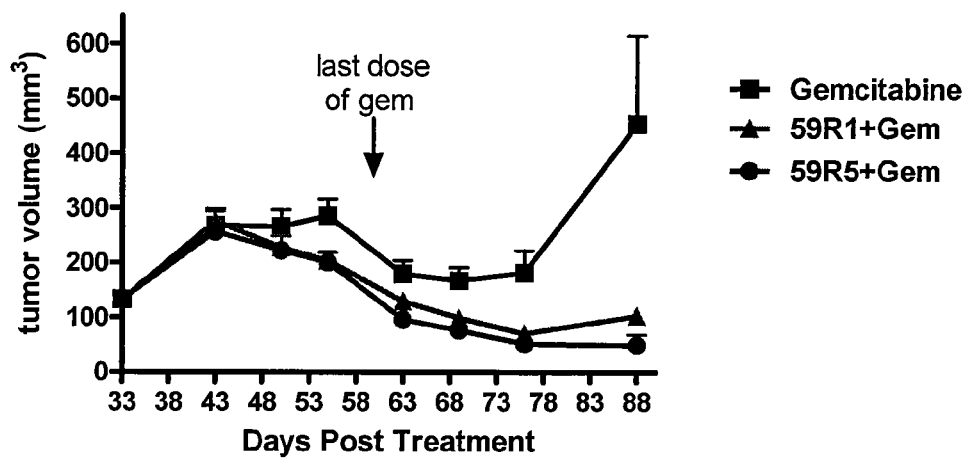
Figure 17:
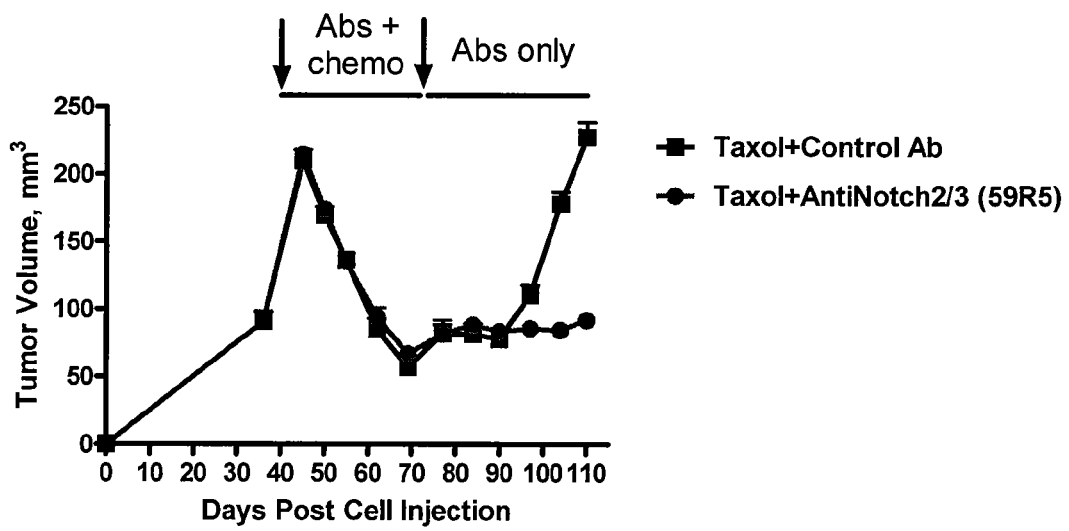

FIG. 17. In vivo treatment of tumors using Notch2/3 antibody 59R5 in combination treatment. (A) Mice were injected with PN8 pancreatic tumor cells. Tumors were allowed to grow for 33 days until they had reached an average volume of 120 mm3. The animals were treated with gemcitabine at 20 mg/kg once per week for four week in combination with either control Ab (squares), 59R1 (triangles), or 59R5 (circles). (B) Mice were injected with PE13 breast tumor cells. Tumors were allowed to grow for 40 days before treatments were initiated. The animals were treated with TAXOL at 15 mg/kg twice per week for 5 weeks, plus either control antibody (squares) or 59R5 (circles). After 5 weeks, the TAXOL treatments were stopped and the antibody treatments continued.

Figure 18:
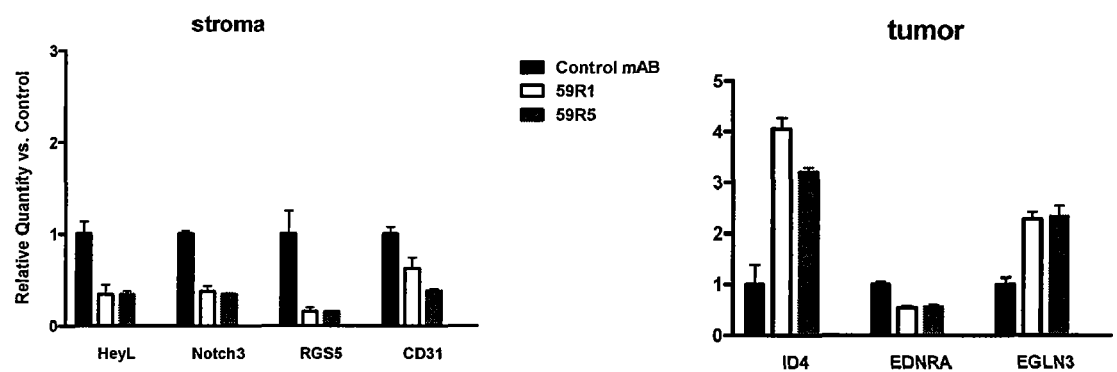

FIG. 18. Regulation of gene expression in tumors after treatment with antibody 59R5. FIG. 18 shows expression levels of selected genes in stromal cells and selected human genes in PE13 tumor cells after treatment with 59R1, 59R5, or control antibody.

FIG. 19. Reduction of PE13 breast cancer stem cell frequency by 59R1. (A) Established tumors were treated with control antibody, taxol plus control antibody, 59R1, or taxol plus 59R1. Tumors were harvested after three weeks of treatment, processed and serial titrations of human cells from each the four treatment groups were transplanted into a new set of mice (n=10 per cell dose). Tumor growth rate was determined after 75 days. Tumor growth rate after 75 days of growth was used to calculate the CSC frequency using the L-calc program (Stem Cell Technologies, Inc.). (B) Cancer stem cell frequency in PE13 breast tumors after treatment with 59R1 and/or taxol. (C) Cancer stem cell frequency in PN4 pancreatic tumors after treatment with 59R1 and/or gemcitabine. (D) Cancer stem cell frequency in PE13 breast tumors after treatment with 59R5 and/or taxol. A single asterisk indicates a statistically significant difference (p<0.05) vs. the control antibody treated group and a double asterisk indicates a significant difference vs. the taxol and control antibody treated group.

DETAILED DESCRIPTION OF THE INVENTION

The present invention provides novel agents, including, but not limited to polypeptides such as antibodies, that bind to one or more human Notch receptors, such as Notch2 and/or Notch3. The Notch-binding agents include antagonists of the human Notch receptor(s). Related polypeptides and polynucleotides, compositions comprising the Notch-binding agents, and methods of making the Notch-binding agents are also provided. Methods of using the novel Notch-binding agents, such as methods of inhibiting tumor growth, inhibiting angiogenesis, and/or treating cancer or other angiogenesis-related disease, are further provided.

The present invention further identifies molecules (e.g., antibodies) that specifically bind to a non-ligand binding region of the extracellular domain of a human Notch receptor and inhibit tumor growth in vivo. The ligand binding region of Notch, which is necessary and sufficient for ligand binding, has been identified as EGF repeats 11 and 12, suggesting this region of the Notch receptor is important in Notch signaling and tumorigenesis (Rebay et al., 1991, *Cell* 67:687; Lei et al., 2003, *Dev.* 130:6411; Hambleton et al., 2004, *Structure* 12:2173). Unexpectedly, antibodies that bind outside the ligand binding domain of the extracellular domain of human Notch receptor have been found to inhibit tumor cell growth in vivo (see U.S. Patent Publication No. 2008/0131434, incorporated by reference herein in its entirety). Thus, antibodies that bind outside the ligand binding domain of the extracellular domain of one or more of the human Notch receptors—Notch1, Notch2, Notch3, and Notch4—have value as potential cancer therapeutics.

Figure 3A:
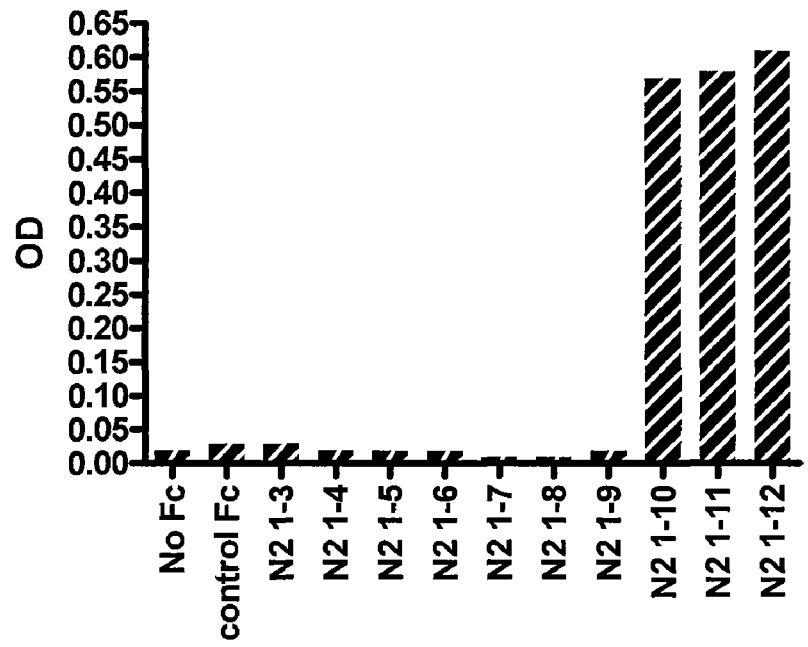
Figure 3A:
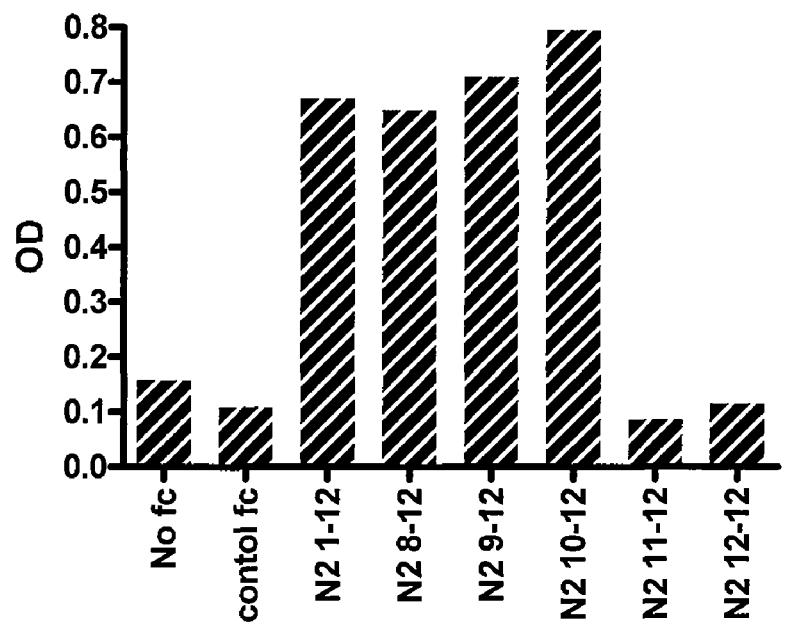
Figure 3B:
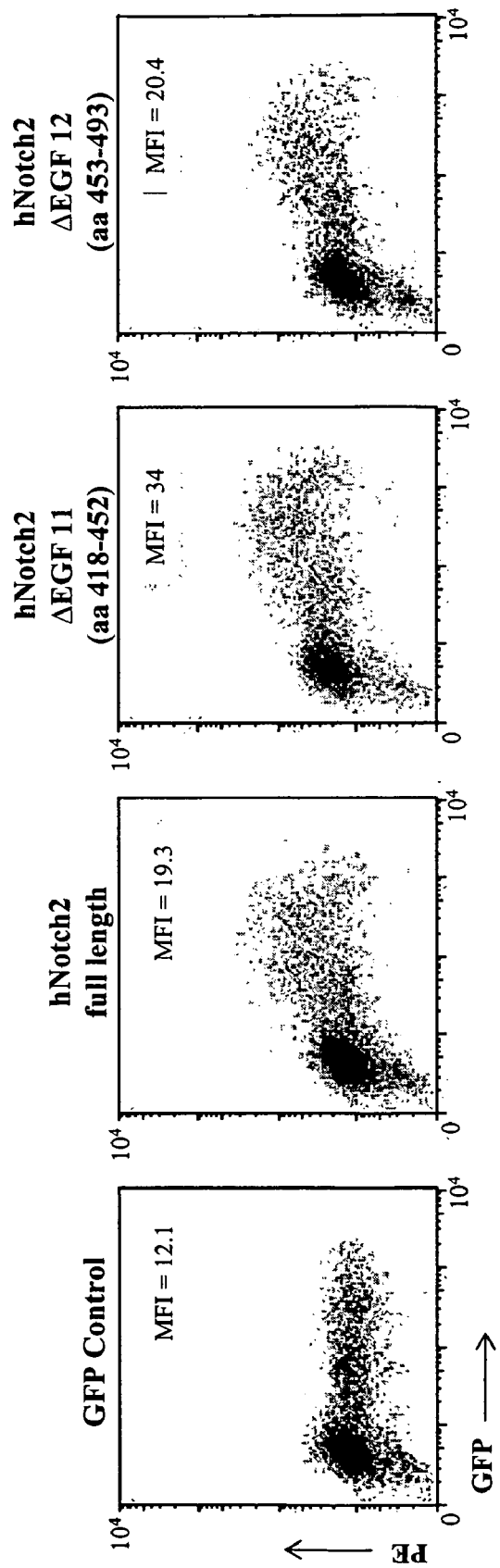
Figure 3C:
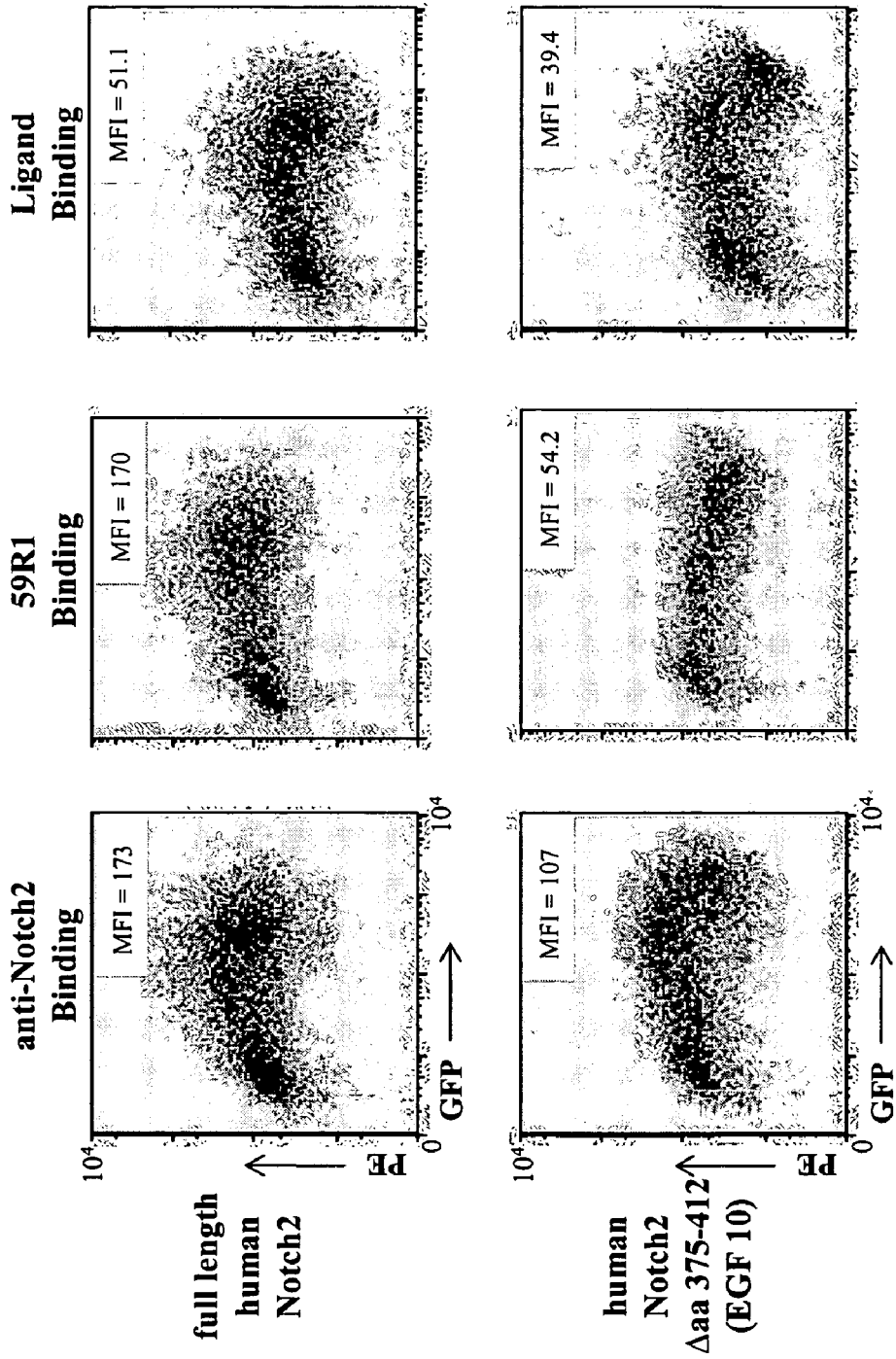

An antibody that specifically binds to an epitope containing residues within EGF repeat 10 of human Notch2 has now been identified (Examples 1 and 3 and FIGS. 3A-3C). The antibody, 59R1, inhibits binding of ligand to Notch2 (Example 1 and FIGS. 1A-1D) and inhibits ligand-induced Notch2 signaling (Example 4 and FIG. 4A-4C), despite binding to Notch2 in a region outside of the ligand-binding region. 59R1 also specifically binds human Notch3 (Example 2 and FIG. 2). The antibody has been found to prevent or inhibit tumor cell growth in vivo in a variety of different xenograft models, either alone or in combination with a second anticancer agent (Examples 5, 6, 7, and 9 and FIGS. 5A-F, 6, 8-10, and 11A-H). The antibody has also been shown to reduce the tumorigenicity of a tumor in vivo in multiple xenograft models by reducing the frequency of cancer stem cells (Examples 8 and 23 and FIGS. 7 and 19A-C). In addition, treatment with 59R1 was found to downregulate expression of RGS5 (a marker for pericytes and/or vascular smooth muscle cells), Notch3, and HeyL in the stroma of various tumors (Example 10 and FIGS. 12A-E) and to upregulate hypoxia in breast and colon tumors (Example 11). Without being bound by theory, these data indicate that the 59R1 antibody has an inhibitory effect on tumor angiogenesis that is due, at least in part, to modulation of the function of pericytes and/or vascular smooth muscle cells. Treatment with 59R1 was also found to regulate additional genes in breast tumors. Cell cycle gene pathways, myc-activating genes and several stem cell gene sets were found to be down-regulated by 59R1 (Example 22).

An additional human antibody, 59R5, has also been developed. 59R5 has properties that are similar to 59R1, such as similar binding affinity to Notch2 and Notch3 and similarities or overlap in their epitopes (Example 13 and FIG. 15B). Antibody 59R5 has been shown to have similar activity as 59R1 in blocking Notch2 and Notch 3 signaling (Example 13 and FIG. 15A). The 59R5 antibody has also been shown to inhibit tumor growth in vivo in several xenograft models, either alone or in combination with a second anti-cancer agent (Examples 14 and 15 and FIGS. 16A-C and 17A-B). In addition, treatment with 59R5, like 59R1, was found to down-regulate expression of RGS5, Notch3, and HeyL in the stroma of various tumors, and 59R5 was also found to regulate the expression of human genes ID4, EDNRA, and EGLN3 in tumor cells to a similar extent as 59R1 (Example 16). 59R5 was further shown to reduce the tumorigenicity in vivo in a xenograft model by reducing the frequency of cancer stem cells (Example 23 and 19D).

DEFINITIONS

An "antagonist" of a Notch receptor is a term that includes any molecule that partially or fully blocks, inhibits, or neutralizes a biological activity of the Notch pathway. Suitable antagonist molecules specifically include antagonist antibodies or antibody fragments.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to Fab, Fab', F(ab')$_2$, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including, but not limited to, by hybridoma, phage selection, recombinant expression, and transgenic animals.

As used herein, the term "humanized antibody" refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues from the complementary determining region (CDR) are replaced by residues from the CDR of a non-human species (e.g. mouse, rat, rabbit, hamster, etc.) that have the desired specificity, affinity, and capability. In some instances, the Fv framework region (FR) residues of a human immunoglobulin are replaced with the corresponding residues in an antibody from a non-human species that has the desired specificity, affinity, and capability. The humanized antibody can be further modified by the substitution of additional residue either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539, herein incorporated by reference.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al 1997, *J. Molec. Biol.* 273:927-948)). In addition, combinations of these two approaches are sometimes used in the art to determine CDRs.

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc.) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Competition between antibodies is determined by an assay in which the immunoglobulin under study inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., 1983, *Methods in Enzymology* 9:242-253); solid phase direct biotin-avidin EIA (see Kirkland et al., *J. Immunol.* 1986, 137:3614-3619); solid phase direct labeled assay, solid phase direct labeled sandwich assay (see Harlow and Lane, 1988, *Antibodies, A Laboratory Manual*, Cold Spring Harbor Press); solid phase direct label RIA using 1-125 label (see Morel et al., 1988, *Molec. Immunol.* 25(1):7-15); solid phase direct biotin-avidin EIA (Cheung et al., 1990, *Virology* 176: 546-552); and direct labeled RIA (Moldenhauer et al., 1990, *Scand. J. Immunol.* 32:77-82). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

That an antibody "selectively binds" or "specifically binds" to an epitope or receptor means that the antibody reacts or associates more frequently, more rapidly, with greater duration, with greater affinity, or with some combination of the above to the epitope or receptor than with alternative substances, including unrelated proteins. "Selectively binds" or "specifically binds" means, for instance, that an antibody binds to a protein with a $K_D$ of about 0.1 mM or less, more usually about 1 µM or less. "Selectively binds" or "specifically binds" means at times that an antibody binds to a protein with a $K_D$ of about 0.1 mM or less, at times about 1 µM or less, at times about 0.1 µM or less, at times about 0.01 µM or less, and at times about 1 nM or less. Because of the sequence identity between homologous proteins in different species, specific binding can include an antibody that recognizes a Notch receptor in more than one species. Likewise, because of homology between different Notch receptors (e.g., Notch2 and Notch3) in certain regions of the polypeptide sequences of the receptors, specific binding can include an antibody that recognizes more than one Notch receptor. It is understood that, in certain embodiments, an antibody or binding moiety that specifically binds to a first target may or may not specifically bind to a second target. As such, "specific binding" does not necessarily require (although it can include) exclusive binding, i.e. binding to a single target. Thus, an antibody may, in certain embodiments, specifically bind to more than one target (e.g., human Notch2 and Notch3). In certain embodiments, the multiple targets may be bound by the same antigen-binding site on the antibody. For example, an antibody may, in certain instances, comprise two identical antigen-binding sites, each of which specifically binds two or more human Notch receptors (e.g., human Notch2 and Notch3). In certain alternative embodiments, an antibody may be bispecific and comprise at least two antigen-binding sites with differing specificities. By way of non-limiting example, a bispecific antibody may comprise one antigen-binding site that recognizes an epitope on one Notch receptor, such as human Notch2, and further comprises a second, different antigen-binding site that recognizes a different epitope on a second Notch receptor, such as human Notch3. Generally, but not necessarily, reference to "binding" herein means "specific binding."

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

The terms "isolated" or "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g. an antibody) or nucleic acid that is the predominant species present in a preparation is substantially purified. In particular, an isolated nucleic acid is separated from open reading frames that naturally flank the gene and encode proteins other than protein encoded by the gene. An isolated antibody is separated from other non-immunoglobulin proteins and from other immunoglobulin proteins with different antigen binding specificity. It can also mean that the nucleic acid or protein is at least 85% pure, at least 95% pure, and in some embodiments, at least 99% pure.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The terms "cancer stem cell" or "tumor stem cell" or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells" or "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur.

The terms "cancer cell" or "tumor cell" and grammatical equivalents refer to the total population of cells derived from a tumor including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the "tumorigenicity" of a tumor refers to the ability of a random sample of cells from the tumor to form palpable tumors upon serial transplantation into immuno-compromised mice.

As used herein, the terms "stem cell cancer marker" or "cancer stem cell marker" or "tumor stem cell marker" or "solid tumor stem cell marker" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g., increased or decreased levels of mRNA or the peptide encoded by the gene).

The terms "cancer stem cell gene signature" or "tumor stem cell gene signature" or "cancer stem cell signature" are used interchangeably herein to refer to gene signatures comprising genes differentially expressed in cancer stem cells compared to other cells or population of cells, for example normal breast epithelial tissue. In some embodiments the cancer stem cell gene signatures comprise genes differentially expressed in cancer stem cells versus normal breast epithelium by a fold change, for example by 2 fold reduced and/or elevated expression, and further limited by using a statistical analysis such as, for example, by the P value of a t-test across multiple samples. In another embodiment, the genes differentially expressed in cancer stem cells are divided into cancer stem cell gene signatures based on the correlation of their expression with a chosen gene in combination with their fold or percentage expression change. Cancer stem cell signatures are predictive both retrospectively and prospectively of an aspect of clinical variability, including but not limited to metastasis and death.

The term "genetic test" as used herein refers to procedures whereby the genetic make-up of a patient or a patient tumor sample is analyzed. The analysis can include detection of DNA, RNA, chromosomes, proteins or metabolites to detect heritable or somatic disease-related genotypes or karyotypes for clinical purposes.

As used herein, the terms "biopsy" or "biopsy tissue" refer to a sample of tissue or fluid that is removed from a subject for the purpose of determining if the sample contains cancerous tissue. In some embodiments, biopsy tissue or fluid is obtained because a subject is suspected of having cancer. The biopsy tissue or fluid is then examined for the presence or absence of cancer.

As used herein an "acceptable pharmaceutical carrier" refers to any material that, when combined with an active ingredient of a pharmaceutical composition such as an antibody, allows the antibody, for example, to retain its biological activity. In addition, an "acceptable pharmaceutical carrier" does not trigger an immune response in a recipient subject. Examples include, but are not limited to, any of the standard pharmaceutical carriers such as a phosphate buffered saline solution, water, and various oil/water emulsions. Some diluents for aerosol or parenteral administration are phosphate buffered saline or normal (0.9%) saline.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs; inhibit and stop tumor metastasis; inhibit and stop tumor growth; relieve to some extent one or more of the symptoms associated with the cancer, or a combination of such effects on cancer cells. To the extent the drug prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. In some embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life. Thus, in certain embodiments, treatment of cancer comprises inhibition of tumor growth in a subject.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA including, but not limited to, 4-acetyl cytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl 2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl 2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2 thiouracil, 2-thiouracil, 4-thiouracil, 5-methyluracil, N-uracil-5-oxyacetic acid methylester, uracil-5-oxyacetic acid, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length polypeptide or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage, and polyadenylation.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors", respectively.

The terms "polypeptide" or "peptide" or "protein" or "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. It is recognized that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, it will be recognized that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Such conservatively modified variants are in addition to and do not exclude polymorphic variants, interspecies homologs, and alleles of the invention. Tables providing functionally similar amino acids useful for conservative amino acid substitutions are well known in the art. Typical conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). (See, also, Table 1 herein).

As used in the present disclosure and claims, the singular forms "a", "an" and "the" include plural forms unless the context clearly dictates otherwise.

It is understood that wherever embodiments are described herein with the language "comprising," otherwise analogous embodiments described in terms of "consisting of" and/or "consisting essentially of" are also provided.

Certain Embodiments of the Present Invention

The present invention provides compositions and methods for studying, diagnosing, characterizing, and treating cancer. In particular, in certain embodiments, the present invention provides agents, including antagonists, that bind Notch receptors and methods of using the agents or antagonists to inhibit tumor growth and treat cancer or other disease in human patients. In certain embodiments, the antagonists are antibodies that specifically recognize one or more human Notch receptors.

In one aspect, the present invention provides an antibody that specifically binds to a non-ligand binding region of the extracellular domain of a human Notch receptor. In some embodiments, the antibody that specifically binds to a non-ligand binding region of the extracellular domain of a human Notch receptor inhibits growth of tumors. In certain embodiments, the antibody that specifically binds to a non-ligand binding region of the extracellular domain of a human Notch receptor and inhibits tumor growth, specifically binds to a non-ligand binding region of the extracellular domain of at least two Notch receptor family members. In certain embodiments, the antibody binds to a non-ligand binding region of the extracellular domain of Notch2 and/or Notch3 receptor. In some embodiments, the antibody binds to a non-ligand binding region of the human Notch2. In some embodiments, the antibody binds to a non-ligand binding region of the extracellular domain of Notch2 and Notch3. In some embodiments, the antibody binds to a non-ligand binding region of the human Notch3. In some embodiments, the antibody binds to Notch1 and/or Notch4.

In certain embodiments, the antibody that specifically binds to a non-ligand binding region of the extracellular domain of a human Notch receptor and inhibits tumor growth is a monoclonal antibody. In certain embodiments, the antibody that specifically binds to a non-ligand binding region of the extracellular domain of a human Notch receptor and inhibits growth of tumors is a chimeric antibody. In certain embodiments, the antibody that specifically binds to a non-ligand binding region of the extracellular domain of a human Notch receptor and inhibits growth of tumors is a humanized antibody. In certain embodiments, the antibody that specifically binds to a non-ligand binding region of the extracellular domain of a human Notch receptor and inhibits tumor growth is a human antibody. In certain embodiments, the antibody that specifically binds to a non-ligand binding region of the extracellular domain of a human Notch receptor and inhibits tumor growth is a monospecific antibody. In certain embodiments, the antibody that specifically binds to a non-ligand binding region of the extracellular domain of a human Notch receptor and inhibits tumor growth is a bispecific antibody. In certain embodiments, the present invention provides a hybridoma producing an antibody that specifically binds to a non-ligand binding region of the extracellular domain of a human Notch receptor and inhibits tumor growth.

In certain embodiments the present invention provides an antibody that specifically binds to a non-ligand binding region comprising EGF repeats 1-10 of the extracellular domain of a human Notch receptor and inhibits tumor growth. In certain embodiments the present invention provides an antibody that specifically binds to a non-ligand binding region comprising EGF repeat 10 (or equivalent) of the extracellular domain of a human Notch receptor and inhibits tumor growth. In certain embodiments the present invention provides an antibody that specifically binds to a non-ligand binding region comprising EGF repeats 13-36 of the extracellular domain of a human Notch receptor and inhibits tumor growth. Certain embodiments provide an antibody that specifically binds to a non-ligand binding region comprising EGF repeats 4 of the extracellular domain of a human Notch receptor and inhibits tumor growth. Certain embodiments provide an antibody that specifically binds to a non-ligand binding region comprising EGF repeat 13 of the extracellular domain of a human Notch receptor and inhibits tumor growth. In certain embodiments, the antibody specifically binds to a non-ligand binding region comprising the LNR-HD domain and inhibits tumor growth.

In certain embodiments the present invention provides a method of treating cancer in a subject in need thereof comprising administering to the subject a therapeutically effective amount of an antibody that specifically binds to a non-ligand binding region of the extracellular domain of a human Notch receptor protein and inhibits tumor growth in the subject. In certain embodiments, the method of treating cancer comprises administering a therapeutically effective amount of an antibody that specifically binds to at least two Notch receptor family members and inhibits tumor growth. In certain embodiments, the method of treating cancer in a subject in need thereof comprises administering to the subject a therapeutically effective amount of an antibody that specifically binds to a non-ligand binding region of the extracellular domain of Notch2 and/or Notch3 receptor and inhibits tumor growth.

In certain embodiments, the method of treating cancer comprises administering a therapeutically effective amount of a monoclonal antibody that specifically binds to a non-ligand binding region of the extracellular domain of a human Notch receptor and inhibits tumor growth. In certain embodiments, the method of treating cancer comprises administering a therapeutically effective amount of a chimeric antibody that specifically binds to a non-ligand binding region of the extracellular domain of a human Notch receptor and inhibits tumor growth. In certain embodiments, the method of treating cancer comprises administering a therapeutically effective amount of a humanized antibody that specifically binds to a non-ligand binding region of the extracellular domain of a human Notch receptor and inhibits tumor growth. In certain embodiments, the method of treating cancer comprises administering a therapeutically effective amount of a human antibody that specifically binds to a non-ligand binding region of the extracellular domain of a human Notch receptor and inhibits tumor growth. In some embodiments, the antibody is a monospecific antibody. In some embodiments, the antibody is a bispecific antibody.

In certain embodiments, the method of treating cancer comprises administering a therapeutically effective amount of an antibody that specifically binds to a non-ligand binding region of the extracellular domain of a human Notch receptor comprising EGF repeats 1-10 and inhibits tumor growth. In certain embodiments, the method of treating cancer comprises administering a therapeutically effective amount of an antibody that specifically binds to a non-ligand binding region of the extracellular domain of a human Notch receptor comprising EGF repeat 10 (or the equivalent if Notch3) and inhibits tumor growth. In certain embodiments, the method of treating cancer comprises administering a therapeutically effective amount of an antibody that specifically binds to a non-ligand binding region of the extracellular domain of a human Notch receptor comprising EGF repeats 13-36 and inhibits tumor growth. In certain embodiments, the method of treating cancer comprises administering a therapeutically effective amount of an antibody that specifically binds to a non-ligand binding region of the extracellular domain of a human Notch receptor comprising EGF repeat 4 and inhibits tumor growth. In certain embodiments, the method of treating cancer comprises administering a therapeutically effective amount of an antibody that specifically binds to a non-ligand binding region of the extracellular domain of a human Notch receptor comprising EGF repeat 4 and inhibits tumor growth. In certain other embodiments, the antibody that is administered specifically binds to the LNR-HD domain of a human Notch receptor.

In certain embodiments, the method of treating cancer comprises administering a therapeutically effective amount of an antibody conjugated to a cytotoxic moiety that specifically binds to a non-ligand binding region of the extracellular domain of a human Notch receptor and inhibits tumor growth. In certain embodiments, the method of treating cancer comprises administering a therapeutically effective amount of an antibody that specifically binds to a non-ligand binding region of the extracellular domain of a human Notch receptor and inhibits tumor growth in combination with radiation therapy. In certain embodiments, the method of treating cancer comprises administering a therapeutically effective amount of an antibody that specifically binds to a non-ligand binding region of the extracellular domain of a human Notch receptor and inhibits tumor growth in combination with chemotherapy. In certain embodiments, the method of treating cancer comprises administering a therapeutically effective amount of an antibody that specifically binds to a non-ligand binding region of the extracellular domain of a human Notch receptor and inhibits tumor growth that are from a breast tumor, colorectal tumor, lung tumor, pancreatic tumor, prostate tumor, or a head and neck tumor.

In certain embodiments, the method of treating cancer comprises identifying patients for treatment with the antibody that specifically binds to a non-ligand binding region of the extracellular domain of a human Notch receptor using a genetic test; and administering a therapeutically effective amount of an antibody that specifically binds to a non-ligand binding region of the extracellular domain of a human Notch receptor and inhibits tumor growth. In certain embodiments, the method of treating cancer comprises identifying patients for treatment with the antibody that specifically binds to a non-ligand binding region of the extracellular domain of a human Notch receptor using a genetic test that detects a cancer stem cell signature; and administering a therapeutically effective amount of an antibody that specifically binds to a non-ligand binding region of the extracellular domain of a human Notch receptor and inhibits tumor growth.

In certain embodiments, the present invention provides a method of identifying a molecule that binds to a non-ligand binding region of an extracellular domain of a human Notch receptor and inhibits tumor growth, the method comprising: i) incubating the molecule with the non-ligand binding domain of the extracellular domain of a human Notch receptor; ii) determining if the molecule binds to the non-ligand binding region of the extracellular domain of the human Notch receptor; and iii) determining if the molecule inhibits tumor growth. In certain embodiments, the invention provides a method of identifying a molecule that binds to a non-ligand binding region of an extracellular domain of a human Notch receptor and inhibits tumor growth, the method comprising: i) incubating the molecule with the non-ligand binding domain of the extracellular domain of a human Notch receptor comprising EGF repeats 1-10; ii) determining if the molecule binds to the non-ligand binding region of the extracellular domain of the human Notch receptor comprising EGF repeats 1-10; and iii) determining if the molecule inhibits tumor growth. In certain embodiments, the invention provides a method of identifying a molecule that binds to a non-ligand binding region of an extracellular domain of a human Notch receptor and inhibits tumor growth, the method comprising: i) incubating the molecule with the non-ligand binding domain of the extracellular domain of a human Notch receptor comprising EGF repeat 10 (or equivalent if Notch3); ii) determining if the molecule binds to the non-ligand binding region of the extracellular domain of the human Notch receptor comprising EGF repeat 10 (or equivalent if Notch3); and iii) determining if the molecule inhibits tumor growth. In certain embodiments, the invention provides a method of identifying a molecule that binds to a non-ligand binding region of an extracellular domain of a human Notch receptor and inhibits tumor growth, the method comprising: i) incubating the molecule with the non-ligand binding domain of the extracellular domain of a human Notch receptor comprising EGF repeats 13-36; ii) determining if the molecule binds to the non-ligand binding region of the extracellular domain of the human Notch receptor comprising EGF repeats 13-36; and iii) determining if the molecule inhibits tumor growth.

In certain embodiments, the present invention provides a pharmaceutical composition comprising an antibody that specifically binds to a non-ligand binding region of the extracellular domain of a human Notch receptor and inhibits tumor growth.

In certain embodiments, the present invention provides a method of making an antibody that specifically binds to a non-ligand binding region of the extracellular domain of a human Notch receptor and inhibits tumor growth.

In certain embodiments, the present invention provides an isolated nucleic acid that encodes an antibody that specifically binds to a non-ligand binding region of the extracellular domain of a human Notch receptor and inhibits tumor growth.

In some embodiments, the invention provides an agent (e.g., an antibody) that specifically binds to an EGF10 domain (or an equivalent of an EGF10 domain if Notch3) of one or more human Notch receptors. In certain embodiments, the agent is an antibody. In certain embodiments, the agent is an antagonist. In certain embodiments, the agent specifically binds to EGF10 of human Notch2 and/or EGF9 of human Notch3. EGF9 is the EGF within human Notch3 that is equivalent to EGF10 in the other human Notch receptors Notch1, Notch2, and Notch4. In certain embodiments, the agent specifically binds human Notch2. In certain embodiments, the agent specifically binds human Notch2 and Notch3. In certain embodiments, the agent specifically binds human Notch3.

In one aspect, the invention provides a 59R1 antibody comprising the heavy chain and light chain sequences provided in SEQ ID NOs:16 and 18 (with or without signal sequence), respectively, or as encoded by the DNA deposited with ATCC on Oct. 15, 2008, and assigned designation number PTA-9547. The invention further provides polypeptides or antibodies that comprise the heavy chain variable region (e.g., SEQ ID NO:14) and/or the light chain variable region (e.g., SEQ ID NO:13) of such a 59R1 antibody. The invention further provides polypeptides or antibodies comprising one or more (e.g., 1, 2, or 3) of the heavy chain CDRs, and/or one or more of the light chain CDRs of the 59R1 antibody. In still further embodiments, the invention provides antibodies that bind to the same epitope as the 59R1 antibody or antibodies that compete for specific binding to human Notch2 and/or Notch3 with the 59R1 antibody.

In another aspect, the invention provides a 59R5 antibody comprising the heavy chain and light chain sequences provided in SEQ ID NOs:49 and 18 (with or without signal sequence), respectively, or as encoded by the DNA deposited with ATCC on Jul. 6, 2009 and assigned designation number PTA-10170. The invention further provides polypeptides or antibodies that comprise the heavy chain variable region and/or the light chain variable region sequences SEQ ID NO:50 and/or SEQ ID NO:13. The invention further provides polypeptides or antibodies comprising one or more (e.g., 1, 2, or 3) of the heavy chain CDRs and/or one or more of the light chain CDRs of the 59R5 antibody. In still further embodiments, the invention provides antibodies that bind to the same epitope as the 59R5 antibody or antibodies that compete for specific binding to human Notch2 and/or Notch3 with the 59R5 antibody.

In certain additional embodiments, the invention provides an antibody that specifically binds to two or more (i.e., at least two or two, three, or four) human Notch receptors. In certain embodiments, the antibody specifically binds to a non-ligand binding region of an extracellular domain of the two or more human Notch receptors. In certain embodiments, the antibody is a monospecific antibody that specifically binds to a non-ligand binding region of an extracellular domain of the two or more human Notch receptors. In certain embodiments, the antibody binds to EGF10 of Notch1, Notch2, or Notch4, and/or to EGF9 of Notch3. In certain embodiments, the non-ligand binding region to which the antibody binds is not EGF4 or does not comprise EGF4. In certain embodiments, the two or more human Notch receptors comprise Notch2 and/or Notch3. In certain embodiments, the two or more human Notch receptors comprise Notch2 and Notch3. In certain embodiments, the antibody is an antagonist of the two or more human Notch receptors.

The invention further provides a method of modulating the function of pericytes and/or vascular smooth muscle cells in a subject, wherein the method comprises administering to the subject an effective amount of an agent that specifically binds human Notch2 and/or human Notch3. In certain embodiments, the agent is an antibody. In certain embodiments, the agent is an antagonist.

The invention further provides a method of inhibiting angiogenesis in a subject, comprising the step of administering to the subject an effective amount of an agent that specifically binds human Notch2 and/or human Notch3. In certain embodiments, the agent is an antibody. In certain embodiments, the agent is an antagonist. In certain embodiments, the antagonist is an antagonist of Notch2. In certain embodiments, the antagonist is an antagonist of Notch3. In certain embodiments, the antagonist is an antagonist of Notch2 and Notch3. In some embodiments, the method of inhibiting angiogenesis comprises modulating the function of pericytes and/or vascular smooth muscle cells. In some embodiments, the angiogenesis is tumor angiogenesis.

In certain embodiments, the Notch-binding agent is an antagonist of the human Notch receptor(s) to which it specifically binds. In some alternative embodiments, the Notch-binding agent is an agonist of the human Notch receptor(s) to which it specifically binds.

In certain embodiments, the agent that specifically binds to one or more Notch receptor(s) and is an antagonist of the one or more Notch receptor(s) inhibits at least about 10%, at least about 20%, at least about 30%, at least about 50%, at least about 75%, at least about 90%, or about 100% of one or more activities of the bound Notch receptor(s).

In certain embodiments, the antagonist of one or more human Notch receptor(s) (e.g., Notch2 and/or Notch3) has one or more of the following effects: inhibit ligand binding to the one or more human Notch receptors, inhibit ligand-induced signaling by the one or more Notch receptors; inhibit proliferation of tumor cells; reduce the tumorigenicity of a tumor by reducing the frequency of cancer stem cells in the tumor; inhibit tumor growth; increase survival, trigger cell death of tumor cells; inhibit angiogenesis; or prevent metastasis of tumor cells.

In certain embodiments, the antagonist has one or more of the following effects: interference with the expression of a Notch receptor; interference with activation of a Notch receptor signal transduction pathway by, for example, sterically inhibiting interactions between the Notch receptor and one or more of its ligands, or binding to a human Notch receptor and triggering cell death or inhibiting cell proliferation.

In certain embodiments, antagonists against a Notch receptor, such as Notch2 or Notch3, act extracellularly to act upon or inhibit the function of the Notch receptor. In certain embodiments, an antagonist is a small molecule that binds to the extracellular domain of a Notch receptor. In certain embodiments, an antagonist of a Notch receptor is proteinaceous. In some embodiments, proteinaceous antagonists of a Notch receptor are antibodies that specifically bind to an extracellular epitope of a Notch receptor. Extracellular binding of an antagonist against a Notch receptor can inhibit the signaling of a Notch receptor protein by inhibiting intrinsic activation (e.g., kinase activity) of a Notch receptor and/or by sterically inhibiting the interaction, for example, of a Notch receptor with one of its ligands. Furthermore, extracellular binding of an antagonist against a Notch receptor can down-regulate cell-surface expression of a Notch receptor such as, for example, by internalization of a Notch receptor and/or decreasing cell surface trafficking of a Notch receptor.

In certain embodiments, the Notch-binding agent or antagonist (e.g., antibody) specifically binds to a non-ligand binding region of an extracellular domain of at least one human Notch receptor, wherein the non-ligand binding region comprises EGF repeat 10 (or the equivalent if Notch3). In certain embodiments, the agent or antagonist specifically binds to Notch2. In certain embodiments, the agent or antagonist specifically binds to Notch3. In certain embodiments, the agent or antagonist specifically binds to both human Notch2 and human Notch3.

In certain embodiments, the Notch-binding agent or antagonist (e.g., antibody) specifically binds to an EGF10 domain of human Notch2. In certain embodiments, the Notch-binding agent or antagonist does not bind to any region of the human Notch2 outside of the EGF 10 domain. In certain alternative embodiments, the Notch-binding agent or antagonist that specifically binds to an EGF10 domain of human Notch2, also further binds to another region of human Notch2. In other words, in some embodiments, the entire epitope of the agent or antagonist falls within EGF10. In certain other embodiments, the epitope of the agent or antagonist that binds to human Notch2 partially overlaps with EGF10. In certain embodiments, the agent or antagonist binds to at least part of the sequence HKGAL (SEQ ID NO:28) within human Notch2 EGF10. In certain embodiments, the agent or antagonist also binds to other amino acids within human Notch2 EGF10 (e.g., the entire epitope of an anti-Notch2 antibody is not necessarily contained entirely within the sequence HKGAL). In certain embodiments, the Notch-binding agent or antagonist further specifically binds to at least one additional human Notch receptor (e.g., Notch1, Notch3, or Notch4). In certain embodiments, the Notch-binding agent or antagonist that binds to EGF10 of human Notch2 further binds to an EGF10 domain of human Notch1, an EGF9 domain of human Notch3, and/or an EGF10 domain of human Notch4. In certain embodiments, the additional human Notch receptor is human Notch3.

In certain embodiments, the Notch-binding agent or antagonist (e.g., antibody) binds to an EGF9 domain of human Notch3. As is apparent from the homology between the sequences of the extracellular domains of human Notch2 and human Notch3, EGF9 is the EGF that is the functional/structural equivalent of Notch2 EGF10 in human Notch3. In certain embodiments, the Notch-binding agent or antagonist does not bind to any region of the human Notch3 outside of EGF9. In certain embodiments, the agent or antagonist binds to at least part of the sequence HEDAI (SEQ ID NO:29) within the human Notch3 EGF9 domain. HEDAI (SEQ ID NO:29) is the sequence within the Notch3 EGF9 domain that corresponds to sequence HKGAL (SEQ ID NO:28) within human Notch2 EGF10. In certain embodiments, the agent or antagonist also binds to other amino acids within human Notch3 EGF9. In certain embodiments, the Notch-binding agent or antagonist binds to an EGF10 domain of at least one additional human Notch receptor (e.g., Notch1, Notch2, and/or Notch4). In certain embodiments, the additional human Notch receptor is human Notch2, such as an agent or antagonist that binds to an EGF10 domain of human Notch2. In certain embodiments, the Notch-binding agent or antagonist does not bind to any region of the human Notch2 outside of EGF10. In certain embodiments, the agent or antagonist binds to at least part of the sequence HKGAL (SEQ ID NO:28) within human Notch2 EGF10. In some embodiments, the agent or antagonist is a monospecific antibody that binds to at least part of the sequence HKGAL (SEQ ID NO:28) in Notch2 and also binds to at least part of the sequence HEDAI (SEQ ID NO:29) in Notch3.

In certain alternative embodiments, the Notch-binding agent or antagonist binds to a portion of the non-ligand binding region of an extracellular domain of a Notch1, Notch2, or Notch4 receptor in a region other than EGF10 or a Notch3 receptor in a region other than EGF9. For example, in certain embodiments, the agent or antagonist binds to the LNR-HD domain of one or more Notch receptors. In certain embodiments, the agent or antagonist binds to EGF1, EGF2, EGF3, EGF4, EGF5, EGF6, EGF7, EGF9, EGF10, EGF13, EGF14, EGF15, EGF16, EGF17, EGF18, EGF19, EGF20, EGF21, EGF22, EGF23, EGF24, EGF25, EGF26, EGF27, EGF28, EGF29, EGF30, EGF31, EGF32, EGF33, EGF34, EGF35, and/or EGF36 of an extracellular domain of one or more Notch receptors.

In certain embodiments, the Notch-binding agent or antagonist binds to the ligand binding region of an extracellular domain of one or more human Notch receptors. Thus, in certain embodiments, the Notch-binding agent or antagonist may bind to EGF11 and/or EGF12 of Notch 1, 2, or 4 (Rebay et al., 1991, *Cell* 67:687; Lei et al., 2003, *Dev.* 130:6411; Hambleton et al., 2004, *Structure* 12:2173) or EGF10 and/or EGF11 of Notch3 (Peters et al., 2004, *Experimental Cell Research*, 299:454-464).

In certain embodiments, the Notch-binding agent (e.g., antibody) specifically binds to two or more human Notch receptors (e.g., Notch1, Notch2, Notch3, and/or Notch4). In other words, in certain embodiments, the agent or antibody binds at least two human Notch receptors (i.e., two, three, or four human Notch receptors). Encompassed are agents and antibodies that specifically bind to two human Notch family receptors (e.g., Notch2 and Notch3, Notch1 and Notch2, Notch1 and Notch3, Notch1 and Notch4, Notch2 and Notch4, or Notch3 and Notch4). Agents and antibodies that specifically bind to three human Notch receptor family members are also envisioned (e.g., agents and antibodies that specifically bind to Notch1, Notch2, and Notch3, Notch1, Notch2, and Notch4, or Notch2, Notch3, and Notch4), as are agents and antibodies that specifically bind to four human Notch receptor family members (e.g., agents and antibodies that specifically bind to Notch1, Notch2, Notch3 and Notch4). In certain embodiments, the agent or antibody specifically binds to both human Notch2 and Notch3. In certain alternative embodiments, the agent or antibody specifically binds to both human Notch1 and Notch2. In some embodiments, the agent or antibody specifically binds to both human Notch1 and Notch3. In still further embodiments, the agent or antibody specifically binds to both human Notch1 and Notch4. In certain embodiments, the agent or antibody is an antagonist of the two or more human Notch receptors.

In certain embodiments, the Notch-binding agent or antagonist binds to a Notch receptor (e.g., Notch2 and/or Notch3) with a dissociation constant of about 1 µM or less, about 100 nM or less, about 40 nM or less, about 20 nM or less, or about 10 nM or less. In certain embodiments, the agent or antagonist binds one or more human Notch receptors, such as human Notch2 and/or human Notch3, with a $K_D$ of 1 nM or less. In some embodiments, the Notch binding agent is an antibody that binds to Notch2 with a $K_D$ of about 1 nM or less. In some embodiments, the Notch binding agent is an antibody that binds to Notch3 with a $K_D$ of about 1 nM or less. In certain embodiments, the dissociation constant for the agent or antagonist with respect to a particular Notch receptor is the dissociation constant determined using a Notch-Fc fusion protein comprising the Notch extracellular domain and/or a portion of the extracellular domain comprising EGF 10 immobilized on a Biacore chip.

In certain embodiments, the antagonist specifically binds to human Notch3 and inhibits binding of a ligand (e.g., DLL4, JAG1, and/or JAG2) to human Notch3 and/or inhibits signaling of human Notch3. In certain embodiments, the antagonist specifically binds to human Notch2 and inhibits binding of a ligand (e.g., DLL4, JAG1, and/or JAG2) to human Notch2 and/or inhibits signaling of human Notch2. In certain embodiments, the antagonist inhibits DLL4-induced Notch2 signaling. In certain embodiments, the antagonist inhibits DLL4-induced Notch3 signaling. In certain embodiments, the antagonist inhibits JAG2-induced Notch2 signaling. In certain embodiments, the antagonist inhibits JAG2-induced Notch3 signaling. In certain embodiments, the signaling by Notch2 and/or Notch3 is reduced by at least about 10%, by at least about 25%, by at least about 50%, by at least about 75%, by at least about 90%, or by at least about 95%. In certain embodiments, the binding of one or more ligands to Notch2 and/or Notch3 is reduced by at least about 10%, by at least about 25%, by at least about 50%, by at least about 75%, by at least about 90%, or by at least about 95%.

In some embodiments, antagonists against a Notch receptor bind to a Notch receptor and have one or more of the following effects: inhibit proliferation of tumor cells, trigger cell death directly in tumor cells, or prevent metastasis of tumor cells. In certain embodiments, antagonists of a Notch receptor trigger cell death via a conjugated toxin, chemotherapeutic agent, radioisotope, or other such agent. For example, an antibody against a Notch receptor is conjugated to a toxin that is activated in tumor cells expressing the Notch receptor by protein internalization. In other embodiments, antagonists of a Notch receptor mediate cell death of a cell expressing the Notch receptor via antibody-dependent cellular cytotoxicity (ADCC). ADCC involves cell lysis by effector cells that recognize the Fc portion of an antibody. Many lymphocytes, monocytes, tissue macrophages, granulocytes and eosinophils, for example, have Fc receptors and can mediate cytolysis (Dillman, 1994, *J. Clin. Oncol.* 12:1497). In some embodiments, an antagonist of a Notch receptor is an antibody that triggers cell death of cell expressing a Notch receptor by activating complement-dependent cytotoxicity (CDC). CDC involves binding of serum complement to the Fc portion an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity are prepared.

The ability of any particular antibody against a Notch receptor to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, the Notch-binding agent or antagonist is an antibody that does not have one or more effector functions. For instance, in some embodiments, the antibody has no antibody-dependent cellular cytoxicity (ADCC) activity and/or no complement-dependent cytoxicity (CDC) activity. In certain embodiments, the antibody does not bind to an Fc receptor and/or complement factors. In certain embodiments, the antibody has no effector function.

In other embodiments, antagonists of a Notch receptor can trigger cell death indirectly by inhibiting angiogenesis. Angiogenesis is the process by which new blood vessels form from pre-existing vessels and is a fundamental process required for normal growth, for example, during embryonic development, wound healing, and in response to ovulation. Solid tumor growth larger than 1-2 $mm^2$ also requires angiogenesis to supply nutrients and oxygen without which tumor cells die. Thus, in certain embodiments, an antagonist of a Notch receptor targets vascular cells that express the Notch receptor including, for example, endothelial cells, smooth muscle cells or components of the extracellular matrix required for vascular assembly. In certain embodiments, an antagonist of a Notch receptor (e.g., Notch2 and/or Notch3)

targets pericytes and/or vascular smooth muscle cells. In other embodiments, an antagonist of a Notch receptor inhibits growth factor signaling required by vascular cell recruitment, assembly, maintenance or survival. In certain embodiments, the antagonist modulates the function of pericytes and/or vascular smooth muscle cells.

In certain embodiments the Notch-binding agents or antagonists (e.g., antibodies), either alone or in combination with a second therapeutic agent, are capable of inhibiting tumor growth. In certain embodiments, the Notch-binding agents or antagonists are capable of inhibiting tumor growth in vivo (e.g., in a xenograft mouse model and/or in a human having cancer). In certain embodiments, the Notch-binding agents or antagonists are capable of inhibiting tumor growth by at least about 10%, at least about 25%, at least about 50%, at least about 75%, at least about 90% at a given time point in a xenograft model. In certain embodiments, the Notch-binding agents or antagonists prevent tumor growth. In certain embodiments, the Notch-binding agents or antagonists inhibit tumor recurrence.

In certain embodiments, the Notch-binding agents are capable of reducing the tumorigenicity of a tumor. In certain embodiments, the agent or antibody is capable of reducing the tumorigenicity of a tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold (e.g., in a xenograft model). In certain embodiments, the reduction in the frequency of cancer stem cells is determined by limiting dilution assay using an animal model. An example of a limiting dilution assay used to test the efficacy of an anti-Notch antibody is provided in Example 8, below. Additional examples and guidance regarding the use of limiting dilution assays to determine a reduction in the number or frequency of cancer stem cells in a tumor can be found, e.g., in International Publication No. WO 2008/042236, U.S. Patent Application Publication Nos. 2008/0064049, and 2008/0178305, each of which is incorporated by reference herein in its entirety.

The present invention provides a variety of polypeptides, including but not limited to, antibodies and fragments of antibodies. In certain embodiments, the polypeptide is isolated. In certain alternative embodiments, the polypeptide is substantially pure.

In certain embodiments, the polypeptides of the present invention can be recombinant polypeptides, natural polypeptides, or synthetic polypeptides comprising the sequence of SEQ ID NOs:2, 4, 13, 14, 16, 18, 19, 20, 39, 40, 49, 50, 52, 53, 54, 55, 56, or 57 (with or without the indicated signal sequences), as well as the polypeptides comprising the polypeptides encoded by the polynucleotides of SEQ ID NOs: 1, 3, 15, 17, 47, 48, 58, 59, or 60 (with or without the indicated signal sequences).

The invention provides a polypeptide comprising the heavy chain and/or the light chain of 59R1 provided in SEQ ID NO:16 and/or SEQ ID NO:18, respectively. In certain embodiments, the polypeptide is an antibody. In certain embodiments, the polypeptide specifically binds Notch2 and/or Notch3. In some embodiments, the polypeptide specifically binds Notch2 and Notch3.

The invention provides a polypeptide comprising the heavy chain and/or the light chain of 59R5 provided in SEQ ID NO:49 and/or SEQ JD NO:18, respectively. In certain embodiments, the polypeptide is an antibody. In certain embodiments, the polypeptide specifically binds Notch2 and/or Notch3. In some embodiments, the polypeptide specifically binds Notch2 and Notch3.

The invention further provides a polypeptide comprising SEQ ID NO:13 and/or SEQ ID NO:14. In certain embodiments, the polypeptide comprises a variable light chain sequence comprising SEQ ID NO:13 and/or a variable heavy chain sequence comprising SEQ ID NO:14. In some embodiments, the polypeptide comprises a variable light chain sequence comprising SEQ ID NO:13 and a variable heavy chain sequence comprising SEQ ID NO:14. In certain embodiments, the polypeptide comprises a variable light chain sequence comprising SEQ ID NO:13 and/or a variable heavy chain sequence comprising SEQ ID NO:50. In some embodiments, the polypeptide comprises a variable light chain sequence comprising SEQ ID NO:13 and a variable heavy chain sequence comprising SEQ ID NO:50. In certain embodiments, the polypeptide comprises a variable light chain sequence comprising SEQ ID NO:13 and/or a variable heavy chain sequence comprising SEQ ID NO:52. In certain embodiments, the polypeptide comprises a variable light chain sequence comprising SEQ ID NO:13 and/or a variable heavy chain sequence comprising SEQ ID NO:53. In certain embodiments, the polypeptide comprises a variable light chain sequence comprising SEQ ID NO:13 and/or a variable heavy chain sequence comprising SEQ ID NO:54. In certain embodiments, the polypeptide comprises a variable light chain sequence comprising SEQ ID NO:13 and/or a variable heavy chain sequence comprising SEQ ID NO:55. In certain embodiments, the polypeptide comprises a variable light chain sequence comprising SEQ ID NO:13 and/or a variable heavy chain sequence comprising SEQ ID NO:56. In certain embodiments, the polypeptide comprises a variable light chain sequence comprising SEQ ID NO:13 and/or a variable heavy chain sequence comprising SEQ ID NO:57. In certain embodiments, the polypeptide is an antibody. In certain embodiments, the polypeptide specifically binds Notch2 and/or Notch3. In some embodiments, the polypeptide specifically binds Notch2 and Notch3. In some embodiments, the polypeptide specifically binds human Notch2. In some embodiments, the polypeptide specifically binds human Notch3.

It will be recognized in the art that some amino acid sequences of the invention can be varied without significant effect of the structure or function of the protein. If such differences in sequence are contemplated, it should be remembered that there will be critical areas on the protein which determine activity. Thus, the invention further includes variations of the polypeptides which show substantial activity. Such mutants include deletions, insertions, inversions, repeats, and type substitutions. Guidance concerning which amino acid changes are likely to be phenotypically silent can be found in Bowie et al., Deciphering the Message in Protein Sequences: Tolerance to Amino Acid Substitutions, 1990, *Science* 247:1306-1310.

Thus, the fragments, derivatives, or analogs of the polypeptides of the invention can be: (i) one in which one or more of the amino acid residues are substituted with a conserved or non-conserved amino acid residue (often a conserved amino acid residue) and such substituted amino acid residue can or cannot be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives, and analogs are deemed to be within the scope of the teachings herein.

Of particular interest are substitutions of a charged amino acid with another charged amino acid and with neutral or negatively charged amino acid. The latter results in proteins with reduced positive charge. Reduced positive charge on a protein can lead to reduction in protein aggregation and the prevention of aggregation is highly desirable. Aggregation of proteins can not only result in a loss of activity but can also be problematic when preparing pharmaceutical formulations, because aggregates can be immunogenic. (Pinckard et al., 1967, *Clin. Exp. Immunol.* 2:331-340; Robbins et al., 1987, *Diabetes* 36:838-845; Cleland et al., 1993, *Crit. Rev. Therapeutic Drug Carrier Systems* 10:307-377).

As indicated, amino acid changes are typically of a minor nature, such as conservative amino acid substitutions that do not significantly affect the folding or activity of the protein (see Table 1.)

TABLE 1

Conservative Amino Acid Substitutions

| Original Amino Acid | Exemplary Conservative Substitutions |
|---|---|
| Alanine | Valine, Isoleucine, Leucine, Glycine, Serine |
| Arginine | Lysine, Histidine, Glutamine, Asparagine |
| Asparagine | Glutamine, Histidine, Lysine, Arginine |
| Aspartic Acid | Glutamic Acid, Asparagine |
| Cysteine | Serine, Alanine, Methionine |
| Glutamine | Asparagine |
| Glutamic Acid | Aspartic Acid, Glutamine |
| Glycine | Proline, Alanine |
| Histidine | Asparagine, Glutamine, Lysine, Arginine |
| Isoleucine | Leucine, Valine, Methionine, Alanine, Phenylalanine, Norleucine |
| Leucine | Norleucine, Isoleucine, Valine, Methionine, Alanine, Phenylalanine |
| Lysine | Arginine, Glutamine, Asparagine, Histidine |
| Methionine | Leucine, Phenylalanine, Isoleucine, Valine, Cysteine |
| Phenylalanine | Leucine, Valine, Isoleucine, Alanine, Tyrosine |
| Proline | Alanine, Glycine |
| Serine | Threonine |
| Threonine | Serine |
| Trytophan | Tyrosine, Phenylalanine |
| Tyrosine | Tryptophan, Phenylalanine, Threonine, Serine |
| Valine | Isoleucine, Methionine, Leucine, Phenylalanine, Alanine, Norleucine |

Of course, the number of amino acid substitutions made depends on many factors, including those described above. In certain embodiments, the number of substitutions for any given polypeptide will not be more than 50, 40, 30, 25, 20, 15, 10, or 3.

In certain embodiment, the polypeptides and polynucleotides of the present invention are provided in an isolated form, and at times are purified to homogeneity.

The polypeptides of the present invention include the polypeptides of SEQ ID NOs: 2, 4, 13, 14, 16, 18, 19, 20, 39, 40, 49, 50, 52, 53 54, 55, 56, or 57 as well as polypeptides which have at least 90% similarity (at certain times at least 90% sequence identity) to the polypeptides of SEQ ID NOs: 2, 4, 13, 14, 16, 18, 19, 20, 39, 40, 49, 50, 52, 53 54, 55, 56, or 57 and at certain times at least 95% sequence identity) to the polypeptides of SEQ ID NOs: 2, 4, 13, 14, 16, 18, 19, 20, 49, 50, 52, 53 54, 55, 56, or 57 and in still other embodiments, polypeptide which have at least 96%, 97%, 98%, or 99% similarity (at certain times 96%, 97%, 98%, or 99% sequence identity) to the polypeptides of SEQ ID NOs: 2, 4, 13, 14, 16, 18, 19, 20, 39, 40, 49, 50, 52, 53 54, 55, 56, or 57. As known in the art, "similarity" between two polypeptides is determined by comparing the amino acid sequence and its conserved amino acid substitutes of one polypeptide to the sequence of a second polypeptide.

Fragments or portions of the polypeptides of the present invention can be employed for producing the corresponding full-length polypeptide by peptide synthesis; therefore, the fragments can be employed as intermediates for producing the full-length polypeptides. Fragments or portions of the polynucleotides of the present invention can be used to synthesize full-length polynucleotides of the present invention.

In certain embodiments, a fragment of the proteins of this invention is a portion or all of a protein which is capable of binding to a Notch receptor protein. This fragment has a high affinity for a Notch receptor or a ligand of a Notch receptor. Certain fragments of fusion proteins are protein fragments comprising at least part of the Notch binding domain of the polypeptide agent or antagonist fused to at least part of a constant region of an immunoglobulin. The affinity is typically in the range of about $10^{-11}$ to $10^{-12}$ M, although the affinity can vary considerably with fragments of different sizes, ranging from $10'^{-7}$ to $10^{-13}$ M. In some embodiments, the fragment is about 10-110 amino acids in length and comprises the Notch binding domain of the polypeptide agent or antagonist linked to at least part of a constant region of an immunoglobulin.

The polypeptides and analogs can be further modified to contain additional chemical moieties not normally part of the protein. Those derivatized moieties can improve the solubility, the biological half life or absorption of the protein. The moieties can also reduce or eliminate any undesirable side effects of the proteins and the like. An overview for those moieties can be found in Remington's Pharmaceutical Sciences, 20th ed., Mack Publishing Co., Easton, Pa. (2000).

The isolated polypeptides described herein can be produced by any suitable method known in the art. Such methods range from direct protein synthesis methods, to constructing a DNA sequence encoding isolated polypeptide sequences and expressing those sequences in a suitable transformed host.

In some embodiments of a recombinant method, a DNA sequence is constructed by isolating or synthesizing a DNA sequence encoding a wild-type protein of interest. Optionally, the sequence can be mutagenized by site-specific mutagenesis to provide functional analogs thereof. See, e.g. Zoeller et al., 1984, *Proc. Nat. Acad. Sci. USA* 81:5662-5066 and U.S. Pat. No. 4,588,585. Another method of constructing a DNA sequence encoding a polypeptide of interest would be by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced.

Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the mutant DNA sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene is operatively linked to transcriptional and translational expression control sequences that are functional in the chosen expression host.

Recombinant expression vectors may be used to amplify and express DNA encoding polypeptides. Recombinant expression vectors are replicable DNA constructs which have synthetic or cDNA-derived DNA fragments encoding a Notch receptor fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. An origin of replication which usually confers the ability to replicate in a host and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, "operatively linked" means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from Esherichia coli, including pCR1, pBR322, pMB9 and their derivatives, and wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example E. coli or Bacilli. Higher eukaryotic cells include established cell lines of mammalian origin as described herein. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman 1981, Cell 23:175, and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, 1988, Bio/Technology 6:47.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In certain embodiments, the Notch-binding agent or antagonist comprises an antibody. In certain embodiments, the antibody is isolated. In certain embodiments, the antibody is substantially pure.

The present invention provides antibodies that compete for specific binding to human Notch2 and/or Notch3 with an antibody comprising a heavy chain variable region comprising SEQ ID NO:14 and a light chain variable region comprising SEQ ID NO:13. The present invention also provides antibodies that compete for specific binding to human Notch2 and/or Notch3 with an antibody that comprises, consists, or consists essentially of a 59R1 IgG2 antibody comprising the heavy chain and light chain of SEQ ID NOs:16 and 18 (with or without signal sequence), respectively, or as encoded by the DNA deposited with the ATCC on Oct. 15, 2008, and assigned designation number PTA-9547.

The invention further provides antibodies that specifically bind to one or more Notch receptors, that comprise one, two, three, four, five, and/or six CDRs of SEQ ID NOs:5-10, 22-27, 30 or 51 with up to four (i.e., 0, 1, 2, 3, or 4) conservative amino acid substitutions (see, e.g., Table 1) per CDR. The invention also provides antibodies that specifically bind to one or more Notch receptors, that comprise one, two, three, four, five, and/or six CDRs of 59R1 (i.e., SEQ ID NOs:5-10), with up to four conservative amino acid substitutions per CDR. Thus, the invention provides antibodies that specifically bind to one or more human Notch receptors that comprise one, two, three, four, five and/or six of the CDRs of 59R1. In certain embodiments, the antibodies comprise the heavy chain CDR3 of 59R1, with up to four conservative amino acid substitutions, and/or the light chain CDR3 of 59R1, with up to four conservative amino acid substitutions. In some embodiments, the antibody comprises (a) a heavy chain CDR1 comprising SSSGMS (SEQ ID NO:5), or a variant thereof comprising 1, 2, 3, or 4 conservative amino acid substitutions; a heavy chain CDR2 comprising VIASSGSNTYYADSVKG (SEQ ID NO:6), or a variant thereof comprising 1, 2, 3, or 4 conservative amino acid substitutions; and/or a heavy chain CDR3 comprising GIFFAI (SEQ ID NO:7), or a variant thereof comprising 1, 2, 3, or 4 conservative amino acid substitutions; and/or (b) a light chain CDR1 comprising RASQSVRSNYLA (SEQ ID NO:8), or a variant thereof comprising 1, 2, 3, or 4 conservative amino acid substitutions; a light chain CDR2 comprising GASSRAT (SEQ ID NO:9), or a variant thereof comprising 1, 2, 3, or 4 conservative amino acid substitutions; and/or a light chain CDR3 comprising QQYSNFPI (SEQ ID NO:10), or a variant thereof comprising 1, 2, 3, or 4 conservative amino acid substitutions.

The invention also provides antibodies that specifically bind to one or more Notch receptors, that comprise one, two, three, four, five, and/or six CDRs of 59R5 (i.e., SEQ ID NOs: 5, 6, 8-10, 51), with up to four conservative amino acid substitutions per CDR. In certain embodiments, the antibodies comprise the heavy chain CDR3 of 59R5, with up to four conservative amino acid substitutions, and/or the light chain CDR3 of 59R5, with up to four conservative amino acid substitutions. In some embodiments, the antibody comprises (a) a heavy chain CDR1 comprising SSSGMS (SEQ ID NO:5), or a variant thereof comprising 1, 2, 3, or 4 conservative amino acid substitutions; a heavy chain CDR2 comprising VIASSGSNTYYADSVKG (SEQ ID NO:6), or a variant thereof comprising 1, 2, 3, or 4 conservative amino acid substitutions; and/or a heavy chain CDR3 comprising SIFYTT (SEQ ID NO:51), or a variant thereof comprising 1, 2, 3, or 4 conservative amino acid substitutions; and/or (b) a light chain CDR1 comprising RASQSVRSNYLA (SEQ ID NO:8), or a variant thereof comprising 1, 2, 3, or 4 conservative amino acid substitutions; a light chain CDR2 comprising GASSRAT (SEQ ID NO:9), or a variant thereof comprising 1, 2, 3, or 4 conservative amino acid substitutions; and/or a light chain CDR3 comprising QQYSNFPI (SEQ ID NO:10), or a variant thereof comprising 1, 2, 3, or 4 conservative amino acid substitutions. In certain embodiments, the antibody comprises a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising SIFYTT (SEQ ID NO:51).

Also provided is an antibody that specifically binds human Notch2 and/or Notch3, wherein the antibody comprises a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising (G/I)(I/S)F(F/Y)(A/P)(I/T/S/N) (SEQ ID NO:30). In certain embodiments, the heavy chain CDR3 is selected from the group consisting of SIFYPT (SEQ ID NO:22), SSFFAS (SEQ ID NO:23), SSFYAS (SEQ ID NO:24), SSFFAT (SEQ ID NO:25), SIFYPS (SEQ ID NO:26), and SSFFAN (SEQ ID NO:27). In certain embodiments, the antibody comprises a heavy chain CDR1 comprising SSSGMS (SEQ ID NO:5), a heavy chain CDR2 comprising VIASSGSNTYYADSVKG (SEQ ID NO:6), and/or a heavy chain CDR3 comprising GIFFAI (SEQ ID NO:7). In certain embodiments, the heavy chain CDR(s) are contained within a variable region of an antibody heavy chain. In certain embodiments, the antibody further comprises a light chain CDR1 comprising RASQSVRSNYLA (SEQ ID NO:8), a light chain CDR2 comprising GASSRAT (SEQ ID NO:9), and/or a light chain CDR3 comprising QQYSNFPI (SEQ ID NO:10). In certain embodiments, the light chain CDR(s) are contained within a variable region of an antibody light chain. In certain embodiments, the heavy chain CDR(s) and/or the light chain CDR(s) have been modified with 1, 2, 3, or 4 conservative amino acid substitutions. In certain embodiments, each of the CDR(s) have been modified by no more than 1-2 conservative amino acid substitutions.

For example, in certain embodiments, the invention provides an antibody that specifically binds human Notch2 and/or Notch3, wherein the antibody comprises: (a) a heavy chain CDR1 comprising SSSGMS (SEQ ID NO:5), a heavy chain CDR2 comprising VIASSGSNTYYADSVKG (SEQ ID NO:6), and a heavy chain CDR3 comprising GIFFAI (SEQ ID NO:7); and/or (b) a light chain CDR1 comprising RASQSVRSNYLA (SEQ ID NO:8), a light chain CDR2 comprising GASSRAT (SEQ ID NO:9), and a light chain CDR3 comprising QQYSNFPI (SEQ ID NO:10). In some embodiments, the antibody comprises both the indicated light and heavy chain CDRs.

In some embodiments, the invention provides an antibody that specifically binds human Notch2 and/or Notch3, wherein the antibody comprises: (a) a heavy chain CDR1 comprising SSSGMS (SEQ ID NO:5), a heavy chain CDR2 comprising VIASSGSNTYYADSVKG (SEQ ID NO:6), and a heavy chain CDR3 comprising SIFYTT (SEQ ID NO:51); and/or (b) a light chain CDR1 comprising RASQSVRSNYLA (SEQ ID NO:8), a light chain CDR2 comprising GASSRAT (SEQ ID NO:9), and a light chain CDR3 comprising QQYSNFPI (SEQ ID NO:10). In certain embodiments, the antibody comprises both the indicated light and heavy chain CDRs.

The invention further provides an antibody that specifically binds human Notch2 and/or Notch3, wherein the antibody comprises a light chain CDR1 comprising RASQSVRSNYLA (SEQ ID NO:8), a light chain CDR2 comprising GASSRAT (SEQ ID NO:9), and/or a light chain CDR3 comprising QQYSNFPI (SEQ ID NO:10).

The invention also provides an antibody that specifically binds human Notch2 and/or Notch3, wherein the antibody comprises: (a) a polypeptide having at least about 80%, at least about 85%, at least about 90%, at least about 95%, or at least about 98% sequence identity to SEQ ID NO:14 or SEQ ID NO:20; and/or (b) a polypeptide having at least about 80%, at least about 85%, at least about 90%, at least about 95%, or at least about 98% sequence identity to SEQ ID NO:13 or SEQ ID NO:19. Accordingly, in certain embodiments, the antibody comprises (a) a heavy chain variable region having at least about 95% sequence identity to SEQ ID NO:14; and/or (b) a light chain variable region having at least about 95% sequence identity to SEQ ID NO:13. In certain embodiments, the antibody comprises: (a) a polypeptide (e.g., a heavy chain variable region) comprising SEQ ID NO:14 or SEQ ID NO:20; and/or (b) a polypeptide (e.g., a light chain variable region) comprising SEQ ID NO:13 or SEQ ID NO:19.

The invention also provides an antibody that specifically binds human Notch2 and/or Notch3, wherein the antibody comprises: (a) a polypeptide having at least about 80%, at least about 85%, at least about 90%, at least about 95%, or at least about 98% sequence identity to SEQ ID NO:50; and/or (b) a polypeptide having at least about 80%, at least about 85%, at least about 90%, at least about 95%, or at least about 98% sequence identity to SEQ ID NO:13. Accordingly, in certain embodiments, the antibody comprises (a) a heavy chain variable region having at least about 95% sequence identity to SEQ ID NO:50; and/or (b) a light chain variable region having at least about 95% sequence identity to SEQ ID NO:13. In certain embodiments, the antibody comprises: (a) a polypeptide (e.g., a heavy chain variable region) comprising SEQ ID NO:50; and/or (b) a polypeptide (e.g., a light chain variable region) comprising SEQ ID NO:13.

In certain embodiments, the antagonists are antibodies that can mediate complement-dependent cytotoxicity or antibody-dependent cellular cytotoxicity to kill tumors expressing a target antigen. In certain alternative embodiments, the antibodies are directly conjugated to toxins or radioisotopes to mediate tumor cell killing. Furthermore, tumor survival depends on neo-vascularization, and in certain embodiments, the antibodies have an anti-angiogenic effect.

The present invention provides isolated antibodies against a Notch receptor such as human Notch2 and/or Notch3. The antibody, or antibody fragment, can be any monoclonal or polyclonal antibody that specifically recognizes the described Notch receptor. In some embodiments, the present invention provides monoclonal antibodies, or fragments thereof, that specifically bind to a Notch receptor described herein. In some embodiments, the monoclonal antibodies, or fragments thereof, are chimeric or humanized antibodies that specifically bind to the extracellular domain of a Notch receptor described herein. In other embodiments, the monoclonal antibodies, or fragments thereof, are human antibodies that specifically bind to the extracellular domain of a Notch receptor described herein. In certain embodiments, the antibodies are IgG1 or IgG2 antibodies.

The antibodies against a Notch receptor find use in the experimental, diagnostic and therapeutic methods described herein. In certain embodiments, the antibodies of the present invention are used to detect the expression of a Notch receptor in biological samples such as, for example, a patient tissue biopsy, pleural effusion, or blood sample. Tissue biopsies can be sectioned and protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of a Notch receptor, for example, on tumor cells, in cell lysates, or in other protein samples. In other embodiments, the antibodies of the present invention are used to inhibit the growth of tumor cells by contacting the tumor cells with the antibodies either in in vitro cell based assays or in vivo animal models. In still other embodiments, the antibodies are used to treat cancer in a human patient by administering a therapeutically effective amount of an antibody against a Notch receptor.

Polyclonal antibodies can be prepared by any known method. Polyclonal antibodies are raised by immunizing an animal (e.g. a rabbit, rat, mouse, donkey, goat, etc.) by multiple subcutaneous or intraperitoneal injections of the relevant antigen (a purified peptide fragment, full-length recombinant protein, fusion protein, etc.) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein, 1975, *Nature* 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, *Monoclonal Antibodies: Principles and Practice*, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, express monoclonal antibodies in the host cells. Also, recombinant monoclonal antibodies or fragments thereof of the desired species can be isolated from phage display libraries, e.g., as described herein.

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

More generally, modified antibodies useful in the present invention may be obtained or derived from any antibody. Further, the parent or precursor antibody, or fragment thereof, used to generate the disclosed modified antibodies may be murine, human, chimeric, humanized, non-human primate or primatized. In other embodiments the modified antibodies of the present invention can comprise single chain antibody constructs (such as that disclosed in U.S. Pat. No. 5,892,019, which is incorporated herein by reference) having altered constant domains as described herein. Consequently, any of these types of antibodies modified in accordance with the teachings herein are compatible with this invention.

According to the present invention, techniques can be adapted for the production of single-chain antibodies specific to a polypeptide of the invention (see U.S. Pat. No. 4,946,778). In addition, methods can be adapted for the construction of Fab expression libraries (Huse et al., 1989, *Science* 246:1275-1281) to allow rapid and effective identification of monoclonal Fab fragments with the desired specificity for Notch, or derivatives, fragments, analogs or homologs thereof. Antibody fragments that contain the idiotypes to a polypeptide of the invention may be produced by techniques in the art including, but not limited to: (a) an F(ab')$_2$ fragment produced by pepsin digestion of an antibody molecule; (b) an Fab fragment generated by reducing the disulfide bridges of an F(ab')$_2$ fragment, (c) an Fab fragment generated by the treatment of the antibody molecule with papain and a reducing agent, and (d) Fv fragments.

Bispecific antibodies are also within the scope of the invention. Bispecific antibodies are monoclonal, preferably human or humanized, antibodies that have binding specificities for at least two different antigens (or, in certain embodiments, two different epitopes on the same antigen). In the present case, one of the binding specificities is for an antigenic polypeptide of the invention (Notch, or a fragment thereof), while the second binding target is any other antigen, and advantageously is a cell surface protein, or receptor or receptor subunit. Bispecific antibodies that comprise one antigen-binding site that specifically binds one human Notch receptor (e.g., Notch2) and further comprise a second, different antigen-binding site that specifically binds a second human Notch receptor (e.g., Notch3) are provided.

Methods for making bispecific antibodies are known in the art. Traditionally the recombinant production of bispecific antibodies is based on the co-expression of two immunoglobulin heavy chain/light chain pairs, where the two heavy chains have different specificities (Milstein and Cuello, 1983, *Nature* 305:537-539). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography.

Alternatively, in certain embodiments, the antibodies described herein may be monospecific. For example, in certain embodiments, each of the one or more antigen-binding sites that an antibody contains is capable of binding (or binds) the same one or more human Notch receptors (e.g., Notch2, Notch3, or homologous epitopes on both Notch2 and Notch3). In certain embodiments, an antigen-binding site of a monospecific antibody described herein is capable of binding (or binds) both the EGF repeat 9 of human Notch3 and EGF repeat 10 of Notch2.

Antibody variable domains with the desired binding specificities can be fused to immunoglobulin constant domain sequences. The fusion is with an immunoglobulin heavy chain constant domain, comprising at least part of the hinge, CH2 and CH3 regions. The first heavy chain constant region (CH1) containing the site necessary for light chain binding can be present in at least one of the fusions. DNA encoding the immunoglobulin heavy chain fusions and, if desired, the immunoglobulin light chain, are inserted into separate expression vectors, and are co-transfected into a suitable host organism. Further details of generating bispecific antibodies can be found in Suresh et al., 1986, *Methods in Enzymology* 121:210.

Bispecific antibodies can be prepared as full-length antibodies or antibody fragments. Techniques for generating bispecific antibodies from antibody fragments have been described in the literature. For example, bispecific antibodies can be prepared using chemical linkage. In addition, Brennan et al., 1985, *Science* 229:81 describe a procedure wherein intact antibodies are proteolytically cleaved to generate F(ab')$_2$ fragments.

Additionally, Fab' fragments can be directly recovered from *E. coli* and chemically coupled to form bispecific antibodies (Shalaby et al., 1992, *J. Exp. Med.* 175:217-225). These methods can be used in the production of a fully humanized bispecific antibody F(ab')$_2$ molecule.

Antibodies with more than two valencies are also contemplated. For example, trispecific antibodies can be prepared (Tuft et al., 1991, *J. Immunol.* 147:60).

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of Notch. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In some embodiments, of the present invention the monoclonal antibody against a Notch receptor is a humanized antibody. Humanized antibodies are antibodies that contain minimal sequences from non-human (e.g., murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g., mouse, rat, rabbit, hamster, etc.) having the desired specificity, affinity, and/or capability (Jones et al., 1986, *Nature* 321:522-525; Riechmann et al., 1988, *Nature* 332:323-327; Verhoeyen et al., 1988, *Science* 239:1534-1536). The humanized antibody can be further modified by the substitution of additional residues either in the Fv framework region and/or within the replaced non-human residues to refine and optimize antibody specificity, affinity, and/or capability.

As an alternative to humanization, human antibodies can be generated. Human antibodies can be prepared using various techniques known in the art, including from transgenic animals, phage libraries, and in vitro activated human B cells.

For example, it is now possible to produce transgenic animals (e.g., mice) containing human immunoglobulin loci that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., 1993, *Proc. Natl. Acad. Sci. USA* 90:2551; Jakobovits et al., 1993, *Nature* 362:255-258; Bruggemann et al., 1993, *Year in Immuno.* 7:33; U.S. Pat. Nos. 5,545,806; 5,569,825; 5,591,669; 5,545,807; 5,545,807; 5,625,126; 5,633,425; and 5,661,016; and WO 97/17852.

Alternatively, phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats. Several sources of V-gene segments can be used for phage display. A diverse array of anti-oxazolone antibodies have been isolated from a small random combinatorial library of V genes derived from the spleens of immunized mice. A repertoire of V genes from unimmunized human donors can be constructed and antibodies to a diverse array of antigens (including self-antigens) can be isolated. Methods of selecting human antibodies from a phage library, where that phage library expresses human antibodies are well known in the art (Vaughan et al., 1996, *Nature Biotechnology* 14:309-314; Sheets et al., 1998, *PNAS* 95:6157-6162; Hoogenboom and Winter, 1991, *J. Mol. Biol.* 227:381; McCafferty et al., 1990, *Nature* 348:552-554; Clackson et al., 1991, *Nature* 352:624-628; and Marks et al., 1991, *J. Mol. Biol.*, 222:581-597). Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.* 376:1182-1200 (each of which is incorporated by reference in its entirety). Affinity maturation strategies, such as chain shuffling (Marks et al., 1992, *Bio/Technology* 10:779-783, incorporated by reference in its entirety), are known in the art and may be employed to generate high affinity human antibodies.

Human antibodies can also be directly prepared using various techniques known in the art. Immortalized human B lymphocytes immunized in vitro or isolated from an immunized individual that produce an antibody directed against a target antigen can be generated. (See, for example, Cole et al., 1985, *Monoclonal Antibodies and Cancer Therapy*, Alan R. Liss, p. 77; Boerner et al., 1991, *J. Immunol.*, 147 (1):86-95; U.S. Pat. Nos. 5,750,373; 5,567,610; and 5,229,275).

It will be appreciated that grafting the entire non-human variable domains onto human constant regions will produce "classic" chimeric antibodies. In the context of the present application the term "chimeric antibodies" will be held to mean any antibody wherein the immunoreactive region or site is obtained or derived from a first species and the constant region (which may be intact, partial or modified in accordance with this invention) is obtained from a second species. In some embodiments, the antigen binding region or site will be from a non-human source (e.g., mouse) and the constant region is human. While the immunogenic specificity of the variable region is not generally affected by its source, a human constant region is less likely to elicit an immune response from a human subject than would the constant region from a non-human source.

The variable domains in both the heavy and light chains are altered by at least partial replacement of one or more CDRs and, if necessary, by partial framework region replacement and sequence modification. Although the CDRs may be derived from an antibody of the same class or even subclass as the antibody from which the framework regions are derived, it is envisaged that the CDRs will be derived from an antibody of different class and preferably from an antibody from a different species. It must be emphasized that it may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089; 5,693,761; and 5,693,762, it will be well within the art, either by carrying out routine experimentation or by trial and error testing to obtain a functional antibody with reduced immunogenicity.

Alterations to the variable region notwithstanding, it will be appreciated that the modified antibodies of this invention will comprise antibodies, or immunoreactive fragments thereof, in which at least a fraction of one or more of the constant region domains has been deleted or otherwise altered so as to provide desired biochemical and/or biological characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention, modified constant regions wherein one or more domains are partially or entirely deleted are contemplated. In other embodiments, the modified antibodies will comprise domain deleted constructs or variants wherein the entire CH2 domain has been removed (ΔCH2 constructs). In still other embodiments, the omitted constant region domain will be replaced by a short amino acid spacer (e.g., 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques.

It will be noted that the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, any spacer added to the construct should be relatively non-immunogenic or, even omitted altogether if the desired biochemical and/or biological qualities of the modified antibodies are to be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g., complement Clq binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Yet other embodiments may comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

This invention also encompasses bispecific antibodies that specifically recognize a Notch receptor. Bispecific antibodies are antibodies that are capable of specifically recognizing and binding at least two different epitopes. The different epitopes can either be within the same molecule (e.g., the same Notch receptor polypeptide) or on different molecules. For example, the antibodies can specifically recognize and bind a Notch receptor as well as, for example, 1) an effector molecule on a leukocyte such as a T-cell receptor (e.g., CD3) or Fc receptor (e.g., CD64, CD32, or CD16) or 2) a cytotoxic agent as described in detail herein. Bispecific antibodies can be intact antibodies or antibody fragments. Techniques for making bispecific antibodies are common in the art (Millstein et al., 1983, *Nature* 305:537-539; Brennan et al., 1985, *Science* 229:81; Suresh et al, 1986, *Methods in Enzymol.* 121:120; Traunecker et al., 1991, *EMBO J.* 10:3655-3659; Shalaby et al., 1992, *J. Exp. Med.* 175:217-225; Kostelny et al., 1992, *J. Immunol.* 148:1547-1553; Gruber et al., 1994, *J. Immunol.* 152:5368; and U.S. Pat. No. 5,731,168).

In certain embodiments of the invention, it can be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, *Journal of Biochemical and Biophysical Methods* 24:107-117 and Brennan et al., 1985, *Science,* 229:81). However, these fragments are now typically produced directly by recombinant host cells as described herein. Thus Fab, Fv, and scFv antibody fragments can all be expressed in and secreted from *E. coli* or other host cells, thus allowing the production of large amounts of these fragments. Alternatively, such antibody fragments can be isolated from the antibody phage libraries discussed herein. The antibody fragments can also be linear antibodies as described in U.S. Pat. No. 5,641,870, for example, and can be monospecific or bispecific. Other techniques for the production of antibody fragments will be apparent.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, Sapaonaria officinalis inhibitor, gelonin, mitogellin, restrictocin, phenomycin, enomycin, and the tricothecenes. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

Conjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

In some embodiments, the antibody of the invention contains human Fc regions that are modified to enhance effector function, for example, antigen-dependent cell-mediated cytotoxicity (ADCC) and/or complement dependent cytotoxicity (CDC). This can be achieved by introducing one or more amino acid substitutions in an Fc region of the antibody. For example, cysteine residue(s) can be introduced in the Fc region to allow interchain disulfide bond formation in this region to improve complement-mediated cell killing and antibody-dependent cellular cytotoxicity (ADCC) (Caron et al., 1992, *J. Exp Med.* 176:1191-1195; Shopes, 1992, *Immunol.* 148:2918-2922). Homodimeric antibodies with enhanced anti-tumor activity can also be prepared using heterobifunctional cross-linkers as described in Wolff et al., 1993, *Cancer Research* 53:2560-2565. Alternatively, an antibody can be engineered which has dual Fc regions (Stevenson et al., 1989, *Anti-Cancer Drug Design* 3:219-230).

Regardless of how useful quantities are obtained, the antibodies of the present invention can be used in any one of a number of conjugated (i.e. an immunoconjugate) or unconjugated forms. The antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. In some embodiments, the antibodies can be conjugated to radioisotopes, including, but not limited to, $^{90}$Y, $^{125}$I, $^{131}$I, $^{123}$I, $^{111}$In, $^{131}$In, $^{212}$Bi, $^{105}$Rh, $^{153}$Sm, $^{67}$Cu, $^{67}$Ga, $^{166}$Ho, $^{177}$Lu, $^{186}$Re and $^{188}$Re using any one of a number of well known chelators or direct labeling. In other embodiments, the disclosed compositions can comprise antibodies coupled to drugs, prodrugs or biological response modifiers such as methotrexate, adriamycin, and lymphokines such as interferon. Still other embodiments of the present invention comprise the use of antibodies conjugated to specific biotoxins such as ricin or diptheria toxin. In yet other embodiments the modified antibodies can be complexed with other immunologically active ligands (e.g., antibodies or fragments thereof) wherein the resulting molecule binds to both the neoplastic cell and an effector cell such as a T cell. The selection of which conjugated or unconjugated modified antibody to use will depend of the type and stage of cancer, use of adjunct treatment (e.g., chemotherapy or external radiation) and patient condition. It will be appreciated that one could readily make such a selection in view of the teachings herein.

The preparation and characterization of anti-Notch antibodies is also taught, e.g., in U.S. Patent Application Publication No. 2008/0131434, which is incorporated by reference herein in its entirety.

In certain embodiments, the Notch-binding agent or antagonist is a polypeptide that is not an antibody. A variety of methods for identifying and producing non-antibody polypeptides that bind with high affinity to a protein target are known in the art. See, e.g., Skerra, 2007, Curr. Opin. Biotechnol., 18:295-304; Hosse et al., 2006, Protein Science, 15:14-27; Gill et al., 2006, Curr. Opin. Biotechnol., 17:653-658; Nygren, 2008, FEBS J., 275:2668-76; and Skerra, 2008, FEBS J., 275:2677-83, each of which is incorporated by reference herein in its entirety. In certain embodiments, phage display technology has been used to identify/produce the Notch-binding polypeptide. In certain embodiments, the polypeptide comprises a protein scaffold of a type selected from the group consisting of protein A, a lipocalin, a fibronectin domain, an ankyrin consensus repeat domain, and thioredoxin.

In some embodiments, the agent is a non-protein molecule. In certain embodiments, the agent is a small molecule. Combinatorial chemistry libraries and techniques useful in the identification of non-protein Notch-binding agents are known to those skilled in the art. See, e.g., Kennedy et al., 2008, J. Comb. Chem., 10:345-354; Dolle et al, 2007, J. Comb. Chem., 9:855-902; and Bhattacharyya, 2001, Curr. Med. Chem., 8:1383-404, each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. Nos. 5,270,163; 5,683,867; 5,763,595; 6,344,321; 7,368,236; 5,582,981; 5,756,291; 5,840,867; 7,312,325; and 7,329,742; International Patent Publication Nos. WO 02/077262; WO 03/070984; U.S. Patent Application Publication Nos. 2005/0239134; 2005/0124565; and 2008/0227735, each of which is incorporated by reference herein in its entirety.

The antibodies of the present invention can be assayed for immunospecific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In some embodiments, of the present invention the immunospecificity of an antibody against a Notch receptor is determined using ELISA. An ELISA assay comprises preparing antigen, coating wells of a 96 well microtiter plate with antigen, adding the antibody against a Notch receptor conjugated to a detectable compound such as an enzymatic substrate (e.g., horseradish peroxidase or alkaline phosphatase) to the well, incubating for a period of time and detecting the presence of the antigen. Alternatively the antibody against a Notch receptor is not conjugated to a detectable compound, but instead a second conjugated antibody that recognizes the antibody against a Notch receptor is added to the well. Further, instead of coating the well with the antigen, the antibody against a Notch receptor can be coated to the well and a second antibody conjugated to a detectable compound can be added following the addition of the antigen to the coated well. The parameters that can be modified to increase the signal detected, as well as other variations of ELISAs are well known in the art (see e.g. Ausubel et al., eds, 1994, Current Protocols in Molecular Biology, Vol. 1, John Wiley & Sons, Inc., New York at 11.2.1).

The binding affinity of an antibody to a Notch receptor and the off-rate of an antibody-antigen interaction can be determined by competitive binding assays. One example of a competitive binding assay is a radioimmunoassay comprising the incubation of labeled antigen (e.g., $^3$H or $^{125}$I), or fragment or variant thereof, with the antibody of interest in the presence of increasing amounts of unlabeled antigen followed by the detection of the antibody bound to the labeled antigen. The affinity of the antibody against a Notch receptor and the binding off-rates can be determined from the data by Scatchard plot analysis. In some embodiments, Biacore kinetic analysis is used to determine the binding on and off rates of antibodies against a Notch receptor. Biacore kinetic analysis comprises analyzing the binding and dissociation of antibodies from chips with immobilized Notch antigens on their surface.

The invention provides isolated polynucleotides encoding the polypeptides of SEQ ID NOs:2, 4, 13, 14, 16, 18, 19, 20, 39, 40, 49, 50, 52, 53, 54, 55, 56, or 57 as well as the polynucleotides of SEQ ID NOs: 1, 3, 15, 17, 47 or 48. The polynucleotides of the invention can be in the form of RNA or in the form of DNA, wherein DNA includes cDNA, genomic DNA, and synthetic DNA. The DNA can be double-stranded or single-stranded, and if single-stranded it can be the coding strand or non-coding (anti-sense) strand. Thus, the term "polynucleotide encoding a polypeptide" encompasses a polynucleotide which includes only coding sequences for the polypeptide as well as a polynucleotide which includes additional coding and/or non-coding sequences. In some embodiments, the invention provides a polynucleotide that hybridizes to a polynucleotide encoding the polypeptides of SEQ ID NOs:2, 4, 13, 14, 16, 18, 19, 20, 39, 40, 49, 50, 52, 53, 54, 55, 56, or 57. In some embodiments, the polynucleotides hybridize to the polynucleotides of SEQ ID NOs: 1, 3, 15, 17, 47, 48, 58, 59 or 60. In some embodiments, the polynucleotides hybridize under stringent hybridization conditions.

As used herein, the phrases "hybridizes" or "selectively hybridizes" or "specifically hybridizes" refer to the binding or duplexing of a molecule only to a particular nucleotide sequence under stringent hybridization conditions when that sequence is present in a complex mixture (e.g., a library of DNAs or RNAs). See, e.g., Andersen (1998) Nucleic Acid Hybridization Springer-Verlag; Ross (ed. 1997) Nucleic Acid Hybridization Wiley.

As used herein, the phrase "stringent hybridization conditions" refers to conditions under which a probe or other polynucleotide will hybridize to its target subsequence or other complementary sequence, typically in a complex mixture of nucleic acid, but generally to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency hybridization, a positive signal is at least two times background, or 10 times background hybridization. Exemplary high stringency or stringent hybridization conditions include: 50% formamide, 5×SSC, and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures can vary from about 32° C. to about 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30-120 sec, an annealing phase lasting 30-120 sec, and an extension phase of about 72° C. for 1-2 min.

The present invention further relates to variants of the hereinabove described polynucleotides which encode for fragments, analogs, and derivatives. The variant of the polynucleotide can be a naturally occurring allelic variant of the polynucleotide or a non-naturally occurring variant of the polynucleotide.

As hereinabove indicated, the polynucleotide can have a coding sequence which is a naturally occurring allelic variant of the coding sequence of the disclosed polypeptides. As known in the art, an allelic variant is an alternate form of a polynucleotide sequence which has a substitution, deletion or addition of one or more nucleotides that does not substantially alter the function of the encoded polypeptide.

The present invention also includes polynucleotides, wherein the coding sequence for the mature polypeptide can be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention can encode for a mature protein, or for a protein having a prosequence or for a protein having both a prosequence and presequence (leader sequence).

The polynucleotides of the present invention can also have the coding sequence fused in frame to a marker sequence which allows for purification of the polypeptide of the present invention. For example, the marker sequence can be a hexa-histidine tag supplied by a pQE-9 vector to provide for purification of the mature polypeptide fused to the marker in the case of a bacterial host. Or for example, the marker sequence can be a hemagglutinin (HA) tag when a mammalian host, e.g. COS-7 cells, is used. The HA tag corresponds to an epitope derived from the influenza hemagglutinin protein (Wilson et al., 1984, *Cell* 37:767).

Further embodiments of the invention include isolated nucleic acid molecules comprising a polynucleotide having a nucleotide sequence at least 90% identical, 95% identical, and in some embodiments, at least 96%, 97%, 98% or 99% identical to SEQ ID NOs:1, 3, 15, 17, 47, 48, 58, 59 or 60. In some embodiments, the polynucleotides comprising a nucleotide sequence at least 90% identical, 95% identical, and in some embodiments, at least 96%, 97%, 98% or 99% identical hybridize to the polynucleotides of SEQ ID NOs:1, 3, 15, 17, 47, 48, 58, 59 or 60. In some embodiments, the polynucleotides comprising a nucleotide sequences at least 90% identical, 95% identical, and in some embodiments, at least 96%, 97%, 98% or 99% identical hybridize to the polynucleotides of SEQ ID NOs:58, 59 or 60. In some embodiments, the polynucleotides hybridize under stringent hybridization conditions. In some embodiments, the polynucleotides hybridize to the polynucleotides of SEQ ID NO:58, 59 or 60 under stringent hybridization conditions. By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule has a certainty percent sequence identity to a reference sequence (for example, has at least about 80%, at least about 90%, at least about 95%, or at least about 97% sequence identity to a reference sequence or is 95%, 96%, 97%, 98% or 99% identical to the reference sequence) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981, *Advances in Applied Mathematics* 2: 482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host such as changing codons in the human mRNA to those preferred by a bacterial host such as *E. coli*.

The present invention further provides pharmaceutical compositions comprising antagonists (e.g., antibodies) that target a Notch receptor. These pharmaceutical compositions find use in inhibiting tumor cell growth and treating cancer in human patients.

Formulations are prepared for storage and use by combining a purified Notch-binding agent or antagonist (e.g., antibody) of the present invention with a pharmaceutically acceptable carrier, excipient, and/or stabilizer as a sterile lyophilized powder, aqueous solution, etc. (Remington, The Science and Practice of Pharmacy 20th Edition Mack Publishing, 2000). Suitable carriers, excipients, or stabilizers comprise: nontoxic buffers such as phosphate, citrate, and other organic acids; salts such as sodium chloride; antioxidants such as ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (less than about 10 amino acid residues); proteins such as serum albumin, gelatin, and immunoglobulins; hydrophilic polymers such as polyvinylpyrrolidone; amino acids such as glycine, glutamine, asparagine, histidine, arginine, and lysine; carbohydrates such as monosacchandes, disaccharides, glucose, mannose, and dextrins; chelating agents such as EDTA; sugars such as sucrose, mannitol, trehalose and sorbitol; salt-forming counter-ions such as sodium; metal complexes such as Zn-protein complexes; and/or non-ionic surfactants such as TWEEN and polyethylene glycol (PEG).

The pharmaceutical composition of the present invention can be administered in any number of ways for either local or systemic treatment. Administration can be topical (such as to mucous membranes including vaginal and rectal delivery) using transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal, intratumoral, or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g., water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc. of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antagonists (e.g., antibodies) of the present invention complexed with liposomes (Epstein, et al., 1985, *Proc. Natl. Acad. Sci. USA* 82:3688; Hwang, et al., 1980, *Proc. Natl. Acad. Sci. USA* 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antagonist (e.g., antibody) can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington's, The Science and Practice of Pharmacy, 20th Ed., Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g., films or microcapsules). Examples of sustained-release matrices include polyesters, hydrogels such as poly (2-hydroxyethyl-methacrylate) or poly(v nylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the Lupron Depot (injectable microspheres composed of lactic acid-glycolic acid copolymer and leuprolide acetate), sucrose acetate isobutyrate, and poly-D(-)-3-hydroxybutyric acid.

In certain embodiments, the pharmaceutical compositions comprise both the Notch-binding agent or antagonist and a second therapeutic agent. In certain embodiments, the second therapeutic agent is an anti-cancer agent and/or an anti-angiogenic agent.

The present invention provides methods for inhibiting the growth or proliferation of tumorigenic cells expressing a Notch receptor using the Notch receptor antagonists described herein. In some embodiments, the methods comprise inhibiting the growth of tumorigenic cells expressing a Notch2 and/or Notch3 receptor using any one the antibodies or polypeptides described herein. In some embodiments, the method of inhibiting the growth of tumorigenic cells expressing a Notch receptor comprises contacting the cell with an antagonist against a Notch receptor in vitro. For example, an immortalized cell line or a cancer cell line that expresses a Notch receptor is cultured in medium to which is added an antibody which specifically binds to Notch2 and/or Notch3 and inhibits cell growth. Or tumor cells and/or tumor stem cells are isolated from a patient sample such as, for example, a tissue biopsy, pleural effusion, or blood sample and cultured in medium to which is added an antibody which specifically binds to Notch2 and/or Notch3 and inhibits cell growth. In some embodiments, the antagonist is an antibody that specifically recognizes an epitope of a Notch2 and/or Notch3 receptor.

In some embodiments, the method of inhibiting the growth or proliferation of tumorigenic cells expressing a Notch receptor comprises contacting the cell with an antagonist against a Notch receptor (e.g., an antagonist of Notch2 and/or Notch3) in vivo. In certain embodiments, contacting a tumorigenic cell with an antagonist to a Notch receptor is undertaken in an animal model. For example, xenografts expressing a Notch receptor are grown in immunocompromised mice (e.g., NOD/SCID mice). The mice are administered an antagonist to the Notch receptor to inhibit tumor growth. Alternatively, cancer stem cells that express a Notch receptor are isolated from a patient sample such as, for example, a tissue biopsy, pleural effusion, or blood sample and injected into immunocompromised mice. The mice are then administered an antagonist against the Notch receptor to inhibit tumor cell growth. In some embodiments, the antagonist of a Notch receptor is administered at the same time or shortly after introduction of tumorigenic cells into the animal to prevent tumor growth. In other embodiments, the antagonist of a Notch receptor is administered as a therapeutic after the tumorigenic cells have grown to a specified size. In some embodiments, the antagonist is a Notch receptor protein fusion that specifically binds to a Notch receptor. In certain embodiments, the antagonist is an antibody that specifically recognizes an epitope of a Notch receptor. In some embodiments, the antibody is any one of the antibodies or polypeptides described herein.

In certain embodiments, contacting a tumorigenic cell with an antagonist to a Notch receptor is undertaken in a human patient diagnosed with cancer. In some embodiments, the antagonist is an antibody that specifically binds to a Notch receptor. In other embodiments, the antagonist is an antibody that specifically recognizes an epitope of a Notch receptor. For example, the invention provides method of inhibiting growth of a tumor in a subject, comprising administering to the subject a therapeutically effective amount of an antagonist of human Notch2 and/or Notch3. In some embodiments, the antagonist is an antibody that binds to Notch2. In some embodiments, the antagonist is an antibody that binds to Notch3. In some embodiments, the antagonist is an antibody that binds to Notch2 and Notch3. In some embodiments, the antagonist is an antibody or polypeptide as described in any one of the aforementioned aspects or embodiments, as well as any other aspects or embodiments described herein. In certain embodiments, the tumor comprises an inactivating deletion or mutation in the phosphatase and tensin homolog (PTEN) gene.

The invention further provides methods of inhibiting Notch signaling (e.g., Notch2 and/or Notch3) in a cell, comprising contacting the cell with an effective amount of the Notch antagonist. These methods may be in vivo or in vitro. In some embodiments, the Notch antagonist is an antibody. In some embodiments, the methods comprise inhibiting Notch2 signaling in a cell comprising contacting the cell with an effective amount of any one of the antibodies or polypeptides of the aforementioned aspects or embodiments, as well as any other aspects or embodiments described herein. In some embodiments, the Notch antagonist is an antibody. In some embodiments, the methods comprise inhibiting Notch3 signaling in a cell comprising contacting the cell with an effective amount of any of the antibodies or polypeptides of the aforementioned aspects or embodiments, as well as any other aspects or embodiments described herein.

The invention further provides a method of modulating the function of pericytes and/or vascular smooth muscle cells, comprising administering an effective amount of an antagonist of human Notch3 to the subject. In some embodiments, the method inhibits angiogenesis by modulating the function of pericytes and/or vascular smooth muscle cells. In some embodiments, the antagonist is an antibody or polypeptide as described in any of the aforementioned aspects or embodiments, as well as any other aspects or embodiments described herein. In certain embodiments, the vascular development that is inhibited is aberrant vascular development. In certain embodiments, the vascular development that is inhibited is in a tumor. In certain embodiments, the method further comprises administering to the subject an antagonist of VEGF or of a VEGF receptor.

In addition, the invention provides methods of inhibiting angiogenesis or vascular development in a subject, comprising administering an effective amount of a Notch antagonist to the subject. In certain embodiments, the Notch antagonist is a Notch3 antagonist. In certain embodiments, the Notch antagonist is a Notch2 antagonist. In certain embodiments, the antagonist is an antagonist of Notch2 and/or 3. In some embodiments, the antagonist is an anti-Notch2/3 antibody. In some embodiments, the methods of inhibiting angiogenesis comprises administering an antibody or polypeptide of any of the aforementioned aspects or embodiments, as well as any other embodiments or aspects described herein. In certain embodiments, the angiogenesis is tumor angiogenesis. In certain embodiments, the vascular development is at the site of a tumor. In certain alternative embodiments, the angiogenesis is not tumor angiogenesis. In certain embodiments, the inhibition of angiogenesis or vascular development is due, at least in part, to modulation of the function of pericytes and/or vascular smooth muscle cells. In certain embodiments, the method further comprises administering to the subject an antagonist of vascular endothelial cell growth factor (VEGF) or of a VEGF receptor.

Methods of reducing the tumorigenicity of a tumor (e.g., a tumor that comprises cancer stem cells) are also provided. In certain embodiments, the methods comprise administering to a subject in need thereof (e.g., subject has a tumor) a therapeutically effective amount of the Notch antagonist. In certain embodiments, the Notch antagonist is an antibody that binds Notch2. In certain embodiments, the Notch antagonist is an antibody that binds Notch3. In certain embodiments, the Notch antagonist is an antibody that binds Notch2 and Notch3. In certain embodiments, the Notch antagonist is an antibody or polypeptide of any of the aforementioned aspects or embodiments, as well as any other embodiments or aspects described elsewhere herein. In certain embodiments, the frequency of cancer stem cells in the tumor is reduced by administration of the antibody. In some embodiments, the tumor is a colorectal tumor, breast tumor, pancreatic tumor or melanoma.

It is further envisioned that the agents and antagonists of the present invention can be used to treat various conditions characterized by expression of and/or increased responsiveness of cells to a Notch receptor. The invention provides methods of treating proliferative disease, such as cancer, diseases associated with angiogenesis (e.g., angiogenesis-dependent diseases), and diseases in which the upregulation or deregulation of Notch signaling plays a role.

In certain embodiments the disease to be treated with the Notch-binding agents or antagonists is a Notch-related disease. In certain embodiments, the disease is characterized by upregulation or deregulation of Notch signaling (e.g., Notch2 and/or Notch3 signaling). In certain embodiments, the disease or tumor is Notch2 and/or Notch3-dependent.

Particularly, it is envisioned that the antagonists (e.g., antibodies) against a Notch receptor will be used to treat proliferative disorders including, but not limited to, benign and malignant tumors of the kidney, liver, bladder, breast, stomach, ovary, colon, rectum, prostate, lung, vulva, thyroid, head and neck, brain (glioblastoma, astrocytoma, medulloblastoma, etc.), blood and lymph (leukemias and lymphomas). In certain embodiments, the proliferative disorder that Notch-binding agent or antagonist is used to treat is colorectal cancer, breast cancer, pancreatic cancer, or melanoma. In certain embodiments, the cancer comprises cancer stem cells.

In certain embodiments, the tumors treated are solid tumors. Examples of solid tumors that can be treated using a therapeutic composition of the instant invention, for example, an antibody that binds Notch include, but are not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. The invention is applicable to sarcomas and epithelial cancers, such as ovarian cancers and breast cancers. In certain embodiments, the tumor is a colorectal tumor, breast tumor, pancreatic tumor, or melanoma. In certain embodiments, the tumor is an ovarian tumor. In certain embodiments, the tumor is a medulloblastoma. In certain embodiments, the tumor comprises cancer stem cells.

In certain embodiments, the disease to be treated with the Notch-binding agent or antagonist is a disease associated with angiogenesis. In certain embodiments, the disease is cancer. In certain other embodiments, the disease is not a cancerous condition. For example, the disease may be wet macular degeneration, age related macular degeneration, diabetic retinopathy, a hemangioma, rheumatoid arthritis, psoriasis, neovascular glaucoma, polycystic ovary disease, endometriosis and inflammatory bowel disorders.

In certain embodiments, the tumor expresses the Notch receptor or receptors to which the Notch-binding agent or antagonist is targeted. In certain embodiments, the tumor expresses Notch2 and/or Notch3. In certain embodiments, the tumor overexpresses Notch2 and/or Notch3. In certain embodiments, the tumor is dependent upon one or more Notch receptors to which the antibody administered specifically binds. For example, in certain embodiments, an antibody that specifically binds Notch2 (or Notch2 and Notch3) may be used to inhibit the growth or otherwise target the Notch2-dependent tumor. In certain embodiments, an antibody that specifically binds Notch3 (or Notch2 and Notch3) may be used to inhibit the growth or otherwise target the Notch3-dependent tumor. In certain embodiments, the tumor comprises cancer stem cells.

In certain embodiments, the tumor is homozygotic or heterozygotic for an inactivating deletion or mutation in the gene encoding the tumor suppressor phosphatase and tensin homolog (PTEN). In certain embodiments, the tumor comprising the deletion or mutation is a breast tumor.

The antagonists are administered as an appropriate pharmaceutical composition to a human patient according with known methods. Suitable methods of administration include intravenous administration as a bolus or by continuous infusion over a period of time, by intramuscular, intraperitoneal, intravenous, intratumoral, intraarterial, intracerobrospinal, subcutaneous, intra-articular, intrasynovial, intrathecal, oral, topical, or inhalation routes.

In certain embodiments, in addition to administering a Notch antagonist, the method or treatment further comprises administering a second therapeutic agent (prior to, concurrently with, and/or subsequently to administration of the Notch antagonist). In certain embodiments, the second therapeutic agent is an anti-cancer and/or anti-angiogenic agent. Pharmaceutical compositions comprising the Notch antagonist and the second therapeutic agent are also provided.

It will be appreciated that the combination of a Notch antagonist (e.g., antibody) and a second therapeutic agent may be administered in any order or concurrently. In selected embodiments, the Notch antagonists will be administered to patients that have previously undergone treatment with the second anti-cancer agent. In certain other embodiments, the Notch antagonist and the second therapeutic agent will be administered substantially simultaneously or concurrently. For example, a subject may be given the Notch antagonist while undergoing a course of treatment with the second therapeutic agent (e.g., chemotherapy). In certain embodiments, the Notch antagonist will be administered within 1 year of the treatment with the second therapeutic agent. In certain alternative embodiments, the Notch antagonist will be administered within 10, 8, 6, 4, or 2 months of any treatment with the second therapeutic agent. In certain other embodiments, the Notch antagonist will be administered within 4, 3, 2, or 1 week of any treatment with the second therapeutic agent. In some embodiments, the Notch antagonist will be administered within 5, 4, 3, 2, or 1 days of any treatment with the second therapeutic agent. It will further be appreciated that the two agents or treatment may be administered to the subject within a matter of hours or minutes (i.e., substantially simultaneously).

Useful classes of anti-cancer agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, performing compounds, purine antimetabolites, puromycins, radiation sensitizers, steroids, taxanes, topoisomerase inhibitors, vinca alkaloids, or the like. In certain embodiments, the second anti-cancer agent is an antimetabolite, a topoisomerase inhibitor, or an angiogenesis inhibitor.

Anticancer agents that may be administered in combination with the Notch antagonists include chemotherapeutic agents. Thus, in some embodiments, the treatment involves the combined administration of an antagonist of the present invention and a chemotherapeutic agent or cocktail of multiple different chemotherapeutic agents. Treatment with an antagonist can occur prior to, concurrently with, or subsequent to administration of chemotherapies. Chemotherapies contemplated by the invention include chemical substances or drugs which are known in the art and are commercially available, such as doxorubicin, 5-fluorouracil, cytosine arabinoside (Ara-C), cyclophosphamide, thiotepa, busulfan, cytoxin, taxol, methotrexate, cisplatin, melphalan, vinblastine and carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically. Preparation and dosing schedules for such chemotherapy are also described in Chemotherapy Service Ed., M. C. Perry, Williams & Wilkins, Baltimore, Md. (1992).

Chemotherapeutic agents useful in the instant invention also include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids such as paclitaxel (TAXOL) and doxetaxel (TAXOTERE, Rhone); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylomithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCL, daunorubicin citrate, mitoxantrone HCL, actinomycin D, etoposide, topotecan HCL, teniposide (VM-26), and irinotecan. In certain embodiments, the second anticancer agent is irinotecan. In certain embodiments, the tumor to be treated is a colorectal tumor and the second anticancer agent is a topoisomerase inhibitor, such as irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second anticancer agent is gemcitabine. In certain embodiments, the tumor to be treated is a pancreatic tumor and the second anticancer agent is an anti-metabolite (e.g., gemcitabine).

In other embodiments, the treatment involves the combined administration of an antagonist of the present invention and radiation therapy. Treatment with an antagonist can occur prior to, concurrently with, or subsequent to administration of radiation therapy. Any dosing schedules for such radiation therapy can be used.

In other embodiments, the treatment can involve the combined administration of antibodies of the present invention with other antibodies against additional tumor associated antigens including, but not limited to, antibodies that bind to the EGF receptor (EGFR) (e.g., Erbitux®), the erbB2 receptor (HER2) (e.g., Herceptin®), and vascular endothelial growth factor (VEGF) (e.g., Avastin®). In certain alternative embodiments, the second anti-cancer agent comprises an antibody that specifically binds to human DLL4 or other ligand of a Notch receptor or an antibody that specifically binds to an additional human Notch receptor. Exemplary, anti-DLL4 antibodies, are described, for example, in U.S. Patent Application Publication No. US 2008/0187532, incorporated by reference herein in its entirety. Additional anti-DLL4 antibodies are described in, e.g., International Patent Publication Nos. WO 2008/091222 and WO 2008/0793326, and U.S. Patent Application Publication Nos. US 2008/0014196, US 2008/0175847; US 2008/0181899; and US 2008/0107648, each of which is incorporated by reference herein in its entirety. Exemplary anti-Notch antibodies, are described, for example, in U.S. Patent Application Publication No. US 2008/0131434, incorporated by reference herein in its entirety. In certain embodiments, the second anti-cancer agent is an inhibitor of Notch signaling. In certain embodiments, the second anti-cancer agent is an antibody that is an angiogenesis inhibitor (e.g., an anti-VEGF antibody). In certain embodiments, the second therapeutic agent is an antibody that specifically binds a VEGF receptor. In certain embodiments, the second therapeutic agent is AVASTIN (bevacizumab), HERCEPTIN (trastuzumab), VECTIBIX (panitumumab), or ERBITUX (cetuximab). Combined administration can include co-administration, either in a single pharmaceutical formulation or using separate formulations, or consecutive administration in either order but generally within a time period such that all active agents can exert their biological activities simultaneously.

Furthermore, treatment can include administration of one or more cytokines (e.g., lymphokines, interleukins, tumor necrosis factors, and/or growth factors) or can be accompanied by surgical removal of cancer cells or any other therapy deemed necessary by a treating physician.

For the treatment of the disease, the appropriate dosage of an antagonist of the present invention depends on the type of disease to be treated, the severity and course of the disease, the responsiveness of the disease, whether the antagonist is administered for therapeutic or preventative purposes, previous therapy, patient's clinical history, and so on, all at the discretion of the treating physician. The antagonist can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antagonist. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

In certain embodiments, the patients under consideration for treatment with the Notch antagonist are screened prior to treatment with the Notch antagonist. In certain embodiments, a tumor in a patient or a tumor that has been removed from a patient is tested for the presence of cancer stem cells. In certain embodiments, the tumor is tested for expression of the one or more Notch receptors (e.g., Notch2 and/or Notch3) to which the antagonist binds. In certain embodiments, the tumor is tested for the presence of an inactivating deletion or mutation in the gene encoding the tumor suppressor phosphatase and tensin homolog (PTEN). In certain embodiments, the tumor so tested is a breast tumor.

For example, the invention provides a method of selecting a subject for treatment with a Notch2 and/or Notch 3 antagonist, wherein the subject has a tumor or has had a tumor removed. In certain embodiments, the method comprises (a) determining if the tumor comprises a deletion or mutation in the PTEN gene, and (b) selecting the subject for treatment with the Notch 3 antagonist if the tumor comprises the deletion or mutation.

In certain alternative embodiments of the present invention, patients screened for the presence of colon adenomas or polyps are tested for allelic loss and somatic mutations via a genetic test. In some embodiments the genetic test screens for loss or mutations in the Wnt pathway including, for example, in APC, Axin2 or beta-catenin.

In another aspect, the present invention provides kits that can be used to perform the methods described herein. In some embodiments, a kit comprises an antibody or antibodies specific for a Notch receptor, a purified antibody or antibodies, in one or more containers. In some embodiments, a kit further comprises a substantially isolated Notch receptor comprising an epitope that is specifically immunoreactive with the antibody or antibodies included in the kit, a control antibody that does not react with the Notch receptor, and/or a means for detecting the binding of an antibody to a Notch receptor (such as, for example, a fluorescent chromophore, an enzymatic substrate, a radioactive compound or a luminescent compound conjugated to the antibody against a Notch receptor or to a second antibody that recognizes the antibody against a Notch receptor). In other embodiments, a kit comprises reagents specific for the detection of mRNA or cDNA (e.g., oligonucleotide probes or primers) of one or more Notch receptor. In some embodiments, the kits contain all of the components necessary and/or sufficient to perform a detection assay, including all controls, directions for performing assays, and any necessary software for analysis and presentation of results.

A compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies or probes used in the methods, containers which contain wash reagents (such as phosphate buffered saline, Tris-buffers, etc.), and containers which contain the reagents used to detect the bound antibody or probe. One will readily recognize that the disclosed polynucleotides, polypeptides and antibodies of the present invention can be readily incorporated into one of the established kit formats which are well known in the art.

In some embodiments, the invention further provides a kit comprising a Notch-binding agent or antagonist and a second therapeutic agent. In certain embodiments, the Notch-binding agent or antagonist is an antibody that specifically binds to Notch 2 and/or Notch3. In certain embodiments, the Notch-binding agent or antagonist is an antibody that specifically binds to Notch 2 and Notch3. In certain embodiments, the second therapeutic agent is an anti-cancer agent and/or an anti-angiogenic agent.

In one aspect, the present invention provides a method of identifying a molecule that binds to a non-ligand binding region of an extracellular domain of a human Notch receptor and inhibits tumor growth, the method comprising: i) incubating the molecule with the non-ligand binding domain of the extracellular domain of the human Notch receptor; ii) determining if the molecule binds to the non-ligand binding region of the extracellular domain of the human Notch receptor; and iii) determining if the molecule inhibits tumor growth. Molecules that specifically bind a non-ligand binding region of an extracellular domain of a human Notch receptor include, but are not limited to, small organic molecules, polypeptides, and antibodies.

Screening can be performed using any suitable method known in the art. In certain embodiments, screening is performed in vitro. In some embodiments, cells expressing a non-ligand binding region of the extracellular domain of a human Notch receptor are incubated with a labeled molecule and specific binding of the labeled molecule to a non-ligand binding region of the extracellular domain of a human Notch receptor is determined by FACS analysis. In some embodiments, a non-ligand binding region of the extracellular domain of a human Notch receptor is expressed by phage display, and molecules that specifically bind to a non-binding region of the extracellular domain of a human Notch receptor are identified. Other suitable methods for identifying molecules that specifically bind to a non-ligand binding region of a human Notch receptor include, but are not limited to, ELISA, Western (or immuno) blotting, and yeast-two-hybrid.

Molecules that specifically bind to a non-ligand binding region of an extracellular domain of a human Notch receptor are then tested for inhibition of tumor cell growth. Testing can be performed using any suitable method known in the art. In certain embodiments, molecules that specifically bind to non-ligand binding region of the extracellular domain of a human Notch receptor are tested for the ability to inhibit tumor growth in vitro. In some embodiments, molecules that specifically bind a non-ligand binding region of the extracellular domain of a human Notch receptor are incubated with tumor cells in culture and proliferation of tumor cells in the presence of a molecule that specifically binds a non-ligand binding region of the extracellular domain of a human Notch receptor is determined and compared to tumor cells incubated with a non-binding control molecule. In certain embodiments, molecules that specifically bind to non-ligand binding region of the extracellular domain of a human Notch receptor are tested for the ability to inhibit tumor growth in vivo. In certain embodiments, molecules that specifically bind a non-ligand binding region of the extracellular domain of a human Notch receptor are injected into an animal xenograft model and the growth of tumors in animals treated with molecules that specifically bind to non-ligand binding region of the extracellular domain of a human Notch receptor is determined and compared to animals treated with a non-binding control molecule.

Briefly, $2 \times 10^{13}$ Fab displaying phage particles were incubated with a passively immobilized, recombinant Notch2 Fc fusion protein (SEQ ID NO:21) comprising the extracellular ligand binding site of Notch2 and surrounding EGF repeats (EGF1-12) in round one. The non-specific phage were washed off, and then the specific phage were eluted with DTT. The eluted output was used to infect TG1 F+bacteria, rescued with helper phage, and then Fab display induced with IPTG (0.25 mM). This process was repeated for two additional rounds and then round three was screened in ELISA against passively immobilized recombinant Notch2 (EGF1-12) Fc fusion (5 µg/ml).

Figure 1A:
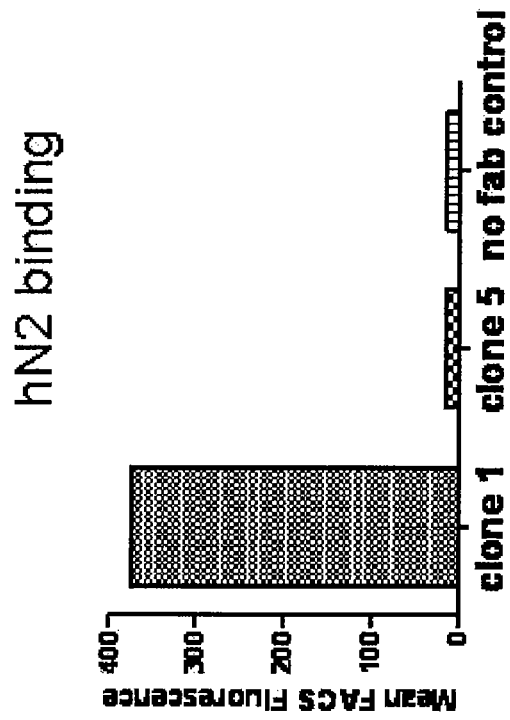
Figure 1C:
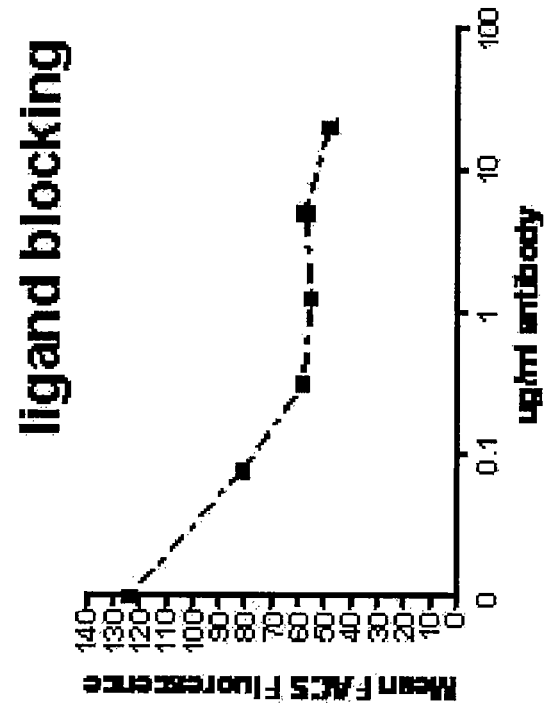

A particular Fab (59R1) was identified that bound the human Notch2 receptor and blocked binding of Jagged1 to human Notch2. Binding of the 59R1 Fab to human Notch2 was verified by FACS assay using a stable human cell line HEK-293 which overexpressed human Notch2 (hN2) (FIG. 1A). Fab binding was detected by phycoerythrin (PE)-conjugated goat anti-human Fab (Jackson Immunochemicals). The 59R1 Fab (referred to in FIG. 1A as clone 1) demonstrated good binding to hN2. The 59R1 Fab also demonstrated good blocking activity against the Notch ligand human Jagged1 in a binding assay using the same stable cell line (FIG. 1B). Ligand binding and blocking was determined by incubating hJagged 1 extracellular domain (ECD) fused to human Fc constant region with the cells and Fabs selected from the phage library and using PE-conjugated goat anti-human Fc gamma specific antibodies (Jackson Immunochemicals) for detection.

The sequences of the VH and VL of the 59R1 Fab are provided in SEQ ID NO: 11 and SEQ ID NO: 12 (including N-terminus bacterial signal sequences that are cleaved upon secretion), respectively. The CDRs of the 59R1 Fab are as indicated in Table 2 below.

TABLE 2

CDRs of 59R1 human Fab and IgG antibodies

| | Heavy Chain | | | Light Chain | | |
|---|---|---|---|---|---|---|
| Lead | CDR1 | CDR2 | CDR3 | CDR1 | CDR2 | CDR3 |
| 59R1 | SSSGMS (SEQ ID NO: 5) | VIASSGSNTYYADSVKG (SEQ ID NO: 6) | GIFFAI (SEQ ID NO: 7) | RASQSVRSNYLA (SEQ ID NO: 8) | GASSRAT (SEQ ID NO: 9) | QQYSNFPI (SEQ ID NO: 10) |

EXAMPLES

It is understood that the examples and embodiments described herein are for illustrative purposes only and that various modifications or changes in light thereof will be suggested to persons skilled in the art and are to be included within the spirit and purview of this application.

Example 1

Production of Human Antibodies to Notch2

Human antibodies that specifically recognize the non-ligand binding portion of the extracellular domain of a Notch2 receptor were isolated using phage display technology. A synthetic antibody library containing human antibody variable domains was screened for specific and high affinity recognition of a Notch2 receptor.

Variable regions based on those of the 59R1 Fab were cloned into Ig expression vectors containing human IgG2 heavy-chain and kappa light-chain along with their respective mammalian signal sequences for expression in Chinese Hamster Ovary (CHO) cells. The VH and VL of the 59R1 IgG antibody are provided as SEQ ID NO: 13 and SEQ ID NO: 14, respectively. The amino acid sequence of the heavy chain and light chain of the 59R1 IgG antibody (including signal sequences) are provided as SEQ ID NO: 16 and SEQ ID NO: 18, respectively. The signal sequence at the N-terminus of the amino acid sequence of each of the chains is cleaved upon secretion. The nucleic acid sequences encoding the heavy and light chains of the 59R1 IgG antibody are provided as SEQ ID NO: 1 and SEQ ID NO: 3, respectively. Protein A purification was used to purify the antibodies. Bacterial plasmid DNA containing a synthetic DNA insert encoding the heavy and light chain of the 59R1 IgG2 antibody DNA was deposited as "59R1" with the ATCC, 10801 University Boulevard, Manassas, Va., USA, under the conditions of the Budapest Treaty on Oct. 15, 2008, and assigned designation number PTA-9547.

Figure 1D:
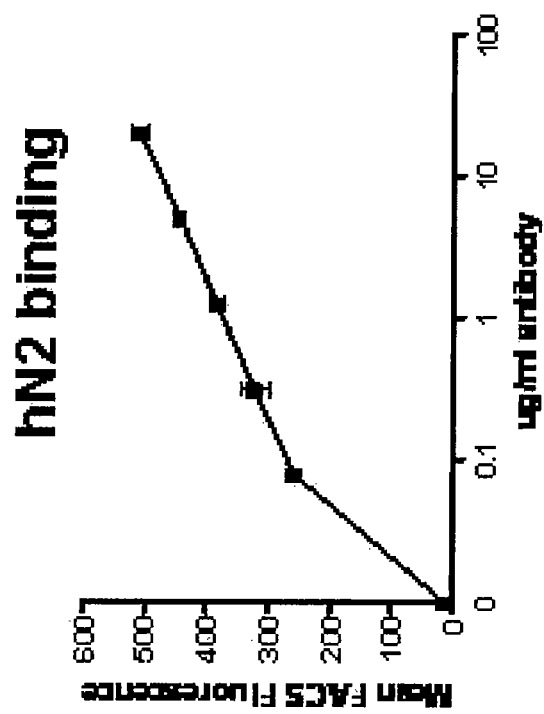

In addition, the 59R1 IgG2 antibody was assayed for its ability to block binding of DLL4 to the human Notch 2 receptor by FACS analysis. HEK-293 cells stably overexpressing human Notch2 were incubated with the antibody at various concentration and then detected for hNotch2 binding (FIG. 1C) by PE-conjugated goat anti-human Fc gamma specific antibody, or ligand blocking activity (FIG. 1D). Ligand blocking was determined by incubating the cells with human DLL4 ECD tagged with the rabbit Fc constant region and the 59R1 antibody at a range of concentrations, and then detecting the hDLL4 by PE-conjugated donkey anti-rabbit antibody. Binding of hNotch2 and ligand blocking activity were thus confirmed for the 59R1 IgG2 antibody.

A germlined variant of 59R1 (referred to herein as "59RGV") was also expressed and purified. The VH and VL of the 59RGV antibody are provided as SEQ ID NO: 19 and SEQ ID NO: 20, respectively. The amino acid sequence of the heavy chain and light chain of the 59RGV antibody (including signal sequences) are provided as SEQ ID NO: 2 and SEQ ID NO: 4, respectively. The signal sequence at the N-terminus of the amino acid sequence of each of the chains is cleaved upon secretion. The nucleic acid sequences encoding the heavy and light chains of the 59RGV antibody are provided as SEQ ID NO: 15 and SEQ ID NO: 17, respectively.

Figure 1E:
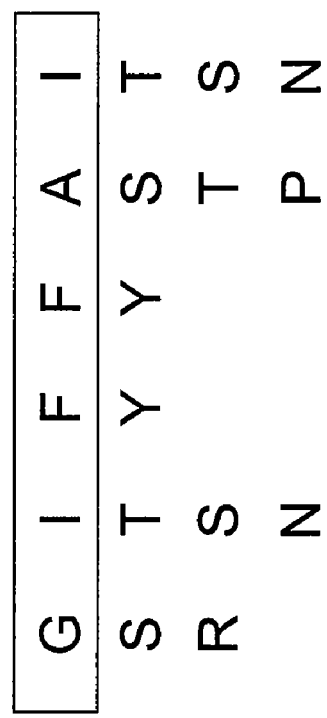
Figure 1F:
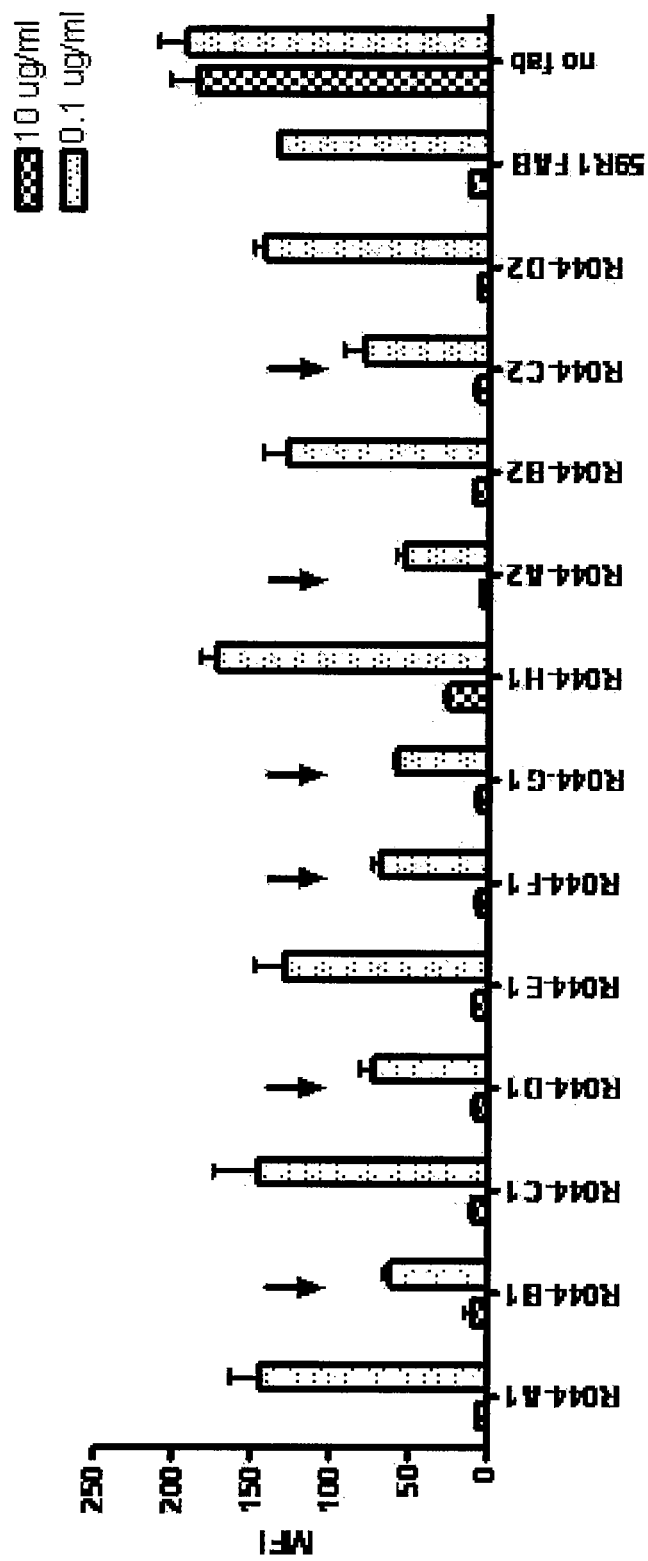

Highly hydrophobic CDRs have the potential, in certain instances, to allow for unfavorable, non-specific binding by an antibody. Since the amino acid sequence of the heavy chain CDR3 of 59R1 had an unusual degree of hydrophobic character, variants of 59R1 that contained heavy chain CDR3 sequences with decreased hydrophobic character were produced. Heavy chain CDR3 affinity maturation was conducted by allowing restricted changes from the parental sequence (GIFFAI; SEQ ID NO:7) as shown in FIG. 1E. Allowed amino acids at each position were allowed to change from parental residues to the residues indicated in FIG. 1E. Improved variants were isolated by screening them for improved JAG1 blocking ability as shown in FIG. 1F (indicated with arrows). Briefly, Fabs (1 and 10 µg/ml) were mixed with hJAG1-rb Fc (preclustered 5 µg/ml to 2 µl/ml PE-conjugated donkey anti-rabbit) and then added to hNotch2 stably transfected 293 cells. hJAG1 binding was then assessed using flow cytometry. Six improved variants (versus 59R1 Fab) were isolated and their HC CDR3 sequences were as follows: SIFYPT (SEQ ID NO:22), SSFFAS (SEQ ID NO:23), SSFYAS (SEQ ID NO:24), SSFFAT (SEQ ID NO:25), SIFYPS (SEQ ID NO:26), and SSFFAN (SEQ ID NO:27). The sequences of the heavy chain variable regions for these variants are sequences SEQ ID NO:52, SEQ ID NO:53, SEQ ID NO:54, SEQ ID NO:55, SEQ ID NO:56, and SEQ ID NO:57.

Example 2

Cross-Reactivity and Binding Affinity of Anti-Notch2/3 59R1 Antibody

The ability of the 59R1 IgG2 antibody to cross-react with other Notch receptors was determined by FACS assay using HEK-293 cells transiently transfected with the human Notch1, Notch2, Notch3 or Notch4 expression plasmid and green fluorescent protein (GFP) as a transfection control. GFP positive cells indicated expression of the transgene. The 59R1 IgG2 was added to the cells at 2 µg/ml and detected by PE-conjugated goat anti-human Fc gamma specific (Jackson Immunochemicals). All Notch constructs were full length. The results are shown in FIG. 2. As shown in FIG. 2, the 59R1 IgG2 antibody specifically binds to both human Notch3 and human Notch2, but does not bind significantly to full-length human Notch1 or human Notch4.

The affinities for human and mouse Notch1, Notch2, Notch3, and Notch4 were determined using a Biacore 2000 instrument. Briefly, recombinant human and mouse Notch proteins (EGF10-15 for Notch1, 2, & 4; EGF9-14 for Notch3) were immobilized on a CM5 chip using standard amine based chemistry (NHS/EDC). For hNotch2, EGF1-12 was also tested for binding. Different antibody concentrations (1-100 nM) were injected over the protein surfaces and kinetic data were collected over time. The data was fit using the simultaneous global fit equation to yield dissociation constants ($K_D$, nM) for each Notch (Table 3).

TABLE 3

| | 59R1 IgG Dissociation Constants ($K_D$) | | | | | | | |
|---|---|---|---|---|---|---|---|---|
| Ab | mNotch1 (nM) | hNotch1 (nM) | mNotch2 (nM) | hNotch2 (nM)* | hNotch2 (nM)** | mNotch3 (nM) | hNotch3 (nM) | hNotch4 (nM) |
| 59R1 | >10 | 86.4 | 0.35 | <0.1 | <0.1 | 0.13 | 0.12 | NB |

*N2(EGF1-12)
**N2(EGF 10-155)

Example 3

Epitope Mapping of Anti-Notch2/3 Antibody 59R1

To identify antibodies that recognize specific non-ligand binding regions of the Notch receptor extracellular domains, epitope mapping was performed.

The binding of anti-Notch2/3 antibodies to supernatant from HEK 293 cells transfected with sequences encoding recombinant human Notch2 Fc fusion proteins comprising the full length human Notch2 protein or various human Notch2 deletion constructs containing various deletions of EGF repeats one to twelve were tested by ELISA. See Table 4 below. HEK-293 cells were transiently transfected with pcDNA 3.1 (Invitrogen) with hNotch2 cDNA's encoding for the indicated amino acids fused to the constant region of human IgG (hFc). Supernatants were harvested 48 hours later. To capture hN2hfc proteins, 96 well plates were first coated with goat anti-human Fc gamma specific IgG (Jackson Immunochemicals, #109-006-098) at 100 ng per well in sodium bicarbonate buffer overnight at 4°. Plates were washed and blocked in 5% bovine serum/PBS-Tween-20. Supernatants were added to plates and incubated at room temperature for 1 hour. Plates were washed in P135-T. 59R1 Fab was added at 10 µg/ml in 5% serum/PBS-T and incubated at room temperature for 1 hour. Plates were washed in PBS-T. Fab binding was detected by goat anti-human Fab specific antibody conjugated to horseradish peroxidase (Thermo,

31414) diluted 1:5000 in 5% serum/PBS-T for 1 hour at room temperature. Plates were washed and developed with 1 Step Ultra TMB (Thermo, #34028). Plates were read on a Perkin Elmer Victor 1420 plate reader. Anti-Notch2/3 59R1 antibody bound only to supernatant from cells expressing recombinant Notch2 proteins comprising EGF10, which consists of amino acids 375-417 of human Notch 2. (FIG. 3A).

TABLE 4

Human Notch2 deletion constructs

| Construct | amino acids |
| --- | --- |
| hN2 1-3 | 1-144 |
| hN2 1-4 | 1-181 |
| hN2 1-5 | 1-221 |
| hN2 1-6 | 1-263 |
| hN2 1-7 | 1-301 |
| hN2 1-8 | 1-341 |
| hN2 1-9 | 1-378 |
| hN2 1-10 | 1-417 |
| hN2 1-11 | 1-456 |
| hN2 1-12 | 1-493 |
| hN2 8-12 | 296-493 |
| hN2 9-12 | 326-493 |
| hN2 10-12 | 375-493 |
| hN2 11-12 | 413-493 |
| hN2 12-12 | 454-493 |

Moreover, FACS analysis shows that 59R1 Fab antibody binding was retained when EGF11 or EGF12 were deleted from full length Notch2 recombinant protein expressed by HEK 293 cells (FIG. 3B). Point mutations were made within EGF10 of Notch2 fusion proteins and binding of 59R1 to each EGF10 mutant was determined by FACS analysis. HEK-293 cells were transiently transfected with the indicated Notch expression plasmid and GFP as a transfection control. GFP positive cells indicated expression of the transgene. The 59R1 Fab antibody was added to the cells at 10 μg/ml and detected by PE-conjugated goat anti-human (Jackson Immunochemicals).

To verify that loss of EGF repeat 10 does not interfere with ligand binding, a mutant hNotch2 missing amino acids 375-412 was generated and tested for binding to 59R1, a hNotch2 monoclonal 59M70 directed against EGF 1-4, and binding to the ligand human DLL4 (FIG. 3C). FACS analysis of HEK-293 cells transiently transfected with the indicated Notch expression plasmid and GFP as a transfection control. GFP positive cells indicate expression of the transgene. Anti-Notch2 (59M70) was added at 20 μg/ml and detected by PE-conjugated goat anti-mouse (Caltag, #3004-4). 59R1 (IgG2) was added to the cells at 2 μg/ml and detected by PE-conjugated goat anti-human Fc gamma specific (Jackson Immunochemicals). Ligand binding was determined by incubation of the cells with human DLL4 extracellular domain (ECD) fused to rabbit IgG constant region at 5 μg/ml and detected by PE-conjugated donkey anti-rabbit. As shown in FIG. 3C, ligand and 59M70 both bind to hNotch2 in the absence of EGF 10, but 59R1 does not.

A comparison analysis of the EGF 10 regions of human Notch1, Notch2, and Notch4 and the EGF 9 region of human Notch3 (the equivalent of EGF 10 in the other Notch receptors) was performed to determine likely binding sites for 59R1 (FIG. 14A). As a result of the analysis, several point mutants were created within full-length Notch2, converting residues within EGF 10 to the corresponding amino acids in human Notch 1. Also, conversely, point mutations were made in hNotch1 EGF 10 converting residues to the corresponding hN2 residues. Mutants in full-length Notch sequences were generated by QuikChange® mutagenesis (Stratagene) and verified by sequencing. Binding to the mutants was determined by FACS analysis (FIGS. 14B and 14C). 59R1 was detected by PE-conjugated goat anti-human Fc gamma specific antibody (Jackson Immunochemicals, #109-116-170). The amino acids necessary for 59R1 binding to hNotch 2 were thus determined to be histidine 385, alanine 388, and leucine 389 (residues within the boxed hNotch2 sequence shown in FIG. 14A). The corresponding residues in hNotch3 are histidine 361, alanine 364, and isoleucine 365.

Example 4

Anti-Notch2/3 Antibody 59R1 Inhibits Notch2 Signaling

Luciferase reporter assays were used to assay the 59R1 antibody for its ability to block hDLL4-, hJAG1-, and hJAG2-induced Notch2 signaling.

Figure 4A:
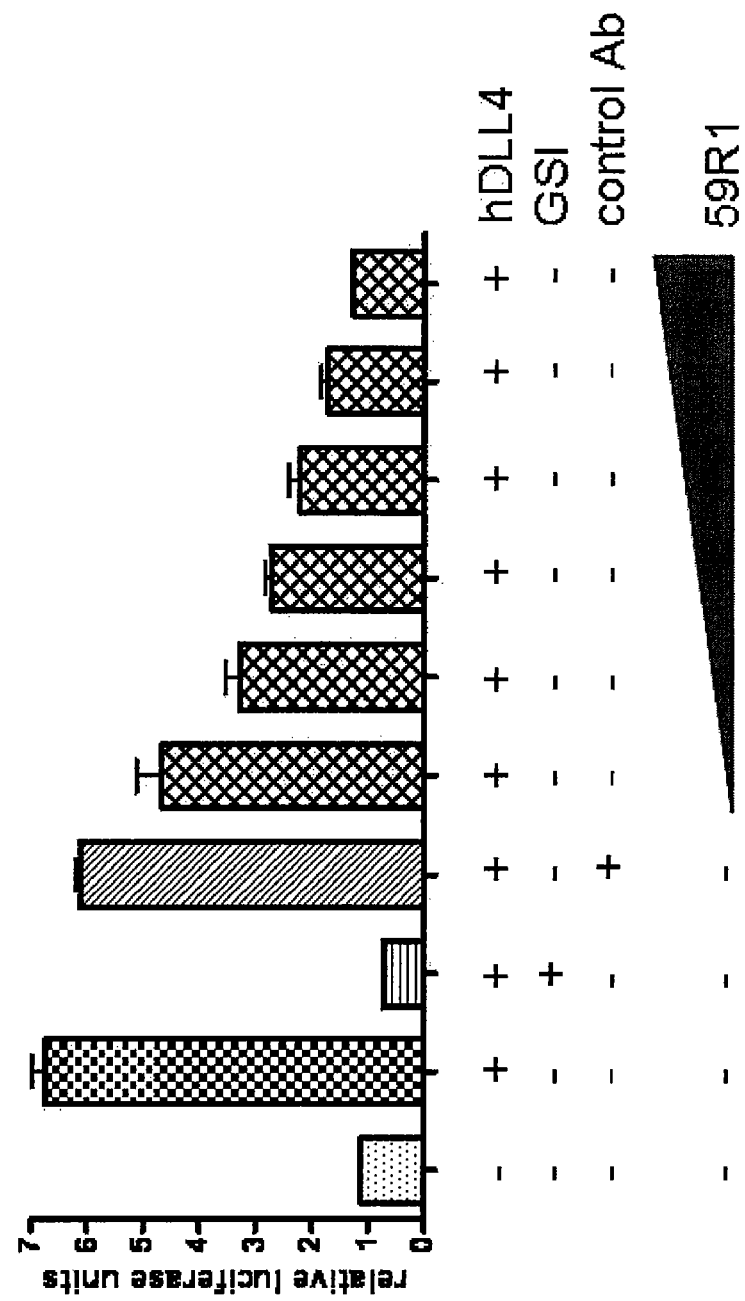

Hela cells that stably overexpress human Notch2 were transiently transfected with firefly luciferase with a synthetic 8×CBS promoter (Ong et al., 2006, *J. of Biological Chemistry*, 281:5106-5119), pSPORT6 MAML-1, and *Renilla* luciferase-CMV as a transfection control. Cells were incubated with 100 ng of immobilized hDLL4 (R&D systems) with the indicated antibodies for 16 hours and then assayed using Dual-Glo (Promega) according to the manufacturer's instructions. Control antibody was at a concentration of 40 μg/ml. 59R1 IgG2 antibody was titrated, starting at 40 μg/ml, and then diluted by one-fourth. The gamma secretase inhibitor (GSI) dibenzazepine (DBZ) was used as a control at 1 μM. As shown in FIG. 4A, the 59R1 antibody was found to inhibit hDLL4-induced Notch2 reporter activity.

Figure 4B:
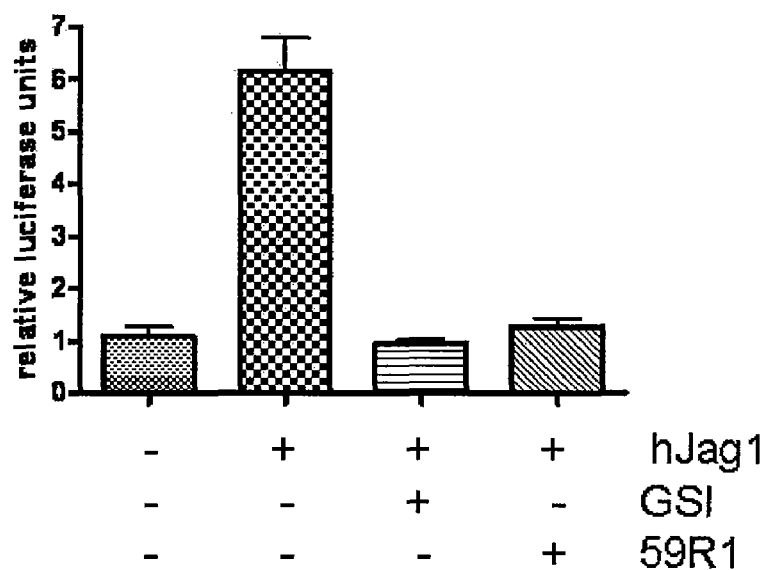
Figure 4C:
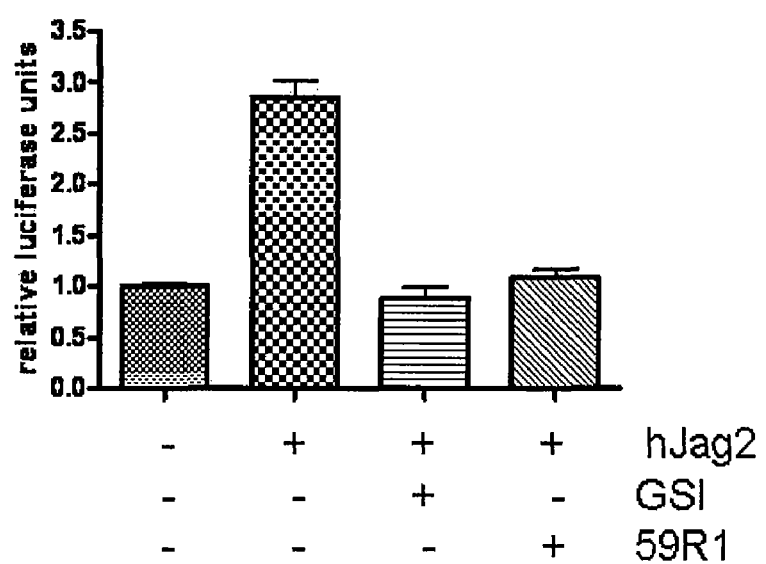

Hela cells that stably overexpress human Notch2 were transiently transfected with firefly luciferase with a synthetic 8×CBS promoter, pSPORT6 MAML-1, and *Renilla* luciferase-CMV as a transfection control. Cells were incubated with either 200 ng of immobilized hJAG1 (R&D systems) or hJAG2 (R&D systems) for 16 hours and then assayed using Dual-Glo (Promega) according to the manufacturer's instructions. 59R1 IgG2 antibody was at a concentration of 40 μg/ml. The gamma secretase inhibitor (GSI) dibenzazepine (DBZ) was used as a control at 1 μM. As shown in FIGS. 4B and 4C, the 59R1 antibody was found to inhibit both hJAG1- and hJAG2-induced Notch2 reporter activity, respectively.

Example 5

Anti-Notch2/3 Antibody 59R1 Prevents In Vivo Tumor Growth

This example describes the use of an anti-Notch2/3 receptor antibody (59R1) that binds a non-ligand binding region of the Notch receptors (EGF10 of Notch2 and EGF10 of Notch3) to prevent tumor growth in a xenograft model.

In certain embodiments, NOD/SCID mice injected with 50,000 PE13 or T3 breast tumor cells were treated with anti-Notch2/3 antibody 59R1 or control antibody 1B7.11 two days following cell injections. Antibodies were dosed at 10 mg/kg twice week. Anti-Notch2/3 antibody 59R1 significantly reduced both PE13 (FIG. 5A) and T3 (FIG. 5B) tumor growth compared to control.

Example 6

In Vivo Treatment of Tumors Using Anti-Notch 2/3 Antibody 59R1

This example describes the use of anti-Notch 2/3 antibodies to treat cancer in a xenograft model.

Figure 5A:
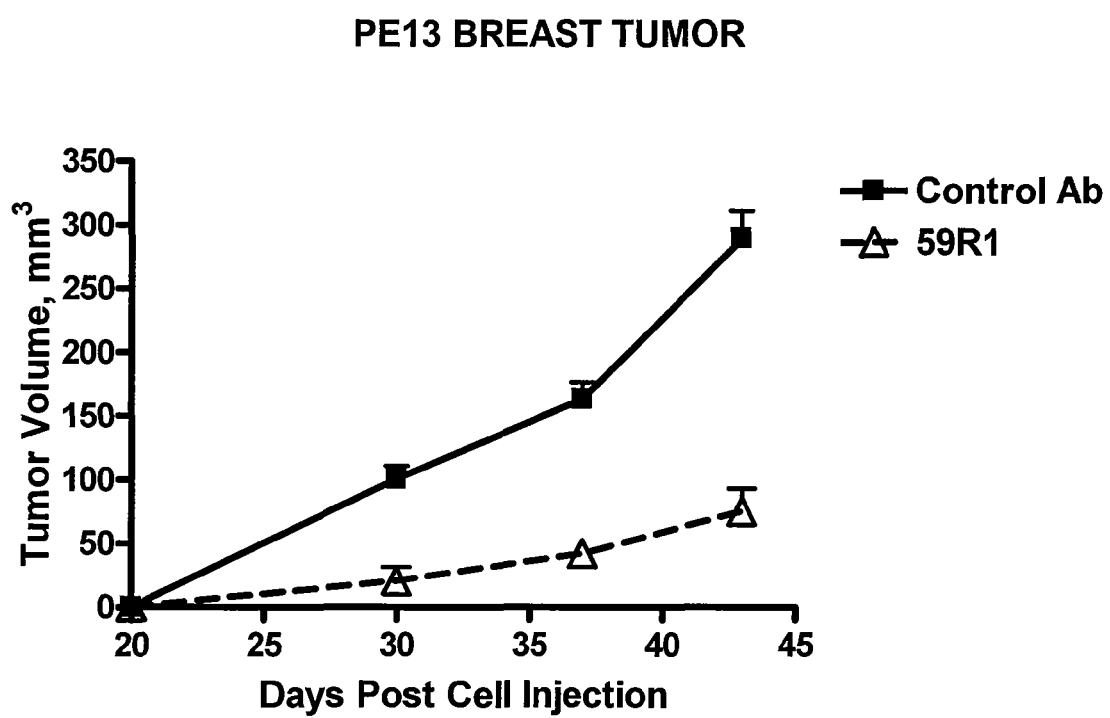
Figure 5B:
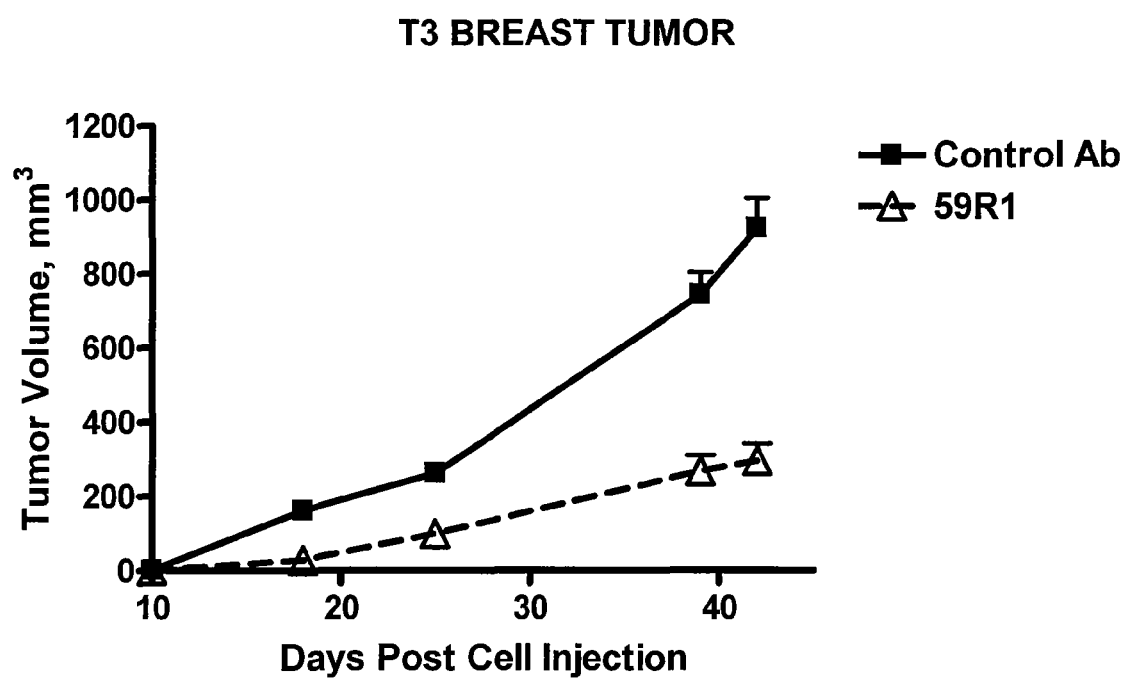
Figure 5C:
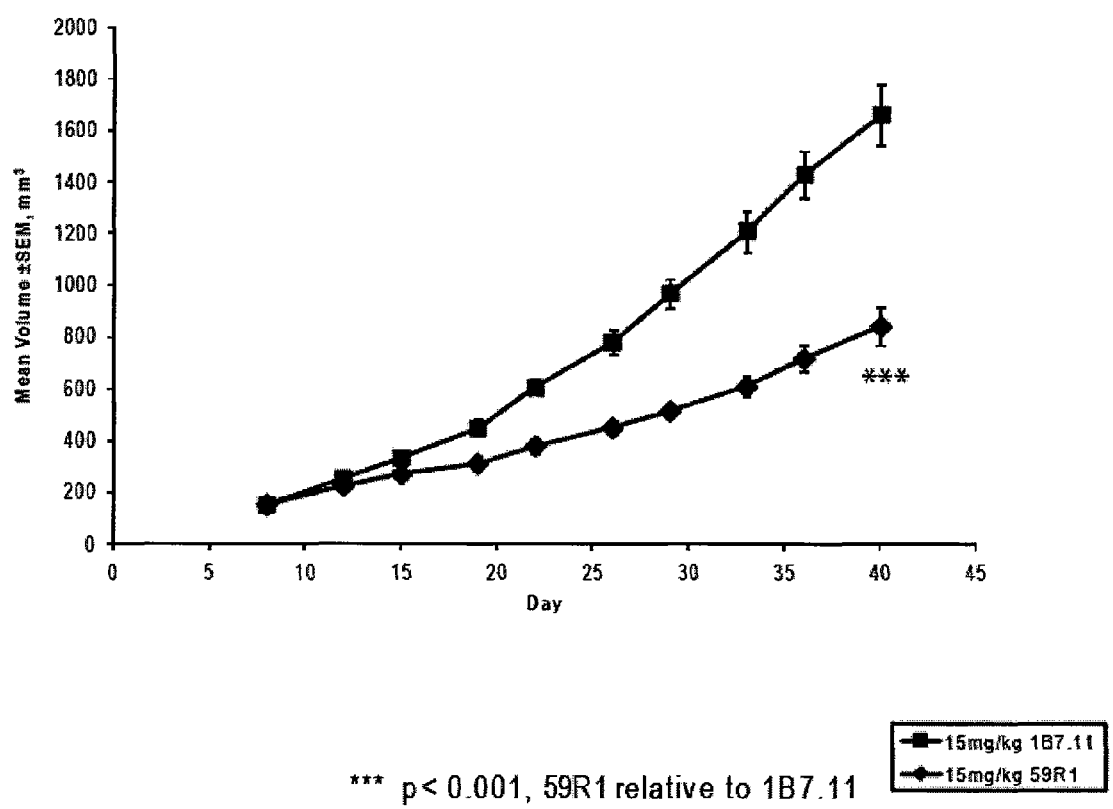

In one experiment, the 1×10⁷ viable Colo-205 colon tumor cells were injected into 6-8 week-old immunodeficient bg/nu XID female mice on a Swiss CD-1 background. Tumors were allowed to grow to a size of between 65 to 200 mm³ after which mice were randomized (n=10 per experimental group), and antibodies administration begun. Animals were treated with 15 mg/kg of either control 1B7.11 antibodies or anti-Notch2/3 59R1 antibodies once weekly. Tumor size was measured twice weekly, and tumor volume was calculated as described (see Michieli et al., 2004, *Cancer Cell*, 6:61-73). Anti-Notch2/3 antibody 59R1 significantly reduced Colo-205 tumor growth compared to control (FIG. 5C).

Figure 5D:
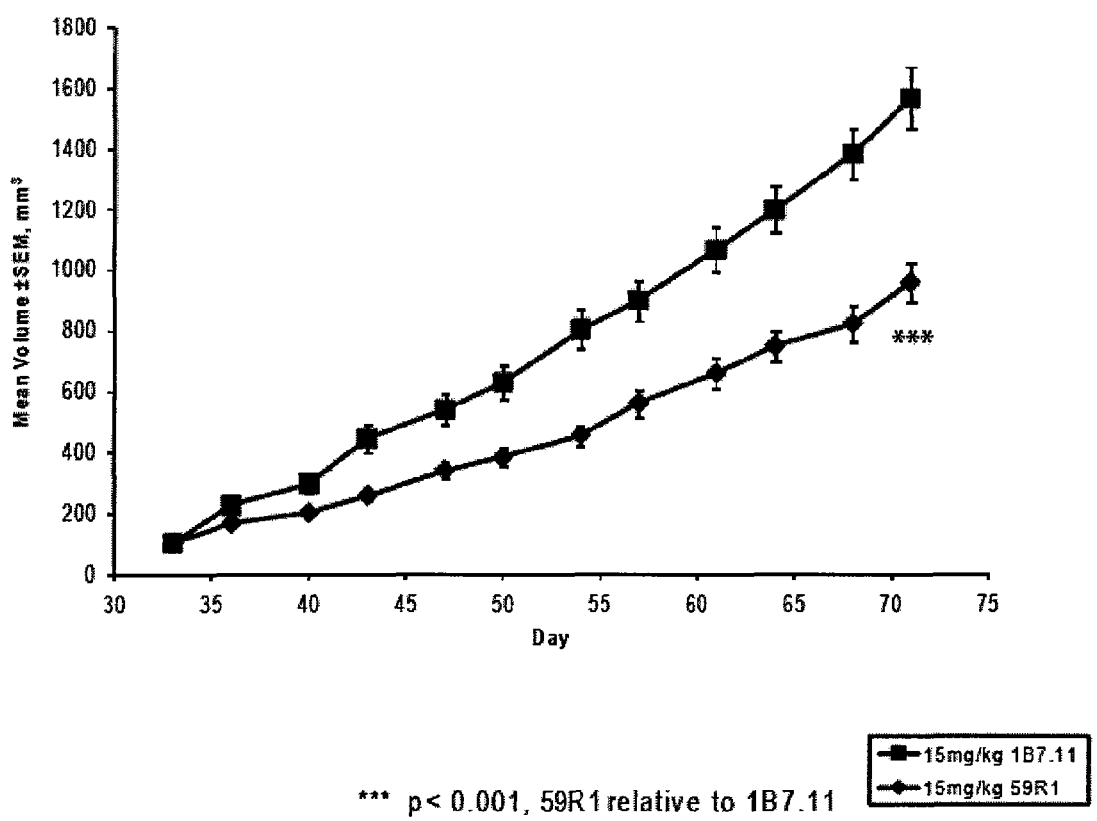
Figure 5E:
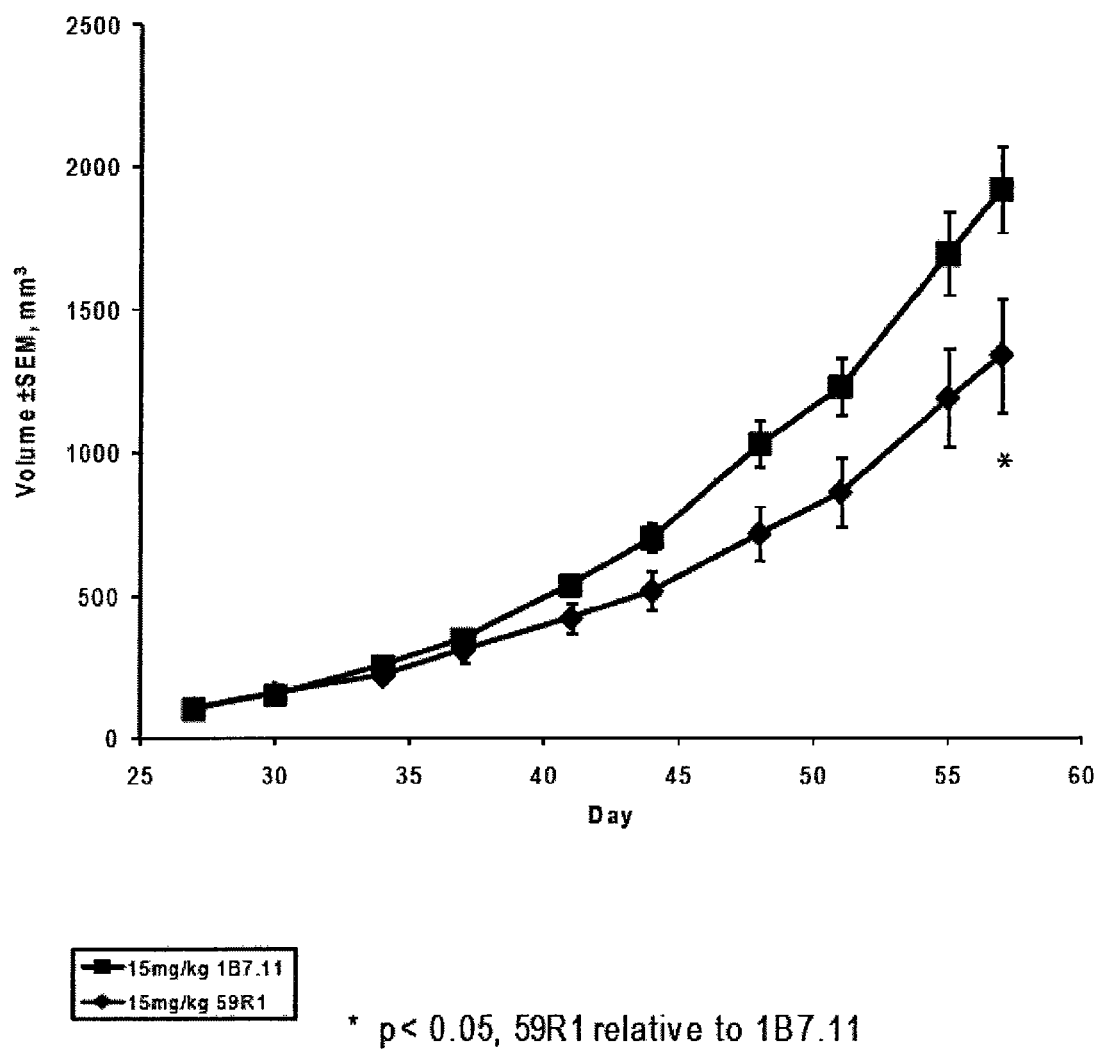
Figure 5F:
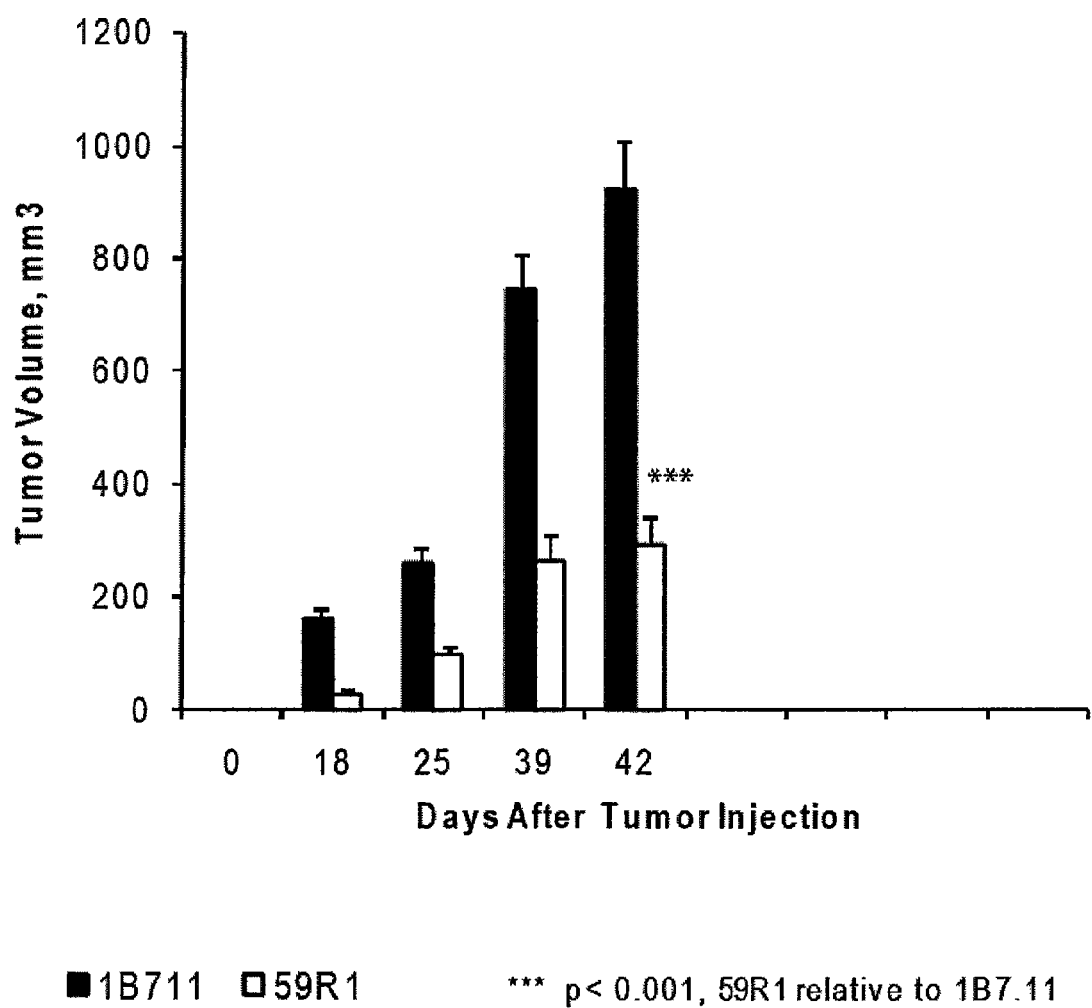

In another experiment, anti-Notch2/3 antibodies were tested for an effect on pancreatic tumor growth. NOD/SCID mice were injected with 30,000 PN4 pancreatic tumor cells sub-cu in the right flank, and tumors were allowed to grow until they had reached an average volume of 100 mm³. Animals were randomized and dosing of anti-Notch2/3 antibody 59R1 or control antibody 1B711 was initiated. Antibodies were dosed at 15 mg/kg given once per week. Anti-Notch2/3 antibody 59R1 significantly reduced PN4 tumor growth compared to control (FIG. 5D).

In a further experiment, anti-Notch2/3 antibodies were tested for an effect on breast tumor growth. NOD/SCID mice were injected with 50,000 PE13 or T3 breast tumor cells, and tumors were allowed to grow to a size of between 65 to 200 mm³ after which mice were randomized (n=10 per experimental group), and antibodies administration begun. Animals were treated with 15 mg/kg of either control 1B7.11 antibodies or anti-Notch2/3 59R1 antibodies twice weekly. Tumor size was measured twice weekly, and tumor volume was calculated as described (see Michieli et al., 2004). Anti-Notch2/3 antibody 59R1 significantly reduced growth of both PE13 (FIG. 5E) and TE (FIG. 5F) tumors compared to control.

At the end point of antibody treatment, tumors may be harvested for further analysis. In some embodiments, a portion of the tumor is analyzed by immunofluorescence to assess antibody penetration into the tumor and tumor response. A portion of each harvested tumor from anti-Notch2/3 antibody treated and control antibody treated mice is fresh-frozen in liquid nitrogen, embedded in O.C.T., and cut on a cryostat as 10 µm sections onto glass slides. Alternatively a portion of each tumor is formalin-fixed, paraffin-embedded, and cut on a microtome as 10 µm section onto glass slides. Sections are post-fixed and incubated with chromophore labeled antibodies that specifically recognize injected antibodies to detect anti-Notch2/3 antibody or control antibodies present in the tumor biopsy. Furthermore, antibodies that detect different tumor and tumor recruited cell types such as, for example, anti-VE cadherin (CD144) or anti-PECAM-1 (CD31) antibodies to detect vascular endothelial cells, anti-smooth muscle alpha-actin antibodies detect vascular smooth muscle cells, anti-Ki67 antibodies to detect proliferating cells, TUNEL assays to detect dying cells, and anti-intracellular domain (ICD) Notch fragment antibodies to detect Notch signaling can be used to assess affects of antibody treatment on angiogenesis, tumor growth, and tumor morphology.

The effect of anti-Notch2/3 antibody treatment on tumor cell gene expression may also be assessed. Total RNA is extracted from a portion of each harvested tumor from Notch2/3 antibody treated and control antibody treated mice and used for quantitative RT-PCR. Expression levels of Notch2/3, components of the Notch2 and/or Notch3 signaling pathway, as well as cancer stem cell markers including, for example, CD44, are analyzed relative to the house-keeping gene GAPDH as an internal control. Changes in tumor cell gene expression upon Notch2/3 antibody treatment are thus determined.

In addition, the effect of anti-Notch2/3 antibody treatment on the presence of cancer stem cells in a tumor may be assessed. Tumor samples from Notch 2/3 antibody versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin-surface cell marker expression as described in detail above.

The tumorigenicity of cells isolated based on ESA+, CD44+, CD24−/low, Lin-expression following anti-Notch2/3 antibody treatment can then assessed. In one example, 5,000, 1,000, 500, and 100 isolated ESA+, CD44+, CD24−/low, Lin-cancer stem cells from Notch 2/3 antibody treated versus control antibody treated mice are re-injected subcutaneously into the mammary fat pads of NOD/SCID mice. The tumorigenicity of cancer stem cells based on the number of injected cells required for consistent tumor formation is thus determined.

Example 7

Anti-Notch 2/3 Antibody 59R1 Delays Tumor Recurrence In Vivo Following Paclitaxel Treatment B51 breast tumor cells (50,000 cells per mouse) were injected sub-cutaneously into the mammary fat pad of NOD-SCID mice. Tumors were allowed to grow for 50 days until they had reached an average volume of ~100 mm³. Animals were randomized (n=10/group) and treatments were initiated. One group received a control antibody (1B711) at 10 mg/kg twice per week and paclitaxel (Taxol) at 15 mg/kg twice per week and the other group received 59R1 at 10 mg/kg twice per week and paclitaxel at 15 mg/kg twice per week. Tumor volumes were measured on the indicated days. Treatments were carried out for 38 days until the tumor volumes had regressed to ~50 mm³, after which the paclitaxel treatments were halted and the antibody treatments continued for the duration of the experiment.

The results are shown in FIG. 6. Tumors were observed to recur more rapidly in the control group compared with the group treated with 59R1.

Example 8

Anti-Notch 2/3 Antibody 59R1 Decreases the Frequency of Cancer Stem Cells in a Tumor In Vivo Limiting dilution assays (LDAs) can be used to assess the effect of a Notch-binding agent on solid tumor cancer stem cells and on the tumorigenicity of a tumor comprising the cancer stem cells. The assays can be sued to determine the frequency of cancer stem cells in tumors from animals treated with the Notch-binding agent or other agent and to compare that frequency to the frequency of cancer stem cells in tumors from control animals.

An LDA was used to assess the effect on the tumorigenicity of the B51 breast tumors that were treated with the combination of control antibody (1B711) plus paclitaxel (Taxol) or treated with the combination of 59R1 and paclitaxel, as described above in Example 7. In addition, the effect of treatment of B51 breast tumors with the control antibody alone or 59R1 alone was also determined by LDA. The doses of antibodies and paclitaxel and the schedule of dosing for the control antibody group and the 59R1 group were the same as described in Example 7, above for the other two treatment groups. After three doses of antibodies and/or paclitaxel, tumors were harvested, processed and dissociated into single cells. The human tumor cells were isolated from the xenograft tumor cells by incubation with biotinylated mouse antibodies (α-mouse CD45-biotin1:200 dilution and rat α-mouse H2 Kd-biotin1:100 dilution, BioLegend, San Diego, Calif.) on ice for 30 min, followed by addition of streptavidin-labeled magnetic beads and removal of the mouse cells with the aid of a magnet. The human cells in the suspension were harvested and counted.

A serial titration of cells (30, 90, 270, and 810 cells) from each of the four treatment groups was injected in a 1:1 (v/v) mixture of FACS buffer and Matrigel into a new set of NOD-SCID mice (n=10/group). Tumors were allowed to grow for 72 days. The percentage of mice with detectable tumors was determined in all groups. The cancer stem cell frequency was then calculated using L-Calc™ software (StemCell Technologies Inc.; downloadable from www.stemcell.com/search/default.asp).

The results are shown in FIG. 7. The frequency of cancer stem cells in the tumor in the control-treated mice ("Control") was determined to be 1:66. The frequency of cancer stem cells in the tumor in the paclitaxel-treated mice ("Taxol") was shown to be 1:25, indicating that treatment with paclitaxel had actually increased the frequency of cancer stem cells in the tumor by more than two-fold relative to the control. Treatment with the 59R1 antibody, either alone ("59R1") or in combination with paclitaxel ("Taxol+59R1"), on the other hand, reduced the frequency of cancer stem cells in the tumors. The 59R1 antibody alone reduced the cancer stem cell frequency in the breast tumors by more than two-fold relative to the control. Treatment with the combination of 59R1 antibody and paclitaxel reduced the frequency of cancer stem cells in the tumor by more than about two-fold relative to treatment with 59R1 alone ($p<0.0001$), by about 4.5-fold relative to treatment with the control antibody, and by about twelve-fold relative to treatment with paclitaxel alone. These results indicate that treatment with the 59R1 antibody is effective at reducing the tumorigenicity of a breast tumor, whether given alone or in combination with paclitaxel, even though treatment with paclitaxel alone has the opposite effect.

Example 9

Additional In Vivo Treatment of Tumors Using Anti-Notch 2/3 Antibody 59R1

PN4 pancreatic tumor cells (50,000 cells per mouse) were injected subcutaneously into the flank region of Nod-Scid mice. Tumors were allowed to grow for 27 days until they had reached an average volume of ~120 mm$^3$. Animals were randomized into four treatment groups (n=10/group) and treatments were initiated. One group received a control antibody (1B711) at 10 mg/kg twice per week; one group received gemcitabine at 40 mg/kg once per week plus the control antibody at 10 mg/kg twice per week; one group received 59R1 at 10 mg/kg twice per week, and the fourth group received the combination of 59R1 at 10 mg/kg twice per week and gemcitabine 40 mg/kg once per week. Tumor volumes were measured on the indicated days. The results are shown in FIG. 8. Tumor growth was found to be inhibited by the combination of 59R1 and gemcitabine ($p<0.001$).

M4 melanoma tumor cells (10,000 cells per mouse) were injected subcutaneously into the flank region of NOD-SCID mice. Tumors were allowed to grow for 25 days until they had reached an average volume of ~80 mm$^3$. Animals were randomized into treatment groups (n=10/group) and treatments were initiated. One group received a control antibody (1B711) at 10 mg/kg twice per week and one group received 59R1 at 10 mg/kg twice per week. Tumor volumes were measured on the indicated days. The results are shown in FIG. 9. Tumor growth was found to be inhibited by 59R1.

C28 colon tumor cells (10,000 cells per mouse) were injected subcutaneously into the flank region of NOD-SCID mice. Tumors were allowed to grow for 24 days until they had reached an average volume of ~130 mm$^3$. Animals were randomized into four treatment groups (n=10/group) and treatments were initiated. One group received a control antibody (1B711) at 10 mg/kg twice per week; one group received irintoecan at 7.5 mg/kg once per week plus the control antibody at 10 mg/kg twice per week; one group received 59R1 at 10 mg/kg twice per week, and the fourth group received the combination of 59R1 at 10 mg/kg twice per week and irinotecan at 7.5 mg/kg once per week. Tumor volumes were measured on the indicated days. The results are shown in FIG. 10. Tumor growth was found to be inhibited by 59R1 alone relative to the control antibody group and by the combination of 59R1 and irinotecan relative to the irinotecan group.

The 59R1 IgG2 antibody was also tested in vivo in the breast tumor xenograft lines OMP-B34, OMP-B39, OMP-B44, PE13, and UM-T1, the pancreas tumor xenograft line OMP-PN8, and the colon tumor xenograft line OMP-C8. These tumor xenograft lines were established by adhering to procedures described in Al-Hajj et al., 2003, *Proc. Natl. Acad. Sci. USA*, 100:3983-3988. Female NOD/SCID immunocompromised mice 7-10 weeks old were used for the establishment of the breast tumor xenografts and male NOD/SCID mice were used for the OMP-Pn8 and OMP-C8 tumor-models (Harlan, Indianapolis, Ind.). The 59R1 IgG2 antibody was also tested in vivo in a Colo-205 colon tumor xenograft model. Female immunodeficient bg/nu XID mice on a Swiss CD-1 background were used for the Colo-205 xenograft tumor model. In case of the breast cancer models, slow-releasing estrogen pellets (0.36 mg) had to be implanted. Mice were subcutaneously injected on the right flank with 50,000 (OMP-B34, OMP-B39, OMP-B44, PE13, and UM-T1) or $1\times10^7$ (Colo-205) viable cells, respectively, in a mixture of PBS (without magnesium or calcium) and Matrigel at a 1:1 ratio. The injected total volume per mouse was 200 μl with 50% being Matrigel. Once the tumor had reached a size between 65-200 mm$^3$, the mice were randomized. Antibodies were administered weekly and tumors measured twice weekly. LZ1 (a human antibody that recognizes lyzozyme) or 1B711 (a murine IgG1 antibody that recognizes the hapten trinitrophenol) was used as a control antibody for treatment of each tumor type. Tumor volume was calculated as described Al-Hajj et al. (2003). Data are expressed as the mean and the mean±S.E.M. Group means were compared using Student's two-tailed, unpaired t-test. Probability (P) values of <0.05 were interpreted as significantly different. All statistical analysis was performed using Microsoft EXCEL and Graph Pad PRISM.

Figure 11A:
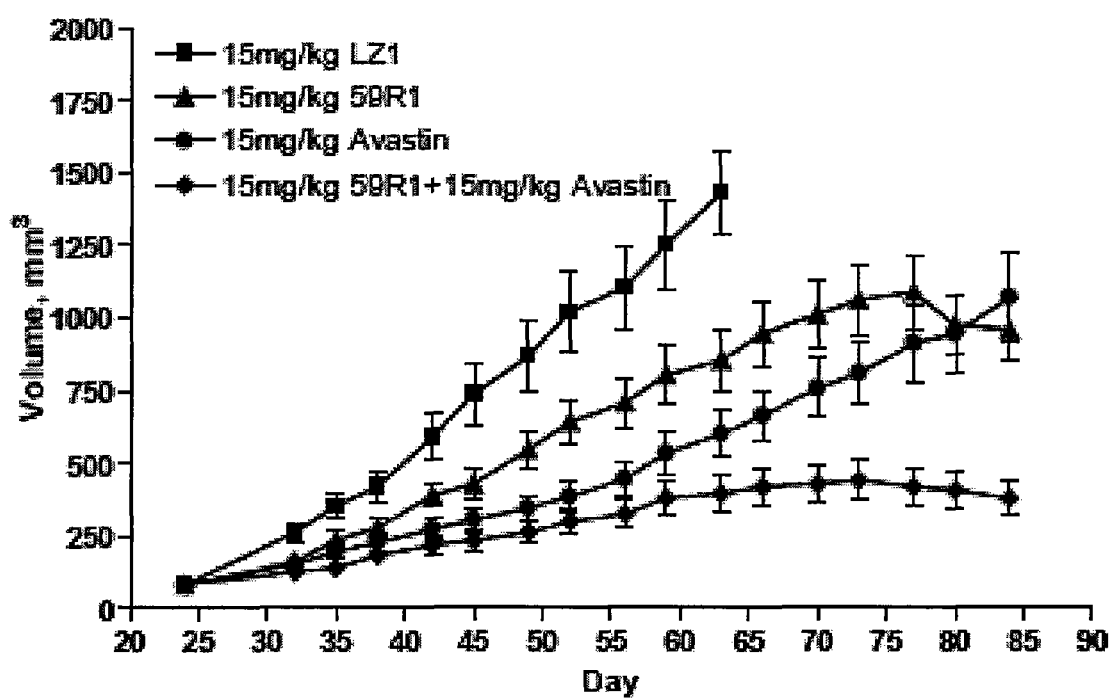
Figure 11B:
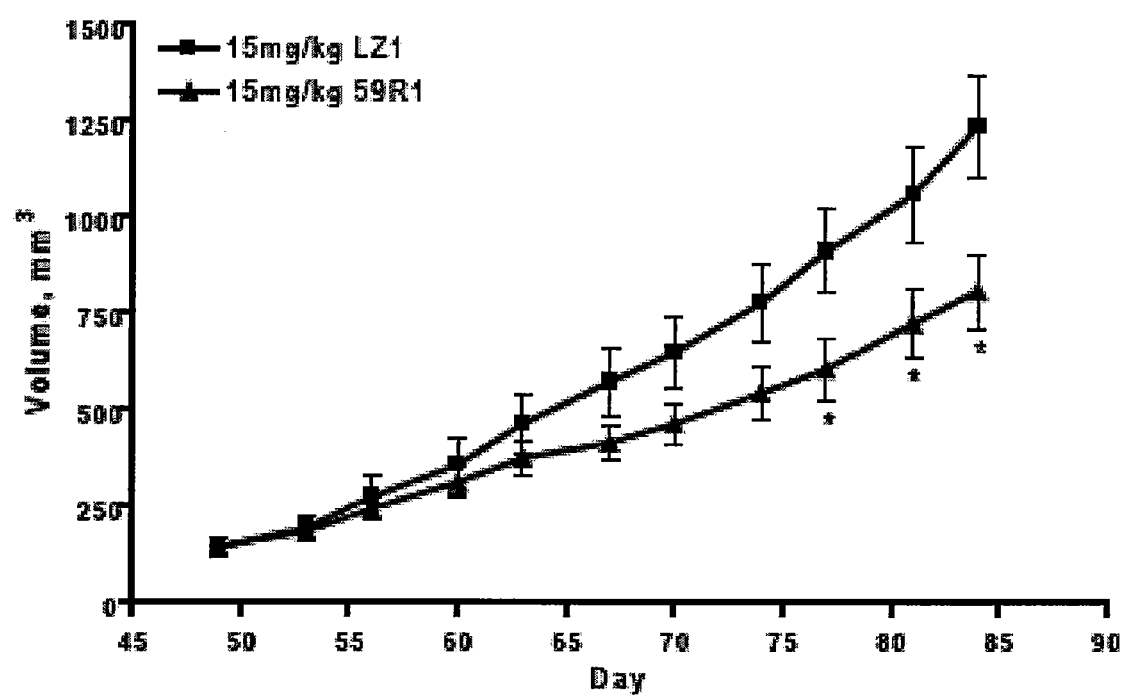
Figure 11C:
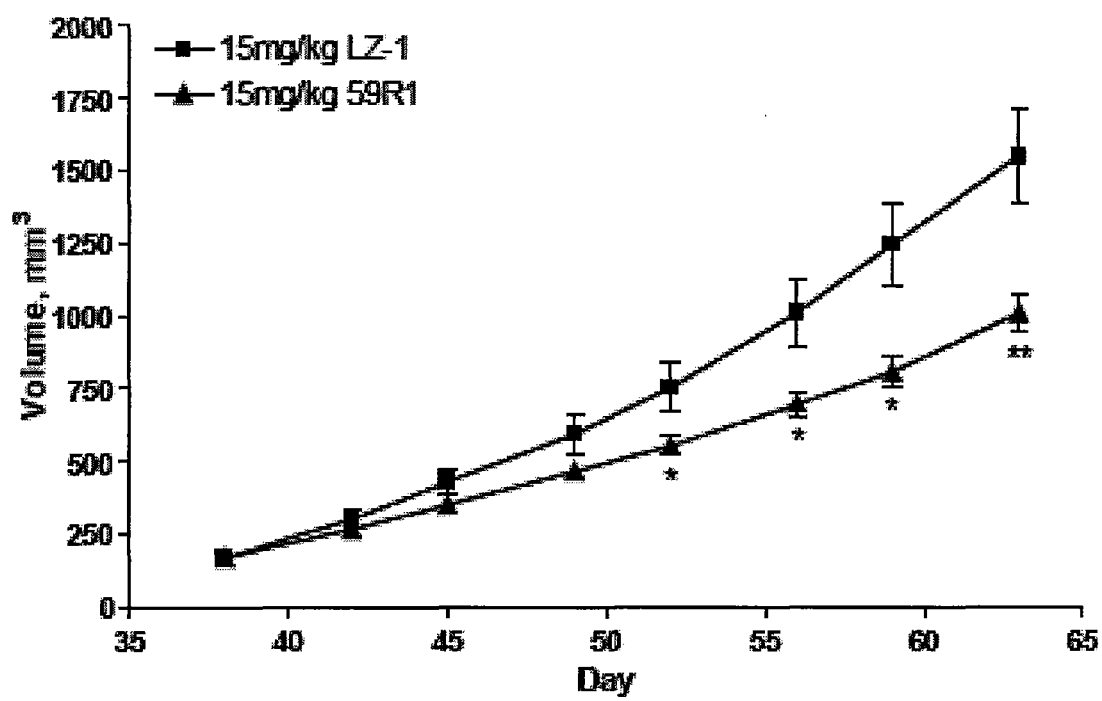
Figure 11D:
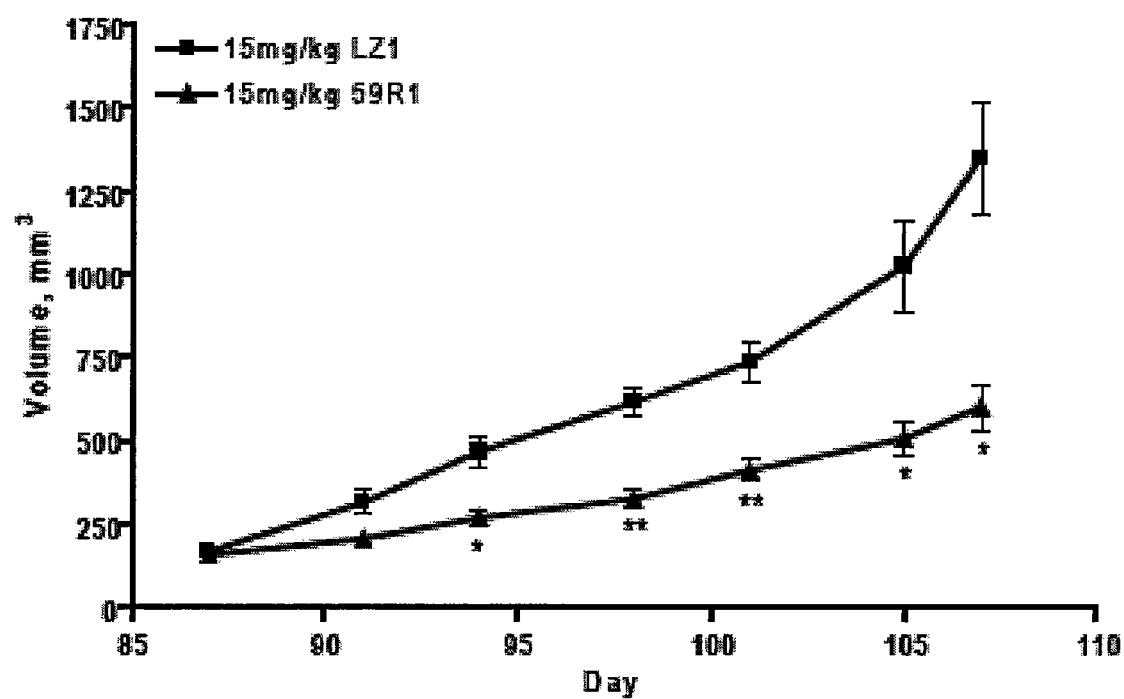
Figure 11E:
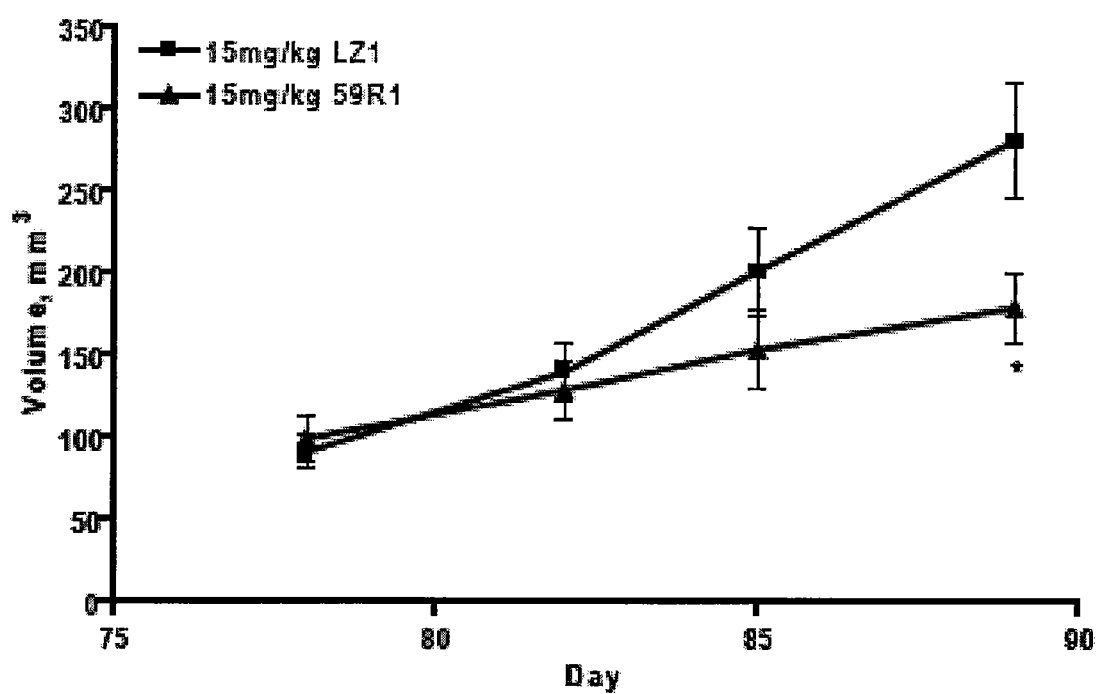
Figure 11F:
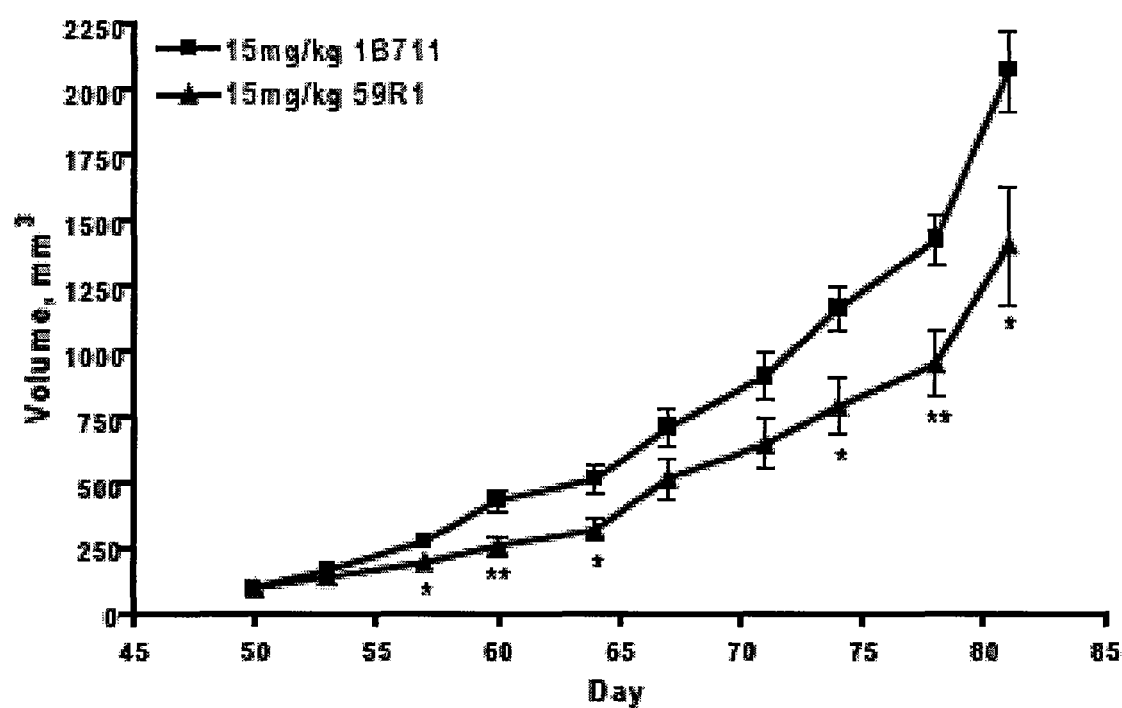
Figure 11G:
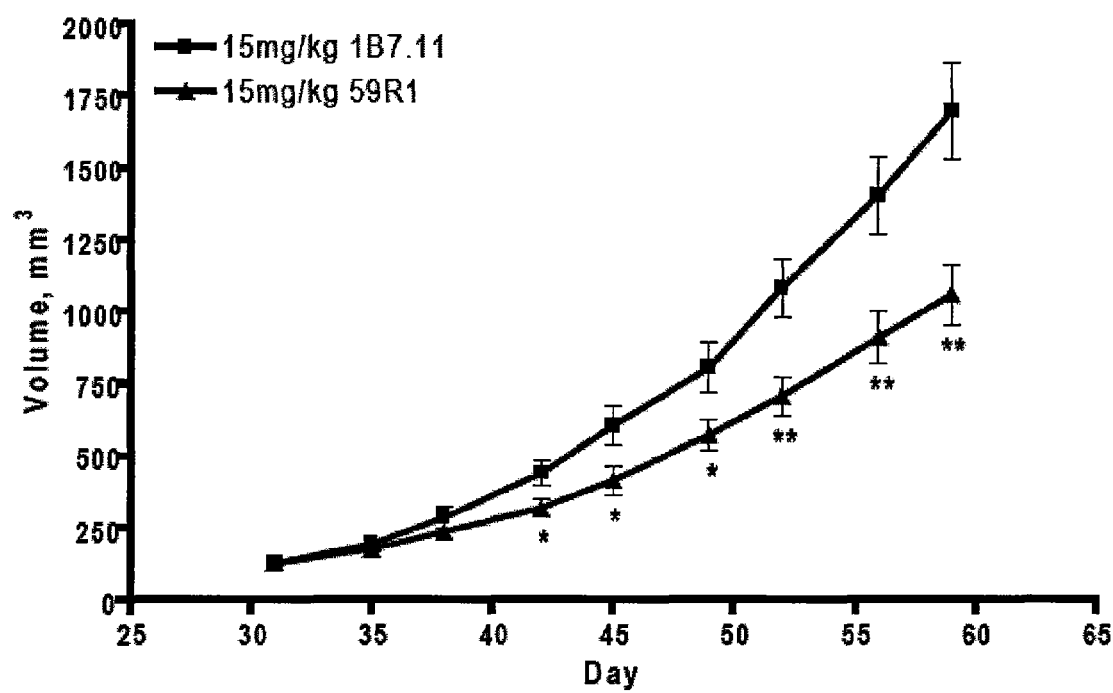
Figure 11H:
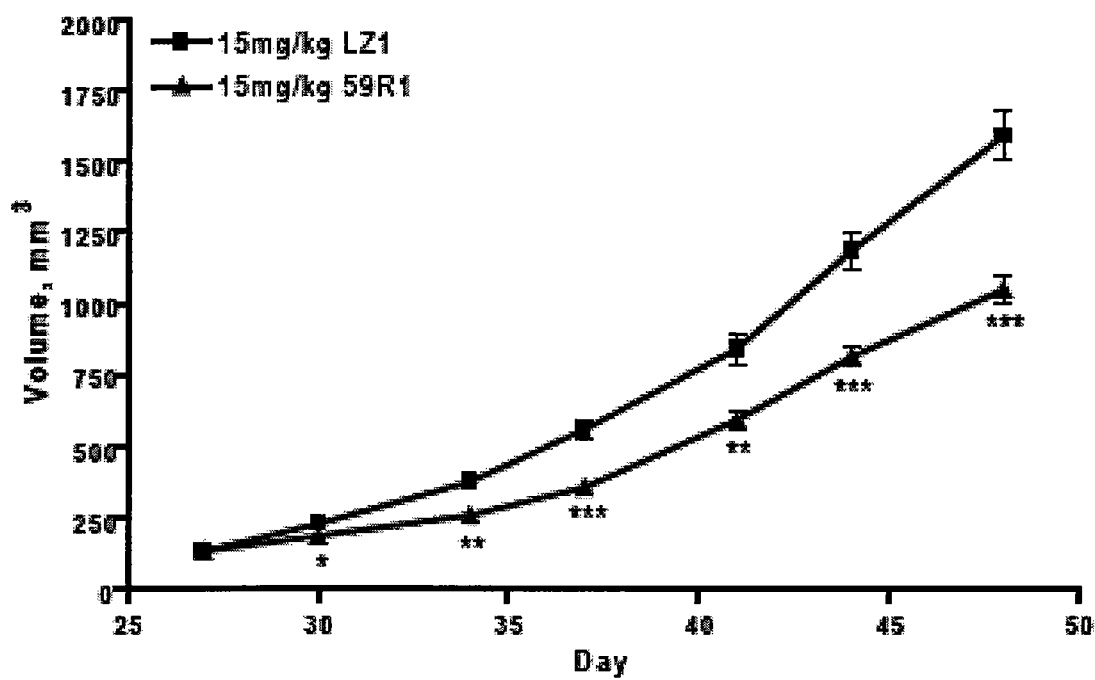

The results of the additional in vivo experiments in Colo205, C8, PNA, B34, B39, B44, PE13, and T1 xenograft models are shown in FIGS. 11A-11H, respectively. As shown in FIG. 11A, monotherapy with the 59R1 antibody significantly inhibited growth of the Colo205 tumor relative to the control antibody (LZ1) ($p<0.01$). Combination therapy with 59R1 plus the anti-VEGF antibody bevacizumab (AVASTIN) provided an even greater inhibition of tumor growth (p<0.001) than either 59R1 or bevacizumab alone. In another colorectal xenograft model, C8, 59R1 was likewise shown to inhibit tumor growth relative to LZ1 control antibody (FIG. 11B). Similarly, 59R1 was found to inhibit pancreatic tumor growth (relative to control antibody) in the PN8 xenograft model (FIG. 11C). 59R1 was also shown to inhibit breast cancer growth relative to a control antibody in each of the five breast cancer xenograft models B34 (FIG. 11D), B39 (FIG. 11E), B44 (FIG. 11F), and PE13 (FIG. 11G). The 59R1 antibody was likewise found to be effective at inhibiting tumor growth in the T1 breast cancer model (FIG. 11H), although it was only effective in the presence of estrogen, despite T1 being an estrogen receptor negative tumor.

ciated differentially regulated genes in selected tumor xenograft models (Colo205, B44, PE13, and T1) are shown in Table 5 below. The P-value (PVal) of each gene is the probability of significant regulation of the gene by 59R1 by chance using Bayesian t-test. A number of genes including the genes encoding regulator of G-protein signaling 5 (RGS5), Notch3, and hairy/enhancer-of-split related with YRPW motif-like (HEYL) protein were shown to be significantly down-regulated in the stroma of the 59R1-treated mice relative to the control mice. (By contrast, these particular genes encoding RGS5, Notch3, and HEYL were not found to be significantly down-regulated in the human cells of the tumors.)

TABLE 5

Differentially expressed genes in stroma of 59R1-treated tumors

| Gene | Colo205 | | B44 | | PE13 | | T1 | |
|---|---|---|---|---|---|---|---|---|
| | Fold | pVal | Fold | pVal | Fold | pVal | Fold | pVal |
| 1420942_s_at (Rgs5) | −5.52 | 7.65E−07 | −2.43 | 5.59E−04 | −4.23 | 2.86E−05 | −1.18 | 9.82E−04 |
| 1417466_at (Rgs5) | −3.39 | 6.62E−07 | −2.22 | 3.11E−04 | −4.03 | 1.31E−10 | −1.99 | 4.11E−04 |
| 1420941_at (Rgs5) | −5.10 | 1.66E−03 | −2.09 | 1.18E−03 | −2.99 | 1.35E−05 | −1.97 | 2.07E−03 |
| 1421964_at (Notch3) | −3.26 | 3.70E−06 | −2.03 | 2.30E−03 | −1.91 | 1.67E−03 | −1.01 | 8.86E−01 |
| 1416286_at (Rgs4) | −3.08 | 2.69E−03 | −1.57 | 3.84E−02 | −1.83 | 6.71E−05 | −1.13 | 4.47E−01 |
| 1434141_at (Gucy1a3) | −2.49 | 2.87E−03 | −1.74 | 1.07E−02 | −4.18 | 1.49E−07 | 1.20 | 5.95E−01 |
| 1459713_s_at (Tmem16a) | −1.90 | 1.90E−03 | −1.70 | 1.01E−02 | −7.28 | 9.89E−10 | −2.14 | 1.79E−04 |
| 1420872_at (Gucy1b3) | −1.94 | 1.90E−02 | −1.65 | 7.68E−03 | −3.06 | 8.52E−10 | −1.01 | 7.13E−01 |
| 1422789_at (Aldh1a2) | −1.73 | 1.20E−02 | −4.92 | 2.42E−08 | −2.17 | 1.58E−04 | −2.16 | 9.27E−04 |
| 1419302_at (Heyl) | −3.28 | 5.61E−03 | −1.12 | 2.36E−01 | −1.77 | 5.72E−04 | −1.07 | 2.39E−02 |
| 1451501_a_at (Ghr) | −1.83 | 1.69E−02 | −2.24 | 2.71E−04 | −1.66 | 8.90E−04 | −1.12 | 3.38E−01 |
| 1417714_x_at (Hba-a1/Hba-a2) | −8.37 | 2.49E−02 | −2.56 | 4.63E−04 | −1.92 | 1.06E−02 | 1.42 | 9.24E−01 |
| 1428361_x_at (Hba-a1/Hba-a2) | −8.91 | 1.93E−02 | −2.42 | 1.08E−03 | −1.73 | 4.27E−02 | 1.73 | 4.67E−01 |
| 1452590_a_at (Plac9) | −1.61 | 1.07E−02 | −1.64 | 1.22E−02 | −1.62 | 6.17E−03 | 1.20 | 7.36E−01 |
| 1449632_s_at (Fkbp10) | −1.72 | 1.69E−02 | −1.57 | 1.12E−02 | −1.63 | 1.80E−04 | 1.07 | 5.97E−01 |
| 1449280_at (Esm1) | 2.07 | 1.06E−02 | 1.55 | 3.48E−02 | 1.56 | 4.35E−02 | 1.18 | 2.44E−01 |
| 1418829_a_at (Eno2) | 1.79 | 2.92E−02 | 1.71 | 1.02E−02 | 1.54 | 5.43E−03 | 1.29 | 9.92E−02 |

Example 10

Effect of Treatment with Anti-Notch2/3 Antibody 59R1 on Gene Regulation in Xenograft Tumor Models Gene expression levels in various xenograft tumor models treated with the 59R1 IgG2 antibody were analyzed by microarray analysis. Global gene expression profiling analysis was performed on Affymetrix HG-U133 plus 2.0 microarray (Affymetrix, Santa Clara, Calif.). Three independent RNA samples of xenograft whole tumors from the control and treatment groups were isolated and hybridized to the microarrays according to the manufacturer's instructions. Scanned array background adjustment and signal intensity normalization were performed with GCRMA algorithm in the opensource bioconductor software (www.bioconductor.org). The expression level of each gene was normalized by z-score transformation across the samples in the control (CTRL) and treatment (59R1) groups. Genes differentially expressed (p<0.05 and fold change >2.0) between the two groups were identified with Bayesian t-test (Baldi et al., 2001, *Bioinformatics*, 17:509-519. The expression patterns of selected asso- The expression levels in the stroma from the xenograft models Colo205, B29, B34, B44, PE13, T1 (without estrogen treatment), T1 (with estrogen treatment), C8, and PN8 of selected genes that had been identified in the microarray analysis as being regulated by treatment with 59R1 (heyl, notch3, rgs5, angpt1, and angpt2) were further analyzed by TaqMan® analysis. The results are shown in FIGS. 12A (heyl), 12B (notch3), 12C (rgs5), 12D (angpt1), and 12E (angpt2).

Figure 12A:
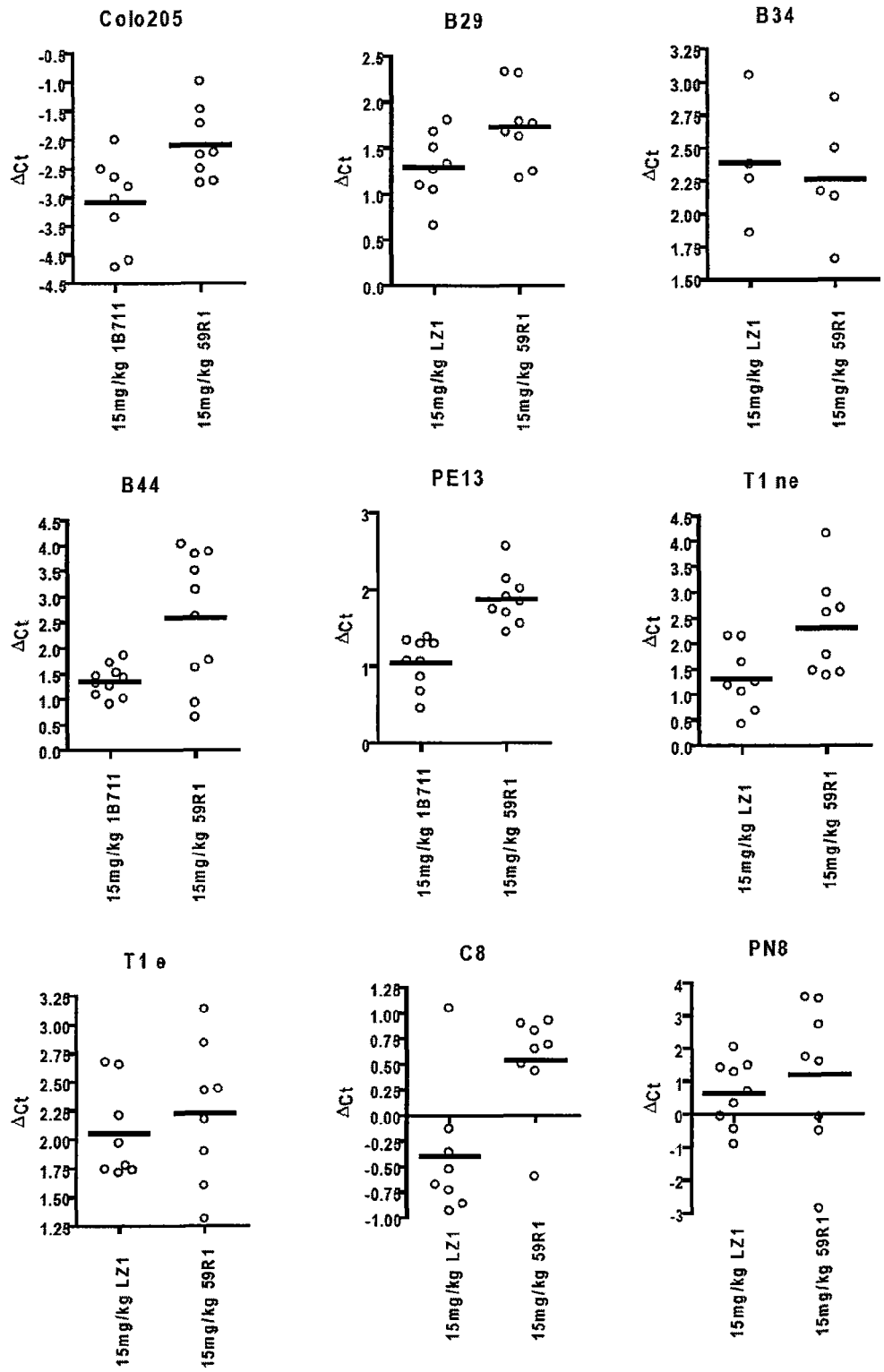
Figure 12B:
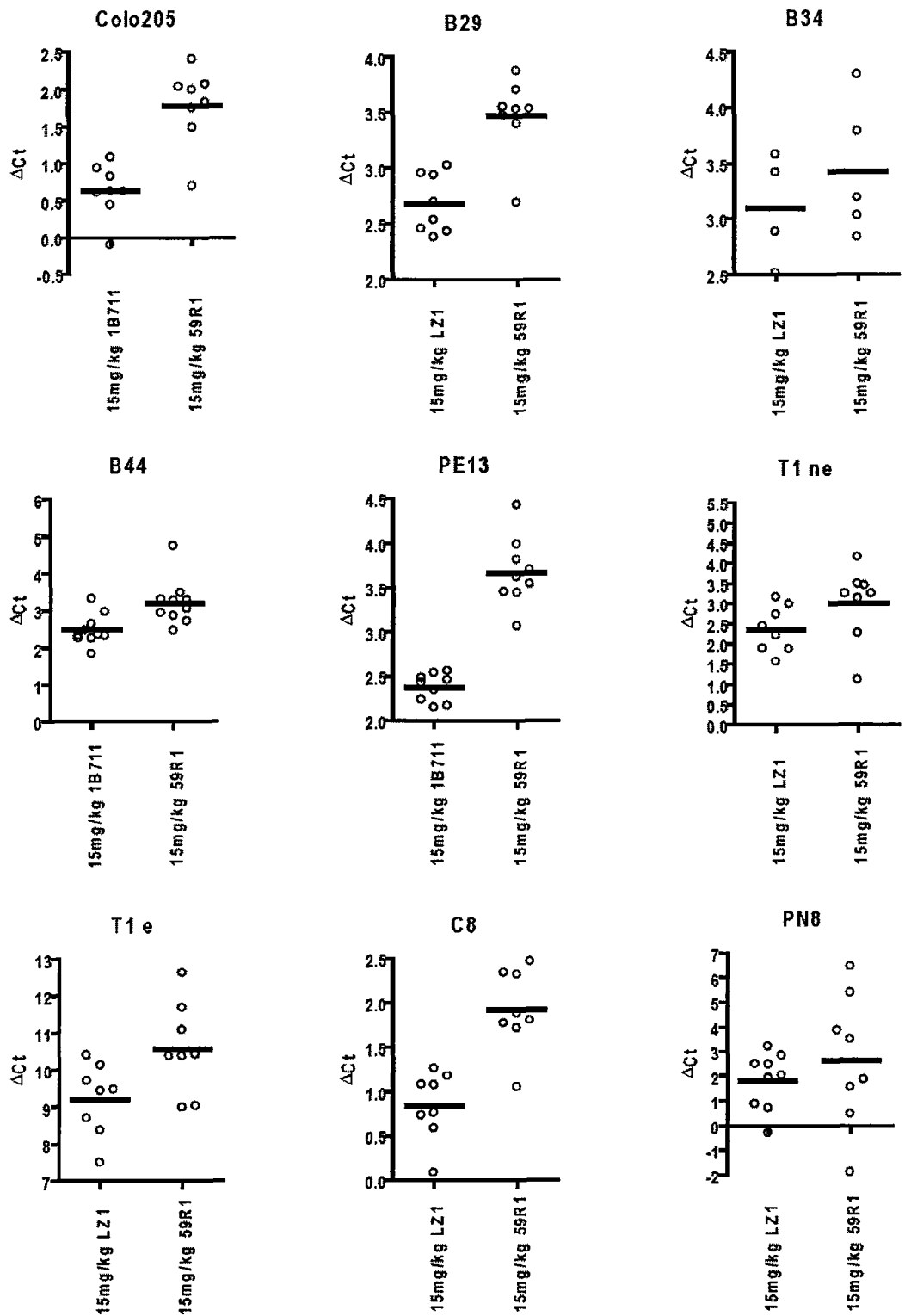
Figure 12C:
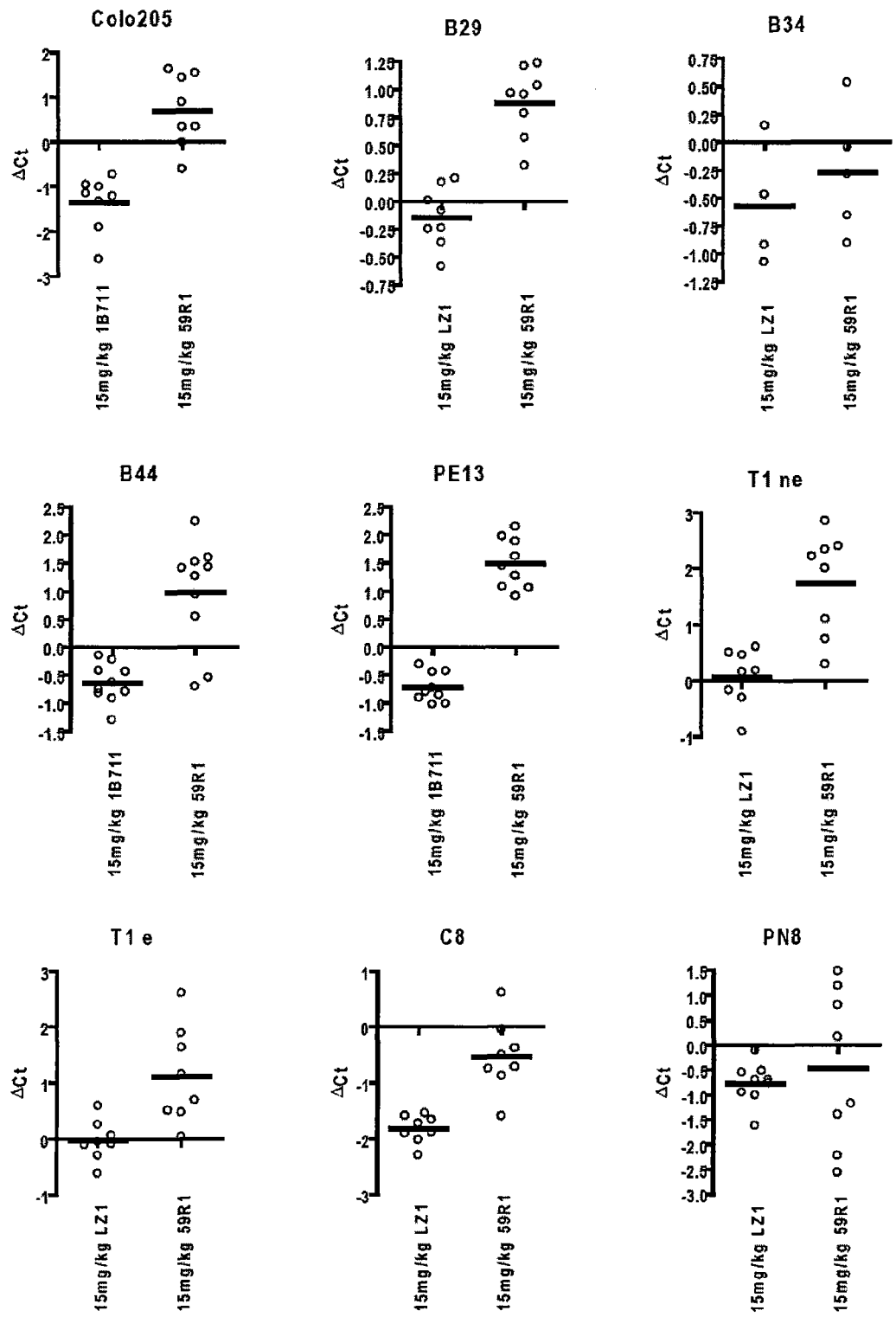

The results of the TaqMan® analysis confirm that notch3 and rgs5 are down-regulated in the stroma of each of the various tumor types in response to treatment with 59R1 (relative to control) (FIGS. 12B and C). RGS5 is a well-known marker of pericytes and vascular smooth muscle cells (Berger et al., 2005, *Blood*, 105:1094-1101; Lovschall et al., 2007, *Int. J. Dev. Biol.*, 51: 715-721; Cho et al., 2003, *FASEB J.*, 17:440-2). Notch3 has been identified as being coexpressed with RGS5 in pericytes during angiogenesis and playing an important role in the regulation of the fate of pericytes and vascular smooth muscle cells (Lovschall et al., 2007, *Int. J. Dev. Biol.*, 51: 715-721; Domenga et al., 2004, *Genes & Dev.*, 18:2730-2735; Sweeney et al., 2004, *FASEB J.*, 18:1421-3; Morrow et al., 2005, *Am. J. Physiol. Cell Physiol.*, 289: C1188-C1196).

In addition, heyl was also confirmed to be downregulated in the stroma of each of the xenograft models except B34 (FIG. 12A). HeyL belongs to the Hey family of downstream transcription factors of Notch signaling (Hey1, Hey2, and HeyL). The downregulation of heyl by 59R1 suggests that the 59R1 antibody directly affects Notch signaling by downregulating heyl.

Figure 12D:
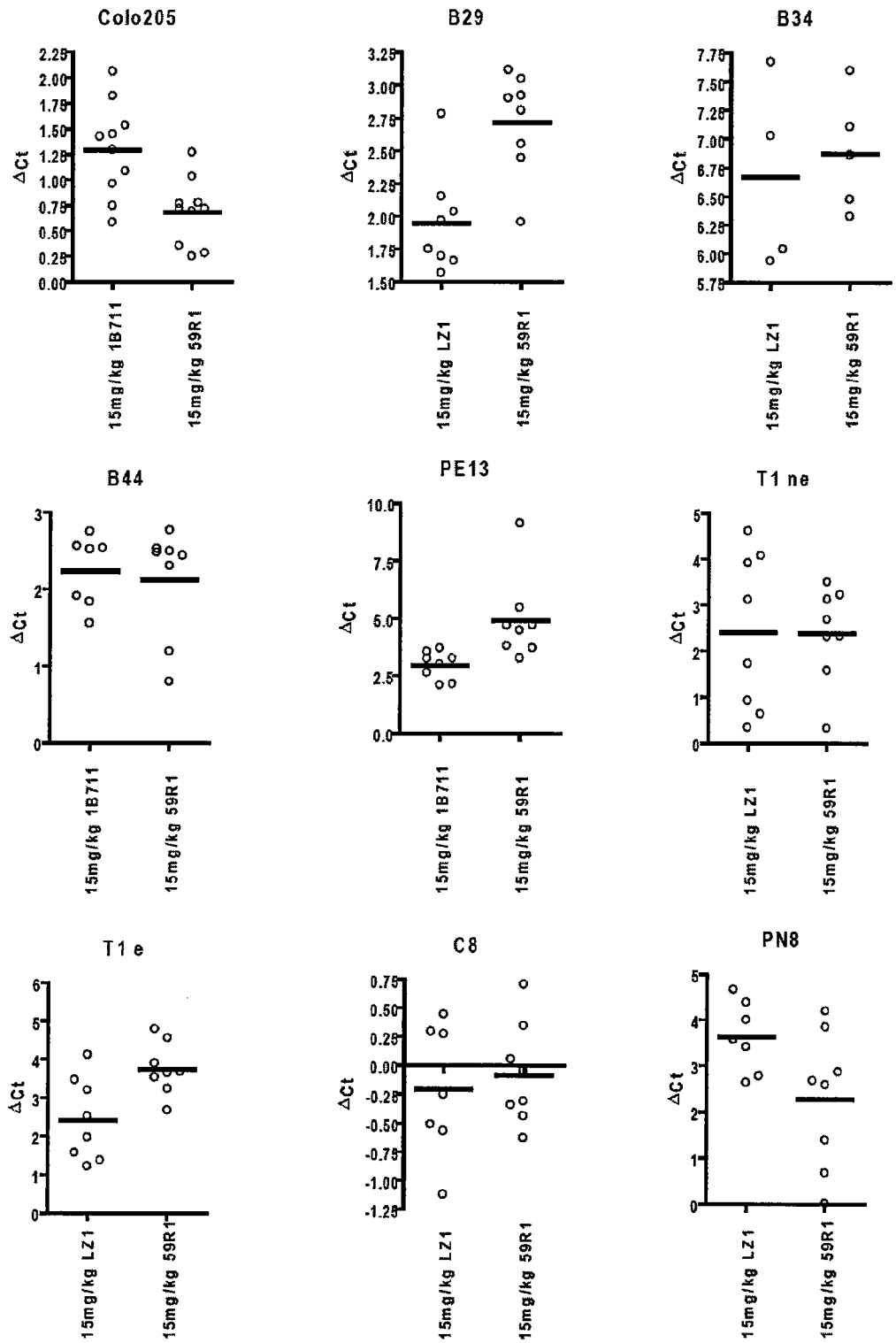
Figure 12E:
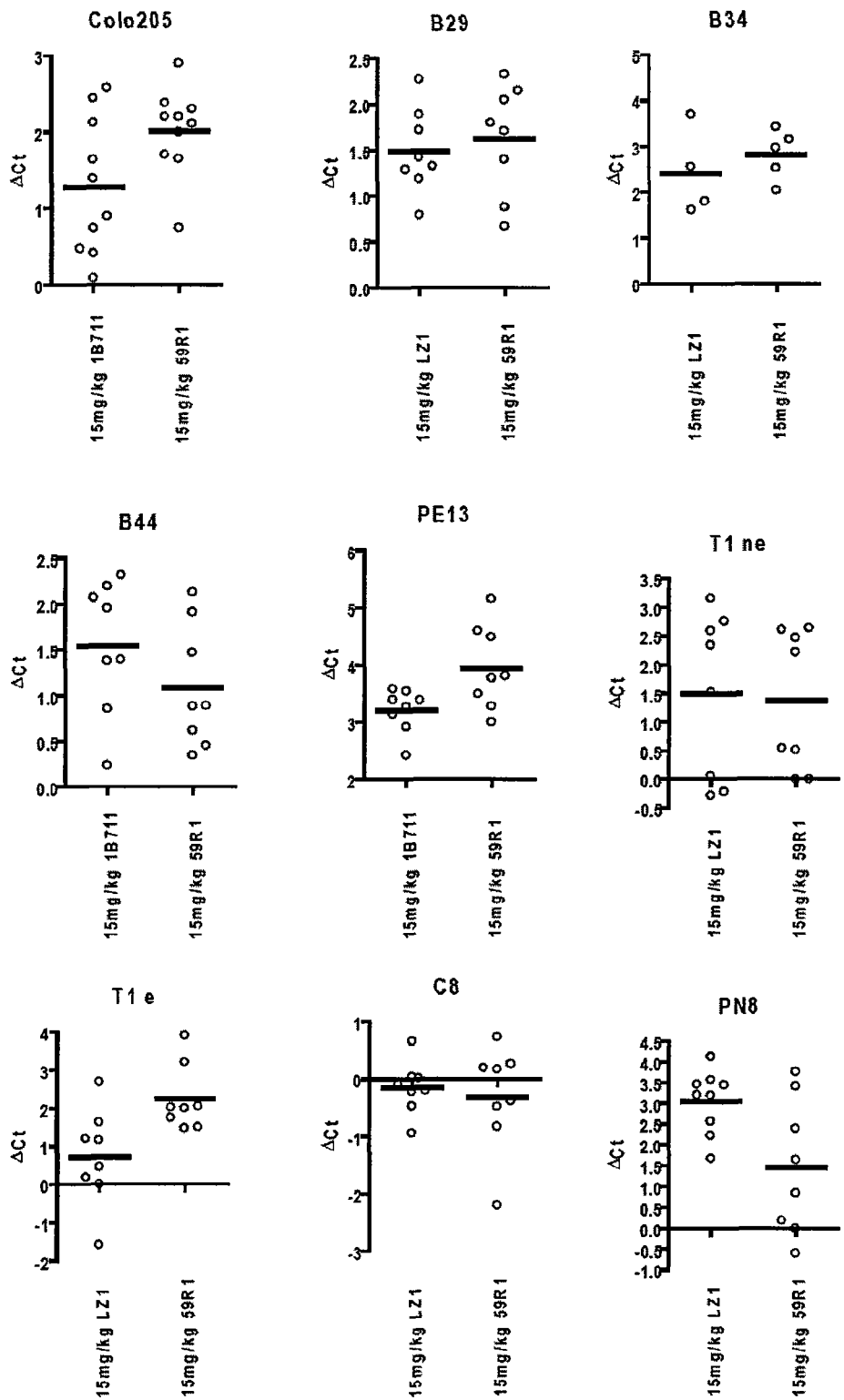

Angiopoietin-1 (angpt1) and angiopoietin-2 (angpt2) were also determined to be down-regulated in the stroma of a number of the breast cancer models (FIGS. 12D and E). ANGPT1 and 2 (angiopoietin-1 and -2) are ligands for the TIE 1 and 2 receptors. TIE receptors, like VEGF, are crucial signaling molecules in neoangiogenesis processes (Jones et al., 2001, *Nature Reviews*, 2:257-267).

Notably, however, angpt1 and angpt2 were down-regulated in the stroma of the T1 model when estrogen treatment was used ("T1 e"), conditions under which treatment with 59R1 was effective against tumor growth, but not in the stroma of the same model in the absence of estrogen treatment ("T1 ne"), conditions under which treatment with 59R1 was ineffective against tumor growth (see Example 9, above). Thus, the effect of 59R1 on the down-regulation of angiopoietin-1 and angiopoietin-2 in the stroma of the T1 tumor is abrogated in the absence of estrogen treatment. One possible explanation of this effect is that in the absence of estrogen treatment, the levels of the growth factors angiopoietin-1 and angiopoietin-2 in the T1 stroma are not sufficiently elevated to provide for measurable decreases in expression levels upon treatment with the 59R1 antibody. Estrogen has been shown to have significant effects on the tumor microenvironment (Banka et al., 2006, *Cancer Res.* 66:3667-3672). One possible explanation of this data is that estrogen leads to a dependence of the tumor on ANGPT2 signaling, which then leads to sensitivity to 59R1 treatment.

Example 11

Anti-Notch2/3 Antibody 59R1 Significantly Induces Hypoxia in Colon and Breast Tumors Staining for hypoxic regions was performed in Colo-205 colon tumors and PE-13 breast tumors that had been treated either with 59R1 IgG2 antibody or with 1B711 control antibody. The staining was performed as described in Ridgway et al., 2006, *Nature* 444:1083-1087. Briefly, to measure hypoxia, pimonidazole-hydrochloride (HypoxyProbe, NPI, Burlington, Mass.), which forms long-lived protein adducts at partial pressure of oxygen less than approximately 10 mm Hg, was injected intraperitoneally at 60 mg/kg 1 hr prior to sacrifice. Tumors were then processed for histological analysis, and tumor sections were stained using anti-pimonidazole antibody following manufacturer's protocol (NPI). Photographs were taken using a BX51 microscope (Olympus, Center Valley, Pa.).

Viable tumor cells were found to be equally present in 1B711 and 59R1-treated tumors, as indicated by a relatively uniform and dense DAPI stain (data not shown). The number of CD31-positive cells also remained unchanged, suggesting that endothelial cell number was not affected by 59R1 treatment. In 59R1-treated Colo-205 and PE13 tumors, however, hypoxic regions (as detected by anti-pimonidazole antibody) were significantly more pronounced than in 1B711 treated tumors (data not shown). AF594-conjugated goat anti-rat F(ab')$_2$ was used to detect anti-CD31 antibody and FITC-conjugated goat anti-rabbit antibody was used to detect anti-pimonidazole antibody.

Example 12

Breast Tumors Comprising Deletions in the PTEN Tumor Suppressor Gene are Responsive to Treatment with 59R1

DNA samples were prepared from tumor cells of xenograft breast cancers. Before the DNA isolation, mouse stroma cells in the xenograft tumors were depleted using magnetic beads conjugated with mouse cell specific antibodies. The purified DNA samples were hybridized to Affymetrix Genome-Wide Human SNP Array 6.0 genechip (Affymetrix, Santa Clara, Calif.), which has more than 946,000 probes for the detection of copy number variations (CNVs), according to the manufacturer's instructions. The copy number state changes were estimated by Hidden Markov Model (HMM) and their variations (CNVs) of each sample were obtained by rank segmentation analysis using Hapmap270 as baseline. Due to the inherent noise in the array, −0.5 and −1.0 log 2 ratios were used as the cutoffs for the heterozygous deletion and homozygous deletion under the significance threshold $<1.0 \times 10^{-6}$ and minimum number of probes per segment=5.

FIG. 13 shows the exon, Affymetrix probe distribution, and the deletions in the gene of the tumor suppressor phosphatase tensin homolog (PTEN) in chromosome 10. The B29, B34, B37, B40, B51, T2, T3, and T6 breast tumors were found to have intact PTEN genes in their genomes. The PTEN gene was determined to harbor homozygous deletions in B39 tumor, while B44, PE13, and T1 tumors were determined to have heterozygous deletions of this gene. As discussed above, 59R1 was determined to have anti-tumor efficacy in each of these four breast tumors comprising homozygous or heterozygous deletions of PTEN. These results suggest that tumors, especially breast tumors, harboring homozygous or heterozygous PTEN deletions may be particularly suitable for treatment with an anti-Notch2/3 antibody such as 59R1.

Example 13

Characterization of 59R5 Antibody

An additional human antibody 59R5 that specifically binds human Notch 2 and human Notch 3 was identified. The sequences of the heavy chain and light chain are provided in SEQ ID NO: 49 and SEQ ID NO:18, respectively. The heavy chain variable region is provided in SEQ ID NO:50 and the light chain variable region is provide SEQ ID NO:13. The heavy chain CDR3 sequence of 59R5 comprises SIFYTT, SEQ ID NO:51. The other CDR sequences of 59R5 are identical to 59R1. Biacore analysis of 59R1 and 59R5 binding affinities indicated that 59R5 had similar binding properties for both Notch2 and Notch3 as 59R1. Both antibodies bind human and murine Notch2 and Notch3 receptors with sub-nanomolar affinity (see Table 6).

TABLE 6

| | IgG Dissociation Constants ($K_D$, nM) | | | | | | |
|---|---|---|---|---|---|---|---|
| | m-Notch1 | h-Notch1 | m-Notch2 | h-Notch2 | m-Notch3 | h-Notch3 | h-Notch4 |
| 59R1 | >10 | >10 | 0.65 | 0.05 | 0.32 | 0.19 | NB |
| 59R5 | >10 | >10 | 0.26 | 0.05 | 0.29 | 0.22 | NB |

59R5 was determined to have similar activity in blocking Notch2 and Notch3 signaling as 59R1. Receptor activation was determined in luciferase-based assays. PC3 tumor cells were transiently transfected with a human or mouse Notch receptor (human Notch2, murine Notch2, human Notch3, or murine Notch3) and GFP inducible reporter construct. Transfected cells were incubated with different concentrations of 59R1 or 59R5 antibody in the presence of passively immobilized DLL4-Fc protein. Notch receptor activation was determined by measuring luciferase activity. As shown in FIG. 15A, 59R5 blocked ligand-induced activation of human Notch2, murine Notch2, human Notch3 and murine Notch3 receptor signaling at similar levels as 59R1.

The binding epitope of 59R5 was determined. As was described in Example 3 for analysis of antibody 59R1, several point mutants were created within full-length Notch1, converting residues within EGF10 to the corresponding amino acids in human Notch 2. Mutants in full-length Notch sequences were generated by QuikChange® mutagenesis (Stratagene) and verified by sequencing. HEK 293 cells were transiently transfected with expression vectors encoding human Notch2, human Notch1, or human Notch1 with residues 382-386 mutated to the corresponding human Notch2 residues. Cells were also co-transfected with a plasmid encoding green fluorescent protein (GFP) to mark those cells that received transfected plasmid. Cells were incubated with 59R1 or 59R5 and fluorescent secondary antibody and then examined by FACS. 59R1 and 59R5 were detected by PE-conjugated goat anti-human Fc gamma specific antibody (Jackson Immunochemicals, #109-116-170). As shown in FIG. 15B, 59R5 bound to Notch2 and did not bind to Notch1. However, when amino acids corresponding to Notch2 amino acids 385-389 were substituted into Notch1, 59R5 was able to bind to the mutated Notch1. This suggested that at least one or more amino acids necessary for 59R5 binding to human Notch 2 were positioned within amino acids 385-389 (residues in the boxed hNotch2 sequence shown in FIG. 14A) and suggested that 59R5 binds the same epitope as 59R1, or an epitope similar to, or overlapping with, the epitope of 59R1.

Example 14

In Vivo Treatment of Tumors Using Notch2/3 Antibody 59R5

In one embodiment, NOD/SCID mice were injected with PE13 breast tumor cells. The mice were treated with anti-Notch2/3 antibody 59R1, anti-Notch2/3 antibody 59R5, or control antibody. Antibodies were dosed at 15 mg/kg once per week in a "preventative" mode where dosing was initiated two days after cell injection. FIG. 16A shows that 59R5 treatment inhibited tumor growth by greater than 80%, similar to the effects seen with 59R1.

In another embodiment, NOD/SCID mice were injected with C28 colon tumor cells. The mice were treated with anti-Notch2/3 antibody 59R1, anti-Notch2/3 antibody 59R5 or control antibody. Antibodies were dosed at 15 mg/kg once per week in a "preventative" mode where dosing was initiated two days after cell injection. FIG. 16B shows that both 59R1 and 59R5 inhibited the growth of C28 colon tumors.

In another embodiment, NOD/SCID mice were injected with Colo205 colon tumor cells. The mice were treated with anti-Notch2/3 antibody 59R1, anti-Notch2/3 antibody 59R5 or control antibody. Antibodies were dosed at 15 mg/kg once per week after tumors had been established. FIG. 16C shows that both 59R1 and 59R5 inhibited the growth of Colo208 colon tumors at similar levels.

Example 15

In Vivo Treatment of Tumors Using Notch2/3 Antibody 59R5 in Combination Treatment In one embodiment, NOD/SCID mice were injected with PN8 pancreatic tumor cells. The tumors were allowed to grow for approximately 33 days until they had reached an average tumor volume of 150 mm$^3$. The mice were treated with gemcitabine at 20 mg/kg once per week for four weeks in combination with control antibody, anti-Notch2/3 antibody 59R1, or anti-Notch2/3 antibody 59R5. As shown in FIG. 17A, antibody 59R5 inhibited tumor growth at a similar level as antibody 59R1 and that combination treatment prolonged tumor recurrence longer than gemcitabine alone.

In one embodiment, to evaluate the effect of 59R5 on cancer stem cells, a tumor recurrence study was carried out in the PE13 breast tumor model. NOD/SCID mice were injected with PE13 breast tumor cells. The tumors were allowed to grow for 40 days before treatments were initiated. The mice were treated with taxol at 15 mg/kg twice per week for 5 weeks, in combination with either control antibody or anti-Notch 2/3 antibody 59R5. After 5 weeks, the taxol treatments were stopped and the antibody treatments were continued. 59R5 was observed to significantly delay tumor recurrence after high-dose taxol treatment (FIG. 17B). These results suggest that 59R5 treatment reduces cancer stem cell frequency.

A summary of the in vivo activity of 59R1 and 59R5 as described in the preceding embodiments is shown in Table 7. Tumor volumes and p values for each experiment are shown relative to the control group. The PE13, C28 and Colo205 studies were carried out as described in Example 14. PN8 studies were carried out as described above. For the PN8 experiment, the control is gemcitabine alone and values for 59R1 and 59R5 are the combinations with gemcitabine. Antibodies were dosed once per week at 15 mg/kg for all experiments.

TABLE 7

| | PE13 | | C28 | | Colo205 | | PN8 | |
|---|---|---|---|---|---|---|---|---|
| | Tumor vol | p value | Tumor vol | p value | Tumor vol | p value | Tumor vol | p value |
| 59R1 | 0.25 | <0.0001 | 0.29 | <0.0001 | 0.68 | 0.003 | 0.27 | 0.026 |
| 59R5 | 0.18 | <0.0001 | 0.38 | <0.0001 | 0.61 | 0.001 | 0.11 | 0.036 |

Example 16

Regulation of Gene Expression in Tumors after 59R5 Treatment

To determine if 59R5 and 59R1 were functioning by the same mechanisms in vivo, the expression of key target genes in tumor cells and tumor stroma were examined. Gene expression was assayed by quantitative PCR in PE13 tumor cells and stromal cells. Gene expression levels relative to the control antibody treated group are shown in FIG. 18. 59R1 and 59R5 regulated the expression of murine HeyL, Notch3, and RGS5 in stromal cells to a similar extent (left panel). The same pattern of regulation was observed in C28 tumors (data not shown). Thus, the mechanism of action previously identified for 59R1 in regulating genes in the tumor stromal critical for function of the tumor vasculature and pericytes was retained by 59R5. Similarly, 59R5 and 59R1 regulated the expression of the human genes ID4, EDNRA, and EGLN3 in tumor cells to the same degree (right panel).

Unlike other members of this gene family, ID4 is generally underexpressed in tumors, and ID4 has been shown to be a tumor suppressor in breast cancer that is frequently silenced by methylation. Loss of expression of ID4 is correlated with a worse prognosis in breast cancer patients (Noetzel et al., 2008, BMC Cancer 8:154). Thus, up-regulation of ID4 in PE13 breast tumor cells may be part of the anti-tumor mechanism of anti-Notch2/3. EDNRA is the gene encoding endothelin receptor which promotes growth of both endothelial and tumor cells and stimulates metastatic activity of tumor cells (Bagnato and Rosano 2008, *Int. J. Biochem. Cell. Biol.* 40:1443-51). EGLN3 (also known as HIF-3α) is a hypoxia inducible gene. Induction of EGLN3 by anti-Notch2/3 is consistent with disruption of functional vasculature in the treated tumors. These data indicated that the biological activities and mechanism of action of 59R1 and 59R5 were very similar.

Table 8 shows results from a microassay analysis of 59R1 and 59R5 treated PE13 tumors. The numbers are mean differential expression values for treated vs. control animals, with 3 animals per group.

TABLE 8

| 59R1 | | 59R5 | | | |
|---|---|---|---|---|---|
| Fold | pVal | Fold | pVal | Symbol | Gene Title |
| −5.10 | 3.21E−05 | −3.00 | 1.10E−03 | Foxc2 | forkhead box C2 |
| −4.40 | 1.26E−05 | −2.46 | 7.45E−04 | Hey2 | hairy/enhancer-of-split related with YRPW motif 2 |
| −4.32 | 8.03E−06 | −2.14 | 1.00E−04 | Rgs5 | regulator of G-protein signaling 5 |
| −3.33 | 5.59E−04 | −2.79 | 3.18E−03 | Heyl | hairy/enhancer-of-split related with YRPW motif-like |
| −2.71 | 4.80E−04 | −2.90 | 1.02E−04 | Rgs4 | regulator of G-protein signaling 4 |
| −2.10 | 2.17E−04 | −1.86 | 4.33E−05 | Notch3 | Notch gene homolog 3 (*Drosophila*) |
| −1.92 | 3.16E−02 | −2.35 | 3.43E−03 | Mmp9 | matrix metallo-peptidase 9 |
| 2.36 | 3.06E−02 | 4.97 | 3.35E−02 | Pdcd1lg2 | programmed cell death 1 ligand 2 |
| 7.42 | 6.25E−07 | 2.80 | 2.07E−03 | Gzma | granzyme A |

Microarray analysis reveals that 59R5 significantly inhibited the Notch pathway (p<0.01) as measured by gene expression (e.g., Foxc2, Hey2, Heyl, Notch3). These results were comparable to 59R1. Foxc2 is a down-stream target of the Hedgehog pathway and is involved in cell differentiation. Additional genes involved in apoptosis (e.g., granzyme A) and tumor-associated tissue remodeling (MMP-9) were also similarly expressed between 59R1 and 59R5. These data suggested that the biological activities and mechanism of action of 59R1 and 59R5 are very similar.

Example 17

Production of Additional Notch2 and/or Notch3 Antibodies

Antigen Production

In certain embodiments, recombinant polypeptide fragments of the human Notch2 or human Notch3 extracellular domain are generated as antigens for antibody production. For example, standard recombinant DNA technology can be used to isolate a polynucleotide encoding amino acids 1-493 of Notch2 (SEQ ID NO: 33), encompassing EGF 1-12. This polynucleotide can be ligated in-frame N-terminal to either a human Fc-tag or histidine-tag and cloned into a transfer plasmid vector for baculovirus mediated expression in insect cells. Standard transfection, infection, and cell culture protocols can be used to produce recombinant insect cells expressing the corresponding Notch2 polypeptide (SEQ ID NO: 34) (O'Reilly et al., 1994, Baculovirus expression vectors: A Laboratory Manual, Oxford: Oxford University Press).

Cleavage of the endogenous signal sequence of human Notch2 was approximated using cleavage prediction software SignalP 3.0, however the actual in vivo cleavage point can differ by a couple of amino acids either direction. The predicted cleavage of Notch2 is between amino acids 1 and 26, thus Notch2 antigen protein comprises approximately amino acid 27 through amino acid 493. Antigen protein can be purified from insect cell conditioned medium using Protein A and $Ni^{++}$-chelate affinity chromatography. Purified antigen protein is then dialyzed against PBS (pH=7), concentrated to approximately 1 mg/ml, and sterile filtered in preparation for immunization.

Immunization

Mice can be immunized with purified Notch2 or Notch3 antigen protein using standard techniques. Blood from individual mice can be screened approximately 70 days after initial immunization for antigen recognition using ELISA and FACS analysis (described in detail below). The animals with the highest antibody titers are then selected for final antigen boost after which spleen cells are isolated for hybridoma production. Hybridoma cells are plated at 1 cell per well in 96 well plates, and the supernatant from each well screened by ELISA and FACS analysis against antigen protein. Several hybridomas with high antibody titer are selected and scaled up in static flask culture. Antibodies are purified from the hybridoma supernatant using protein A or protein G agarose chromatography and antibodies are tested by FACS as described below.

FACS Analysis

To select monoclonal antibodies produced by hybridomas, clones that recognize native cell-surface Notch2 (and/or Notch3) protein, FACs analysis is used. HEK293 cells are co-transfected with expression vectors encoding a full-length cDNA clone of Notch2 and the transfection marker GFP. Twenty-four to forty-eight hours post-transfection, cells are collected in suspension and incubated on ice with anti-Notch2 (or anti-Notch3 or anti-Notch2/3) antibodies or control IgG to detect background antibody binding. The cells are washed and primary antibodies detected with anti-mouse secondary antibodies conjugated to a fluorescent chromophore. Labeled cells are then sorted by FACS to identify anti-Notch2, anti-Notch3, or anti-Notch2/3 antibodies that specifically recognize cell surface expression of native cell-surface Notch2 and/or Notch3 protein.

Chimeric Antibodies

After monoclonal antibodies that specifically recognize a non-ligand binding domain of a Notch receptor are identified, these antibodies are modified to overcome the human anti-mouse antibody (HAMA) immune response when rodent antibodies are used as therapeutics agents. The variable regions of the heavy-chain and light-chain of the selected monoclonal antibody are isolated by RT-PCR from hybridoma cells and ligated in-frame to human IgG1 heavy-chain and kappa light chain constant regions, respectively, in mammalian expression vectors. Alternatively a human Ig expression vector such as TCAE 5.3 is used that contains the human IgG1 heavy-chain and kappa light-chain constant region genes on the same plasmid (Preston et al., 1998, *Infection & Immunity* 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against a Notch2 or Notch3 receptor can require further humanization. To generate humanized antibodies the three short hypervariable sequences, or complementary determining regions (CDRs), of the chimeric antibody heavy- and light-chain variable domains described above are engineered using recombinant DNA technology into the variable domain framework of a human heavy- and light-chain sequences, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Example 18

Additional In Vitro Assays to Evaluate Antibodies Against a Notch Receptor

This example describes methods for in vitro assays to test the activity of antibodies generated against a Notch2 and/or Notch3 receptor on cell proliferation and cytotoxicity.

Proliferation Assay

Antibodies against Notch2 and/or Notch3 are tested for their effect on tumor cell growth in vitro using a BrdU based assay. Freshly dissociated, Lin-depleted breast tumor cells are cultured in low oxygen for between 2-5 days. Cells are then cultured at 20,000 cells/well with 2.5 µg/mL or 5.0 µg/mL anti-Notch antibody, control non-specific murine IgG, or no antibody for three days followed by 18 hours BrdU labeling. All experiments are performed with multiple replicates. The ability of anti-Notch antibodies to inhibit cell proliferation compared to control antibodies is then determined.

Complement-Dependent Cytotoxicity Assay

Cancer cell lines expressing a Notch2 receptor and/or a Notch3 receptor or, alternatively, cancer stem cells isolated from a patients sample passaged as a xenograft in immuno-compromised mice are used to measure complement dependent cytotoxicity (CDC) mediated by an antibody against a Notch 2 and/or Notch3 receptor. Cells are suspended in 200 µl RPMI 1640 culture medium supplemented with antibiotics and 5% FBS at $10^6$ cells/ml. Suspended cells are then mixed with 200 µl serum or heat-inactivated serum with antibodies against a Notch2 and/or Notch3 receptor or control antibodies in triplicate. Cell mixtures are incubated for 1 to 4 hours at 37° C. in 5% $CO_2$. Treated cells are then collected, resuspended in 100 µl FITC-labeled annexin V diluted in culture medium and incubated at room temperature for 10 min. One hundred µl of a propidium iodide solution (25 µg/ml) diluted in HESS is added and incubated for 5 min at room temperature. Cells are collected, resuspended in culture medium and analyzed by flow cytometry. Flow cytometry of FITC stained cells provides total cell counts, and propidium iodide uptake by dead cells as a percentage of total cell numbers is used to measure cell death in the presence of serum and antibodies against a Notch2 and/or Notch3 receptor compared to heat-inactivated serum and control antibodies. The ability of anti-Notch2/3 antibodies to mediated complement-dependent cytotoxicity is thus determined.

Antibody-Dependent Cellular Cytotoxicity Assay

Cancer cell lines expressing a Notch2 receptor and/or a Notch3 receptor or, alternatively, cancer stem cells isolated from a patients sample passaged as a xenograft in immuno-compromised mice (described in detail below) are used to measure antibody dependent cellular cytotoxicity (ADCC) mediated by an antibody against a Notch2 and/or Notch3 receptor. Cells are suspended in 200 µl phenol red-free RPMI 1640 culture medium supplemented with antibiotics and 5% FBS at $10^6$ cells/ml. Peripheral blood mononuclear cells (PBMCs) are isolated from heparinized peripheral blood by Ficoll-Paque density gradient centrifugation for use as effector cells. Target cells (T) are then mixed with PBMC effector cells (E) at E/T ratios of 25:1, 10:1 and 5:1 in 96-well plates in the presence of a Notch2 or Notch3 receptor or control antibodies. Controls include incubation of target cells alone and effector cells alone in the presence of antibody. Cell mixtures are incubated for 1 to 6 hours at 37° C. in 5% $CO_2$. Released lactate dehydrogenase (LDH), a stable cytosolic enzyme released upon cell lysis, is then measured by a colorimetric assay (e.g., CytoTox96 Non-radioactive Cytotoxicity Assay; Promega; Madison, Wis.). Absorbance data at 490 nm are collected with a standard 96-well plate reader and background corrected. The percentage of specific cytotoxicity is calculated according to the formula: % cytotoxicity=100×(experimental LDH release−effector spontaneous LDH release−target spontaneous LDH release)/(target maximal LDH release−target spontaneous LDH release). The ability of antibodies against a Notch2 and/or Notch3 receptor to mediated antibody dependent cellular cytotoxicity is thus determined.

Example 19

Production of Antibodies Against EGF 10 (or Equivalent EGF) of Notch Receptors

Identification of an antibody that specifically binds the tenth EGF repeat of Notch2 and the corresponding EGF repeat of Notch3 (the ninth EGF repeat) that reduces tumor growth in animals suggests the importance of the non-ligand binding domain, and the tenth EGF repeat (or its equivalent) in particular, for effective cancer therapies. To target the EGF repeat 10 (or equivalent EGF) in Notch receptor family members, antibodies against EGF10 of Notch1, Notch2, or Notch4 or against EGF9 of Notch3 are produced and analyzed. Specifically, mice are immunized with antigens comprising the tenth EGF repeat of Notch1 (SEQ ID NO:35); Notch2 (SEQ ID NO:36), or Notch4 (SEQ ID NO:38) or the ninth EGF repeat of Notch3 (SEQ ID NO:37). Antibodies that recognize specific Notch receptors as well as antibodies that recognize different combinations of the four Notch receptors are identified using FACS analysis of HEK 293 cells transfected with each Notch receptor as described in detail above. Antibodies that recognize the tenth EGF repeat (or equivalent EGF) of two Notch receptor family members are envisioned (e.g. antibodies that recognize the Notch1 EGF10 and Notch2 EGF10; Notch1 EGF10 and Notch3 EGF9; Notch1 EGF10 and Notch4 EGF10; Notch2 EGF10 and Notch3 EGF9; Notch2 EGF10 and Notch4 EGF10; or Notch3 EGF9 and Notch4 EGF10). Antibodies that recognize the tenth EGF repeat (or equivalent EGF) of three Notch receptor family members are likewise contemplated (e.g., antibodies that recognize the Notch1 EGF10, Notch2 EGF10, and Notch3 EGF9; Notch1 EGF10, Notch2 EGF10, and Notch4 EGF10; or Notch2 EGF10, Notch3 EGF9, and Notch4 EGF10). And antibodies that recognize the tenth EGF repeat (or equivalent EGF) of four Notch receptor family members are envisioned (e.g. antibodies that recognize the Notch1 EGF10, Notch2 EGF10, Notch3 EGF9 and Notch4 EGF10).

Example 20

Treatment of Human Cancer Using Anti-Notch Receptor Antibodies

This example describes methods for treating cancer using antibodies against a Notch receptor to target tumors comprising cancer stem cells and/or tumor cells in which Notch receptor expression has been detected.

The presence of cancer stem cell marker expression can first be determined from a tumor biopsy. Tumor cells from a biopsy from a patient diagnosed with cancer are removed under sterile conditions. In some embodiments, the tissue biopsy is fresh-frozen in liquid nitrogen, embedded in O.C.T., and cut on a cryostat as 10 µm sections onto glass slides. Alternatively the tissue biopsy is formalin-fixed, paraffin-embedded, and cut on a microtome as 10 µm section onto glass slides. Sections are incubated with antibodies against a Notch receptor to detect protein expression. Additionally, the presence of cancer stem cells can be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, and -Lin, antibodies to detect cancer stem cells, and the presence of ESA+, CD44+, CD24-/low, Lin-tumor stem cells is determined by flow cytometry as described in detail above.

Cancer patients whose tumors are diagnosed as expressing a Notch receptor are treated with anti-Notch receptor antibodies. Humanized or human monoclonal anti-Notch receptor antibodies generated as described above are purified and formulated with a suitable pharmaceutical carrier in PBS for injection. Patients are treated with the Notch antibodies once a week for at least 10 weeks, but in certain cases once a week for at least about 14 weeks. Each administration of the antibody should be a pharmaceutically effective dose about 2 to about 100 mg/ml and in certain cases between about 5 to about 40 mg/ml. The antibody can be administered prior to, concurrently with, or after standard radiotherapy regimens or chemotherapy regimens using one or more chemotherapeutic agent, such as paclitaxel, gemcitabine, irinotecan, oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

Example 21

Production of Antibodies Against Notch1, Notch2, Notch3, and/or Notch4 EGF Repeat 4

To target the EGF repeat 4 in Notch receptor family members, antibodies against Notch1, Notch2, Notch3, and/or NOTCH4 EGF repeat 4 are produced and analyzed. Specifically, mice are immunized with antigens comprising the fourth EGF repeat of Notch1 (SEQ ID NO:41), Notch2 (SEQ ID NO:42), Notch3 (SEQ ID NO: 43), or Notch4 (SEQ ID NO:44). Antibodies that recognize specific Notch receptors as well as antibodies that recognize different combinations of the four Notch receptors are identified using FACS analysis of HEK 293 cells transfected with each Notch receptor as described in detail above. Antibodies that recognize the fourth EGF repeat of two Notch receptor family members are envisioned (e.g. antibodies that recognize the fourth EGF repeat of Notch1 and Notch2; Notch1 and Notch3; Notch1 and Notch4; Notch2 and Notch3; Notch2 and Notch4; or Notch3 and Notch4). Antibodies that recognize the fourth EGF repeat of three Notch receptor family members are envisioned (e.g. antibodies that recognize the fourth EGF repeat of Notch1, Notch2, and Notch3; Notch1, Notch2, and Notch4; or Notch2, Notch3, and Notch4). And antibodies that recognize the fourth EGF repeat of four Notch receptor family members are envisioned (e.g. antibodies that recognize the fourth EGF repeat of Notch1, Notch2, Notch3 and Notch4).

A description of the exemplary production and characterization of a monoclonal antibody, 13M57, that binds EGF4 of Notch1 can be found in U.S. Patent Application Publication No. 2008/0131434, which is incorporated by reference herein in its entirety.

Example 22

Additional Gene Expression Assays in Tumor Cells Treated with 59R1

Changes in gene expression in response to 59R1 treatment in tumor cells in xenograft models were identified.

Several pathways/gene sets that are regulated by antibody 59R1 in tumor cells were identified (Table 9) using Gene Set Enrichment Analysis (Mootha et al., 2003, *Nature Genetics* 34:267-73; Subramanian et al., 2005, *Proc. Natl. Acad. Sci. USA* 102:15545-50) in the breast tumors T1, PE13, and B51. Notably, cell cycle gene pathways, myc-activating genes and several stem cell gene sets are down-regulated by 59R1 in this analysis. cMyc has been shown to be a direct target of the Notch pathway (Weng et al., 2006, *Genes Dev.* 20:2096-109). The stem cell gene sets down-regulated by 59R1 were derived from a molecular signature derived from five distinct populations: human fetal hematopoietic stem cells (HCS), murine fetal and adult HSCs, neural stem cells (NSC), and embryonic stem cells (ESC) (Ivanova et al., 2002, *Science* 298:601-604), and also a recently described core ESC gene set (Ben-Porath et al., 2008, *Nature Genetics* 40:499-507) and an ESC self-renewal gene set whose down-regulation causes differentiation (Hu et al., 2009, *Genes Dev.* 23:837-48).

TABLE 9

| Name | Size | FDR | Description |
|---|---|---|---|
| NGUYEN KERATO UP NOTCH | 27 | 0.0774 | Genes concomitantly modulated by activated Notch1 in mouse and human primary keratinocytes-Up |
| CELLCYCLEPATHWAY | 22 | 0.0798 | Cyclins interact with cyclin-dependent kinases to form active kinase complexes that regulate progression thr |
| YU CMYC UP | 28 | 0.0884 | Myc-activated genes |
| HSC STHSC FETAL | 27 | 0.0885 | Up-regulated in mouse short-term functional hematopoietic stem cells from fetal liver (ST-HSC Shared) |
| HSC STHSC SHARED | 27 | 0.0907 | Up-regulated in mouse short-term functional hematopoietic stem cells from both adult bone marrow an |
| WEINBERG ESC EXP2 | 30 | 0.1001 | 40 genes specifically overexpressed in hES cells according to Meta-analysis of 8 profiling studies (Natu |
| ESC SELF RENEWAL | 30 | 0.1087 | Genes identified by a genome-wide RNAI screen, whose down-regulation caused mESC differentiation |
| BRENTANI REPAIR | 33 | 0.1122 | Cancer related genes involved in DNA repair |

FDR < 15%

Example 23

Reduction of Cancer Stem Cell Frequency by Notch2/3 Antibodies

Figure 19A:
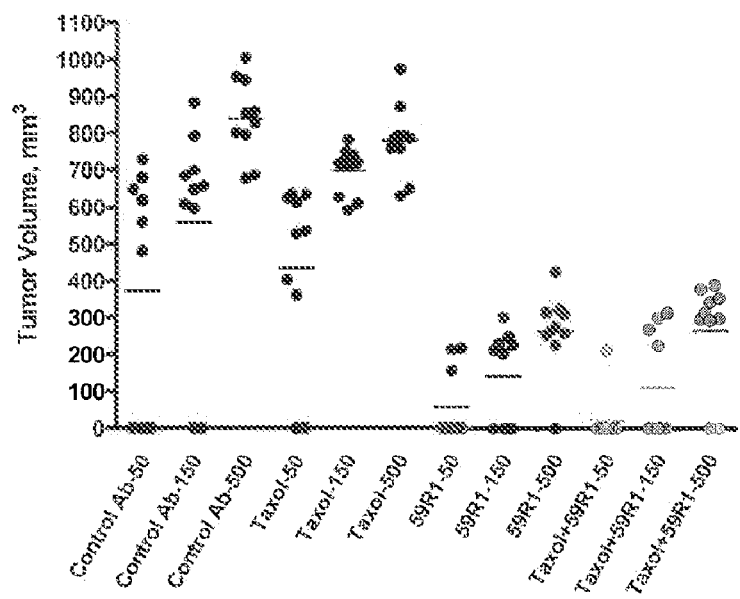
Figure 19B:
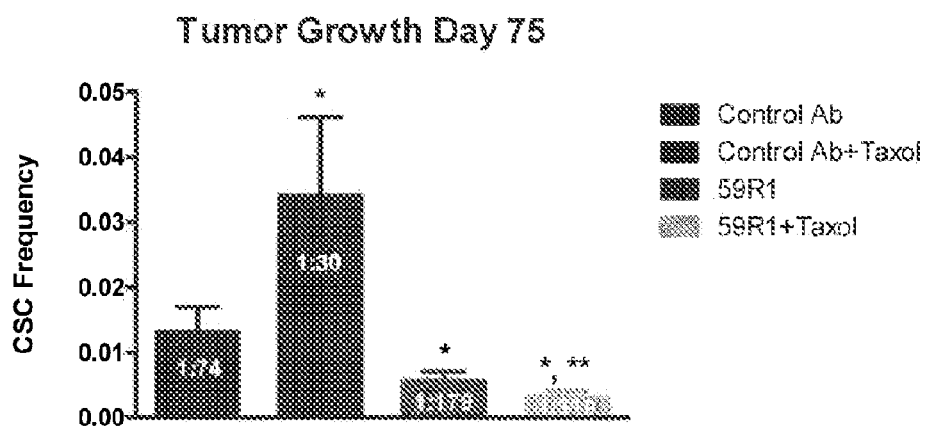

Using a similar experimental study as described in Example 8, an analysis of cancer stem cell frequency by limiting dilution analysis was carried out in PE13 breast cancer cells. Animals bearing PE13 breast tumors were treated with control antibody, taxol plus control antibody, 59R1, or taxol plus 59R1 for three weeks. Tumors were harvested after three weeks, and CSC frequency in the treated tumors was analyzed. Serial titrations of human cells from each the four treatment groups were transplanted into a new set of mice (n=10 per cell dose). Tumor growth rate after 75 days of growth (FIG. 19A) was used to calculate the CSC frequency using the L-calc program (Stem Cell Technologies, Inc.). The control antibody treated tumors were determined to have a tumor initiating cell frequency of 1:74. Treatment with taxol alone increased the CSC frequency to 1:30. In contrast, treatment with 59R1 decreased CSC frequency to 1:179 and the combination of 59R1 plus taxol decreased CSC frequency to 1:319 (FIG. 19B). A single asterisk indicates a statistically significant difference (p<0.05) vs. the control antibody treated group and a double asterisk indicates a significant difference vs. the taxol and control antibody treated group. This experiment indicated that 59R1 treatment of PE13 breast tumors reduced CSC frequency as a single agent and more dramatically, in combination with taxol treatment. In contrast, treatment with taxol alone, while effective at reducing tumor volume, increased the CSC frequency of treated tumors indicating that tumor initiating cells are preferentially resistant to the effects of this chemotherapeutic agent.

In addition to investigating the effects of 59R1 in tumors and the effect on CSC frequency, gene changes were studied following 59R1 treatment in combination with taxol. The experiment was performed in PE13 breast tumors where a decrease in CSC frequency after treatment with 59R1 alone or 59R1 plus taxol treatment had previously been observed (and described herein). Microarray analysis was performed on tumors from the same experiment where limiting dilution analyses of PE13 were carried out for CSC quantification (FIG. 19). Animals bearing PE13 breast tumors were treated three weeks with 59R1 plus taxol, control and taxol prior to harvesting for microarray analysis. Mean differential expression values for taxol vs. control and 59R1 plus taxol vs. taxol treated animals (3 animals per group) were calculated. Strikingly, in the gene expression microarray data, it was found that 59R1 in combination with taxol affected apoptosis, hypoxia, differentiation, and stem-cell related genes in the opposite fold direction than the gene changes observed following with taxol alone (Table 10) consistent with the effects of these compounds on the CSC frequency.

TABLE 10

| Taxol vs. control | | 59R1 Taxol vs. Taxol | | | |
|---|---|---|---|---|---|
| Fold | pval | Fold | pval | Symbol | Name |
| 10.2 | 6.8E-03 | -4.3 | 2.3E-01 | BMPR1B | bone morphogenetic protein receptor, type IB |
| -2.1 | 4.2E-05 | 1.8 | 6.9E-05 | BNIP3 | BCL2/adenovirus E1B 19 kDa interacting protein 3 |
| -21.1 | 1.0E-02 | 11.9 | 3.9E-04 | EGLN3 | egl nine homolog 3 |
| 13.4 | 5.9E-05 | -1.8 | 1.2E-01 | HSPB6 | heat shock protein, alpha-crystallin-related, B6 |
| 2.2 | 1.5E-02 | -2.5 | 1.9E-03 | ITGAM | integrin, alpha M |
| 4.6 | 3.6E-03 | -4.4 | 5.2E-03 | LHX8 | LIM homeobox 8 |
| -9.0 | 2.0E-06 | 6.4 | 1.8E-05 | NDRG1 | N-myc downstream regulated gene 1 |
| 6.4 | 6.9E-06 | -2.2 | 7.4E-03 | RARRES1 | retinoic acid receptor responder 1 |
| 2.6 | 3.5E-04 | -1.7 | 1.1E-03 | RARRES3 | retinoic acid receptor responder 3 |
| 4.8 | 3.9E-05 | -2.2 | 1.6E-02 | RBP2 | retinol binding protein 2, cellular |
| 10.6 | 1.3E-10 | -1.5 | 5.9E-02 | XAF1 | XIAP associated factor 1 |

The apoptosis-related genes regulated in this dataset include BNIP3, NDRG1 HSPB6, and XAF1. BNIP3 (Bcl-2/E1B 19 kDa interacting protein) is a pro-apoptotic member of the Bcl-2 family that is expressed in hypoxic regions of tumors (Kothari et al., 2003, *Oncogene* 22:4734-44). BNIP3 is down-regulated by taxol alone and up-regulated by the combination therapy, suggesting that 59R1 plus taxol may promote apoptosis. Consistent with this idea is the observation that HSPB6 is down-regulated in taxol treated tumors; HSPB6 over-expression may protect against apoptosis in some biological systems (Fan et al., 2005, *Trends Cardiovasc. Med.* 15:138-41). NDRG1 (N-myc downstream regulated gene1), which is up-regulated in the combination treatment, is necessary for p53-dependent apoptosis (Stein et al., 2004, *J. Biol. Chem.* 279:48930-40). Interestingly, NDRG1 is also a putative suppressor of colorectal cancer metastases. Its increased expression is associated with improved survival in prostate and breast cancer (Shah et al., 2005, *Clin. Cancer Res.* 11:3296-302). Additionally, NDRG1 is involved in promoting differentiation. The expression of NDRG1 has been shown to be highly expressed in well-differentiated pancreatic cancer cells, and not expressed in the less differentiated tumor cells (Angst et al., 2006, *Br. J. Cancer* 95:307-13). It was also observed that other stem cell-related genes such BMPR1B and homeobox containing gene, LHX8, were up-regulated by taxol alone, and then down-regulated with 59R1 treatment in combination with taxol.

Several genes involved in the metabolism of retinoids (RARRES1, RARRES3, RBP2), which are similar functionally to the putative stem cell marker, ALDH1a1, were up-regulated by taxol, and then down-regulated with taxol plus 59R1 treatment. Retinoic acid signaling has been shown to be linked to cellular differentiation (Appel and Eisen, 2003, *Neuron* 40:461-4). Taken together, these data show that 59R1 has significant effects on gene expression in PE13 breast tumor cells and may begin to elucidate some of the mechanisms that underlie the observed decrease in cancer stem cell frequency in this tumor following treatment with 59R1 and taxol combination therapy.

Figure 19C:
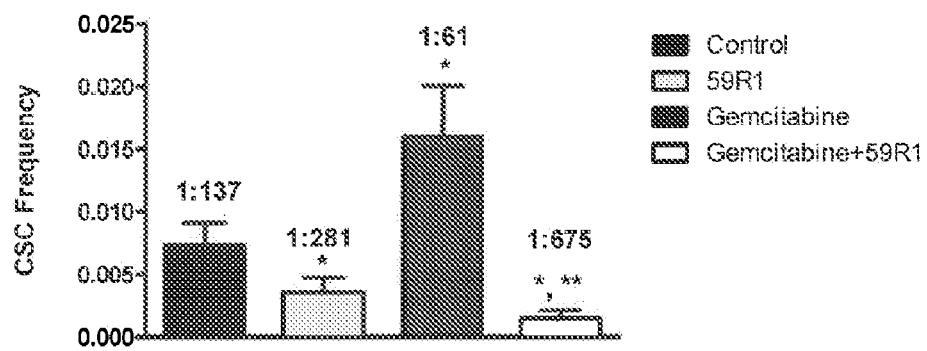

In another embodiment, a PN4 pancreatic tumor model was used to test for reduction in cancer stem cell frequency after treatment with 59R1. PN4 pancreatic tumors were treated with control antibody, anti-Notch2/3 59R1, gemcitabine, or a combination of 59R1 and gemcitabine for a period of three weeks. Antibodies were dosed at 10 mg/kg, twice per week and gemcitabine was dosed at 50 mg/kg, twice per week. Tumors from each group were harvested and processed to obtain single cell suspensions. The human tumors cells in the xenograft were isolated and counted. A titration of cells (30, 90 or 210 cells) were re-injected into NOD-SCID mice (n=10 per group). Tumor growth was assayed on day 84 and tumor initiating cell frequency was calculated from the tumor take rate. The control antibody treated tumors were determined to have a tumor initiating cell frequency of 1:137. Treatment with gemcitabine alone increased the CSC frequency to 1:61. In contrast, treatment with 59R1 decreased CSC frequency to 1:281 and the combination of 59R1 plus gemcitabine decreased CSC frequency to 1:675 (FIG. 19C). A single asterisk indicates a statistically significant difference ($p<0.05$) vs. the control antibody treated group and a double asterisk indicates a significant difference vs. the gemcitabine and control antibody treated group.

Figure 19D:
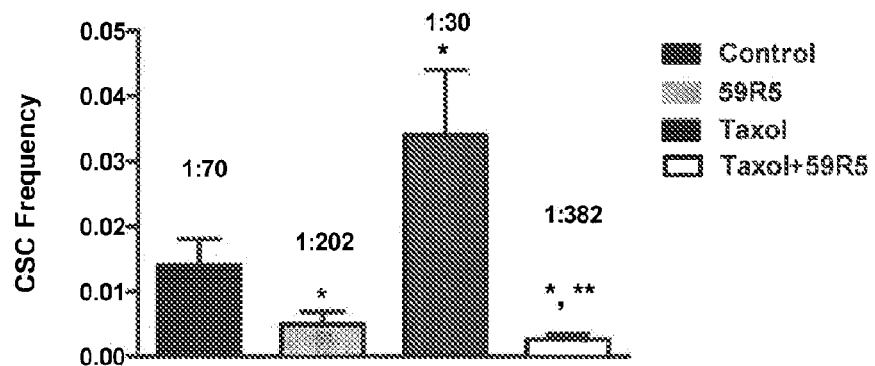

In another embodiment, a PE13 breast tumor model was used to test for reduction in cancer stem cell frequency after treatment with 59R5. PE13 breast tumors were treated with control antibody, anti-Notch 2/3 59R5, taxol, or a combination of 59R5 and taxol for a period of three weeks. Antibodies were dosed at 20 mg/kg, once per week and taxol was dosed at 15 mg/kg, twice per week. Tumors from each group were harvested and processed to obtain single cell suspensions. The human tumors cells in the xenograft were isolated and counted. A titration of cells (50, 150 or 450 cells) were re-injected into NOD-SCID mice (n=10 per group). Tumor growth was assayed on day 39 and tumor initiating cell frequency was calculated from the tumor take rate. The control antibody treated tumors were determined to have a tumor initiating cell frequency of 1:70. Treatment with taxol alone increased the CSC frequency to 1:30. In contrast, treatment with 59R5 decreased CSC frequency to 1:202 and the combination of 59R5 plus taxol decreased CSC frequency to 1:382 (FIG. 19D). A single asterisk indicates a statistically significant difference ($p<0.05$) vs. the control antibody treated group and a double asterisk indicates a significant difference vs. the taxol and control antibody treated group.

As observed in other experiments, these results indicated that 59R1 treatment of PN4 pancreatic tumors and 59R5 treatment of PE13 breast tumors reduced CSC frequency as a single agent and more dramatically, in combination with gemcitabine or taxol treatment, respectively. In contrast, treatment with taxol or gemcitabine alone, while effective at reducing tumor volume, increased the CSC frequency of treated tumors indicating that tumor initiating cells are preferentially resistant to the effects of these chemotherapeutic agents.

All publications and patents mentioned in the above specification are herein incorporated by reference. Various modifications and variations of the described method and system of the invention will be apparent to those in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those in the relevant fields are intended to be within the scope of the following claims.

Sequences

Human Anti-Notch2/3 Antibody Sequences
SEQ ID NO:1: Nucleotide sequence encoding anti-Notch2/3 IgG2 59R1 heavy chain, plus signal sequence. The sequence encoding the signal sequence is underlined.

```
ATGAAACACCTGTGGTTCTTCCTCCTGCTGGTGGCAGCTCCCAGATGGGT

CCTGTCCCAGGTGCAATTGGTGGAAAGCGGCGGCGGCCTGGTGCAACCGG

GCGGCAGCCTGCGTCTGAGCTGCGCGGCCTCCGGATTTACCTTTTCTTCT

TCTGGTATGTCTTGGGTGCGCCAAGCCCCTGGGAAGGGTCTCGAGTGGGT

GAGCGTTATCGCTTCTTCTGGTAGCAATACCTATTATGCGGATAGCGTGA

AAGGCCGTTTTACCATTTCACGTGATAATTCGAAAAACACCCTGTATCTG

CAAATGAACAGCCTGCGTGCGGAAGATACGGCCGTGTATTATTGCGCGCG

TGGTATTTTTTTTGCTATTTGGGGCCAAGGCACCCTGGTGACGGTTAGCT

CAGCCAGCACAAAGGGCCCTAGCGTCTTCCCTCTGGCTCCCTGCAGCAGG

AGCACCAGCGAGAGCACAGCCGCCCTGGGCTGCCTGGTCAAGGACTACTT

CCCCGAACCGGTGACGGTGTCGTGGAACTCAGGCGCTCTGACCAGCGGCG

TGCACACCTTCCCAGCTGTCCTACAGTCCTCAGGACTCTACTCCCTCAGC

AGCGTGGTGACCGTGCCCTCCAGCAACTTCGGCACCCAGACCTACACCTG

CAACGTAGATCACAAGCCCAGCAACACCAAGGTGGACAAGACAGTTGAGC

GCAAATGTTGTGTCGAGTGCCCACCGTGCCCAGCACCACCTGTGGCAGGA

CCGTCAGTCTTCCTCTTCCCCCCAAAACCCAAGGACACCCTCATGATCTC

CCGGACCCCTGAGGTCACGTGCGTGGTGGTGGACGTGAGCCACGAAGACC

CCGAGGTCCAGTTCAACTGGTACGTGGACGGCGTGGAGGTGCATAATGCC

AAGACAAAGCCACGGGAGGAGCAGTTCAACAGCACGTTCCGTGTGGTCAG

CGTCCTCACCGTTGTGCACCAGGACTGGCTGAACGGCAAGGAGTACAAGT

GCAAGGTCTCCAACAAAGGCCTCCCAGCCCCCATCGAGAAAACCATCTCC

AAAACCAAAGGGCAGCCCCGAGAACCACAGGTGTACACCCTGCCCCCATC

CCGGGAGGAGATGACCAAGAACCAGGTCAGCCTGACCTGCCTGGTCAAAG

GCTTCTACCCCAGCGACATCGCCGTGGAGTGGGAGAGCAATGGGCAGCCG

GAGAACAACTACAAGACCACACCTCCCATGCTGGACTCCGACGGCTCCTT

CTTCCTCTACAGCAAGCTCACCGTGGACAAGAGCAGGTGGCAGCAGGGGA
```

-continued

ACGTCTTCTCATGCTCCGTGATGCATGAGGCTCTGCACAACCACTACACG

CAGAAGAGCCTCTCCCTGTCTCCGGGTAAATGA

SEQ ID NO:16: Predicted protein sequence of anti-Notch2/3 59R1 IgG2 heavy chain, plus signal sequence. The signal sequence is underlined.

MKHLWFFLLLLVAAPRWVLSQVQLVESGGGLVQPGGSLRLSCAASGFTFSS

SGMSWVRQAPGKGLEWVSVIASSGSNTYYADSVKGRFTISRDNSKNTLYL

QMNSLRAEDTAVYYCARGIFFAIWGQGTLVTVSSASTKGPSVFPLAPCSR

STSESTAALGCLVKDYFPEPVTVSWNSGALTSGVHTFPAVLQSSGLYSLS

SVVTVPSSNFGTQTYTCNVDHKPSNTKVDKTVERKCCVECPPCPAPPVAG

PSVFLFPPKPKDTLMTSRTPEVTCVVVDVSHEDPEVQFNWYVDGVEVHNA

KTKPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNGQP

ENNYKTTPPMLDSDGSFFLYSKLTVDKSRWQQGNVFSCSVMHEALHNHYT

QKSLSLSPGK

SEQ ID NO:3: Nucleotide sequence encoding anti-Notch2/3 59R1 light chain, plus signal sequence. The sequence encoding the signal sequence is underlined.

ATGGTGTTGCAGACCCAGGTCTTCATTTCTCTGTTGCTCTGGATCTCTGG

TGCCTACGGGGATATCGTGCTGACCCAGAGCCCGGCGACCCTGAGCCTGT

CTCCGGGCGAACGTGCGACCCTGAGCTGCAGAGCGAGCCAGTCTGTTCGT

TCTAATTATCTGGCTTGGTACCAGCAGAAACCAGGTCAAGCACCGCGTCT

ATTAATTTATGGTGCTTCTTCTCGTGCAACTGGGGTCCCGGCGCGTTTTA

GCGGCTCTGGATCCGGCACGGATTTTACCCTGACCATTAGCAGCCTGGAA

CCTGAAGACTTTGCGGTTTATTATTGCCAGCAGTATTCTAATTTTCCTAT

TACCTTTGGCCAGGGTACGAAAGTTGAAATTAAACGTACGGTGGCTGCAC

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAAGTCTACGCCTGCGAAGT

CACCCATCAGGGCCTGAGCTCGCCCGTCACAAAGAGCTTCAACAGGGGAG

AGTGTTAG

SEQ ID NO:18: Predicted protein sequence of anti-Notch2/3 59R1 light chain, plus signal sequence. The signal sequence is underlined.

MVLQTQVFISLLLWISGAYGDIVLTQSPATLSLSPGERATLSCRASQSVR

SNYLAWYQQKPGQAPRLLIYGASSRATGVPARFSGSGSGTDFTLTISSLE

PEDFAVYYCQQYSNFPITFGQGTKVEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

SEQ ID NO:5: 59R1 Heavy chain CDR1

SSSGMS

SEQ ID NO:6: 59R1 Heavy chain CDR2

VIASSGSNTYYADSVKG

SEQ ID NO:7: 59R1 Heavy chain CDR3

GIFFAI

SEQ ID NO:8: 59R1 Light chain CDR1

RASQSVRSNYLA

SEQ ID NO:9: 59R1 Light chain CDR2

GASSRAT

SEQ ID NO:10: 59R1 Light chain CDR3

QQYSNFPI

SEQ ID NO:11: 59R1 Light chain VL of 59R1 Fab plus signal sequence. The signal sequence is underlined.

MKKTAIAIAVALAGFATVAQADIVLTQSPATLSLSPGERATLSCRASQSV

RSNYLAWYQQKPGQAPRLLIYGASSRATGVPARFSGSGSGTDFTLTISSL

EPEDFAVYYCQQYSNFPITFGQGTKVEIKR

SEQ ID NO:12: 59R1 Heavy chain VH of 59R1 Fab plus signal sequence. The signal sequence is underlined.

MKQSTIALALLPLLFTPVTKAQVQLVESGGGLVQPGGSLRLSCAASGFTF

SSSGMSWVRQAPGKGLEWVSVIASSGSNTYYADSVKGRFTISRDNSKNTL

YLQMNSLRAEDTAVYYCARGIFFAIWGQGTLVTVSSA

SEQ ID NO:13: 59R1 Light chain VL of 59R1 IgG antibody

DIVLTQSPATLSLSPGERATLSCRASQSVRSNYLAWYQQKPGQAPRLLIY

GASSRATGVPARFSGSGSGTDFTLTISSLEPEDFAVYYCQQYSNFPITFG

QGTKVEIKR

SEQ ID NO:14: 59R1 Heavy chain VH of 59R1 IgG antibody

QVQLVESGGGLVQPGGSLRLSCAASGFTFSSSGMSWVRQAPGKGLEWVSV

IASSGSNTYYADSVKGRFTISRDNSKNTLYLQMNSLRAEDTAVYYCARGI

FFAIWGQGTLVTVSSA

SEQ ID NO:39: 59R1 light chain VL plus mammalian signal sequence (underlined)

MVLQTQVFISLLLWISGAYGDIVLTQSPATLSLSPGERATLSCRASQSVR

SNYLAWYQQKPGQAPRLLIYGASSRATGVPARFSGSGSGTDFTLTISSLE

PEDFAVYYCQQYSNFPITFGQGTKVEIKR

SEQ ID NO:40: 59R1 heavy chain VH plus mammalian signal sequence (underlined)

MKHLWFFLLLVAAPRWVLSQVQLVESGGGLVQPGGSLRLSCAASGFTFSS

SGMSWVRQAPGKGLEWVSVIASSGSNTYYADSVKGRFTISRDNSKNTLYL

QMNSLRAEDTAVYYCARGIFFAIWGQGTLVTVSSA

SEQ ID NO:15: Nucleotide sequence encoding the heavy chain of anti-Notch2/3 59RGV IgG2 antibody (germlined variant of 59R1), plus signal sequence. The sequence encoding the signal sequence is underlined.

ATGAAGCACCTGTGGTTCTTTCTGCTGCTGGTCGCCGCTCCTAGATGGGT
GCTGTCCGAGGTGCAGCTGGTCGAGTCTGGCGGCGGACTGGTGCAGCCTG
GCGGCTCCCTGAGACTGTCCTGCGCTGCCTCCGGCTTCACCTTCTCCTCC
TCCGGCATGTCCTGGGTGCGCCAGGCTCCCGGCAAGGGCCTGGAGTGGGT
GTCCGTGATCGCCTCCAGCGGCTCCAACACCTACTACGCCGACTCCGTGA
AGGGCCGGTTCACCATCTCCCGGGACAACTCCAAGAACACCCTGTACCTG
CAGATGAACTCCCTGCGGGCCGAGGACACCGCCGTGTACTACTGCGCCAG
GGGCATCTTCTTCGCCATCTGGGGCCAGGGCACCCTGGTGACCGTGTCCT
CCGCCTCCACCAAGGGCCCTTCCGTGTTCCCTCTGGCCCCTTGCTCCCGG
TCCACCTCCGAGTCCACCGCCGCTCTGGGCTGCCTGGTGAAGGACTACTT
CCCTGAGCCTGTGACAGTGTCCTGGAACTCTGGCGCCCTGACCTCCGGCG
TGCACACCTTCCCTGCCGTGCTGCAGTCCTCCGGCCTGTACTCCCTGTCC
TCCGTGGTGACAGTGCCTTCCTCCAACTTCGGCACCCAGACCTACACCTG
CAACGTGGACCACAAGCCTTCCAACACCAAGGTGGACAAGACCGTGGAGC
GGAAGTGCTGCGTGGAGTGCCCTCCTTGCCCTGCCCCTCCTGTGGCTGGC
CCTAGCGTGTTCCTGTTCCCTCCTAAGCCTAAGGACACCCTGATGATCTC
CCGGACCCCTGAGGTGACCTGCGTGGTGGTGGACGTGTCCCACGAGGACC
CTGAGGTGCAGTTCAATTGGTACGTGGACGGCGTGGAGGTGCACAACGCC
AAGACCAAGCCTCGGGAGGAACAGTTCAACTCCACCTTCCGGGTGGTGTC
CGTGCTGACCGTGGTGCACCAGGACTGGCTGAACGGCAAGGAATACAAGT
GCAAAGTCTCCAACAAGGGCCTGCCTGCCCCTATCGAGAAAACCATCAGC
AAGACCAAGGGCCAGCCTCGCGAGCCTCAGGTGTACACCCTGCCTCCATC
CAGGGAGGAAATGACCAAGAACCAGGTGTCCCTGACCTGTCTGGTGAAGG
GCTTCTACCCTTCCGATATCGCCGTGGAGTGGGAGTCCAACGGCCAGCCT
GAGAACAACTACAAGACCACCCCTCCTATGCTGGACTCCGACGGCTCCTT
CTTCCTGTACTCCAAGCTGACAGTGGACAAGTCCCGGTGGCAGCAGGGCA
ACGTGTTCTCCTGCTCCGTGATGCACGAGGCCCTGCACAACCACTACACC
CAGAAGTCCCTGTCCCTGAGCCCTGGCAAGTAG

SEQ ID NO:2: Predicted protein sequence of the heavy chain of anti-Notch2/3 59RGV (germlined variant of 59R1), plus signal sequence. The signal sequence is underlined.

MKHLWFFLLLVAAPRWVLSEVQLVESGGGLVQPGGSLRLSCAASGFTFSS
SGMSWVRQAPGKGLEWVSVIASSGSNTYYADSVKGRFTISRDNSKNTLYL
QMNSLRAEDTAVYYCARGIFFAIWGQGTLVTVSSASTKGPSVFPLAPCSR
STSESTAALGCLVKDYFPEPVTVSWNSGALTSGVHTFPAVLQSSGLYSLS
SVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNA
KTKPREEQFNSTFRVVSVLTVVHQDWLNGKEYKCKVSNKGLPAPIEKTIS
KTKGQPREPQVYTLPPSREEMTKNQVSLTCLVKGFYPSDIAVEWESNGQP
ENNYKTTPPMLDSDGSFFLYSKLTVDKSRWQQGNVFSCSVMHEALHNHYT
QKSLSLSPGK

SEQ ID NO:17: Nucleotide sequence of the anti-Notch2/3 59RGV antibody (germlined variant of 59R1), plus signal sequence. The sequence encoding the signal sequence is underlined.

ATGGTGCTGCAGACCCAGGTGTTCATCTCCCTGCTGCTGTGGATCTCCGG
CGCCTACGGCGAGATCGTGCTGACCCAGTCCCCTGCCACACTGAGCCTGA
GCCCTGGCGAGAGAGCCACCCTGAGCTGCAGGCGGGCCTCCCAGTCCGTG
CGGTCCAACTACCTGGCTTGGTATCAGCAGAAACCCGGACAGGCCCCTCG
GCTGCTGATCTACGGCGCCTCCTCCCGGGCTACCGGCATCCCTGCCCGGT
TCTCCGGCTCCGGCAGCGGCACCGACTTCACCCTGACCATCTCCTCCCTG
GAGCCTGAGGACTTCGCCGTGTACTACTGCCAGCAGTACTCCAACTTCCC
TATCACCTTCGGCCAGGGCACCAAGGTGGAGATCAAGCGGACCGTGGCCG
CTCCTTCCGTGTTCATCTTCCCCCCTTCCGACGAGCAGCTGAAGTCCGGC
ACCGCCTCCGTGGTGTGCCTGCTGAACAACTTCTACCCTCGGGAGGCCAA
GGTGCAGTGGAAGGTGGACAACGCCCTGCAGTCCGGCAACTCCCAGGAAT
CCGTCACCGAGCAGGACTCCAAGGACAGCACCTACTCCCTGTCCTCCACC
CTGACCCTGTCCAAGGCCGACTACGAGAAGCACAAGGTGTACGCCTGCGA
GGTGACCCACCAGGGCCTGTCCAGCCCTGTGACCAAGTCCTTCAACCGGG
GCGAGTGCTAG

SEQ ID NO:4: Predicted protein sequence of the light chain of anti-Notch2/3 59RGV antibody (germlined variant of 59R1), plus signal sequence. The signal sequence is underlined.

MVLQTQVFISLLLWISGAYGEIVLTQSPATLSLSPGERATLSCRRASQSV
RSNYLAWYQQKPGQAPRLLIYGASSRATGIPARFSGSGSGTDFTLTISSL
EPEDFAVYYCQQYSNFPITFGQGTKVEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC

SEQ ID NO:19: 59R1 Light chain VL of 59RGV antibody (germlined variant of 59R1)

EIVLTQSPATLSLSPGERATLSCRRASQSVRSNYLAWYQQKPGQAPRLLI
YGASSRATGIPARFSGSGSGTDFTLTISSLEPEDFAVYYCQQYSNFPITF
GQGTKVEIKR

SEQ ID NO:20: 59R1 Heavy chain VH of 59RGV antibody (germlined variant of 59R1)

EVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARGI
FFAIWGQGTLVTVSSA

SEQ ID NO:22 (alternative heavy chain CDR3)

```
SIFYPT
```

SEQ ED NO:23 (alternative heavy chain CDR3)

```
SSFFAS
```

SEQ ID NO:24 (alternative heavy chain CDR3)

```
SSFYAS
```

SEQ ID NO:25 (alternative heavy chain CDR3)

```
SSFFAT
```

SEQ ID NO:26 (alternative heavy chain CDR3)

```
SIFYPS
```

SEQ ID NO:27 (alternative heavy chain CDR3)

```
SSFFAN
```

SEQ ID NO:30 (heavy chain CDR3 consensus sequence):

```
(G/S) (I/S) F (F/Y) (A/P) (I/T/S/N)
```

SEQ ID NO:47: 59R5 Light Chain nucleotide sequence (without signal sequence)

GACATCGTGCTGACCCAGTCCCCCGCCACACTGTCCCTGTCTCCCGGCGA
GAGAGCCACCCTGAGCTGTCGGGCCTCCCAGTCCGTGCGGTCCAACTACC
TGGCCTGGTATCAGCAGAAGCCCGGCCAGGCCCCTCGGCTGCTGATCTAC
GGCGCCTCCTCCAGGGCTACCGGCGTGCCTGCCCGGTTCTCCGGCTCCGG
CTCTGGCACCGACTTCACCCTGACCATCTCCAGCCTGGAGCCTGAGGACT
TCGCCGTGTACTACTGCCAGCAGTACTCCAACTTCCCTATCACCTTCGGC
CAGGGCACCAAGGTGGAGATCAAGCGGACCGTGGCCGCTCCTTCCGTGTT
CATCTTCCCCCCTTCCGACGAGCAGCTGAAGTCCGGCACCGCCTCCGTGG
TGTGCCTGCTGAACAACTTCTACCCTCGGGAGGCCAAGGTGCAGTGGAAG
GTGGACAACGCCCTGCAGTCCGGCAACTCCCAGGAGTCCGTCACCGAGCA
GGACTCCAAGGACTCTACCTACTCCCTGTCCTCCACCCTGACCCTGAGCA
AGGCCGACTACGAGAAGCACAAGGTGTACGCCTGCGAGGTGACCCACCAG
GGCCTGTCCTCTCCCGTGACCAAGTCCTTCAACCGGGGCGAGTGC

SEQ ID NO:48: 59R5 Heavy chain nucleotide sequence (without signal sequence)

GAGGTGCAGCTGGTCGAGTCTGGCGGCGGACTGGTGCAGCCTGGCGGCTC
CCTGAGACTGTCCTGCGCCGCTTCCGGCTTCACCTTCTCCTCCAGCGGCA
TGTCCTGGGTGCGCCAGGCACCTGGCAAAGGACTCGAGTGGGTGTCCGTG
ATCGCCTCCTCCGGCTCCAACACCTACTACGCCGACTCCGTGAAGGGCCG
GTTCACCATCTCCCGGGACAACTCCAAGAACACCCTGTACCTGCAGATGA
ACTCCCTGCGGGCCGAGGACACCGCCGTGTACTACTGCGCCCGGTCCATC
TTCTACACCACCTGGGGCCAGGGCACCCTGGTGACCGTGTCCTCCGCCTC
CACCAAGGGCCCCTCCGTGTTCCCTCTGGCCCCTTGCTCCCGGTCCACCT
CTGAGTCTACCGCCGCTCTGGGCTGCCTGGTGAAGGACTACTTCCCTGAG
CCTGTGACCGTGTCCTGGAACTCTGGCGCCCTGACCTCTGGCGTGCACAC
CTTCCCTGCCGTGCTGCAGTCCTCCGGCCTGTACTCCCTGTCCTCCGTGG
TGACCGTGCCTTCCTCCAACTTCGGCACCCAGACCTACACCTGCAACGTG
GACCACAAGCCTTCCAACACCAAGGTGGACAAGACCGTGGAGCGGAAGTG
CTGCGTGGAGTGCCCTCCTTGTCCTGCTCCTCCTGTGGCTGGCCCTTCTG
TGTTCCTGTTCCCTCCTAAGCCTAAGGACACCCTGATGATCTCCCGGACC
CCTGAAGTGACCTGCGTGGTGGTGGACGTGTCCCACGAGGACCCTGAGGT
GCAGTTCAATTGGTACGTGGACGGCGTGGAGGTGCACAACGCCAAGACCA
AGCCTCGGGAGGAACAGTTCAACTCCACCTTCCGGGTGGTGTCTGTGCTG
ACCGTGGTGCACCAGGACTGGCTGAACGGCAAAGAATACAAGTGCAAGGT
GTCCAACAAGGGCCTGCCTGCCCCTATCGAAAAGACCATCTCTAAGACCA
AGGGCCAGCCTCGCGAGCCTCAGGTCTACACCCTGCCTCCTAGCCGGGAG
GAAATGACCAAGAACCAGGTGTCCCTGACCTGTCTGGTGAAGGGCTTCTA
CCCTTCCGATATCGCCGTGGAGTGGGAGTCTAACGGCCAGCCTGAGAACA
ACTACAAGACCACCCCTCCTATGCTGGACTCCGACGGCTCCTTCTTCCTG
TACTCCAAGCTGACAGTGGACAAGTCCCGGTGGCAGCAGGGCAACGTGTT
CTCCTGCTCCGTGATGCACGAGGCCCTGCACAACCACTACACCCAGAAGT
CCCTGTCCCTGTCTCCTGGCAAG

SEQ ID NO:49: 59R5 Heavy chain

EVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSI
FYTTWGQGTLVTVSSASTKGPSVFPLAPCSRSTSESTAALGCLVKDYFPE
PVTVSWNSGALTSGVHTFPAVLQSSGLYSLSSVVTVPSSNFGTQTYTCNV
DHKPSNTKVDKTVERKCCVECPPCPAPPVAGPSVFLFPPKPKDTLMISRT

-continued

PEVTCVVVDVSHEDPEVQFNWYVDGVEVHNAKTKPREEQFNSTFRVVSVL
TVVHQDWLNGKEYKCKVSNKGLPAPIEKTISKTKGQPREPQVYTLPPSRE
EMTKNQVSLTCLVKGFYPSDIAVEWESNGQPENNYKTTPPMLDSDGSFFL
YSKLTVDKSRWQQGNVFSCSVMHEALHNHYTQKSLSLSPGK

SEQ ID NO:50: 59R5 Heavy chain variable region

EVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSI
FYTTWGQGTLVTVSSAST

SEQ ID NO:51: 59R5 Heavy chain CDR3

SIFYTT

SEQ ID NO:52: Variant 59R1 Heavy chain variable region

QVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSI
FYPTWGQGTLVTVSSA

SEQ ID NO:53: Variant 59R1 Heavy chain variable region

QVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSS
FEASWGQGTLVTVSSA

SEQ ID NO:54: Variant 59R1 Heavy chain variable region

QVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSS
FYASWGQGTLVTVSSA

SEQ ID NO:55: Variant 59R1 Heavy chain variable region

QVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSS
FFATWGQGTLVTVSSA

SEQ ID NO:56: Variant 59R1 Heavy chain variable region

QVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSI
FYPSWGQGTLVTVSSA

SEQ ID NO:57: Variant 59R1 Heavy chain variable region

QVQLVESGGGLVQPGGSLRLSCAASGFTFSSSGMSWVRQAPGKGLEWVSV
IASSGSNTYYADSVKGRFTISRDNSKNTLYLQMNSLRAEDTAVYYCARSS
FFANWGQGTLVTVSSA

SEQ ID NO:58: 59R5 Heavy chain variable region nucleotide sequence (without signal sequence)

GAGGTGCAGCTGGTCGAGTCTGGCGGCGGACTGGTGCAGCCTGGCGGCTC
CCTGAGACTGTCCTGCGCCGCTTCCGGCTTCACCTTCTCCTCCAGCGGCA
TGTCCTGGGTGCGCCAGGCACCTGGCAAAGGACTCGAGTGGGTGTCCGTG
ATCGCCTCCTCCGGCTCCAACACCTACTACGCCGACTCCGTGAAGGGCCG
GTTCACCATCTCCCGGGACAACTCCAAGAACACCCTGTACCTGCAGATGA
ACTCCCTGCGGGCCGAGGACACCGCCGTGTACTACTGCGCCCGGTCCATC
TTCTACACCACCTGGGGCCAGGGCACCCTGGTGACCGTGTCCTCCGCCTC
CACC

SEQ ID NO:59: 59R1 Light chain variable region nucleotide sequence (without signal sequence)

GATATCGTGCTGACCCAGAGCCCGGCGACCCTGAGCCTGTCTCCGGGCGA
ACGTGCGACCCTGAGCTGCAGAGCGAGCCAGTCTGTTCGTTCTAATTATC
TGGCTTGGTACCAGCAGAAACCAGGTCAAGCACCGCGTCTATTAATTTAT
GGTGCTTCTTCTCGTGCAACTGGGGTCCCGGCGCGTTTTAGCGGCTCTGG
ATCCGGCACGGATTTTACCCTGACCATTAGCAGCCTGGAACCTGAAGACT
TTGCGGTTTATTATTGCCAGCAGTATTCTAATTTTCCTATTACCTTTGGC
CAGGGTACGAAAGTTGAAATTAAACGT

SEQ ID NO:60: 59R1 Heavy chain variable region nucleotide sequence (without signal sequence)

CAGGTGCAATTGGTGGAAAGCGGCGGCGGCCTGGTGCAACCGGGCGGCAG
CCTGCGTCTGAGCTGCGCGGCCTCCGGATTTACCTTTTCTTCTTCTGGTA
TGTCTTGGGTGCGCCAAGCCCCTGGGAAGGGTCTCGAGTGGGTGAGCGTT
ATCGCTTCTTCTGGTAGCAATACCTATTATGCGGATAGCGTGAAAGGCCG
TTTTACCATTTCACGTGATAATTCGAAAAACACCCTGTATCTGCAAATGA
ACAGCCTGCGTGCGGAAGATACGGCCGTGTATTATTGCGCGCGTGGTATT
TTTTTTGCTATTTGGGGCCAAGGCACCCTGGTGACGGTTAGCTCAGCC

Human Notch-Related sequences:
SEQ ID NO:21: Notch2(EGF1-12) Fc fusion protein amino acid sequence MPALRPALLWALLALWLCCAAPAHALQCRDGYEPCVNEGMCVTYHNGTGY
CKCPEGFLGEYCQHRDPCEKNRCQNGGTCVAQAMLGKATCRCASGFTGED
CQYSTSHPCFVSRPCLNGGTCHMLSRDTYECTCQVGFTGKECQWTDACLS
HPCANGSTCTTVANQFSCKCLTGFTGQKCETDVNECDIPGHCQHGGTCLN
LPGSYQCQCPQGFTGQYCDSLYVPCAPSPCVNGGTCRQTGDFTFECNCLP
GFEGSTCERNIDDCPNHRCQNGGVCVDGVNTYNCRCPPQWTGQFCTEDVD
ECLLQPNACQNGGTCANRNGGYGCVCVNGWSGDDCSENIDDCAFASCTPG
STCIDRVASFSCMCPEGKAGLLCHLDDACISNPCHKGALCDTNPLNGQYI
CTCPQGYKGADCTEDVDECAMANSNPCEHAGKCVNTDGAFHCECLKGYAG

```
PRCEMDINECHSDPCQNDATCLDKIGGFTCLCMPGFKGVHCELGRADKTH

TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFS

CSVMHEALHNHYTQKSLSLSPGK
```

SEQ ID NO:28 (potential component of 59R1 binding site within EGF10 of human Notch2):

```
HKGAL
```

SEQ ID NO:29 (site within human Notch3 EGF9 that corresponds to the potential component of 59R1 binding site within human Notch2 EGF10):

```
HEDAI
```

SEQ ID NO:45: hNotch1
Amino Acids 1-1732 Extracellular domain. (underlined)
Amino Acids 372-414 EGF repeat 10 (double underlined and italicized)

```
MPPLLAPLLCLALLPALAARGPRCSQPGETCLNGGKCEAANGTEACVCGG

AFVGPRCQDPNPCLSTPCKNAGTCHVVDRRGVADYACSCALGFSGPLCLT

PLDNACLTNPCRNGGTCDLLTLTEYKCRCPPGWSGKSCQQADPCASNPCA

NGGQCLPFEASYICHCPPSFHGPTCRQDVNECGQKPGLCRHGGTCHNEVG

SYRCVCRATHTGPNCERPYVPCSPSPCQNGGTCRPTGDVTHECACLPGFT

GQNCEENIDDCPGNNCKNGGACVDGVNTYNCRCPPEWTGQYCTEDVDECQ

LMPNACQNGGTCHNTHGGYNCVCVNGWTGEDCSENIDDCASAACFHGATC

HDRVASFYCECPHGRTGLLCHLNDACISNPCNEGSNCDTNPVNGKAICTC

PSGYTGPACSQDVDECSLGANPCEHAGKCINTLGSFECQCLQGYTGPRCE

IDVNECVSNPCQNDATCLDQIGEFQCICMPGYEGVHCEVNTDECASSPCL

HNGRCLDKINEFQCECPTGFTGHLCQYDVDECASTPCKNGAKCLDGPNTY

TCVCTEGYTGTHCEVDIDECDPDPCHYGSCKDGVATFTCLCRPGYTGHHC

ETNINECSSQPCRHGGTCQDRDNAYLCFCLKGTTGPNCEINLDDCASSPC

DSGTCLDKIDGYECACEPGYTGSMCNINIDECAGNPCHNGGTCEDGINGF

TCRCPEGYHDPTCLSEVNECNSNPCVHGACRDSLNGYKCDCDPGWSGTNC

DINNNECESNPCVNGGTCKDMTSGYVCTCREGFSGPNCQTNINECASNPC

LNQGTCIDDVAGYKCNCLLPYTGATCEVVLAPCAPSPCRNGGECRQSEDY

ESFSCVCPTGWQGQTCEVDINECVLSPCRHGASCQNTHGGYRCHCQAGYS

GRNCETDIDDCRPNPCHNGGSCTDGINTAFCDCLPGFRGTFCEEDINECA

SDPCRNGANCTDCVDSYTCTCPAGFSGIHCENNTPDCTESSCFNGGTCVD

GINSFTCLCPPGFTGSYCQHDVNECDSQPCLHGGTCQDGCGSYRCTCPQG

YTGPNCQNLVHWCDSSPCKNGGKCWQTHTQYRCECPSGWTGLYCDVPSVS

CEVAAQRQGVDVARLCQHGGLCVDAGNTHHCRCQAGYTGSYCEDLVDECS

PSPCQNGATCTDYLGGYSCKCVAGYHGVNCSEEIDECLSHPCQNGGTCLD

LPNTYKCSCPRGTQGVHCEINVDDCNPPVDPVSRSPKCFNNGTCVDQVGG

YSCTCPPGFVGERCEGDVNECLSNPCDARGTQNCVQRVNDFHCECRAGHT

GRRCESVINGCKGKPCKNGGTCAVASNTARGFICKCPAGFEGATCENDAR

TCGSLRCLNGGTCISGPRSPTCLCLGPFTGPECQFPASSPCLGGNPCYNQ

GTCEPTSESPFYRCLCPAKFNGLLCHILDYSFGGGAGRDIPPPLIEEACE

LPECQEDAGNKVCSLQCNNHACGWDGGDCSLNFNDPWKNCTQSLQCWKYF

SDGHCDSQCNSAGCLFDGFDCQRAEGQCNPLYDQYCKDHFSDGHCDQGCN

SAECEWDGLDCAEHVPERLAAGTLVVVVLMPPEQLRNSSFHFLRELSRVL

HTNVVFKRDAHGQQMIFPYYGREEELRKHPIKRAAEGWAAPDALLGQVKA

SLLPGGSEGGRRRRELDPMDVRGSIVYLEIDNRQCVQASSQCFQSATDVA

AFLGALASLGSLNIPYKIEAVQSETVEPPPPAQLHFMYVAAAAFVLLFFV

GCGVLLSRKRRRQHGQLWFPEGFKVSEASKKKRREPLGEDSVGLKPLKNA

SDGALMDDNQNEWGDEDLETKKFRFEEPVVLPDLDDQTDHRQWTQQHLDA

ADLRMSAMAPTPPQGEVDADCMDVNVRGPDGFTPLMIASCSGGGLETGNS

EEEEDAPAVISDFIYQGASLHNQTDRTGETALHLAARYSRSDAAKRLLEA

SADANIQDNMGRTPLHAAVSADAQGVFQILIRNRATDLDARMHDGTTPLI

LAARLAVEGMLEDLINSHADVNAVDDLGKSALHWAAAVNNVDAAVVLLKN

GANKDMQNNREETPLFLAAREGSYETAKVLLDHFANRDITDHMDRLPRDI

AQERMHHDIVRLLDEYNLVRSPQLHGAPLGGTPTLSPPLCSPNGYLGSLK

PGVQGKKVRKPSSKGLACGSKEAKDLKARRKKSQDGKGCLLDSSGMLSPV

DSLESPHGYLSDVASPPLLPSPFQQSPSVPLNHLPGMPDTHLGIGHLNVA

AKPEMAALGGGGRLAFETGPPRLSHLPVASGTSTVLGSSSGGALNFTVGG

STSLNGQCEWLSRLQSGMVPNQYNPLRGSVAPGPLSTQAPSLQHGMVGPL

HSSLAASALSQMMSYQGLPSTRLATQPHLVQTQQVQPQNLQMQQQNLQPA

NIQQQQSLQPPPPPPQPHLGVSSAASGHLGRSFLSGEPSQADVQPLGPSS

LAVHTILPQESPALPTSLPSSLVPPVTAAQFLTPPSQHSYSSPVDNTPSH

QLQVPEHPFLTPSPESPDQWSSSSPHSNVSDWSEGVSSPPTSMQSQIARI

PEAFK
```

SEQ ID NO:31: human Notch2
Amino Acids 1-1677: Extracellular domain (underlined)
Amino Acids 375-417: EGF repeat 10 (double underlined and italicized)

```
MPALRPALLWALLALWLCCAAPAHALQCRDGYEPCVNEGMCVTYHNGTGY

CKCPEGFLGEYCQHRDPCEKNRCQNGGTCVAQAMLGKATCRCASGFTGED

CQYSTSHPCFVSRPCLNGGTCHMLSRDTYECTCQVGFTGKECQWTDACLS

HPCANGSTCTTVANQFSCKCLTGFTGQKCETDVNECDIPGHCQHGGTCLN

LPGSYQCQCPQGFTGQYCDSLYVPCAPSPCVNGGTCRQTGDFTFECNCLP

GFEGSTCERNIDDCPNHRCQNGGVCVDGVNTYNCRCPPQWTGQFCTEDVD

ECLLQPNACQNGGTCANRNGGYGCVCVNGWSGDDCSENIDDCAFASCTPG

STCIDRVASFSCMCPEGKAGLLCHLDDACISNPCHKGALCDTNPLNGQYI
```

*CTCPQGYKGADCTEDVD*ECAMANSNPCEHAGKCVNTDGAFHCECLKGYAG
PRCEMDINECHSDPCQNDATCLDKIGGFTCLCMPGFKGVHCELEINECQS
NPCVNNGQCVDKVNRFQCLCPPGFTGPVCQIDIDDCSSTPCLNGAKCIDH
PNGYECQCATGFTGVLCEENIDNCDPDPCHHGQCQDGIDSYTCICNPGYM
GAICSDQIDECYSSPCLNDGRCIDLVNGYQCNCQPGTSGVNCEINFDDCA
SNPCIHGICMDGINRYSCVCSPGFTGQRCNIDIDECASNPCRKGATCING
VNGFRCICPEGPHHPSCYSQVNECLSNPCIHGNCTGGLSGYKCLCDAGWV
GINCEVDKNECLSNPCQNGGTCDNLVNGYRCTCKKGFKGYNCQVNIDECA
SNPCLNQGTCFDDISGYTCHCVLPYTGKNCQTVLAPCSPNPCENAAVCKE
SPNFESYTCLCAPGWQGQRCTIDIDECISKPCMNHGLCHNTQGSYMCECP
PGFSGMDCEEDIDDCLANPCQNGGSCMDGVNTFSCLCLPGFTGDKCQTDM
NECLSEPCKNGGTCSDYVNSYTCKCQAGFDGVHCENNINECTESSCFNGG
TCVDGINSFSCLCPVGFTGSFCLHEINECSSHPCLNEGTCVDGLGTYRCS
CPLGYTGKNCQTLVNLCSRSPCKNKGTCVQKKAESQCLCPSGWAGAYCDV
PNVSCDIAASRRGVLVEHLCQHSGVCINAGNTHYCQCPLGYTGSYCEEQL
DECASNPCQHGATCSDFIGGYRCECVPGYQGVNCEYEVDECQNQPCQNGG
TCIDLVNHFKCSCPPGTRGLLCEENIDDCARGPHCLNGGQCMDRIGGYSC
RCLPGFAGERCEGDINECLSNPCSSEGSLDCIQLTNDYLCVCRSAFTGRH
CETFVDVCPQMPCLNGGTCAVASNMPDGFICRCPPGFSGARCQSSCGQVK
CRKGEQCVHTASGPRCFCPSPRDCESGCASSPCQHGGSCHPQRQPPYYSC
QCAPPFSGSRCELYTAPPSTPPATCLSQYCADKARDGVCDEACNSHACQW
DGGDCSLTMENPWANCSSPLPCWDYINNQCDELCNTVECLFDNFECQGNS
KTCKYDKYCADHFKDNHCDQGCNSEECGWDGLDCAADQPENLAEGTLVIV
VLMPPEQLLQDARSFLRALGTLLHTNLRIKRDSQGELMVYPYYGEKSAAM
KKQRMTRRSLPGEQEQEVAGSKVFLEIDNRQCVQDSDHCFKNTDAAAALL
ASHAIQGTLSYPLVSVVSESLTPERTQLLYLLAVAVVIILFIILLGVIMA
KRKRKHGSLWLPEGFTLRRDASNHKRREPVGQDAVGLKNLSVQVSEANLI
GTGTSEHWVDDEGPQPKKVKAEDEALLSEEDDPIDRRPWTQQHLEAADIR
RTPSLALTPPQAEQEVDVLDVNVRGPDGCTPLMLASLRGGSSDLSDEDED
AEDSSANIITDLVYQGASLQAQTDRTGEMALHLAARYSRADAAKRLLDAG
ADANAQDNMGRCPLHAAVAADAQGVFQILIRNRVTDLDARMNDGTTPLIL
AARLAVEGMVAELINCQADVNAVDDHGKSALHWAAAVNNVEATLLLLKNG
ANRDMQDNKEETPLFLAAREGSYEAAKILLLDHFANRDITDHMDRLPRDVA
RDRMHHDIVRLLDEYNVTPSPPGTVLTSALSPVICGPNRSFLSLKHTPMG
KKSRRPSAKSTMPTSLPNLAKEAKDAKGSRRKKSLSEKVQLSESSVTLSP
VDSLESPHTYVSDTTSSPMITSPGILQASPNPMLATAAPPAPVHAQHALS
FSNLHEMQPLAHGASTVLPSVSQLLSHHHIVSPGSGSAGSLSRLHPVPVP
ADWMNRNEVNETQYNEMFGMVLAPAEGTHPGIAPQSRPPEGKHITTPREP
LPPIVTFQLIPKGSIAQPAGAPQPQSTCPPAVAGPLPTMYQIPEMARLPS
VAFPTAMMPQQDGQVAQTILPAYHPFPASVGKYPTPPSQHSYASSNAAER

TPSHSGHLQGEHPYLTPSPESPDQWSSSSPHSASDWSDVTTSPTPGGAGG
GQRGPGTHMSEPPHNNMQVYA

SEQ ID NO:32: human Notch3
Amino Acids 1-1640: Extracellular domain (underlined)
Amino Acids 351-393: EGF repeat 9 (double underlined and italicized)

MGPGARGRRRRRRPMSPPPPPPPVRALPLLLLLAGPGAAAPPCLDGSPCA
NGGRCTQLPSREAACLCPPGWVGERCQLEDPCHSGPCAGRGVCQSSVVAG
TARFSCRCPRGFRGPDCSLPDPCLSSPCAHGARCSVGPDGRFLCSCPPGY
QGRSCRSDVDECRVGEPCRHGGTCLNTPGSFRCQCPAGYTGPLCENPAVP
CAPSPCRNGGTCRQSGDLTYDCACLPGFEGQNCEVNVDDCPGHRCLNGGT
CVDGVNTYNCQCPPEWTGQFCTEDVDECQLQPNACHNGGTCFNTLGGHSC
VCVNGWTGESCSQNIDDCATAVCFHGATCHDRVASFYCACPMGKTGLLCH
*LDDACVSNPCHEDAICDTNPVNGRAICTCPPGFTGGACDQDVD*ECSIGAN
PCEHLGRCVNTQGSFLCQCGRGYTGPRCETDVNECLSGPCRNQATCLDRI
GQFTCICMAGFTGTYCEVDIDECQSSPCVNGGVCKLRVNGFSCTCPSGFS
GSTCQLDVDECASTPCRNGAKCVDQPDGYECRCAEGFEGTLCDRNVDDCS
PDPCHHGRCVDIASFSCACAPGYTGTRCESQVDECRSQPCRHGGKCLDL
VDKYLCRCPSGTTGVNCEVNIDDCASNPCTFGVCRDGINRYDCVCQPGFT
GPLCNVEINECASSPCGEGGSCVDGENGFRCLCPPGSLPPLCLPPSHPCA
HEPCSHGICYDAPGGFRCVCEPGWSGPRCSQSLARDACESQPCRAGGTCS
SDGMGFHCTCPPGVQGRQCELLSPCTPNPCEHGGRCESAPGQLPVCSCPQ
GWQGPRCQQDVDECAGPAPCGPHGICTNLAGSFSCTCHGGYTGPSCDQDI
NDCDPNPCLNGGSCQDGVGSFSCSCLPGFAGPRCAPDVDECLSNPCGPGT
CTDHVASFTCTCPPGYGGFHCEQDLPDCSPSSCFNGGTCVDGVNSFSCLC
RPGYTGAHCQHEADPCLSRPCLHGGVCSAAHPGFRCTCLESFTGPQCQTL
VDWCSRQPCQNGGRCVQTGAYCLCPPGWSGRLCDIRSLPCREAAAQIGVR
LEQLCQAGGQCVDEDSSHYCVCPEGRTGSHCEQEVDPCLAQPCQHGGTCR
GYMGGYMCECLPGYNGDNCEDDVDECASQPCQHGGSCIDLVARYLCSCPP
GTLGVLCEINEDDCGPGPPLDSGPRCLHNGTCVDLVGGFRCTCPPGYTGL
RCEADINECRSGACHAAHTRDCLQDPGGGFRCLCHAGFSGPRCQTVLSPC
ESQPCQHGGQCRPSPGPGGGLTFTCHCAQPFWGPRCERVARSCRELQCPV
GVPCQQTPRGPRCACPPGLDGPDCRSFPGSPPGASNASCAAAPCLHGGSC
RPAPLAPFFRCACAQGWTGPRCEAPAAAPEVSEEPRCPRAACQAKRGDQR
CDRECNSPGCGWDGGDCSLSVGDPWRQCEALQCWRLFNNSRCDPACSSPA
CLYDNFDCHAGGRERTCNPVYEKYCADHFADGRCDQGCNTEECGWDGLDC
ASEVPALLARGVLVLTVLLPPEELLRSSADFLQRLSAILRTSLRFRLDAH
GQAMVFPYHRPSPGSEPRARRELAPEVIGSVVMLEIDNRLCLQSPENDHC
FPDAQSAADYLGALSAVERLDFPYPLRDVRGEPLEPPEPSVPLLPLLVAG
AVLLLVILVLGVMVARRKREHSTLWFPEGFSLHKDVASGHKGRREPVGQD

-continued

```
ALGMKNMAKGESLMGEVATDWMDTECPEAKRLKVEEPGMGAEEAVDCRQW
TQHHLVAADIRVAPAMALTPPQGDADADGMDVNVRGPDGFTPLMLASFCG
GALEPMPTEEDEADDTSASIISDLICQGAQLGARTDRTGETALHLAARYA
RADAAKRLLDAGADTNAQDHSGRTPLHTAVTADAQGVFQILIRNRSTDLD
ARMADGSTALILAARLAVEGMVEELIASHADVNAVDELGKSALHWAAAVN
NVEATLALLKNGANKDMQDSKEETPLFLAAREGSYEAAKLLLDHFANREI
TDHLDRLPRDVAQERLHQDIVRLLDQPSGPRSPPGPHGLGPLLCPPGAFL
PGLKAAQSGSKKSRRPPGKAGLGPQGPRGRGKKLTLACPGPLADSSVTLS
PVDSLDSPRPFGGPPASPGGFPLEGPYAAATATAVSLAQLGGPGRAGLGR
QPPGGCVLSLGLLNPVAVPLDWARLPPPAPPGPSFLLPLAPGPQLLNPGT
PVSPQERPPPYLAVPGHGEEYPVAGAHSSPPKARFLRVPSEHPYLTPSPE
SPEHWASPSPPSLSDWSESTPSPATATGAMATTTGALPAQPLPLSVPSSL
AQAQTQLGPQPEVTPKRQVLA
```

SEQ ID NO:46: hNotch4
Amino Acids 1-1444 Extracellular domain (underlined)
Amino Acids 392-434 EGF repeat 10 (double underlined and italicized)

```
MQPPSLLLLLLLLLLLCVSVVRPRGLLCGSFPEPCANGGTCLSLSLGQGT
CQCAPGFLGETCQFPDPCQNAQLCQNGGSCQALLPAPLGLPSSPSPLTPS
FLCTCLPGFTGERCQAKLEDPCPPSFCSKRGRCHIQASGRPQCSCMPGWT
GEQCQLRDFCSANPCVNGGVCLATYPQIQCHCPPGFEGHACERDVNECFQ
DPGPCPKGTSCHNTLGSFQCLCPVGQEGPRCELRAGPCPPRGCSNGGTCQ
LMPEKDSTFHLCLCPPGFIGPDCEVNPDNCVSHQCQNGGTCQDGLDTYTC
LCPETWTGWDCSEDVDECETQGPPHCRNGGTCQNSAGSFHCVCVSGWGGT
SCEENLDDCIAATCAPGSTCIDRVGSFSCLCPPGRTGLLCHLEDMCLSQP
CHGDAQCSTNPLTGSTLCLCQPGYSGPTCHQDLDECLMAQQGPSPCEHGG
SCLNTPGSFNCLCPPGYTGSRCEADHNECLSQPCHPGSTCLDLLATFHCL
CPPGLEGQLCEVETNECASAPCLNHADCHDLLNGFQCICLPGFSGTRCEE
DIDECRSSPCANGGQCQDQPGAFHCKCLPGFEGPRCQTEVDECLSDPCPV
GASCLDLPGAFFCLCPSGFTGQLCEVPLCAPNLCQPKQICKDQKDKANCL
CPDGSPGCAPPEDNCTCHHGHCQRSSCVCDVGWTGPECEAELGGCISAPC
AHGGTCYPQPSGYNCTCPTGYTGPTCSEEMTACHSGPCLNGGSCNPSPGG
YYCTCPPSHTGPQCQTSTDYCVSAPCFNGGTCVNRPGTFSCLCAMGFQGP
RCEGKLRPSCADSPCRNRATCQDSPQGPRCLCPTGYTGGSCQTLMDLCAQ
KPCPRNSHCLQTGPSFHCLCLQGWTGPLCNLPLSSCQKAALSQGIDVSSL
CHNGGLCVDSGPSYFCHCPPGFQGSLCQDHVNPCESRPCQNGATCMAQPS
GYLCQCAPGYDGQNCSKELDACQSQPCHNHGTCTPKPGGFHCACPPGFVG
LRCEGDVDECLDQPCHPTGTAACHSLANAFYCQCLPGHTGQWCEVEIDPC
HSQPCFHGGTCEATAGSPLGFICHCPKGFEGPTCSHRAPSCGFHHCHHGG
LCLPSPKPGFPPRCACLSGYGGPDCLTPPAPKGCGPPSPCLYNGSCSETT
GLGGPGFRCSCPHSSPGPRCQKPGAKGCEGRSGDGACDAGCSGPGGNWDG
GDCSLGVPDPWKGCPSHSRCWLLFRDGQCHPQCDSEECLFDGYDCETPPA
CTPAYDQYCHDHFHNGHCEKGCNTAECGWDGGDCRPEDGDPEWGPSLALL
VVLSPPALDQQLFALARVLSLTLRVGLWVRKDRDGRDMVYPYPGARAEEK
LGGTRDPTYQERAAPQTQPLGKETDSLSAGFVVVMGVDLSRCGPDHPASR
CPWDPGLLLRFLAAMAAVGALEPLLPGPLLAVHPHAGTAPPANQLPWPVL
CSPVAGVILLALGALLVLQLIRRRRREHGALWLPPGFTRRPRTQSAPHRR
RPPLGEDSIGLKALKPKAEVDEDGVVMCSGPEEGEEVGQAEETGPPSTCQ
LWSLSGGCGALPQAAMLTPPQESEMEAPDLDTRGPDGVTPLMSAVCCGEV
QSGTFQGAWLGCPEPWEPLLDGGACPQAHTVGTGETPLHLAARFSRPTAA
RRLLEAGANPNQPDRAGRTPLHAAVAADAREVCQLLLRSRQTAVDARTED
GTTPLMLAARLAVEDLVEELIAAQADVGARDKWGKTALHWAAAVNNARAA
RSLLQAGADKDAQDNREQTPLFLAAREGAVEVAQLLLGLGAARELRDQAG
LAPADVAHQRNHWDLLTLLEGAGPPEARHKATPGREAGPFPRARTVSVSV
PPHGGGALPRCRTLSAGAGPRGGGACLQARTWSVDLAARGGGAYSHCRSL
SGVGAGGGPTPRGRRFSAGMRGPRPNPAIMRGRYGVAAGRGGRVSTDDWP
CDWVALGACGSASNIPIPPPCLTPSPERGSPQLDCGPPALQEMPINQGGE
GKK
```

SEQ ID NO:33: Polynucleotide sequence encoding human Notch2 EGF 1-12

```
ATGCCCGCCCTGCGCCCCGCTCTGCTGTGGGCGCTGCTGGCGCTCTGGCT
GTGCTGCGCGGCCCCCGCGCATGCATTGCAGTGTCGAGATGGCTATGAAC
CCTGTGTAAATGAAGGAATGTGTGTTACCTACCACAATGGCACAGGATAC
TGCAAATGTCCAGAAGGCTTCTTGGGGAATATTGTCAACATCGAGACCC
CTGTGAGAAGAACCGCTGCCAGAATGGTGGGACTTGTGTGGCCCAGGCCA
TGCTGGGGAAAGCCACGTGCCGATGTGCCTCAGGGTTTACAGGAGAGGAC
TGCCAGTACTCAACATCTCATCCATGCTTTGTGTCTCGACCCTGCCTGAA
TGGCGGCACATGCCATATGCTCAGCCGGGATACCTATGAGTGCACCTGTC
AAGTCGGGTTTACAGGTAAGGAGTGCCAATGGACGGATGCCTGCCTGTCT
CATCCCTGTGCAAATGGAAGTACCTGTACCACTGTGGCCAACCAGTTCTC
CTGCAAATGCCTCACAGGCTTCACAGGGCAGAAATGTGAGACTGATGTCA
ATGAGTGTGACATTCCAGGACACTGCCAGCATGGTGGCACCTGCCTCAAC
CTGCCTGGTTCCTACCAGTGCCAGTGCCCTCAGGGCTTCACAGGCCAGTA
CTGTGACAGCCTGTATGTGCCCTGTGCACCCTCACCTTGTGTCAATGGAG
GCACCTGTCGGCAGACTGGTGACTTCACTTTTGAGTGCAACTGCCTTCCA
GGTTTTGAAGGGAGCACCTGTGAGAGGAATATTGATGACTGCCCTAACCA
CAGGTGTCAGAATGGAGGGTTTGTGTGGATGGGGTCAACACTTACAACT
GCCGCTGTCCCCCACAATGGACAGGACAGTTCTGCACAGAGGATGTGGAT
GAATGCCTGCTGCAGCCCAATGCCTGTCAAAATGGGGGCACCTGTGCCAA
CCGCAATGGAGGCTATGGCTGTGTATGTGTCAACGGCTGGAGTGGAGATG
ACTGCAGTGAGAACATTGATGATTGTGCCTTCGCCTCCTGTACTCCAGGC
```

TCCACCTGCATCGACCGTGTGGCCTCCTTCTCTTGCATGTGCCCAGAGGG

GAAGGCAGGTCTCCTGTGTCATCTGGATGATGCATGCATCAGCAATCCTT

GCCACAAGGGGCACTGTGTGACACCAACCCCCTAAATGGGCAATATATT

TGCACCTGCCCACAAGGCTACAAAGGGGCTGACTGCACAGAAGATGTGGA

TGAATGTGCCATGGCCAATAGCAATCCTTGTGAGCATGCAGGAAAATGTG

TGAACACGGATGGCGCCTTCCACTGTGAGTGTCTGAAGGGTTATGCAGGA

CCTCGTTGTGAGATGGACATCAATGAGTGCCATTCAGACCCCTGCCAGAA

TGATGCTACCTGTCTGGATAAGATTGGAGGCTTCACATGTCTGTGCATGC

CAGGTTTCAAAGGTGTGCATTGTGAATTA

SEQ ID NO:34: Human Notch2 EGF 1-12 polypeptide sequence

MPALRPALLWALLALWLCCAAPAHALQCRDGYEPCVNEGMCVTYHNGTY

CKCPEGFLGEYCQHRDPCEKNRCQNGGTCVAQAMLGKATCRCASGFTGED

CQYSTSHPCFVSRPCLNGGTCHMLSRDTYECTCQVGFTGKECQWTDACLS

HPCANGSTCTTVANQFSCKCLTGFTGQKCETDVNECDIPGHCQHGGTCLN

LPGSYQCQCPQGFTGQYCDSLYVPCAPSPCVNGGTCRQTGDFTFECNCLP

GFEGSTCERNIDDCPNHRCQNGGVCVDGVNTYNCRCPPQWTGQFCTEDVD

ECLLQPNACQNGGTCANRNGGYGCVCVNGWSGDDCSENIDDCAFASCTPG

STCIDRVASFSCMCPEGKAGLLCHLDDACISNPCHKGALCDTNPLNGQYI

CTCPQGYKGADCTEDVDECAMANSNPCEHAGKCVNTDGAFHCECLKGYAG

PRCEMDINECHSDPCQNDATCLDKIGGFTCLCMPGFKGVHCEL

SEQ ID NO:35: Human Notch1 EGF10

LNDACISNPCNEGSNCDTNPVNGKAICTCPSGYTGPACSQDVD

SEQ ID NO:36: Human Notch2 EGF10

LDDACISNPCHKGALCDTNPLNGQYICTCPQGYKGADCTEDVD

SEQ ID NO:37: Human Notch3 EGF9 (EGF9 is the EGF of human Notch3 that corresponds to EGF10 of the other Notch receptors including Notch2)

LDDACVSNPCHEDAICDTNPVNGRAICTCPPGFTGGACDQDVD

SEQ ID NO:38: Human Notch4 EGF10

LEDMCLSQPCHGDAQCSTNPLTGSTLCLCQPGYSGPTCHQDLD

SEQ ID NO:41: Notch1 EGF repeat 4

QADPCASNPCANGGQCLPFEASYICHCPPSFHGPTCRQ

SEQ ID NO:42: Notch2 EGF repeat 4

TDACLSHPCANGSTCTTVANQFSCKCLTGFTGQKCET

SEQ ID NO:43: Notch3 EGF repeat 4

SDVDECRVGEPCRHGGTCLNTPGSFRCQCPAGYTGPLCEN

SEQ ID NO:44: Notch4 EGF repeat 4

RDFCSANPCVNGGVCLATYPQIQCHCPPGFEGHACER

---

What is claimed is:

1. An isolated antibody encoded by the polynucleotide deposited with ATCC as PTA-9547.

2. An isolated cell comprising or producing the antibody of claim 1.

3. A pharmaceutical composition comprising the antibody of claim 1.

4. An isolated antibody that specifically binds human Notch2 and/or Notch3, wherein the antibody comprises:
   (a) a heavy chain CDR1 comprising SSSGMS (SEQ ID NO:5), a heavy chain CDR2 comprising VIASSGSN-TYYADSVKG (SEQ ID NO:6), and a heavy chain CDR3 comprising SIFYTT (SEQ ID NO:51); and
   (b) a light chain CDR1 comprising RASQSVRSNYLA (SEQ ID NO:8), a light chain CDR2 comprising GAS-SRAT (SEQ ID NO:9), and a light chain CDR3 comprising QQYSNFPI (SEQ ID NO:10).

5. The antibody of claim 4, which is a monoclonal antibody, a chimeric antibody, a humanized antibody, a human antibody, or an antibody fragment.

6. An isolated cell comprising or producing the antibody of claim 4.

7. A pharmaceutical composition comprising the antibody of claim 4.

8. An isolated antibody that specifically binds human Notch2 and/or Notch3, wherein the antibody comprises:
   (a) a heavy chain CDR1 comprising SSSGMS (SEQ ID NO:5), a heavy chain CDR2 comprising VIASSGSN-TYYADSVKG (SEQ ID NO:6), and a heavy chain CDR3 comprising GIFFAI (SEQ ID NO:7); and (b) a light chain CDR1 comprising RASQSVRSNYLA (SEQ ID NO:8), a light chain CDR2 comprising GASSRAT (SEQ ID NO:9), and a light chain CDR3 comprising QQYSNFPI (SEQ ID NO:10).

9. The antibody of claim 8, which is a monoclonal antibody, a chimeric antibody, a humanized antibody, a human antibody, or an antibody fragment.

10. An isolated cell comprising or producing the antibody of claim 8.

11. A pharmaceutical composition comprising the antibody of claim 8.

12. An isolated antibody that specifically binds human Notch2 and/or Notch3, wherein the antibody comprises:
   (a) a heavy chain variable region having at least about 90% sequence identity to SEQ ID NO:50, SEQ ID NO:14, or SEQ ID NO:20; and
   (b) a light chain variable region having at least about 90% sequence identity to SEQ ID NO:13 or SEQ ID NO:19.

13. The antibody of claim 12, which comprises:
   (a) a heavy chain variable region having at least about 95% sequence identity to SEQ ID NO:50; and
   (b) a light chain variable region having at least about 95% sequence identity to SEQ ID NO:13.

14. The antibody of claim 13, which comprises:
   (a) a heavy chain variable region comprising SEQ ID NO:50; and
   (b) a light chain variable region comprising SEQ ID NO:13.

15. The antibody of claim 12, which comprises:
   (a) a heavy chain variable region having at least about 95% sequence identity to SEQ ID NO:14; and
   (b) a light chain variable region having at least about 95% sequence identity to SEQ ID NO:13.

16. The antibody of claim 15, which comprises:
   (a) a heavy chain variable region comprising SEQ ID NO:14; and
   (b) a light chain variable region comprising SEQ ID NO:13.

17. The antibody of claim 12, which is a monoclonal antibody, a chimeric antibody, a humanized antibody, a human antibody, or an antibody fragment.

18. An isolated cell comprising or producing the antibody of claim 12.

19. A pharmaceutical composition comprising the antibody of claim 12.

20. An isolated polypeptide comprising a sequence selected from the group consisting of SEQ ID NO:50, SEQ ID NO:2, SEQ ID NO:4, SEQ ID NO:16, SEQ ID NO:18, SEQ ID NO:13, SEQ ID NO:14, SEQ ID NO:19, SEQ ID NO:20, and SEQ ID NO:49.

21. An isolated antibody encoded by the polynucleotide deposited with ATCC as PTA-10170.

22. An isolated cell comprising or producing the antibody of claim 21.

23. A pharmaceutical composition comprising the antibody of claim 21.

* * * * *

UNITED STATES PATENT AND TRADEMARK OFFICE
CERTIFICATE OF CORRECTION

| | |
|---|---|
| PATENT NO. | : 8,226,943 B2 |
| APPLICATION NO. | : 12/499627 |
| DATED | : July 24, 2012 |
| INVENTOR(S) | : Gurney et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 274 days.

Signed and Sealed this
Twenty-seventh Day of November, 2012

David J. Kappos
*Director of the United States Patent and Trademark Office*